United States Patent
Patel et al.

(10) Patent No.: US 11,071,721 B2
(45) Date of Patent: Jul. 27, 2021

(54) BICYCLIC AMIDE COMPOUNDS AND METHODS OF USE THEREOF

(71) Applicant: Genentech, Inc., South San Francisco, CA (US)

(72) Inventors: Snahel Patel, Foster City, CA (US); Gregory Hamilton, South San Francisco, CA (US); Guiling Zhao, South San Francisco, CA (US); Huifen Chen, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/828,271

(22) Filed: Nov. 30, 2017

(65) Prior Publication Data

US 2018/0153831 A1 Jun. 7, 2018

Related U.S. Application Data

(60) Provisional application No. 62/429,558, filed on Dec. 2, 2016.

(51) Int. Cl.
| | |
|---|---|
| *C07D 471/04* | (2006.01) |
| *A61K 31/16* | (2006.01) |
| *A61P 9/10* | (2006.01) |
| *C07D 519/00* | (2006.01) |
| *A61P 9/00* | (2006.01) |
| *A61P 29/00* | (2006.01) |
| *A61P 43/00* | (2006.01) |
| *A61K 31/396* | (2006.01) |
| *A61K 31/397* | (2006.01) |
| *A61K 31/4025* | (2006.01) |
| *A61K 31/416* | (2006.01) |
| *A61K 31/4196* | (2006.01) |
| *A61K 31/44* | (2006.01) |
| *A61K 31/5383* | (2006.01) |
| *C07D 487/04* | (2006.01) |
| *C07D 491/04* | (2006.01) |
| *C07D 491/048* | (2006.01) |

(52) U.S. Cl.
CPC .......... *A61K 31/16* (2013.01); *A61K 31/396* (2013.01); *A61K 31/397* (2013.01); *A61K 31/4025* (2013.01); *A61K 31/416* (2013.01); *A61K 31/4196* (2013.01); *A61K 31/44* (2013.01); *A61K 31/5383* (2013.01); *A61P 9/00* (2018.01); *A61P 9/10* (2018.01); *A61P 29/00* (2018.01); *A61P 43/00* (2018.01); *C07D 471/04* (2013.01); *C07D 487/04* (2013.01); *C07D 491/04* (2013.01); *C07D 491/048* (2013.01); *C07D 519/00* (2013.01)

(58) Field of Classification Search
CPC .. C07D 471/04; C07D 487/04; C07D 491/04; C07D 491/048; A61K 31/16
See application file for complete search history.

(56) References Cited

U.S. PATENT DOCUMENTS

| | | | |
|---|---|---|---|
| 3,948,903 | A | 4/1976 | Doub et al. |
| 2018/0170927 | A1* | 6/2018 | Patel ..................... A61P 1/18 |
| 2019/0100530 | A1* | 4/2019 | Patel ..................... C07D 235/12 |
| 2019/0127382 | A1 | 5/2019 | Patel et al. |
| 2020/0283446 | A1 | 9/2020 | Chen et al. |

FOREIGN PATENT DOCUMENTS

| | | |
|---|---|---|
| EP | 0244098 A2 | 11/1987 |
| FR | 94123 E | 7/1969 |
| WO | 98/27092 A1 | 6/1998 |
| WO | 98/56376 A1 | 12/1998 |
| WO | 01/58869 A2 | 8/2001 |
| WO | 2004/017908 A2 | 3/2004 |
| WO | 2004/098589 A1 | 11/2004 |
| WO | 2009/092565 * | 9/2007 |
| WO | 2009/092565 A1 | 7/2009 |
| WO | 2010/100070 A1 | 9/2010 |
| WO | 2013/067260 A1 | 5/2013 |
| WO | 2014/125444 A1 | 8/2014 |
| WO | 2015/006280 A1 | 1/2015 |
| WO | 2015/144609 A1 | 10/2015 |
| WO | 2016/027253 A1 | 2/2016 |
| WO | 2017/004500 A1 | 1/2017 |
| WO | 2017/096301 A1 | 6/2017 |
| WO | 2017/109724 A1 | 6/2017 |
| WO | 2017/136727 A2 | 8/2017 |
| WO | 2018/100070 A1 | 6/2018 |
| WO | 2019/012063 A1 | 1/2019 |
| WO | 2019/072942 A1 | 4/2019 |
| WO | 2019/086494 A1 | 5/2019 |

OTHER PUBLICATIONS

Bertrand et al., "cIAP1 and cIAP2 facilitate cancer cell survival by functioning as E3 ligases that promote RIP1 ubiquitination" Mol Cell 30(6):689-700 (Jun. 2008).
Chen, "Ubiquitination in signaling to and activation of IKK" Immunol Rev. 246(1):95-106 (2012).
Cho et al., "Phosphorylation-driven assembly of the RIP1-RIP3 complex regulates programmed necrosis and virus-induced inflammation" Cell 137(6):1112-23 (Jun. 2009).
De Almagro, "Necroptosis: Pathway diversity and characteristics" Semin Cell Dev Biol. 39:56-62 (Mar. 2015).

(Continued)

*Primary Examiner* — D Margaret M Seaman
(74) *Attorney, Agent, or Firm* — Andre T. Krammer

(57) ABSTRACT

The invention provides novel compounds having the general formula I:

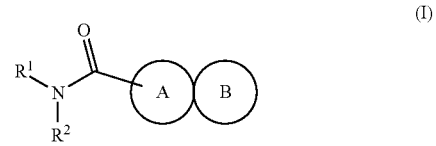

wherein $R^1$, $R^2$, the A ring and the B ring are as described herein, pharmaceutical compositions including the compounds and methods of using the compounds.

17 Claims, No Drawings

(56) References Cited

OTHER PUBLICATIONS

Degterev et al., "Chemical inhibitor of nonapoptotic cell death with therapeutic potential for ischemic brain injury" Nat Chem Biol. 1(2):112-9 (Jul. 2005).
Degterev et al., "Identification of RIP1 kinase as a specific cellular target of necrostatins" Nat Chem Biol. 4(5):313-21 (May 2008).
Feoktistova et al., "cIAPs block Ripoptosome formation, a RIP1/caspase-8 containing intracellular cell death complex differentially regulated by cFLIP isoforms" Mol Cell. 43(3):449-63 (Aug. 2011).
Harris et al., "Discovery of Small Molecule RIP1 Kinase Inhibitors for the Treatment of Pathologies Associated with Necroptosis" ACS Medicinal Chemistry Letters 4(12):1238-1243 ( 2013).
He et al., "Receptor interacting protein kinase-3 determines cellular necrotic response to TNF-alpha" Cell 137(6):1100-11 (Jun. 2009).
ISR for PCT/EP2017/080996.
Kaiser et al., "Toll-like receptor 3-mediated necrosis via TRIF, RIP3, and MLKL" J Biol Chem. 288(43):31268-79 (Oct. 2013).
Kazuko Ohta et al., "Formation of pyridines by the reaction of isoxazoles with enamines" (with English Abstract), 9:1593-1600 ( 1989).
Linkermann et al., "Necroptosis" N Engl J Med. (Send to), 370(5):455-65 (Jan. 2014).
Najjar et al., "Structure Guided Design of Potent and Selective Ponatinib-Based Hybrid Inhibitors for RIPKI" Cell Rep. 10(11):1850-60 (Mar. 24, 2015).
Newton et al., "Activity of protein kinase RIPK3 determines whether cells die by necroptosis or apoptosis" Science 343(6177):1357-60 (Mar. 2014).
Newton, "RIPK1 and RIPK3: critical regulators of inflammation and cell death" Trends Cell Biol. 25(6):347-5 (Jun. 2015).
O'Donnell et al., "Ubiquitination of RIP1 regulates an NF-kappaB-independent cell-death switch in TNF signaling" Curr Biol. 17(5):418-24 (Mar. 2007).
Sun et al., "Mixed lineage kinase domain-like protein mediates necrosis signaling downstream of RIP3 kinase" Cell 148(1-2):213-27 (Jan. 2012).
Takahashi et al., "Necrostatin-1 analogues: critical issues on the specificity, activity and in vivo use in experimental disease models" Cell Death Dis. (Send to), 3:e43 (Nov. 2012).
Vanden et al., "Regulated necrosis: the expanding network of non-apoptotic cell death pathways" Nature Reviews Molecular Cell Biology 15:135-147.
Wang et al., "TNF-alpha induces two distinct caspase-8 activation pathways" Cell 133(4):693-703 (May 2008).
Yogesh B. Surase et al., "Identification and synthesis of novel inhibitors of *Mycobacterium* ATP synthase" Bioorganic & Medicinal Chemistry Letters 27(15):3454-3459 ( 2017).
Zhao et al., "Mixed lineage kinase domain-like is a key receptor interacting protein 3 downstream component of TNF-induced necrosis" Proc Natl Acad Sci U S A. 109(14):5322-27 (Apr. 2012).
Harris et al., "Discovery of a First-in-Class Receptor Interacting Protein 1 (RIP1) Kinase Specific Clinical Candidate (GSK2982772) for the Treatment of Inflammatory Diseases", Journal of Medicinal Chemistry 60(4):1247-1261 (2017).
International Search Report and Written Opinion for PCT/EP2018/079772.
International Search Report and Written Opinion for PCT/EP2018/068998.
International Search Report and Written Opinion for PCT/EP2017/076385, dated Dec. 7, 2017, 12 pages.
Written Opinion of the International Searching Authority for PCT/EP2017/082851, dated Feb. 20, 2018, 8 pages.
CAS Registry Compunds, RN:1554480-89-5, 1554480-83-9, 1542201-50-2, 1540456-83-4, 1539697-89-6, 1536914-91-6, 1529444-36-7, 1528724-76-6, 1526961-09-0,1515103-12-2; 1517186-33-2, 2092781-81-0, 1991193-96-4, 1989442-07-0, 1979877-21-8, 1979849-45-0, 1979849-27-8, 1554480-89-5, dated Aug. 25, 2016 through Apr. 20, 2017, pp. 1-7 (Oct. 3, 2019).
International Preliminary Report on Patentability for PCT/EP2017/076385, dated Apr. 23, 2019, 7 pages.
International Preliminary Report on Patentability for PCT/EP2017/080996, dated Jun. 13, 2019, 10 pages.
International Search Report for PCT/EP2017/082851, dated Feb. 20, 2018, 8 pages.
Jensen et al., "Biochemical characterization and lysosomal localization of the mannose-6-phosphate protein p76 (hypothetical protein LOC196463)" Biochem. J. 402:449-463 (2007).
Joseph G. Cannon Chapter Nineteen in Burger's Medicinal Chemistry and Drug Discovery Fifth edition, vol. 1: Principles and Practice: 783-802 (1995).
Lipson et al., "Reactions of 3-amino-1,2,4-triazoles with cinnamic aldehydes" Russ. Chem. Bull., Intl. Ed. 58(7):1141-1444 (2009).
USPTO Non-Final Office Action, U.S. Appl. No. 16/034,207, dated Oct. 10, 2019, 9 pages.
USPTO Non-Final Office Action, U.S. Appl. No. 16/175,206, dated Jun. 25, 2019, 18 pages.
USPTO Notice of Allowance, U.S. Appl. No. 16/034,207, dated May 13, 2020, 10 pages.
USPTO Notice of Allowance, U.S. Appl. No. 16/175,206, dated Jan. 21, 2020, 11 pages.
USPTO Restriction Requirement, U.S. Appl. No. 16/034,207, dated Apr. 8, 2019, 9 pages.
Waly el al., "A novel Synthesis of Imidazo (4,5-d)azepine Ring System" Polish J. Chem. 70(3): 296-301 (1996).
Written Opinion of the International Searching Authority for PCT/EP2017/080996, dated Feb. 7, 2018, 8 pages.
https://pubchem.ncbi.nlm.nih.gov/compound/11845422; compound name: 6,7-Dihydro-4H-pyrazolo [5,1-c][1,4]oxazine-2-carbaldehyde; created Nov. 6, 2006.
https://pubchem.ncbi.nlm.nih.gov/compound/20744102; compound name: 1-(5,6-Dihydro-4H-pyrrolo[1,2-b]pyrazol-2-yl)ethanone; created Dec. 5, 2007.
https://pubchem.ncbi.nlm.nih.gov/compound/82594726; 5H-pyrrolo[1,2-a]imidazol-2-yl)ethanone; created Oct. 20, 2014.
https://pubchem.ncbi.nlm.nih.gov/compound/83875142; 1-(5-Methyl-5,6,7,8-tetrahydro-[1,2,4]triazolo [1,5-a]pyridin-2-yl)ethanone; created Oct. 20, 2014.
Rojas-Rivera, D. et al., "When PERK inhibitors turn out to be new potent RIPK1 inhibitors: critical issues on the specificity and use of GSK2606414 and GSK2656157" Cell Death Differ. 24(6):1100-1110 (2017).
https://pubchem.ncbi.nlm.nih.gov/compound/82594726; compound name: 1-(6,7-Dihydro-5H-pyrrolo[1,2a]imidazol-2-yl)ethanone; created Oct. 20, 2014.
https://pubchem.ncbi.nlm.nih.gov/compound/83875142; compound name: 1-(5-Methyl-5,6,7,8-tetrahydro-[1,2,4]triazolo[1,5-a]pyridin-2-yl)ethanone; created Oct. 20, 2014.
https://pubchem.ncbi.nlm.nih.gov/compound/11845422; compound name: 6,7-Dihydro-4H-pyrazolo [5,1-c][1,4]oxazine-2-carbaldehyde; created Nov. 6, 2006; 14 pages.
https://pubchem.ncbi.nlm.nih.gov/compound/20744102; compound name: 1-(5,6-Dihydro-4H-pyrrolo[1,2-b]pyrazol-2-yl)ethanone; created Dec. 5, 2007; 10 pages.
https://pubchem.ncbi.nlm.nih.gov/compound/82594726; compound name: 1-(6,7-Dihydro-5H-pyrrolo[1,2-a]imidazol-2-yl)ethanone; created Oct. 20, 2014; 10 pages.
https://pubchem.ncbi.nlm.nih.gov/compound/83875142; compound name: 1-(5-Methyl-5,6,7,8-tetrahydro-[1,2,4]triazolo[1,5-a]pyridin-2-yl)ethanone; created Oct. 20, 2014; 8 pages.

\* cited by examiner

BICYCLIC AMIDE COMPOUNDS AND METHODS OF USE THEREOF

CROSS-REFERENCE TO RELATED APPLICATIONS

This application claims priority to U.S. Provisional Patent Application No. 62/429,558, filed on Dec. 2, 2016, the entire contents of which are hereby incorporated by reference.

FIELD OF THE INVENTION

The present invention relates to organic compounds useful for therapy and/or prophylaxis in a mammal, and in particular to inhibitors of RIP1 kinase useful for treating diseases and disorders associated with inflammation, cell death and others.

BACKGROUND OF THE INVENTION

Receptor-interacting protein-1 ("RIP1") kinase is a serine/threonine protein kinase. RIP1 is a regulator of cell signaling that is involved, among other things, in the mediation of programmed cell death pathways, e.g., necroptosis. The best studied form of necroptotic cell death is initiated by TNFα (tumor necrosis factor), but necroptosis can also be induced by other members of the TNFα death ligand family (Fas and TRAIL/Apo2L), interferons, Toll-like receptors (TLRs) signaling and viral infection via the DNA sensor DAI (DNA-dependent activator of interferon regulatory factor) [1-3]. Binding of TNFα to the TNFR1 (TNF receptor 1) prompts TNFR1 trimerization and formation of an intracellular complex, Complex-I. TRADD (TNF receptor associated death domain protein) binds to the intracellular death domain of TNFR1 and recruits the protein kinase RIP1 (receptor-interacting protein 1) through the death domain present in both proteins [4]. Following initial recruitment into TNFR1-associated signaling complex, RIP1 translocates to a secondary cytoplasmatic complex, Complex-II [5-7]. Complex-II is formed by the death domain containing protein FADD (Fas-associated Protein), RIP1, caspase-8 and cFLIP. If caspase-8 is not fully activated or its activity is blocked, the protein kinase RIP3 gets recruited to the complex, forming a necrosome, which will lead to necroptotic cell death initiation [8-10]. Once the necrosome is formed, RIP1 and RIP3 engage in a series of auto and cross phosphorylation events that are essential for necroptotic cell death. Necroptosis can be completely blocked either by the kinase inactivating mutation in any of the two kinases, or chemically by RIP1 kinase inhibitors (necrostatins), or RIP3 kinase inhibitors [11-13]. Phosphorylation of RIP3 allows the binding and phosphorylation of pseudokinase MLKL (mixed lineage kinase domain-like), a key component of necroptotic cell death [14, 15].

Necroptosis has crucial pathophysiological relevance in myocardial infarction, stroke, atherosclerosis, ischemia-reperfusion injury, inflammatory bowel diseases, retinal degeneration and a number of other common clinical disorders [16]. Therefore, selective inhibitors of RIP1 kinase activity are therefore desired as a potential treatment of diseases mediated by this pathway and associated with inflammation and/or necroptotic cell death.

Inhibitors of RIP1 kinase have been previously described. The first published inhibitor of RIP1 kinase activity was necrostatin 1 (Nec-1) [17]. This initial discovery was followed by modified versions of Nec-1 with various abilities to block RIP1 kinase activity [11, 18]. Recently, additional RIP1 kinase inhibitors have been described that differ structurally from necrostatin class of compounds [19, 20, 21].

References cited above, each of which is hereby incorporated by reference in its entirety:
1) Vanden Berghe, T., Linkermann, A., Jouan-Lanhouet, S., Walczak, H. and Vandenabeele, P. (2014) Regulated necrosis: the expanding network of non-apoptotic cell death pathways. Nature reviews. Molecular cell biology. 15, 135-147.
2) Newton, K. (2015) RIPK1 and RIPK3: critical regulators of inflammation and cell death. Trends in cell biology. 25, 347-353.
3) de Almagro, M. C. and Vucic, D. (2015) Necroptosis: Pathway diversity and characteristics. Semin Cell Dev Biol. 39, 56-62.
4) Chen, Z. J. (2012) Ubiquitination in signaling to and activation of IKK. Immunological reviews. 246, 95-106.
5) O'Donnell, M. A., Legarda-Addison, D., Skountzos, P., Yeh, W. C. and Ting, A. T. (2007) Ubiquitination of RIP1 regulates an NF-kappaB-independent cell-death switch in TNF signaling. Curr Biol. 17, 418-424.
6) Feoktistova, M., Geserick, P., Kellert, B., Dimitrova, D. P., Langlais. C., Hupe, M., Cain, K., MacFarlane, M., Hacker, G. and Leverkus, M. (2011) cIAPs block Ripoptosome formation, a RIP1/caspase-8 containing intracellular cell death complex differentially regulated by cFLIP isoforms. Molecular cell. 43, 449-463.
7) Bertrand, M. J., Milutinovic, S., Dickson, K. M., Ho, W. C., Boudreault, A., Durkin, J., Gillard. J. W., Jaquith, J. B., Morris, S. J. and Barker, P. A. (2008) cIAP1 and cIAP2 facilitate cancer cell survival by functioning as E3 ligases that promote RIP1 ubiquitination. Mol Cell. 30, 689-700.
8) Wang, L., Du, F. and Wang. X. (2008) TNF-alpha induces two distinct caspase-8 activation pathways. Cell. 133, 693-703.
9) He, S., Wang, L., Miao, L., Wang, T., Du, F., Zhao, L. and Wang, X. (2009) Receptor interacting protein kinase-3 determines cellular necrotic response to TNF-alpha. Cell. 137, 1100-1111.
10) Cho, Y. S., Challa, S., Moquin, D., Genga, R., Ray, T. D., Guildford, M. and Chan, F. K. (2009) Phosphorylation-driven assembly of the RIP1-RIP3 complex regulates programmed necrosis and virus-induced inflammation. Cell. 137, 1112-1123.
11) Degterev, A., Hitomi, J., Germscheid, M., Ch'en, I. L., Korkina, O., Teng, X., Abbott, D., Cuny, G. D., Yuan, C., Wagner, G., Hedrick, S. M., Gerber, S. A., Lugovskoy, A. and Yuan, J. (2008) Identification of RIP1 kinase as a specific cellular target of necrostatins. Nat Chem Biol. 4, 313-321.
12) Newton, K., Dugger, D. L., Wickliffe. K. E., Kapoor, N., de Almagro, M. C., Vucic, D., Komuves, L., Ferrando, R. E., French, D. M., Webster, J., Roose-Girma, M., Warming, S. and Dixit, V. M. (2014) Activity of protein kinase RIPK3 determines whether cells die by necroptosis or apoptosis. Science. 343, 1357-1360.
13) Kaiser, W. J., Sridharan, H., Huang, C., Mandal, P., Upton, J. W., Gough, P. J., Sehon, C. A., Marquis, R. W., Bertin, J. and Mocarski, E. S. (2013) Toll-like receptor 3-mediated necrosis via TRIF, RIP3, and MLKL. The Journal of biological chemistry. 288, 31268-31279.
14) Zhao, J., Jitkaew, S., Cai, Z., Choksi, S., Li, Q., Luo, J. and Liu, Z. G. (2012) Mixed lineage kinase domain-like is a key receptor interacting protein 3 downstream component of TNF-induced necrosis. Proceedings of the National Academy of Sciences of the United States of America. 109, 5322-5327.

15) Sun, L., Wang. H., Wang, Z., He, S., Chen, S., Liao, D., Wang, L., Yan, J., Liu, W., Lei, X. and Wang, X. (2012) Mixed Lineage Kinase Domain-like Protein Mediates Necrosis Signaling Downstream of RIP3 Kinase. Cell. 148, 213-227.
16) Linkermann, A. and Green, D. R. (2014) Necroptosis. The New England journal of medicine. 370, 455-465.
17) Degterev, A., Huang. Z., Boyce. M., Li, Y., Jagtap. P., Mizushima, N., Cuny, G. D., Mitchison, T. J., Moskowitz, M. A. and Yuan, J. (2005) Chemical inhibitor of nonapoptotic cell death with therapeutic potential for ischemic brain injury. Nat Chem Biol. 1, 112-119.
18) Takahashi, N., Duprez, L., Grootjans, S., Cauwels, A., Nerinckx, W., DuHadaway, J. B., Goossens, V., Roelandt, R., Van Hauwermeiren, F., Libert. C., Declercq, W., Callewaert. N., Prendergast, G. C., Degterev, A., Yuan, J. and Vandenabeele, P. (2012) Necrostatin-1 analogues: critical issues on the specificity, activity and in vivo use in experimental disease models. Cell Death Dis. 3, e437.
19) Harris, P. A., Bandyopadhyay, D., Berger, S. B., Campobasso, N., Capriotti, C. A., Cox, J. A., Dare, L., Finger, J. N., Hoffman, S. J., Kahler, K. M., Lehr, R., Lich, J. D., Nagilla, R., Nolte, R. T., Ouellette, M. T., Pao, C. S., Schaeffer, M. C., Smallwood. A., Sun, H. H., Swift, B. A., Totoritis, R. D., Ward, P., Marquis, R. W., Bertin, J. and Gough, P. J. (2013) Discovery of Small Molecule RIP1 Kinase Inhibitors for the Treatment of Pathologies Associated with Necroptosis. ACS medicinal chemistry letters. 4, 1238-1243.
20) Najjar, M., Suebsuwong, C., Ray, S. S., Thapa, R. J., Maki, J. L., Nogusa, S., Shah, S., Saleh, D., Gough, P. J., Bertin. J., Yuan, J., Balachandran, S., Cuny, G. D. and Degterev, A. (2015) Structure Guided Design of Potent and Selective Ponatinib-Based Hybrid Inhibitors for RIPK1. Cell Rep.
21) International Patent Publication No. WO 2014/125444.

SUMMARY OF THE INVENTION

Provided herein are compounds of formula I:

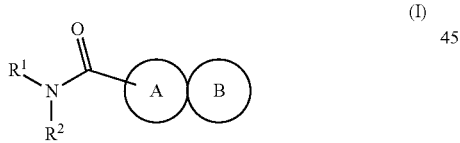

(I)

or pharmaceutically acceptable salts thereof, wherein $R^1$ and $R^2$:
  (a) are each independently selected from the group consisting of $C_1$-$C_6$ alkyl, $C_3$-$C_6$ cycloalkyl, $C_1$-$C_6$ haloalkyl, $C_1$-$C_6$ alkoxy. $C_1$-$C_6$ haloalkoxy, $C_1$-$C_6$ thioalkyl, $C_1$-$C_6$ alkyl-N($R^N$)$_2$, phenyl, 5 to 6 membered heteroaryl, and 4 to 5 membered heterocyclyl;
  (b) together with the adjacent amide N, form a 4 to 7 membered unsaturated heterocyclic ring optionally substituted by one or two $R^3$, wherein the unsaturated heterocyclic ring contains zero or one additional heteroatom selected from the group consisting of $NR^N$, O and S; or
  (c) together with the adjacent amide N, form a bicyclic heteroaryl moiety optionally substituted by one or two $R^3$, wherein the bicyclic heterocyclic moiety contains zero to three additional heteroatoms selected from the group consisting of N, O and S, wherein only one of the additional heteroatoms is O or S;
  each $R^3$ is independently selected from the group consisting of F, Cl, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_1$-$C_6$ hydroxyalkyl, and phenoxy; or, when $R^1$ and $R^2$ together with the adjacent amide N form a 6 membered ring, two $R^3$ may together form a 1 to 2 carbon bridge or a $C_3$-$C_5$ spirocycloalkyl;
  each $R^N$ is independently selected from the group consisting of H, $C_1$-$C_6$ alkyl, $C_3$-$C_6$ cycloalkyl, $C_1$-$C_6$ alkoxy and $C_1$-$C_6$ haloalkyl; or two $R^N$ may together with the adjacent N form a 4-6 membered ring;
  the A ring is a 5 or 6 membered heteroaryl having 1 to 3 heteroatoms selected from the group consisting of nitrogen, oxygen and sulfur; wherein the A ring is optionally substituted with 1 to 2 substituents selected from the group consisting of halogen, $C_1$-$C_6$ alkyl, $C_3$-$C_6$ cycloalkyl, $C_1$-$C_6$ haloalkyl, $C_1$-$C_6$ alkoxy and $C_1$-$C_6$ haloalkoxy; and wherein if a nitrogen atom in the A ring is substituted, the substituent is not halogen, $C_1$-$C_6$ alkoxy or $C_1$-$C_6$ haloalkoxy having an oxygen or sulfur atom directly bonded to the nitrogen atom;
  the B ring is a 5 to 7 membered cycloalkyl, or a 5 to 7 membered heterocyclyl having 1 to 3 heteroatoms selected from the group consisting of nitrogen, oxygen and sulfur; wherein the B ring is substituted according to (a), (b), or both (a) and (b):
    (a) 1 to 2 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, and cyano, wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom; wherein two substituents on the B ring together may form a 1 to 2 carbon bridge or $C_3$-$C_5$ spirocycloalkyl group:
    (b) 1 substituent selected from the group consisting of phenyl, benzyl, $CH_2$—($C_3$-$C_6$ cycloalkyl), and $CH_2CH_2$—($C_3$-$C_6$ cycloalkyl), $CH_2$-(4 to 6 membered heterocyclyl), $CH_2CH_2$-(4 to 6 membered heterocyclyl), 5 or 6 membered heteroaryl, and $CH_2$-(5 or 6 membered heteroaryl); wherein when a phenyl ring is present it may be substituted by 1 or 2 substituents selected from the group consisting of halogen, $C_1$-$C_4$ alkyl, $C_1$-$C_4$ haloalkyl, $C_1$-$C_4$ alkoxy. $C_1$-$C_4$ haloalkoxy, and cyano;
  provided that if the B ring is substituted by only one substituent, it is not halogen or methyl.

In the following description, all references to formula I also include subembodiments of formula I (i.e., formulae Ia, Ib, etc.).

Also provided herein are pharmaceutical compositions comprising a compound of formula I, or a pharmaceutically acceptable salt thereof, and one or more pharmaceutically acceptable carriers or excipients. Specific embodiments include pharmaceutical compositions suitable for intravenous or oral delivery.

Also provided herein are oral formulations of a compound of formula I, or a pharmaceutically acceptable salt thereof, and one or more pharmaceutically acceptable carriers or excipients suitable for oral delivery.

Also provided herein are parenteral formulations of a compound of formula I, or a pharmaceutically acceptable salt thereof, and one or more pharmaceutically acceptable carriers or excipients suitable for parenenteral delivery.

In some embodiments, provided herein are uses of a compound of formula I, or a pharmaceutically acceptable salt thereof, for the treatment of diseases and disorders. In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, antiphospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury(AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease. Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis, Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome), HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis. Alpha-mannosidosis, Aspartylglucosaminuria, Cholesterl Ester storage disease, Chronic Hexosaminidase A Deficiency, Cystinosis, Danon disease, Fabry disease, Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders, Multiple sulfatase deficiency, Niemann-Pick Disease, Neuronal Ceroid Lipofuscinoses, Pompe disease, Pycnodysostosis, Sandhoff disease, Schindler disease. Sialic Acid Storage Disease, Tay-Sachs and Wolman disease).

In some embodiments, the diseases and disorders to be treated are selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa and retinal degeneration.

In some embodiments, provided herein are methods for the treatment or prevention of a disease or disorder with a therapeutically effective amount of a compound of formula I, or a pharmaceutically acceptable salt thereof, wherein the disease or disorder is associated with inflammation and/or necroptosis. In some embodiments said disease or disorder is selected from the specific diseases and disorders recited herein.

In some embodiments, provided herein are methods of inhibiting RIP1 kinase activity by contacting a cell with a compound of formula I or a pharmaceutically acceptable salt thereof.

DETAILED DESCRIPTION OF THE INVENTION

Definitions

As provided herein, all chemical formulae and generic chemical structures should be interpreted to provide proper valence and chemically stable bonds between atoms as understood by one of ordinary skill in the art. Where appropriate, substituents may be bonded to more than one adjacent atom (e.g., alkyl includes methylene where two bonds are present).

In the chemical formulae provided herein, "halogen" or "halo' refers to flurorine, chlorine, and bromine (i.e., F, Cl, Br).

Alkyl, unless otherwise specifically defined, refers to an optionally substituted, straight-chain or branched $C_1$-$C_{12}$ alkyl group. In some embodiments, alkyl refers to a $C_1$-$C_6$ alkyl group. Exemplary alkyl groups include methyl, ethyl, propyl, iso-propyl, n-butyl, iso-butyl, tert-butyl, sec-butyl, n-pentyl, n-hexyl, n-heptyl, and n-oxtyl. Substituted alkyl groups provided herein are substituted by one or more substituents selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl). $SO_2N(C_1$-$C_4$ alkyl)$_2$, and $NHSO_2(C_1$-$C_4$ alkyl). In some embodiments, the substituted alkyl group has 1 or 2 substituents. In some embodiments, the alkyl group is unsubstituted.

Cycloalkyl, unless otherwise specifically defined, refers to an optionally substituted $C_3$-$C_{12}$ cycloalkyl group and includes fused, spirocyclic, and bridged bicyclic groups, wherein the substituents are selected from the group consisting of halogen, cyano, trifluoromethyl, methoxy, ethoxy, difluoromethoxy, trifluoromethoxy, $C_3$-$C_6$ cycloalkyl, phenyl, OH, $CO_2H$, $CO_2(C_1$-$C_4$ alkyl), $NH_2$, $NH(C_1$-$C_4$ alkyl), $N(C_1$-$C_4$ alkyl)$_2$, $NH(C=O)C_1$-$C_4$ alkyl, $(C=O)NH(C_1$-$C_4$ alkyl), $(C=O)N(C_1$-$C_4$ alkyl)$_2$, $S(C_1$-$C_4$ alkyl), $SO(C_1$-$C_4$ alkyl), $SO_2(C_1$-$C_4$ alkyl), $SO_2NH(C_1$-$C_4$ alkyl), $SO_2N(C_1$-$C_4$ alkyl)$_2$, and $NHSO_2(C_1$-$C_4$ alkyl). In some embodiments, cycloalkyl refers to a $C_3$-$C_6$ cycloalkyl group. In some embodiments, the $C_3$-$C_6$ cycloalkyl group is optionally substituted with 1 to three halogen atoms. In some embodiments, the $C_3$-$C_6$ cycloalkyl group is optionally substituted with 1 to three fluorine atoms. Exemplary $C_3$-$C_6$ cycloalkyl groups include cyclopropyl, cyclobutyl, cyclopentyl and cyclohexyl. Exemplary $C_3$-$C_{12}$ cycloalkyl groups further include bicyclo[3.1.0]hexyl, bicyclo[2.1.1]hexyl, cycloheptyl, bicyclo[4.1.0]heptyl, spiro[4.2]heptyl, cyclooctyl, spiro[4.3]octyl, spiro[5.2]octyl, bicyclo[2.2.1]heptanyl, bicycle[2.2.2]octanyl, adamantanyl, decalinyl, and spiro[5.4]decanyl. Where appropriate, cycloalkyl groups may be fused to other groups such that more than one chemical bond exists between the cycloalkyl group and another ring system (e.g., the C ring of formula I). In some embodiments, the cycloalkyl group is unsubstituted.

Haloalkyl, unless otherwise specifically defined, refers to a straight-chain or branched $C_1$-$C_{12}$ alkyl group, wherein one or more hydrogen atoms are replaced by a halogen. In some embodiments, haloalkyl refers to a $C_1$-$C_6$ haloalkyl group. In some embodiments, 1 to 3 hydrogen atoms of the haloalkyl group are replaced by a halogen. In some embodiments, every hydrogen atom of the haloalkyl group is replaced by a halogen (e.g, trifluoromethyl). In some embodiments, the haloalkyl is as defined herein wherein the halogen in each instance is fluorine. Exemplary haloalkyl groups include fluoromethyl, difluoromethyl, trifluoromethyl, trifluoroethyl, and pentafluoroethyl.

Alkoxy, unless otherwise specifically defined, refers to a straight-chain or branched $C_1$-$C_{12}$ alkyl group, wherein one or more oxygen atoms are present, in each instance between two carbon atoms. In some embodiments, alkoxy refers to a $C_1$-$C_6$ alkoxy group. In some embodiments, $C_1$-$C_6$ alkoxy groups provided herein have one oxygen atom. Exemplary alkoxy groups include methoxy, ethoxy, $CH_2OCH_3$, $CH_2CH_2OCH_3$, $CH_2OCH_2CH_3$, $CH_2CH_2OCH_2CH_3$, $CH_2OCH_2CH_2CH_3$, $CH_2CH_2CH_2OCH_3$, $CH_2OCH(CH_3)_2$, $CH_2OC(CH_3)_3$, $CH(CH_3)OCH_3$, $CH_2CH(CH_3)OCH_3$, $CH(CH_3)OCH_2CH_3$, $CH_2OCH_2OCH_3$, $CH_2CH_2OCH_2CH_2OCH_3$, and $CH_2OCH_2OCH_2OCH_3$.

Cycloalkoxy, unless otherwise specifically defined, refers to a $C_4$-$C_{10}$ or a $C_4$-$C_6$ alkoxy group as defined above wherein the group is cyclic and contains one oxygen atom. Exemplary cycloalkoxy groups include oxetanyl, tetrahydrofuranyl, and tetrahydropyranyl.

Haloalkoxy, unless otherwise specifically defined, refers to a $C_1$-$C_6$ haloalkyl group as defined above, wherein one or two oxygen atoms are present, in each instance between two carbon atoms. In some embodiments, $C_1$-$C_6$ haloalkoxy groups provided herein have one oxygen atom. Exemplary haloalkoxy groups include $OCF_3$, $OCHF_2$ and $CH_2OCF_3$.

Thioalkyl, unless otherwise specifically defined, refers to a $C_1$-$C_{12}$ or a $C_1$-$C_6$ alkoxy group as defined above wherein the oxygen atom is replaced by a sulfur atom. In some embodiments, thioalkyl groups may include sulfur atoms substituted by one or two oxygen atoms (i.e., alkylsulfones and alkylsulfoxides). Exemplary thioalkyl groups are those exemplified in the definition of alkoxy above, wherein each oxygen atom is replaced by a sulfur atom in each instance.

Thiocycloalkyl, unless otherwise specifically defined, refers to a $C_4$-$C_{10}$ or a $C_4$-$C_6$ thioalkyl group as defined above wherein the group is cyclic and contains one sulfur atom. In some embodiments, the sulfur atom of the thiocycloalkyl group is substituted by one or two oxygen atoms (i.e., a cyclic sulfone or sulfoxide). Exemplary thiocycloalkyl groups include thietanyl, thiolanyl, thianyl, 1,1-dioxothiolanyl, and 1,1-dioxothianyl.

Heterocyclyl, unless otherwise specifically defined, refers to a single saturated or partially unsaturated 4 to 8 membered ring that has at least one atom other than carbon in the ring, wherein the atom is selected from the group consisting of oxygen, nitrogen and sulfur; the term also includes multiple condensed ring systems that have at least one such saturated or partially unsaturated ring, which multiple condensed ring systems have from 7 to 12 atoms and are further described below. Thus, the term includes single saturated or partially unsaturated rings (e.g., 3, 4, 5, 6, 7 or 8 membered rings) from about 1 to 7 carbon atoms and from about 1 to 4 heteroatoms selected from the group consisting of oxygen, nitrogen and sulfur in the ring. The ring may be C-branched (i.e., substituted by $C_1$-$C_4$ alkyl). The ring may be substituted with one or more (e.g., 1, 2 or 3) oxo groups and the sulfur and nitrogen atoms may also be present in their oxidized forms. Exemplary heterocycles include but are not limited to azetidinyl, tetrahydrofuranyl and piperidinyl. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heterocycle) can be at any position of the multiple condensed ring system. It is also to be understood that the point of attachment for a heterocycle or heterocycle multiple condensed ring system can be at any suitable atom of the heterocyclyl group including a carbon atom and a nitrogen atom. Exemplary heterocycles include, but are not limited to aziridinyl, azetidinyl, pyrrolidinyl, piperidinyl, homopiperidinyl, morpholinyl, thiomorpholinyl, piperazinyl, tetrahydrofuranyl, dihydrooxazolyl, tetrahydropyranyl, tetrahydrothiopyranyl, 1,2,3,4-tetrahydroquinolyl, benzoxazinyl, dihydrooxazolyl, chromanyl, 1,2-dihydropyridinyl, 2,3-dihydrobenzofuranyl, 1,3-benzodioxolyl, 1,4-benzodioxanyl, spiro[cyclopropane-1,1'-isoindolinyl]-3'-one, isoindolinyl-1-one, 2-oxa-6-azaspiro[3.3]heptanyl, imidazolidin-2-one N-methylpiperidine, imidazolidine, pyrazolidine, butyrolactam, valerolactam, imidazolidinone, hydantoin, dioxolane, phthalimide, 1,4-dioxane, thiomorpholine, thiomorpholine-S-oxide, thiomorpholine-S,S-oxide, pyran, 3-pyrroline, thiopyran, pyrone, tetrhydrothiophene, quinuclidine, tropane, 2-azaspiro[3.3]heptane, (1R,5S)-3-azabicyclo[3.2.1]octane, (1s,4s)-2-azabicyclo[2.2.2]octane. (1R,4R)-2-oxa-5-azabicyclo[2.2.2]octane and pyrrolidin-2-one.

In some embodiments, the heterocyclyl is a $C_4$-$C_{10}$ heterocyclyl having 1 to 3 heteroatoms selected from the group consisting of nitrogen, oxygen and sulfur. In some embodiments, the heterocyclyl group is neither bicyclic nor spirocyclic. In some embodiments, the heterocyclyl is a $C_5$-$C_6$ heterocylcyl having 1 to 3 heteroatoms, wherein at least 2 are nitrogen if 3 heteroatoms are present.

Aryl, unless otherwise specifically defined, refers to a single all carbon aromatic ring or a multiple condensed all carbon ring system wherein at least one of the rings is aromatic and wherein the aryl group has 6 to 20 carbon atoms, 6 to 14 carbon atoms, 6 to 12 carbon atoms, or 6 to 10 carbon atoms. Aryl includes a phenyl radical. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., carbocycle). Such multiple condensed ring systems are optionally substituted with one or more (e.g., 1, 2 or 3) oxo groups on any carbocycle portion of the multiple condensed ring system. The rings of the multiple condensed ring system can be connected to each other via fused, spiro and bridged bonds when allowed by valency requirements. It is to be understood that the point of attachment of a multiple condensed ring system, as defined above, can be at any position of the ring system including an aromatic or a carbocycle portion of the ring. Exemplary aryl groups include phenyl, indenyl, naphthyl, 1, 2, 3, 4-tetrahydronaphthyl, anthracenyl, and the like.

Heteroaryl, unless otherwise specifically defined, refers to a 5 to 6 membered aromatic ring that has at least one atom other than carbon in the ring, wherein the atom is selected from the group consisting of oxygen, nitrogen and sulfur "heteroaryl" also includes multiple condensed ring systems having 8 to 16 atoms that have at least one such aromatic ring, which multiple condensed ring systems are further described below. Thus, "heteroaryl" includes single aromatic rings of from about 1 to 6 carbon atoms and about 1-4 heteroatoms selected from the group consisting of oxygen, nitrogen and sulfur. The sulfur and nitrogen atoms may also be present in an oxidized form provided the ring is aromatic. Exemplary heteroaryl ring systems include but are not limited to pyridyl, pyrimidinyl, oxazolyl or furyl. "Heteroaryl" also includes multiple condensed ring systems (e.g., ring systems comprising 2 or 3 rings) wherein a heteroaryl group, as defined above, is condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1,2,3,4-tetrahydro-1,8-naphthyridinyl), carbocycles (to form for example 5,6,7,8-tetrahydroquinolyl) and aryls (to form for example indazolyl) to form the multiple condensed ring system. Thus, a heteroaryl (a single aromatic ring or multiple condensed ring system) has 1 to 15 carbon atoms and about 1-6 heteroatoms within the heteroaryl ring. Such multiple condensed ring systems may be optionally substituted with one or more (e.g., 1, 2, 3 or 4) oxo groups on the carbocycle or heterocycle portions of the condensed ring. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system. It is also to be understood that the point of attachment for a heteroaryl or heteroaryl multiple condensed ring system can be at any suitable atom of the heteroaryl or heteroaryl multiple condensed ring system including a carbon atom and a heteroatom (e.g., a nitrogen). Exemplary heteroaryls include but are not limited to pyridyl, pyrrolyl, pyrazinyl, pyrimidinyl, pyridazinyl, pyrazolyl, thienyl, indolyl, imidazolyl, oxazolyl, isoxazolyl, thiazolyl, furyl, oxadiazolyl, thiadiazolyl, quinolyl, isoquinolyl, benzothiazolyl, benzoxazolyl, indazolyl, quinoxalyl, quinazolyl, 5,6,7,8-tetrahydroisoquinolinyl benzofuranyl, benzimidazolyl, thianaphthenyl, pyrrolo[2,3-b]pyridinyl, quinazolinyl-4(3H)-one, triazolyl, 4,5,6,7-tetrahydro-1H-indazole and 3b,4,4a,5-tetrahydro-1H-cyclopropa[3,4]cyclopenta[1,2-c]pyrazole.

As used herein, the term "chiral" refers to molecules which have the property of non-superimposability of the mirror image partner, while the term "achiral" refers to molecules which are superimposable on their mirror image partner.

As used herein, the term "stereoisomers" refers to compounds which have identical chemical constitution, but differ with regard to the arrangement of the atoms or groups in space.

As used herein a wavy line "⌇" that intersects a bond in a chemical structure indicates the point of attachment of the bond that the wavy bond intersects in the chemical structure to the remainder of a molecule.

As used herein, the term "C-linked" means that the group that the term describes is attached the remainder of the molecule through a ring carbon atom.

As used herein, the term "N-linked" means that the group that the term describes is attached to the remainder of the molecule through a ring nitrogen atom.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers can separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention can contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer can also be referred to as an enantiomer, and a mixture of such isomers is often called an enantiomeric mixture. A 50:50 mixture of enantiomers is referred to as a racemic mixture or a racemate, which can occur where there has been no stereoselection or stereospecificity in a chemical reaction or process. The terms "racemic mixture" and "racemate" refer to an equimolar mixture of two enantiomeric species, devoid of optical activity.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 97% the absolute stereoisomer depicted. In another embodiment, the compound may be at least 98% the absolute stereoisomer depicted. In another embodiment, the compound may be at least 99% the absolute stereoisomer depicted.

As used herein, the term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

As used herein, the term "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

As used herein, the term "protecting group" refers to a substituent that is commonly employed to block or protect a particular functional group on a compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethyleneoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. For a general description of protecting groups and their use, see P.G.M. Wuts and T.W. Greene, Greene's Protective Groups in Organic Synthesis 4$^{th}$ edition, Wiley-Interscience, New York, 2006.

As used herein, the term "mammal" includes, but is not limited to, humans, mice, rats, guinea pigs, monkeys, dogs, cats, horses, cows, pigs, and sheep.

As used herein, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example. Berge, S. M., et al., "Pharmaceutical Salts", Journal of Pharmaceutical Science, 1977, 66, 1-19). Certain specific compounds of the present invention contain both basic and acidic functionalities that allow the compounds to be converted into either base or acid addition salts.

The neutral forms of the compounds can be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. As used herein the term "prodrug" refers to those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Prodrugs of the invention include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of the invention can be derivatized as an amide or alkyl ester. As another example, compounds of this invention comprising free hydroxy groups can be derivatized as prodrugs by converting the hydroxy group into a group such as, but not limited to, a phosphate ester, hemisuccinate, dimethylaminoacetate, or phosphoryloxymethyloxycarbonyl group, as outlined in Fleisher, D. et al., (1996) Improved oral drug delivery: solubility limitations overcome by the use of prodrugs Advanced Drug Delivery Reviews, 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group can be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as ($C_{1-6}$)alkanoyloxymethyl, 1-(($C_{1-6}$)alkanoyloxy)ethyl, 1-methyl-1-(($C_{1-6}$)alkanoyloxy)ethyl, ($C_{1-6}$)alkoxycarbonyloxymethyl, N—($C_{1-6}$)alkoxycarbonylaminomethyl, succinoyl, ($C_{1-6}$)alkanoyl, alpha-amino($C_{1-4}$)alkanoyl, arylacyl and alpha-aminoacyl, or alpha-aminoacyl-alpha-aminoacyl, where each alpha-aminoacyl group is independently selected from the naturally occurring L-amino acids, $P(O)(OH)_2$, —$P(O)(O(C_{1-6})alkyl)_2$ or glycosyl (the radical resulting from the removal of a hydroxyl group of the hemiacetal form of a carbohydrate).

For additional examples of prodrug derivatives, see, for example, a) Design of Prodrugs, edited by H. Bundgaard, (Elsevier, 1985) and Methods in Enzymology, Vol. 42, p. 309-396, edited by K. Widder, et al. (Academic Press, 1985); b) A Textbook of Drug Design and Development, edited by Krogsgaard-Larsen and H. Bundgaard, Chapter 5 "Design and Application of Prodrugs," by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Additionally, the present invention provides for metabolites of compounds of the invention. As used herein, a "metabolite" refers to a product produced through metabolism in the body of a specified compound or salt thereof. Such products can result for example from the oxidation, reduction, hydrolysis, amidation, deamidation, esterification, deesterification, enzymatic cleavage, and the like, of the administered compound.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention can exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention.

The term "composition," as used herein, is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "treat" and "treatment" refer to both therapeutic treatment and/or prophylactic treatment or preventative measures, wherein the object is to prevent or slow down (lessen) an undesired physiological change or disorder, such as, for example, the development or spread of cancer. For purposes of this invention, beneficial or desired clinical results include, but are not limited to, alleviation of symptoms, diminishment of extent of disease or disorder, stabilized (i.e., not worsening) state of disease or disorder, delay or slowing of disease progression, amelioration or palliation of the disease state or disorder, and remission (whether partial or total), whether detectable or undetectable. "Treatment" can also mean prolonging survival as compared to expected survival if not receiving treatment. Those in need of treatment include those already with the disease or disorder as well as those prone to have the disease or disorder or those in which the disease or disorder is to be prevented.

The phrase "therapeutically effective amount" or "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

Inhibitors of RIP1 Kinase

The present invention provides novel compounds having the general formula I:

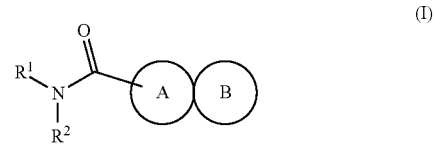

or pharmaceutically acceptable salts thereof, wherein $R^1$ and $R^2$:
  (a) are each independently selected from the group consisting of $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, phenyl, 5 to 6 membered heteroaryl, and 4 to 5 membered heterocyclyl;
  (b) together with the adjacent amide N, form a 4 to 7 membered unsaturated heterocyclic ring optionally substituted by one or two $R^3$, wherein the unsaturated heterocyclic ring contains zero or one additional heteroatom selected from the group consisting of $NR^N$, O and S; or
  (c) together with the adjacent amide N, form a bicyclic heteroaryl moiety optionally substituted by one or two $R^3$, wherein the bicyclic heterocyclic moiety contains zero to three additional heteroatoms selected from the group consisting of N, O and S, wherein only one of the additional heteroatoms is O or S;
each $R^3$ is independently selected from the group consisting of F, Cl, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_1$-$C_6$ hydroxyalkyl, and phenoxy; or, when $R^1$ and $R^2$ together with the adjacent amide N form a 6 membered ring, two $R^3$ may together form a 1 to 2 carbon bridge or a $C_3$-$C_5$ spirocycloalkyl;
each $R^N$ is independently selected from the group consisting of H, $C_1$-$C_6$ alkyl, $C_3$-$C_6$ cycloalkyl, $C_1$-$C_6$ alkoxy and $C_1$-$C_6$ haloalkyl; or two $R^N$ may together with the adjacent N form a 4-6 membered ring:
the A ring is a 5 or 6 membered heteroaryl having 1 to 3 heteroatoms selected from the group consisting of nitrogen, oxygen and sulfur, wherein the A ring is optionally substituted with 1 to 2 substituents selected from the group consisting of halogen, $C_1$-$C_6$ alkyl, $C_3$-$C_6$ cycloalkyl, $C_1$-$C_6$ haloalkyl, $C_1$-$C_6$ alkoxy and $C_1$-$C_6$ haloalkoxy; and wherein if a nitrogen atom in the A ring is substituted, the substituent is not halogen. $C_1$-$C_6$ alkoxy or $C_1$-$C_6$ haloalkoxy having an oxygen or sulfur atom directly bonded to the nitrogen atom;
the B ring is a 5 to 7 membered cycloalkyl, or a 5 to 7 membered heterocyclyl having 1 to 3 heteroatoms selected from the group consisting of nitrogen, oxygen and sulfur; wherein the B ring is substituted according to (a), (b), or both (a) and (b):
  (a) 1 to 2 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy. $C_1$-$C_6$ thioalkyl, $C_1$-$C_6$ alkyl-N($R^N$)$_2$, and cyano; wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom: wherein two substituents on the B ring together may form a 1 to 2 carbon bridge or $C_3$-$C_5$ spirocycloalkyl group;
  (b) 1 substituent selected from the group consisting of phenyl, benzyl, $CH_2$—($C_3$-$C_6$ cycloalkyl), and $CH_2CH_2$—($C_3$-$C_6$ cycloalkyl), $CH_2$-(4 to 6 membered heterocyclyl), $CH_2CH_2$-(4 to 6 membered heterocyclyl), 5 or 6 membered heteroaryl, and $CH_2$-(5 or 6 membered heteroaryl); wherein when a phenyl ring is present it may be substituted by 1 or 2 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;
provided that if the B ring is substituted by only one substituent, it is not halogen or methyl.

Also provided herein are compounds of formula I, or pharmaceutically acceptable salts thereof, wherein $R^1$ and $R^2$:
  (a) are each independently selected from the group consisting of $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$; or
  (b) together with the adjacent amide N, form a 4 to 6 membered unsaturated heterocyclic ring optionally substituted by one or two $R^3$, containing zero or one additional heteroatom selected from the group consisting of O and S:
each $R^3$ is independently selected from the group consisting of F, Cl, $C_1$-$C_6$ alkyl, $C_3$-$C_6$ cycloalkyl, $C_1$-$C_6$ haloalkyl, $C_1$-$C_6$ alkoxy and $C_1$-$C_6$ haloalkoxy; or, when $R^1$ and $R^2$ together with the adjacent amide N form a 6 membered ring, two $R^3$ may together form a 1 to 2 carbon bridge or a $C_3$-$C_5$ spirocycloalkyl;
each $R^N$ is independently selected from the group consisting of H, $C_1$-$C_6$ alkyl, $C_3$-$C_6$ cycloalkyl, $C_1$-$C_6$ alkoxy and $C_1$-$C_6$ haloalkyl; or two $R^N$ may together with the adjacent N form a 4-6 membered ring;
the A ring is a 5 or 6 membered heteroaryl having 1 to 3 heteroatoms selected from the group consisting of nitrogen, oxygen and sulfur, wherein the A ring is optionally substituted with 1 to 2 substituents selected from the group consisting of halogen, $C_1$-$C_6$ alkyl, $C_3$-$C_6$ cycloalkyl, $C_1$-$C_6$ haloalkyl, $C_1$-$C_6$ alkoxy and $C_1$-$C_6$ haloalkoxy; and wherein if a nitrogen atom in the A ring is substituted, the substituent is not halogen, $C_1$-$C_6$ alkoxy or $C_1$-$C_6$ haloalkoxy having an oxygen or sulfur atom directly bonded to the nitrogen atom;
the B ring is a 5 to 7 membered cycloalkyl, or a 5 to 7 membered heterocyclyl having 1 to 3 heteroatoms selected from the group consisting of nitrogen, oxygen and sulfur, wherein the B ring is substituted according to (a), (b), or both (a) and (b):
  (a) 1 to 2 substituents selected from the group consisting of halogen, $C_1$-$C_6$ alkyl, $C_1$-$C_6$ haloalkyl, $C_3$-$C_6$ cycloalkyl, $C_1$-$C_6$ alkoxy, $C_1$-$C_6$ haloalkoxy, $C_1$-$C_6$ thioalkyl, $C_1$-$C_6$ alkyl-N($R^N$)$_2$, and cyano; wherein if a nitrogen atom in the B ring is substituted, the substituent is not halogen, cyano, or a $C_1$-$C_6$ alkoxy, $C_1$-$C_6$ haloalkoxy or $C_1$-$C_6$ thioalkyl having an oxygen or sulfur atom directly bonded to the nitrogen atom; wherein two substituents on the B ring together may form a 1 to 2 carbon bridge or $C_3$-$C_5$ spirocycloalkyl group;
  (b) 1 substituent selected from the group consisting of phenyl, benzyl, $CH_2$—($C_3$-$C_6$ cycloalkyl), and $CH_2CH_2$—($C_3$-$C_6$ cycloalkyl), $CH_2$-(4 to 6 membered heterocyclyl), $CH_2CH_2$-(4 to 6 membered heterocyclyl), 5 or 6 membered heteroaryl, and $CH_2$-(5 or 6 membered heteroaryl); wherein when a phenyl ring is present it may be substituted by 1 or 2 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;
provided that if the B ring is substituted by only one substituent, it is not halogen or methyl.

In some embodiments, $R^1$ and $R^2$ are each independently selected from the group consisting of $C_1$-$C_6$ alkyl, $C_3$-$C_6$ cycloalkyl, $C_1$-$C_6$ haloalkyl, $C_1$-$C_6$ alkoxy, $C_1$-$C_6$ alkyl-N($R^N$)$_2$. In some embodiments, $R^1$ and $R^2$ are each a $C_1$-$C_6$ alkyl. In some embodiments, $R^1$ and $R^2$ are each methyl.

In some embodiments, $R^1$ is selected from the group consisting of $C_1$-$C_3$ alkyl, $C_3$-$C_5$ cycloalkyl, and $C_1$-$C_3$ haloalkyl, and $R^2$ is selected from the group consisting of $C_1$-$C_3$ alkyl, $C_3$-$C_5$ cycloalkyl, $C_1$-$C_4$ alkoxy, phenyl, and 4 to 5 membered heterocyclyl.

In some embodiments, wherein $R^1$ is selected from the group consisting of methyl, cyclopropyl, —$CH_2CF_2H$ and —$CH_2CF_3$; and $R^2$ is selected from the group consisting of methyl, cyclopropyl, —$CH_2CH_2CH_3$, phenyl, and oxetan-3-yl.

In some embodiments, each $R^N$ is independently selected from the group consisting of H and $C_1$-$C_6$ alkyl. In some embodiments, each $R^N$ is a $C_1$-$C_4$ alkyl. In some embodiments, each $R^N$ is methyl.

Also provided herein are compounds of Formula (Ia):

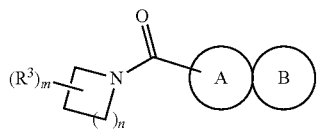

(Ia)

wherein $R^3$, ring A and ring B are as defined herein; m is 0, 1 or 2; and n is 1, 2 or 3.

In some embodiments of Formula (Ia), m is 0. In some embodiments, m is 1 and each $R^3$ is selected from the group consisting of F, Cl, $C_1$-$C_6$ alkyl, $C_1$-$C_6$ haloalkyl, $C_1$-$C_6$ alkoxy and $C_1$-$C_6$ haloalkoxy. In some embodiments, m is 2 and each $R^3$ is selected from the group consisting of F, $C_1$-$C_6$ alkyl, and $C_1$-$C_6$ haloalkyl. In some embodiments, m is 2 and each $R^3$ is F.

In some embodiments of Formula (Ia), each $R^3$ is selected from the group consisting of methyl, ethyl, F and Cl. In some embodiments, each $R^3$ is methyl or F.

In some embodiments, n is 1. In some embodiments, n is 2. In some embodiments, n is 3.

In some embodiments of Formula (Ia),

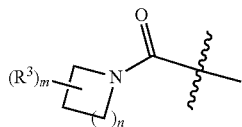

is selected from the group consisting of:

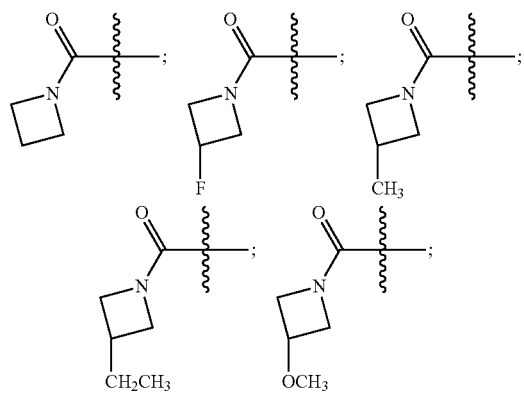

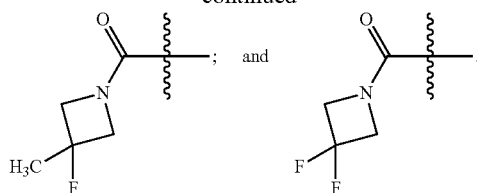

In some embodiments of Formula (Ia),

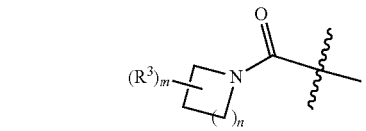

is selected from the group consisting of:

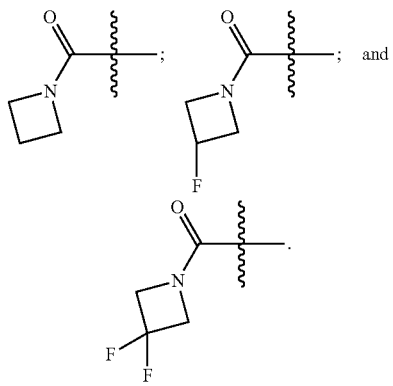

In some embodiments of Formula (Ia),

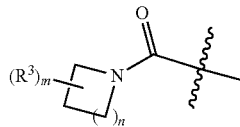

is selected from the group consisting of:

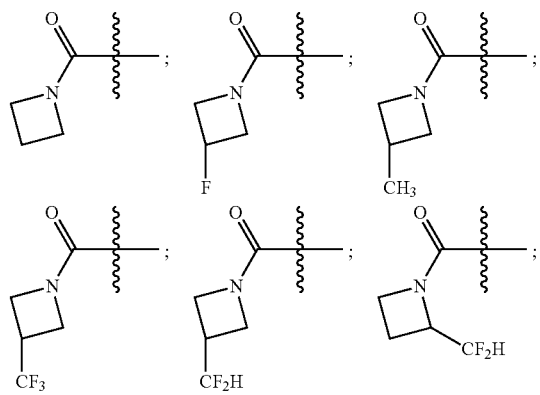

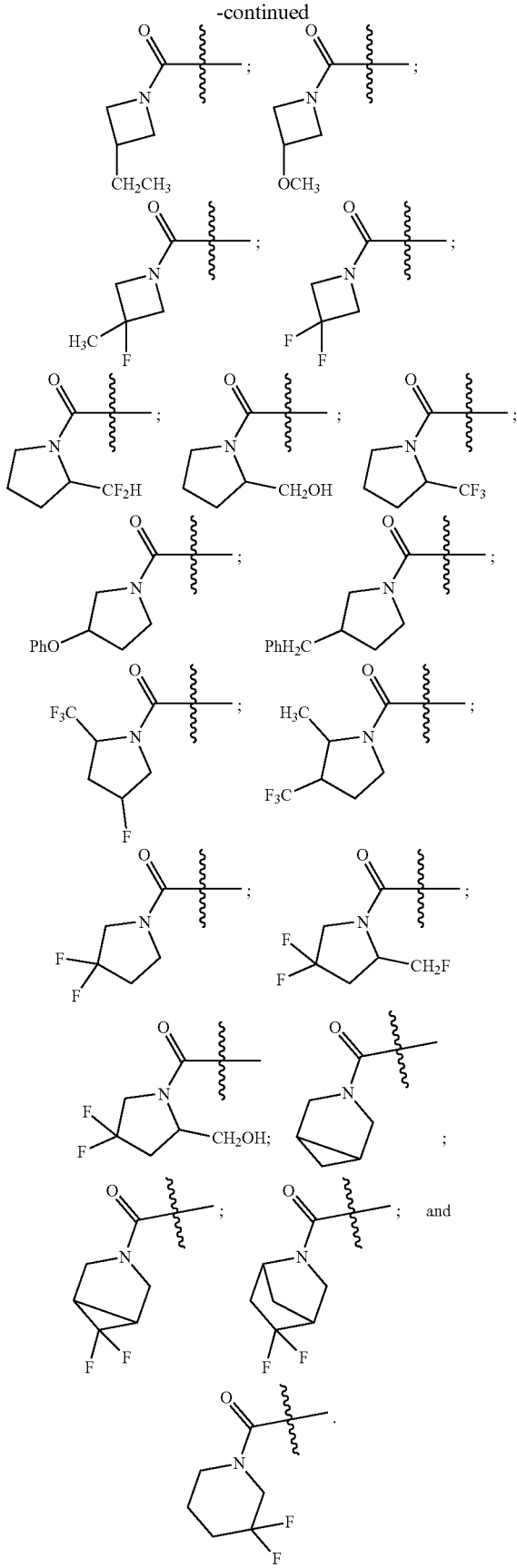

Also provided herein are compounds of Formula (Ib) or (Ic):

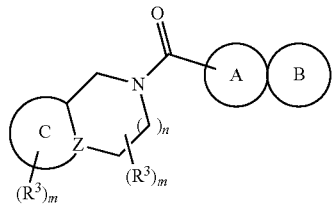

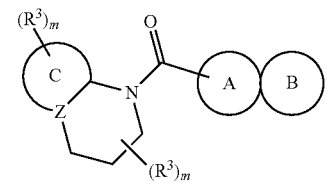

wherein, in each instance,
the C ring is phenyl or a 5 to 6 membered heteroaryl ring;
Z is C or N;
each $R^3$ is independently selected from the group consisting of F, Cl, $C_1$-$C_3$ alkyl, $C_3$-$C_5$ cycloalkyl, $C_1$-$C_3$ haloalkyl, $C_1$-$C_3$ alkoxy, and $C_1$-$C_3$ haloalkoxy;
n is 1 or 2; and
m is 0, 1 or 2.

In some embodiments of Formulae (Ib) or (Ic), each $R^3$ is independently selected from the group consisting of F and $C_1$-$C_3$ alkyl.

In some embodiments of Formulae (Ib) or (Ic),

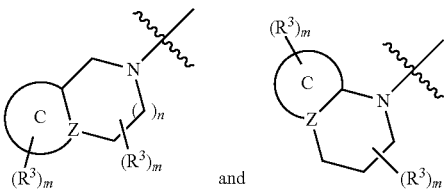

and are selected from the group consisting of:

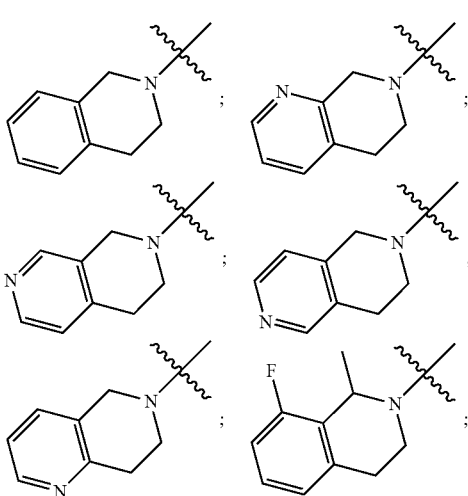

-continued

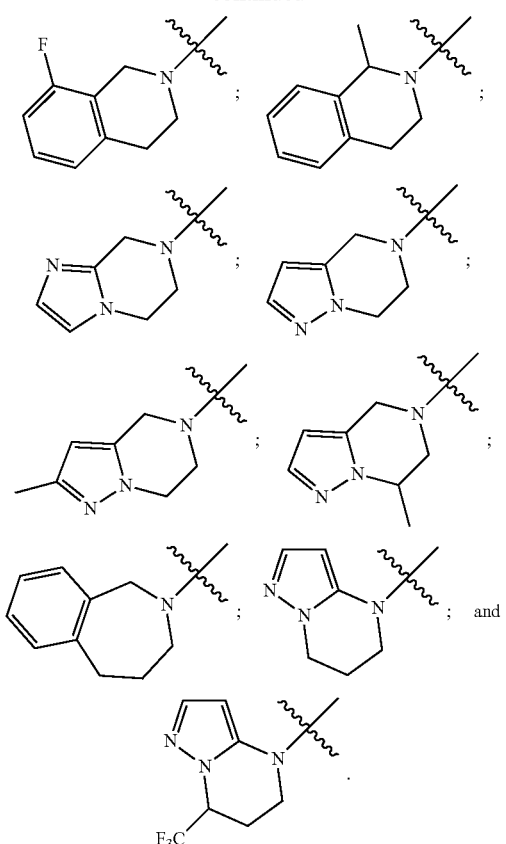

In some embodiments,

is selected from the group consisting of:

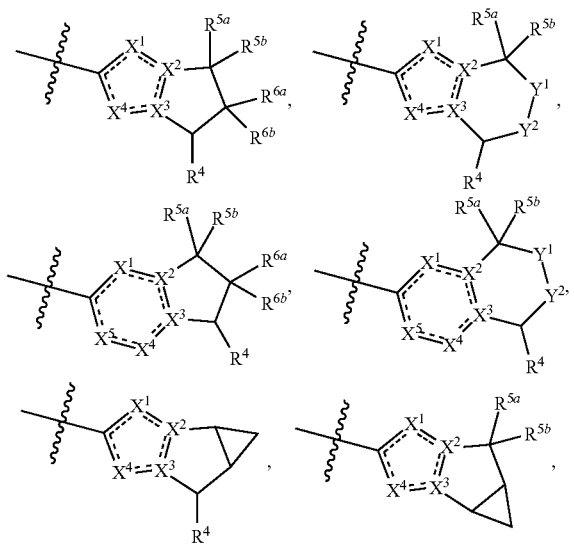

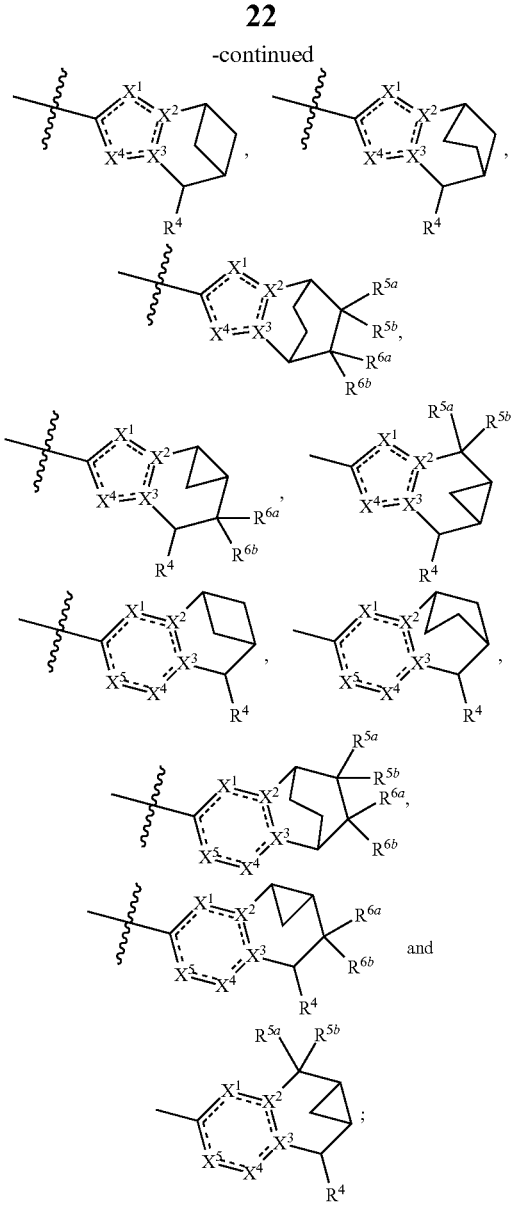

wherein
X$^1$, X$^4$, X$^5$ are each selected from the group consisting of NR$^7$ and CR$^8$;
X$^2$ and X$^3$ are each selected from the group consisting of N or C;
Y$^1$ and Y$^2$ are each selected from the group consisting of O, S, SO, SO$_2$, and CR$^{6a}$R$^{6b}$;
R$^4$ is selected from the group consisting of phenyl and 5 to 6 membered heteroaryl, wherein the heteroaryl has one or two heteroatoms selected from O, S and N, and phenyl may be substituted by 1 or 2 substituents selected from the group consisting of halogen, C$_1$-C$_4$ alkyl, C$_1$-C$_4$ haloalkyl, C$_1$-C$_4$ alkoxy, C$_1$-C$_4$ haloalkoxy, and cyano;
each R$^{5a}$ and R$^{5b}$ is independently selected from the group consisting of H, F, Cl, C$_1$-C$_6$ alkyl, C$_3$-C$_4$ cycloalkyl, C$_1$-C$_6$ haloalkyl, C$_1$-C$_6$ alkoxy, C$_1$-C$_6$ haloalkoxy; wherein R$^{5a}$ and R$^{5b}$ together with the carbon to which they are attached may form a 3 or 4 membered cycloalkyl optionally substituted by one or two F, or a 4 membered cycloalkoxy;
each R$^{6a}$ and R$^{6b}$ is independently selected from the group consisting of H, F, Cl, and C$_1$-C$_4$ alkyl;

each $R^7$ is independently selected from the group consisting of H and $C_1$-$C_4$ alkyl;

each $R^8$ is independently selected from the group consisting of H, halo, cyano, $C_1$-$C_4$ alkyl, $C_1$-$C_4$ haloalkyl, $C_1$-$C_4$ alkoxy, and $C_1$-$C_4$ haloalkoxy:

provided that only one of $X^2$ and $X^3$ is N, and the ring comprising $X^1$-$X^4$ or $X^1$-$X^5$ has 1, 2 or 3 nitrogen atoms;

further provided that one of $Y^1$ or $Y^2$ is $CR^{6a}R^{6b}$.

In some embodiments,

is selected from the group consisting of:

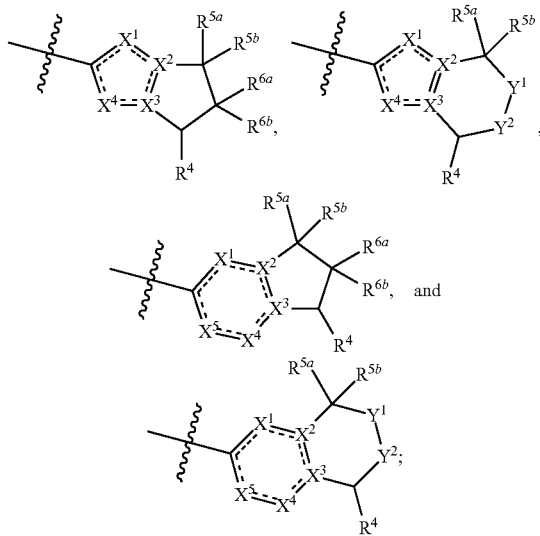

wherein $X^1$, $X^4$, $X^5$ are each selected from the group consisting of $NR^7$ and $CR^8$;

$X^2$ and $X^3$ are each selected from the group consisting of N or C;

$Y^1$ and $Y^2$ are each selected from the group consisting of O, S, SO, $SO_2$, and $CR^{6a}R^{6b}$;

$R^4$ is selected from the group consisting of phenyl and 5 to 6 membered heteroaryl, wherein the heteroaryl has one or two heteroatoms selected from O, S and N, and phenyl may be substituted by 1 or 2 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;

each $R^{5a}$ and $R^{5b}$ is independently selected from the group consisting of H, F, Cl, $C_1$-$C_6$ alkyl, $C_3$-$C_4$ cycloalkyl, $C_1$-$C_6$ haloalkyl, $C_1$-$C_6$ alkoxy, $C_1$-$C_6$ haloalkoxy; wherein $R^{5a}$ and $R^{5b}$ together with the carbon to which they are attached may form a 3 or 4 membered cycloalkyl optionally substituted by one or two F, or a 4 membered cycloalkoxy:

each $R^{6a}$ and $R^{6b}$ is independently selected from the group consisting of H, F, Cl, and $C_1$-$C_4$ alkyl;

each $R^7$ is independently selected from the group consisting of H and $C_1$-$C_4$ alkyl;

each $R^8$ is independently selected from the group consisting of H, halo, cyano, $C_1$-$C_4$ alkyl, $C_1$-$C_4$ haloalkyl, $C_1$-$C_4$ alkoxy, and $C_1$-$C_4$ haloalkoxy;

provided that only one of $X^2$ and $X^3$ is N, and the ring comprising $X^1$-$X^4$ or $X^1$-$X^5$ has 1, 2 or 3 nitrogen atoms;

further provided that one of $Y^1$ or $Y^2$ is $CR^{6a}R^{6b}$.

In some embodiments, $R^4$ is phenyl. In some embodiments, $R^4$ is mono- or difluorophenyl.

In some embodiments, each $R^{5a}$ and $R^{5b}$ is independently selected from the group consisting of H, $C_1$-$C_6$ alkyl, $C_3$-$C_4$ cycloalkyl, $C_1$-$C_6$ haloalkyl, $C_1$-$C_6$ alkoxy, $C_1$-$C_6$ haloalkoxy; wherein $R^{5a}$ and $R^{5b}$ together with the carbon to which they are attached may form a 3 or 4 membered cycloalkyl optionally substituted by one or two F, or a 4 membered cycloalkoxy.

In some embodiments, $R^{5a}$ and $R^{5b}$ are each independently H or F. In some embodiments, $R^{5a}$ and $R^{5b}$ are each independently H or F; and $R^{6a}$ and $R^{6b}$ are each H. In some embodiments, $R^{5a}$, $R^{5b}$, $R^{6a}$, and $R^{6b}$ are each H. In some embodiments. $R^{5a}$ and $R^{5b}$ are each F.

In some embodiments, each $R^{6a}$ and $R^{6b}$ is independently selected from the group consisting of H and $C_1$-$C_4$ alkyl. In some embodiments, $R^{6a}$ and $R^{6b}$ are each H.

In some embodiments, $Y^1$ and $Y^2$ are each $CR^{6a}R^{6b}$. In some embodiments, $Y^1$ is $CH_2$ and $Y^2$ is $CR^{6a}R^{6b}$. In some embodiments. $Y^1$ is $CR^{6a}R^{6b}$ and $Y^2$ is $CH_2$. In some embodiments, $Y^1$ and $Y^2$ are each $CH_2$. In some embodiments, $Y^1$ is O and $Y^2$ is $CR^{6a}R^{6b}$. In some embodiments, $Y^1$ is $CR^{6a}R^{6b}$ and $Y^2$ is O. In some embodiments, $Y^1$ is O and $Y^2$ is $CH_2$. In some embodiments, $Y^1$ is $CH_2$ and $Y^2$ is O.

In some embodiments, each $R^7$ is independently selected from the group consisting of H and methyl. In some embodiments, each $R^7$ is H.

In some embodiments, each $R^8$ is H.

In some embodiments, $X^1$, $X^4$, $X^5$ are each selected from the group consisting of $NR^7$ and $CR^8$;

$X^2$ and $X^3$ are each selected from the group consisting of N or C;

$Y^1$ and $Y^2$ are each selected from the group consisting of O and $CR^{6a}R^{6b}$; and each of $R^{6a}$, $R^{6b}$, $R^7$ and $R^8$ are as defined above;

provided that only one of $X^2$ and $X^3$ is N. and the ring comprising $X^1$-$X^4$ or $X^1$-$X^5$ has 1 or 2 nitrogen atoms;

further provided that one of $Y^1$ or $Y^2$ is $CR^{6a}R^{6b}$.

In some embodiments,

is selected from the group consisting of:

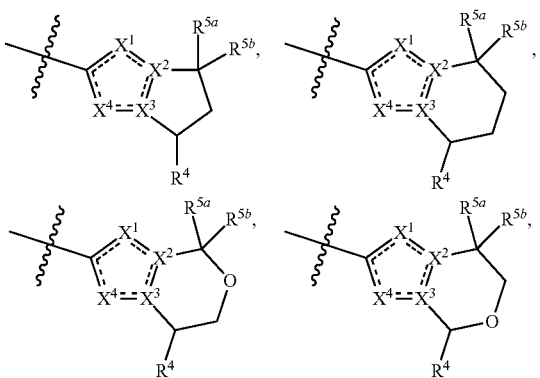

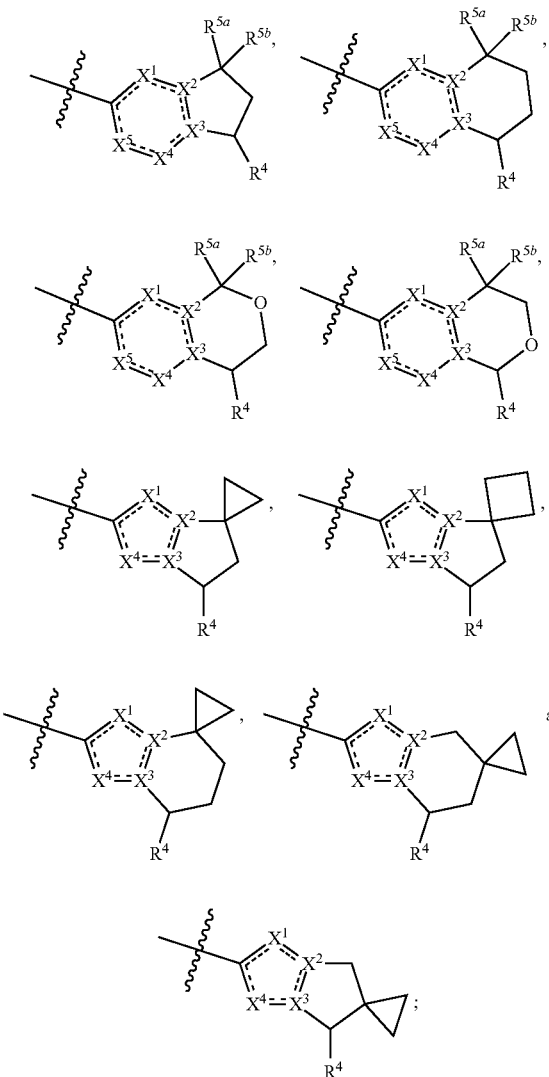
wherein
$X^1, X^2, X^3, X^4, X^5, R^4, R^{5a}, R^{5b}, R^{6a}$ and $R^{6b}$ are as defined above.
In some embodiments,
is selected from the group consisting of: consisting of:

-continued

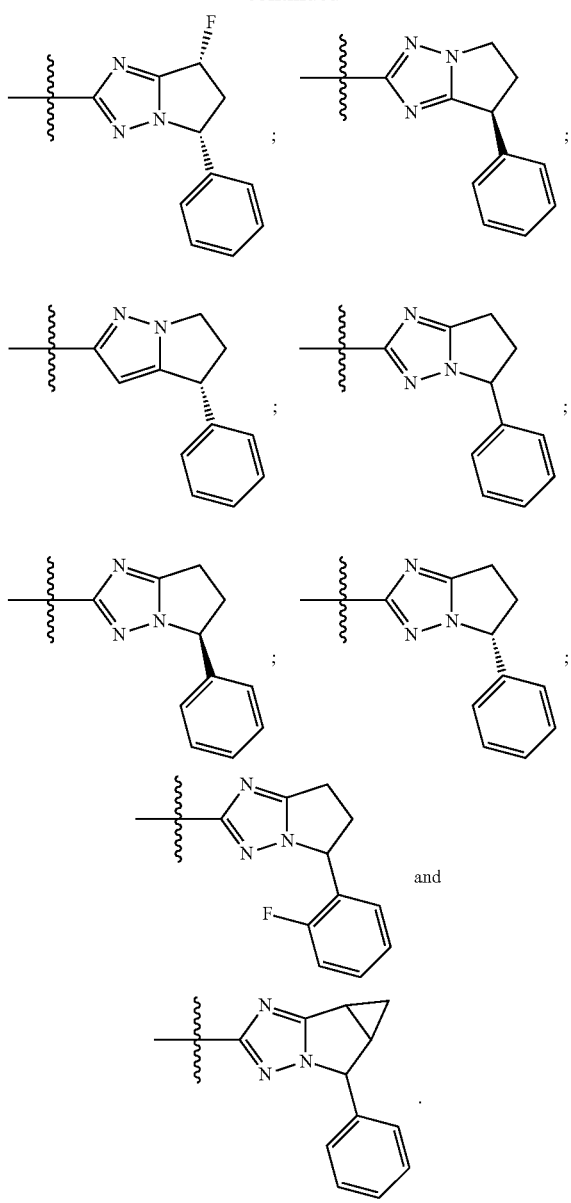

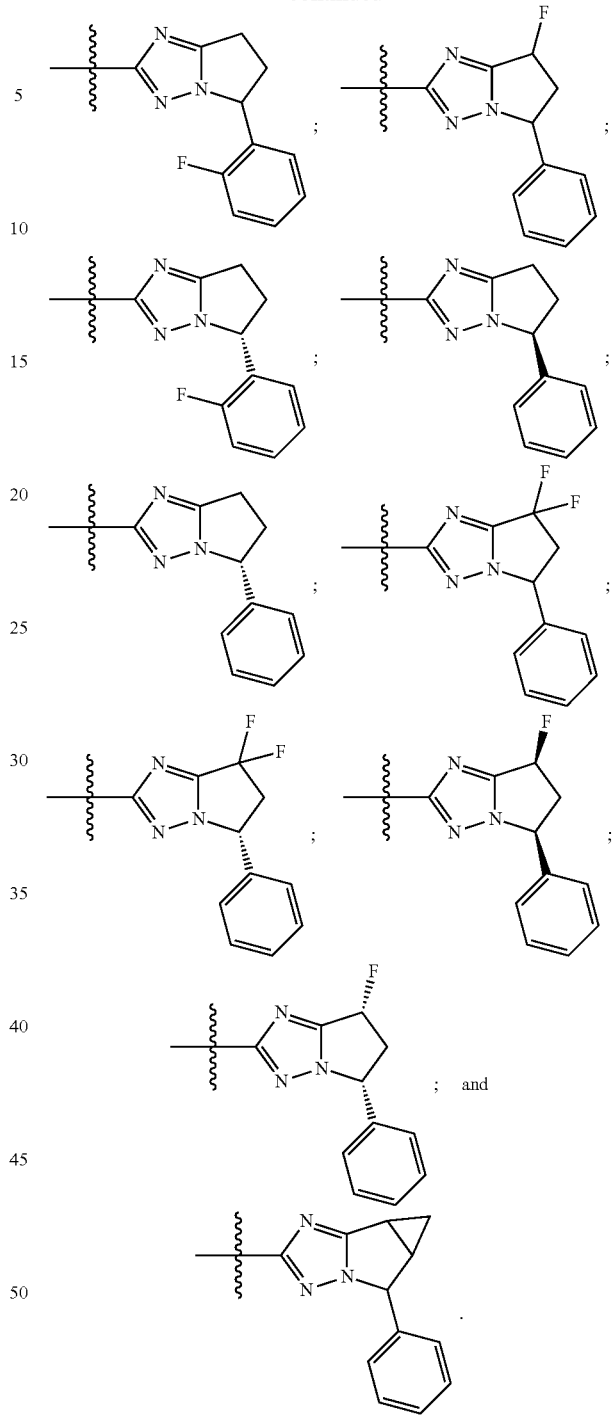

In some embodiments,

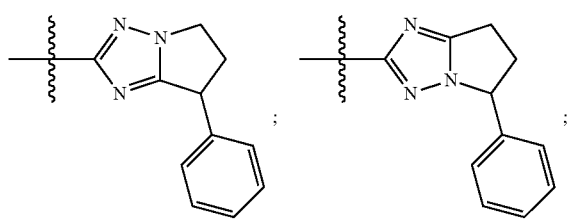

is selected from the group consisting of:

Also provided herein are embodiments corresponding to each of those described above, wherein each substituent is unsubstituted unless explicitly provided in the embodiment.

In another embodiment, provided herein is a compound selected from the compounds of Table 1 below. In another embodiment, provided herein is a compound selected from the compounds of Table 2 below.

Also provided herein is a method for the treatment or prophylaxis of a disease or disorder in a human, the method comprising administration to the human of an effective amount of a compound provided herein, wherein the disease or disorder is selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

Also provided herein is a method for the treatment of a disease or disorder in a human, the method comprising administration to the human of an effective treatment amount of a compound provided herein, wherein the disease or disorder is selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cisplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), chronic obstructive pulmonary disease (COPD).

Pharmaceutical Compositions and Administration

Provided herein are pharmaceutical compositions or medicaments containing the compounds of the invention (or stereoisomers, geometric isomers, tautomers, solvates, metabolites, isotopes, pharmaceutically acceptable salts, or prodrugs thereof), and a therapeutically inert carrier, diluent or excipient, as well as methods of using the compounds of the invention to prepare such compositions and medicaments. In one example, compounds of formula I may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I is formulated in an acetate buffer, at pH 5. In another embodiment, the compounds of formula I are sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. In some embodiments, the "effective amount" of the compound to be administered will be governed by such considerations, and is the minimum amount necessary to inhibit RIP1 kinase activity in order to provide a therapeutic effect in the mammal being treated. In addition, such an effective amount may be below the amount that is toxic to normal cells, or the mammal as a whole.

In one example, the pharmaceutically effective amount of the compound of the invention administered intravenously or parenterally will be in the per dose range of about 0.1 to 100 mg/kg, alternatively about 0.1 to 20 mg/kg of patient body weight per day, or alternatively about 0.3 to 15 mg/kg/day.

In another embodiment, oral unit dosage forms, such as tablets and capsules, preferably contain from about 1 to about 1000 mg (e.g., 1 mg, 5 mg, 10 mg. 15 mg, 20 mg, 25 mg, 30 mg, 40 mg, 50 mg, 100 mg, 200 mg, 250 mg, 400 mg, 500 mg, 600 mg, 700 mg, 800 mg, 900 mg, or 1000 mg) of the compound of the invention. The daily does is, in certain embodiments, given as a single daily dose or in divided doses two to six times a day, or in sustained release form. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

In some embodiments, a low dose of the compound of the invention is administered in order to provide therapeutic benefit while minimizing or preventing adverse effects.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration. In specific embodiments, the compound of formula I is administered orally. In other specific embodiments, the compound of formula I is administered intravenously.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which a compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol: 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). A active pharmaceutical ingredient of the invention (e.g., compound of formula I or an embodiment thereof) can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington: The Science and Practice of Pharmacy: Remington the Science and Practice of Pharmacy (2005) $21^{st}$ Edition, Lippincott Williams & Wilkins, Philadelphia, Pa.

Sustained-release preparations of a compound of the invention (e.g., compound of formula I or an embodiment thereof) can be prepared. Suitable examples of sustained-release preparations include semipermeable matrices of solid hydrophobic polymers containing a compound of formula I or an embodiment thereof, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate (Sidman et al., Biopolymers 22:547, 1983), non-degradable ethylene-vinyl acetate (Langer et al., J. Biomed. Mater. Res. 15:167, 1981), degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid (EP 133,988A). Sustained release compositions also include liposomally entrapped compounds, which can be prepared by methods known per se (Epstein et al., Proc. Natl. Acad. Sci. U.S.A. 82:3688, 1985; Hwang et al., Proc. Natl. Acad. Sci. U.S.A. 77:4030, 1980; U.S. Pat. Nos. 4,485,045 and 4,544,545; and EP 102,324A). Ordinarily, the liposomes are of the small (about 200-800 Angstroms) unilamelar type in which the lipid content is greater than about 30 mol % cholesterol, the selected proportion being adjusted for the optimal therapy.

In one example, compounds of formula I or an embodiment thereof may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula I (or an embodiment thereof) is formulated in an acetate buffer, at pH 5. In another embodiment, the compounds of formula I or an embodiment thereof are sterile. The compound may be stored, for example, as a solid or amorphous composition, as a lyophilized formulation or as an aqueous solution.

An example of a suitable oral dosage form provided herein is a tablet containing about 1 to about 500 mg (e.g., about 1 mg, 5 mg, 10 mg, 25 mg, 30 mg, 50 mg, 80 mg, 100 mg, 150 mg, 250 mg, 300 mg and 500 mg) of the compound of the invention compounded with suitable amounts of anhydrous lactose, sodium croscarmellose, polyvinylpyrrolidone (PVP) K30, and magnesium stearate. The powdered ingredients are first mixed together and then mixed with a solution of the PVP. The resulting composition can be dried, granulated, mixed with the magnesium stearate and compressed to tablet form using conventional equipment.

Formulations of a compound of the invention (e.g., compound of formula I or an embodiment thereof) can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally acceptable diluent or solvent, such as a solution in 1,3-butanediol or prepared as a lyophilized powder. Among the acceptable vehicles and solvents that can be employed are water, Ringer's solution and isotonic sodium chloride solution. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The amount of active ingredient that can be combined with the carrier material to produce a single dosage form will vary depending upon the host treated and the particular mode of administration. For example, a time-release formulation intended for oral administration to humans can contain approximately 1 to 1000 mg of active material compounded with an appropriate and convenient amount of carrier material which can vary from about 5 to about 95% of the total compositions (weight:weight). The pharmaceutical composition can be prepared to provide easily measurable amounts for administration. For example, an aqueous solution intended for intravenous infusion can contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which can contain anti-oxidants, buffers, bacteriostats and solutes which render the formulation isotonic with the blood of the intended recipient; and aqueous and non-aqueous sterile suspensions which can include suspending agents and thickening agents.

The formulations can be packaged in unit-dose or multi-dose containers, for example sealed ampoules and vials, and can be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described.

An embodiment, therefore, includes a pharmaceutical composition comprising a compound of formula I, or pharmaceutically acceptable salt thereof. In a further embodiment includes a pharmaceutical composition comprising a compound of formula I, or a pharmaceutically acceptable salt thereof, together with a pharmaceutically acceptable carrier or excipient.

When the binding target is located in the brain, certain embodiments of the invention provide for a compound of formula I (or an embodiment thereof) to traverse the blood-brain barrier. In these embodiments, the compounds provided herein exhibit sufficient brain penetration as potential therapeutics in neurological diseases. In some embodiments, brain penetration is assessed by evaluating free brain/plasma ratio ($B_u/P_u$) as measured in vivo pharmacokinetic studies in rodents or by other methods known to persons skilled in the art (see, e.g., Liu, X. et al., J. Pharmacol. Exp. Therap., 325:349-56, 2008).

Certain neurological diseases are associated with an increase in permeability of the blood-brain barrier, such that a compound of formula I (or an embodiment thereof) can be readily introduced to the brain. When the blood-brain barrier remains intact, several art-known approaches exist for transporting molecules across it, including, but not limited to, physical methods, lipid-based methods, and receptor and channel-based methods. Physical methods of transporting a compound of formula I (or an embodiment thereof) across the blood-brain barrier include, but are not limited to, circumventing the blood-brain barrier entirely, or by creating openings in the blood-brain barrier.

Circumvention methods include, but are not limited to, direct injection into the brain (see, e.g., Papanastassiou et al., Gene Therapy 9:398-406, 2002), interstitial infusion/convection-enhanced delivery (see, e.g., Bobo et al., Proc. Natl. Acad. Sci. U.S.A. 91:2076-2080, 1994), and implanting a delivery device in the brain (see, e.g., Gill et al., Nature Med. 9:589-595, 2003; and Gliadel Wafers™, Guildford.

Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Volumes 1 and 2, Plenum Press, N.Y., 1989)), and permeabilization by, e.g., bradykinin or permeabilizer A-7 (see, e.g., U.S. Pat. Nos. 5,112,596, 5,268,164, 5,506,206, and 5,686,416).

Lipid-based methods of transporting a compound of formula I or I-I (or an embodiment thereof) across the blood-brain barrier include, but are not limited to, encapsulating the a compound of formula I or I-I (or an embodiment thereof) in liposomes that are coupled to antibody binding fragments that bind to receptors on the vascular endothelium of the blood-brain barrier (see, e.g., U.S. Patent Publication No. 2002/0025313), and coating a compound of formula I (or an embodiment thereof) in low-density lipoprotein particles (see, e.g., U.S. Patent Publication No. 2004/0204354) or apolipoprotein E (see, e.g., U.S. Patent Publication No. 2004/0131692).

Receptor and channel-based methods of transporting a compound of formula I (or an embodiment thereof) across the blood-brain barrier include, but are not limited to, using glucocorticoid blockers to increase permeability of the blood-brain barrier (see, e.g., U.S. Patent Publication Nos. 2002/0065259, 2003/0162695, and 2005/0124533); activating potassium channels (see, e.g., U.S. Patent Publication No. 2005/0089473), inhibiting ABC drug transporters (see, e.g., U.S. Patent Publication No. 2003/0073713); coating a compound of formula I or I-I (or an embodiment thereof) with a transferrin and modulating activity of the one or more transferrin receptors (see, e.g., U.S. Patent Publication No. 2003/0129186), and cationizing the antibodies (see, e.g., U.S. Pat. No. 5,004,697).

For intracerebral use, in certain embodiments, the compounds can be administered continuously by infusion into the fluid reservoirs of the CNS, although bolus injection may be acceptable. The inhibitors can be administered into the ventricles of the brain or otherwise introduced into the CNS or spinal fluid. Administration can be performed by use of an indwelling catheter and a continuous administration means such as a pump, or it can be administered by implantation, e.g., intracerebral implantation of a sustained-release vehicle. More specifically, the inhibitors can be injected through chronically implanted cannulas or chronically infused with the help of osmotic minipumps. Subcutaneous pumps are available that deliver proteins through a small tubing to the cerebral ventricles. Highly sophisticated pumps can be refilled through the skin and their delivery rate can be set without surgical intervention. Examples of suitable administration protocols and delivery systems involving a subcutaneous pump device or continuous intracerebroventricular infusion through a totally implanted drug delivery system are those used for the administration of dopamine, dopamine agonists, and cholinergic agonists to Alzheimer's disease patients and animal models for Parkinson's disease, as described by Harbaugh, J. Neural Transm. Suppl. 24:271, 1987; and DeYebenes et al., Mov. Disord. 2: 143, 1987.

Indications and Methods of Treatment

The compounds of the invention inhibit RIP1 kinase activity. Accordingly, the compounds of the invention are useful for the treatment of diseases and disorders mediated by this pathway and associated with inflammation and/or necroptotic cell death. Compounds of the invention are therefore useful for the treatment or prevention of a disease or disorder selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD).

In another embodiment, compounds of the invention are useful for the treatment of one or more symptoms of the above diseases and disorders. In some embodiments, the disease or disorder is an irritable bowel disorder. In some embodiments, the disease or disorder is irritable bowel syndrome (IBS), Crohn's disease, or ulcerative colitis. In some embodiments, the disease or disorder is an ischemia-reperfusion injury of kidneys, liver and lungs. In some embodiments, the disease or disorder is a chronic kidney disease. In some embodiments, the disease or disorder is acute respiratory distress syndrome (ARDS). In some embodiments, the disease or disorder is chronic obstructive pulmonary disease (COPD).

In some embodiments, the disease or disorder to be treated is selected from the group consisting of inflammatory bowel diseases (including Crohn's disease and ulcerative colitis), psoriasis, retinal detachment, retinitis pigmentosa, macular degeneration, pancreatitis, atopic dermatitis, arthritis (including rheumatoid arthritis, osteoarthritis, spondylarthritis, gout, systemic onset juvenile idiopathic arthritis (SoJIA), psoriatic arthritis), systemic lupus erythematosus (SLE), Sjogren's syndrome, systemic scleroderma, anti-phospholipid syndrome (APS), vasculitis, liver damage/diseases (non-alcohol steatohepatitis, alcohol steatohepatitis, autoimmune hepatitis autoimmune hepatobiliary diseases, primary sclerosing cholangitis (PSC), acetaminophen toxicity, hepatotoxicity), kidney damage/injury (nephritis, renal transplant, surgery, administration of nephrotoxic drugs e.g. cisplatin, acute kidney injury(AKI)), Celiac disease, autoimmune idiopathic thrombocytopenic purpura, transplant rejection, ischemia reperfusion injury of solid organs, sepsis, systemic inflammatory response syndrome (SIRS), cerebrovascular accident (CVA, stroke), myocardial infarction (MI), atherosclerosis, Huntington's disease. Alzheimer's disease, Parkinson's disease, amyotrophic lateral sclerosis (ALS), spinal muscular atropy (SMA), allergic diseases (including asthma and atopic dermatitis), multiple sclerosis, type I diabetes, Wegener's granulomatosis, pulmonary sarcoidosis. Behcet's disease, interleukin-1 converting enzyme (ICE, also known as caspase-1) associated fever syndrome, chronic obstructive pulmonary disease (COPD), tumor necrosis factor receptor-associated periodic syndrome (TRAPS), periodontitis, NEMO-deficiency syndrome (F-kappa-B essential modulator gene (also known as IKK gamma or IKKG) deficiency syndrome). HOIL-1 deficiency ((also known as RBCK1) heme-oxidized IRP2 ubiquitin ligase-1 deficiency), linear ubiquitin chain assembly complex (LUBAC) deficiency syndrome, hematological and solid organ malignancies, bacterial infections and viral infections (such as tuberculosis and influenza), and Lysosomal storage diseases (particularly, Gaucher Disease, and including GM2, Gangliosidosis, Alpha-mannosidosis, Aspartylglucosaminuria, Cholesteryl Ester storage disease, Chronic Hexosaminidase A Deficiency, Cystinosis, Danon disease, Fabry disease. Farber disease, Fucosidosis, Galactosialidosis, GM1 gangliosidosis, Mucolipidosis, Infantile Free Sialic Acid Storage Disease, Juvenile Hexosaminidase A Deficiency, Krabbe disease, Lysosomal acid lipase deficiency, Metachromatic Leukodystrophy, Mucopolysaccharidoses disorders. Multiple sulfatase deficiency, Niemann-Pick Disease, Neuronal Ceroid Lipofuscinoses, Pompe disease, Pycnodysostosis, Sandhoff disease, Schindler disease, Sialic Acid Storage Disease, Tay-Sachs and Wolman disease).

Also provided herein is the use of a compound of the invention in therapy. In some embodiments, provided herein is the use of a compound of the invention for the treatment or prevention of the above diseases and disorders. Also provided herein is the use of a compound of the invention in the manufacture of a medicament for the treatment or prevention of the above diseases and disorders.

Also provided herein is a method of treating a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a symptom of a disease or disorder in a mammal in need of such treatment, said disease or disorder being selected from the group consisting of irritable bowel disorders (IBD), irritable bowel syndrome (IBS), Crohn's disease, ulcerative colitis, myocardial infarction, stroke, traumatic brain injury, atherosclerosis, ischemia-reperfusion injury of kidneys, liver and lungs, cysplatin-induced kidney injury, sepsis, systemic inflammatory response syndrome (SIRS), pancreatits, psoriasis, retinitis pigmentosa, retinal degeneration, chronic kidney diseases, acute respiratory distress syndrome (ARDS), and chronic obstructive pulmonary disease (COPD), wherein the method comprises administering to said mammal a therapeutically effective amount of a compound of formula I, or a pharmaceutically acceptable salt thereof.

Also provided herein is a method of treating a disease or disorder in a mammal in need of such treatment, said disease or disorder being selected from the group consisting of irritable bowel disorders (IBD), irritable bowel syndrome (IBS), Crohn's disease, and ulcerative colitis, wherein the method comprises orally administering to said mammal a therapeutically effective amount of a compound of formula I, or a pharmaceutically acceptable salt thereof, as an orally acceptable pharmaceutical composition.

Combination Therapy

Compounds of the invention may be combined with one or more other compounds of the invention or one or more other therapeutic agent as any combination thereof, in the treatment of the diseases and disorders provided herein. For example, a compound of the invention may be administered simultaneously, sequentially or separately in combination with other therapeutic agents known to be useful for the treatment of a disease or disorder selected from those recited above.

In some embodiments, a compound provided herein may be combined with another therapeutically active agent as recited in WO 2016/027253, the contents of which are hereby incorporated by reference in their entirety. In such embodiments, the compound that inhibits RIP1 kinase in the combinations recited in WO 2016/027253 is replaced by a compound of formula I of the present disclosure.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise. "combination" may include formulations of a compound of the invention with another thera-

37 peutic agent. Dosage forms, routes of administration and pharmaceutical compositions include, but are not limited to, those described herein.

EXAMPLES

The invention will be more fully understood by reference to the following examples. They should not, however, be construed as limiting the scope of the invention.

These examples serve to provide guidance to a skilled artisan to prepare and use the compounds, compositions and methods of the invention. While particular embodiment of the present invention are described, the skilled artisan will appreciate that various changes and modifications can be made without departing from the spirit and scope of the inventions.

The chemical reactions in the examples described can be readily adapted to prepare a number of other compounds of the invention, and alternative methods for preparing the compounds of this invention are deemed to be within the scope of this invention. For example, the synthesis of non-exemplified compounds according to the invention can be successfully performed by modifications apparent to those skilled in the art, for example, by appropriately protecting interfering group, by utilizing other suitable reagents known in the art, for example, by appropriately protecting interfering groups by utilizing other suitable reagents known in the art other than those described, and/or by making routine modifications of reaction conditions.

In the examples below, unless otherwise indicated all temperatures are set forth in degrees Celsius. Commercially available reagents were purchased from suppliers such as Aldrich Chemical Company, Lancaster, TCI or Maybridge and were used without further purification unless otherwise indicated. The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried. $^1$H NMR spectra were obtained in deuterated CDCl$_3$, d$_6$-DMSO, CH$_3$OD or d$_6$-acetone solvent solutions (reported in ppm) using or trimethylsilane (TMS) or residual non-deuterated solvent peaks as the reference standard. When peak multiplicities are reported, the following abbreviates are used: s (singlet), d (doublet), t (triplet), q (quartet), m (multiplet, br (broadened), dd (doublet of doublets), dt (doublet of triplets). Coupling constants, when given, ar reported in Hz (Hertz).

In the examples below, LCMS methods were performed for 10 or 30 minutes according to the following conditions:

Agilent 10 min LCMS Method: Experiments performed on an Agilent 1290 UHPLC coupled with Agilent MSD (6140) mass spectrometer using ESI as ionization source. The LC separation was using a Phenomenex XB-C18, 1.7 mm, 50×2.1 mm column with a 0.4 ml/minute flow rate. Solvent A is water with 0.1% FA and solvent B is acetonitrile with 0.1% FA. The gradient consisted with 2-98% solvent B over 7 min and hold 98% B for 1.5 min following equilibration for 1.5 min. LC column temperature is 40° C. UV absorbance was collected at 220 nm and 254 nm and mass spec full scan was applied to all experiment.

Agilent 30 min LCMS Method: Experiments performed on an Agilent 1100 HPLC coupled with Agilent MSD mass spectrometer using ESI as ionization source. The LC separation was using an Agilent Eclipse XDB-C18, 3.5 mm, 100×3.0 mm column with a 0.7 ml/minute flow rate. Solvent A is water with 0.1% FA and solvent B is acetonitrile with 0.1% FA. The gradient consisted with 2-98% solvent B over 25.5 min and hold 98% B for 2.5 min following equilibration for 1.5 min. UV absorbance were collected at 220 nm and 254 nm and mass spec full scan was applied to all experiment.

All abbreviations used to describe reagents, reaction conditions or equipment are intended to be consistent with the definitions set forth in the following list of Abbreviations. The chemical names of discrete compounds of the invention were typically obtained using the structure naming feature of ChemDraw naming program.

ABBREVIATIONS

ACN Acetonitrile
Boc tert-Butoxycarbonyl
DMF N,N-Dimethylformamide
DMSO Dimethyl sulfoxide
HPLC High Pressure Liquid Chromatography
LCMS Liquid Chromatography Mass Spectrometry
RP Reverse phase
RT or R$_T$ Retention time
SEM 2-(Trimethylsilyl)ethoxymethyl
THF Tetrahydrofuran Example 1

Synthetic Method #1

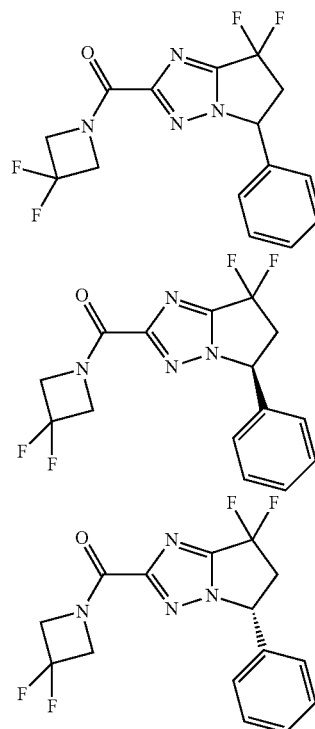

(3,3-difluoroazetidin-1-yl)-(7,7-difluoro-5-phenyl-5,6-dihydropyrrolo[1,2-b][1,2,4]triazol-2-yl)methanone, (S)-(7,7-difluoro-5-phenyl-6,7-dihydro-5H-pyrrolo[1,2-b][1,2,4]triazol-2-yl)(3,3-difluoroazetidin-1-yl)methanone and (R)-(7,7-difluoro-5-phenyl-6,7-dihydro-5H-pyrrolo[1,2-b][1,2,4]triazol-2-yl)(3,3-difluoroazetidin-1-yl)methanone

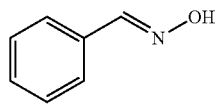

Step 1: (E)-benzaldehyde oxime

To a solution of benzaldehyde (45.0 g, 424.1 mmol) in ethanol (100 mL) was added sodium carbonate (112.3 g. 1060.1 mmol) and hydroxylamine hydrochloride (35.3 g, 508.9 mmol). The reaction mixture was stirred at 25° C. for 3 h and filtered. The filtrate was concentrated under reduced pressure and the residue was diluted with water (50 mL). The resulting mixture was extracted with ethyl acetate (3×150 mL). The combined organic layers were washed with brine (60 mL), dried over anhydrous sodium sulfate and concentrated under reduced pressure to afford crude (E)-benzaldehyde oxime as colorless oil (51.0 g, 99%), used in the next step without further purification.

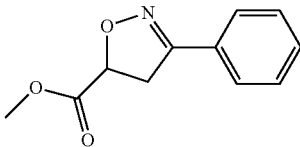

Step 2: methyl 3-phenyl-4,5-dihydroisoxazole-5-carboxylate

To a solution of (E)-benzaldehyde oxime (20.0 g, 165.1 mmol) in 1,4-dioxane (500 mL) was added methyl acrylate (14.2 g, 165.1 mmol), sodium iodide (24.7 g, 165.1 mmol). 2,6-lutidine (17.6 g, 165.1 mmol) and hypochlorous acid tert-butyl ester (17.9 g, 165.1 mmol). The reaction mixture was stirred at 25° C. for 24 h and subsequently concentrated under reduced pressure. The residue was purified by column chromatography (silica gel, 100-200 mesh, 0 to 20% ethyl acetate in petroleum ether) to afford methyl 3-phenyl-4,5-dihydroisoxazole-5-carboxylate as a yellow solid (25.0 g, 74%). LCMS $R_T$=0.871 min, m/z=206.2 [M+H]$^+$.

LCMS (10 to 80% acetonitrile in water+0.03% trifluoacetic acid over 2.0 mins) retention time 0.871 min, ESI+ found [M+H]=206.2.

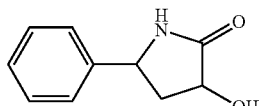

Step 3: 3-hydroxy-5-phenyl-pyrrolidin-2-one

A mixture of methyl 3-phenyl-4, 5-dihydroisoxazole-5-carboxylate (25.0 g, 121.8 mmol) and palladium (10% on carbon, 2.5 g) in ethanol (800 mL) was hydrogenated (50 psi) at 25° C. for 2 h and then filtered and the filtrate was concentrated under reduced pressure to afford crude 3-hydroxy-5-phenyl-pyrrolidin-2-one as a yellow solid (18.0 g, 83%), used in the next step without further purification. LCMS $R_T$=0.270 min, m/z=177.8 [M+H]$^+$.

LCMS (5 to 95% acetonitrile in water+0.03% trifluoacetic acid over 1.5 mins) retention time 0.270 min, ESI+ found [M+H]=177.8.

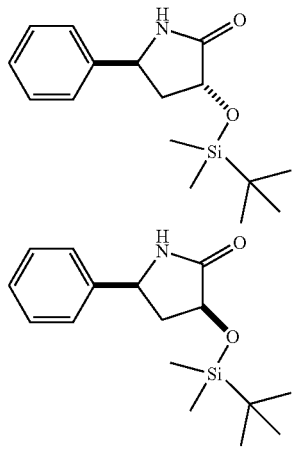

Step 4: cis-3-[tert-butyl(dimethyl)silyl]oxy-5-phenyl-pyrrolidin-2-one & trans-3-[tert-butyl(dimethyl)silyl]oxy-5-phenyl-pyrrolidin-2-one To a solution of 3-hydroxy-5-phenyl-pyrrolidin-2-one (15.0 g, 84.6 mmol) in dichloromethane (300 mL) was added tert-butyldimethylchlorosilane (19.1 g, 126.9 mmol) and imidazole (11.5 g, 169.3 mmol). The reaction mixture was stirred at 25° C. for 16 h and subsequently concentrated under reduced pressure. The residue was purified by column chromatography (silica gel. 100-200 mesh, 0 to 30% ethyl acetate in petroleum ether) to afford cis-3-[tert-butyl(dimethyl)silyl]oxy-5-phenyl-pyrrolidin-2-one (12.4 g, 51%). $^1$H NMR (400 MHz, CDCl$_3$) δ 7.37-7.25 (m, 5H). 4.88-4.53 (m, 1H), 4.54-4.46 (m, 1H), 2.89-2.79 (m, 1H), 1.80-1.71 (m, 1H), 0.93-0.90 (m, 9H), 0.19-0.12 (m, 6H) and trans-3-[tert-butyl(dimethyl)silyl]oxy-5-phenyl-pyrrolidin-2-one as a colorless oil (9.3 g, 38%). $^1$H NMR (400 MHz, CDCl$_3$) δ 7.44-7.34 (m, 2H), 7.29-7.24 (m, 3H), 4.87-4.80 (m, 1H), 4.44-4.41 (m, 1H), 2.45-2.37 (m, 1H), 2.27-2.22 (m, 1H), 0.93-0.90 (m, 9H), 0.16-0.13 (m, 6H).

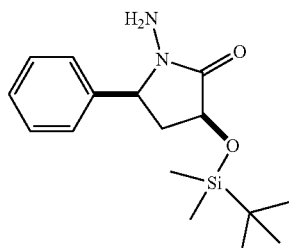

Step 5: cis-1-amino-3-[tert-butyl(dimethyl)silyl]oxy-5-phenyl-pyrrolidin-2-one To a solution of cis-3-[tert-butyl(dimethyl)silyl]oxy-5-phenyl-pyrrolidin-2-one (12.4 g, 42.8 mmol) in N,N-dimethylformamide (400 mL) was slowly added sodium hydride (60%, 2.6 g, 64.1 mmol) at 0° C. After addition, the mixture was stirred at 0° C. for 20 min and subsequently O-(diphenylphosphoryl)hydroxylamine (14.9 g, 64.1 mmol) was added. The reaction mixture was stirred at 25° C. for 16 h and then filtered. The filtrate was concentrated under reduced pressure to afford the crude cis-1-amino-3-[tert-butyl(dimethyl)silyl]oxy-5-phenyl-pyrrolidin-2-one as a yellow oil (9.5 g, 73%), used in the next step without further purification. LCMS $R_T$=0.877 min, m/z=307.0 [M+H]$^+$.

LCMS (5 to 95% acetonitrile in water+0.03% trifluoacetic acid over 1.5 mins) retention time 0.877 min, ESI+ found [M+H]=307.0.

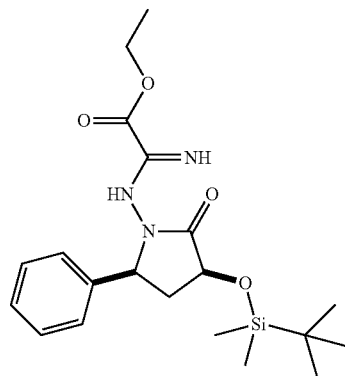 [SMILES: CCOC(=O)C(=N)NN1C(=O)[C@@H](O[Si](C)(C)C(C)(C)C)C[C@H]1c1ccccc1]

Step 6: ethyl 2-[[cis-3-[tert-butyl(dimethyl)silyl]oxy-2-oxo-5-phenyl-pyrrolidin-1-yl]amino]-2-imino-acetate To a solution of cis-1-amino-3-[tert-butyl(dimethyl)silyl]oxy-5-phenyl-pyrrolidin-2-one (9.5 g, 31.0 mmol) in ethanol (250 mL) was added ethyl 2-ethoxy-2-imino-acetate (6.7 g, 46.5 mmol). The reaction mixture was stirred at 60° C. for 6 h and subsequently concentrated under reduced pressure to afford crude ethyl 2-[[cis-3-[tert-butyl(dimethyl)silyl]oxy-2-oxo-5-phenyl-pyrrolidin-1-yl]amino]-2-imino-acetate as a yellow oil (10.6 g, 84%), used in the next step without further purification. LCMS $R_T$=2.106 min, m/z=406.2 [M+H]$^+$.

LCMS (10 to 80% acetonitrile in water+0.1% ammonia water over 3.0 mins) retention time 2.106 min, ESI+ found [M+H]=406.2.

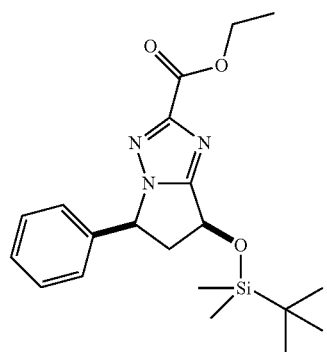 [SMILES: CCOC(=O)c1nc2n(n1)[C@H](c1ccccc1)C[C@@H]2O[Si](C)(C)C(C)(C)C]

Step 7: ethyl cis-7-[tert-butyl(dimethyl)silyl]oxy-5-phenyl-6,7-dihydro-5H-pyrrolo[1,2-b][1,2,4]triazole-2-carboxylate To a solution of ethyl 2-[[cis-3-[tert-butyl(dimethyl)silyl]oxy-2-oxo-5-phenyl-pyrrolidin-1-yl]amino]-2-imino-acetate (10.6 g, 26.1 mmol) in toluene (200 mL) was added p-toluenesulfonic acid (4.5 g, 26.1 mmol). The reaction mixture was heated at 120° C. for 24 h and subsequently concentrated under reduced pressure. The residue was purified by column chromatography (silica gel, 100-200 mesh, 0 to 80% ethyl acetate in petroleum ether) to afford ethyl cis-7-[tert-butyl(dimethyl)silyl]oxy-5-phenyl-6,7-dihydro-5H-pyrrolo[1,2-b][1,2,4]triazole-2-carboxylate as a white solid (6.5 g, 64%), used as is in the next step.

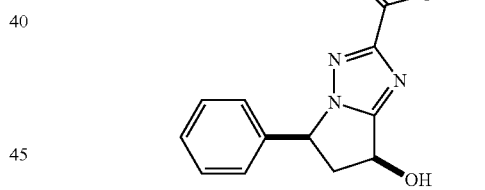

Step 8: ethyl cis-7-hydroxy-5-phenyl-6,7-dihydro-5H-pyrrolo[1,2-b][1,2,4]triazole-2-carboxylate A mixture of ethyl 2-[[cis-3-[tert-butyl(dimethyl)silyl]oxy-2-oxo-5-phenyl-pyrrolidin-1-yl]amino]-2-imino-acetate (3.1 g, 7.6 mmol) and tert-butylammonium fluoride (1.0 M in THF, 7.6 mL, 7.6 mmol) in tetrahydrofuran (60 mL) was heated at 60° C. for 18 h and subsequently concentrated under reduced pressure. The residue was purified by column chromatography (silica gel, 100-200 mesh, 0 to 100% ethyl acetate in petroleum ether) to give ethyl cis-7-hydroxy-5-phenyl-6,7-dihydro-5H-pyrrolo[1,2-b][1,2,4]triazole-2-carboxylate as white solid (1.4 g, 69%). $^1$H NMR (400 MHz, CDCl$_3$) δ7.39-7.32 (m, 5H), 5.73 (d, J=3.5 Hz, 1H), 5.50 (m, 1H), 4.41 (q, J=7.1 Hz, 2H), 3.73-3.65 (m, 1H), 2.76 (td, J=4.5 Hz, 13.9 Hz, 1H), 1.35 (t. J=7.1 Hz, 3H).

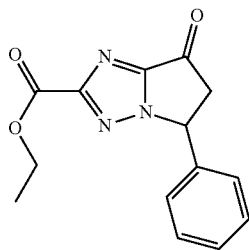 [SMILES: CCOC(=O)c1nc2n(n1)C(c1ccccc1)CC2=O]

Step 9: ethyl 7-oxo-5-phenyl-5,6-dihydropyrrolo[1,2-b][1,2,4]triazole-2-carboxylate To a solution of cis-7-hydroxy-5-phenyl-6,7-dihydro-5H-pyrrolo[1,2-b][1,2,4]triazole-2-carboxylate (1.0 g, 3.6 mmol) in dichloromethane (100 mL) was added manganese dioxide (0.9 g, 10.9 mmol). The mixture was heated at reflux for 3 h and subsequently filtered. The filtrate was concentrated under reduced pressure and the residue was purified by column chromatography (silica gel, 100-200 mesh, 0 to 50% ethyl acetate in petroleum ether) to afford ethyl 7-oxo-5-phenyl-5,6-dihydropyrrolo[1,2-b][1,2,4]triazole-2-carboxylate (350 mg, 35%) as a pink solid. LCMS $R_T$=0.725 min, m/z=271.9 [M+H]$^+$.

LCMS (5 to 95% acetonitrile in water+0.03% trifluoacetic acid over 1.5 mins) retention time 0.725 min, ESI+ found [M+H]=271.9.

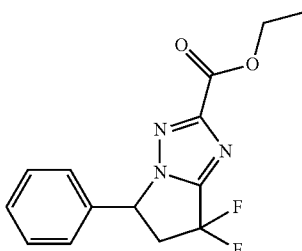

Step 10: ethyl 7,7-difluoro-5-phenyl-5,6-dihydropyrrolo[1,2-b][1,2,4]triazole-2-carboxylate To a solution of ethyl 7-oxo-5-phenyl-5,6-dihydropyrrolo[1,2-b][1,2,4]triazole-2-carboxylate (300 mg, 1.1 mmol) in dichloromethane (10 mL) was added diethylaminosulfur trifluoride (1.78 g, 11.1 mmol) at 0° C. The reaction mixture was stirred at 25° C. for 2 h and subsequently quenched by addition of ice-water (20 mL). The mixture was extracted with dichloromethane (3×20 mL). The combined organic layers were washed with water (20 mL), brine (20 mL), dried over anhydrous sodium sulfate and concentrated under reduced pressure to afford crude ethyl 7,7-difluoro-5-phenyl-5,6-dihydropyrrolo[1,2-b][1,2,4]triazole-2-carboxylate as a yellow oil (280 mg, 86%), used in the next step without further purification. LCMS $R_T$=0.834 min, m/z=294.1 [M+H]$^+$.

LCMS (5 to 95% acetonitrile in water+0.03% trifluoacetic acid over 1.5 mins) retention time 0.834 min, ESI+ found [M+H]=294.1.

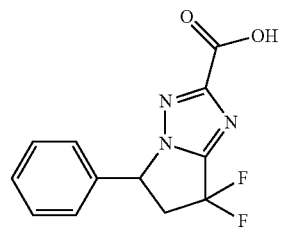 [SMILES: O=C(O)c1nc2n(n1)C(c1ccccc1)CC2(F)F]

Step 11: 7,7-difluoro-5-phenyl-5,6-dihydropyrrolo[1,2-b][1,2,4]triazole-2-carboxylic acid To a solution of ethyl 7,7-difluoro-5-phenyl-5,6-dihydropyrrolo[1,2-b][1,2,4]triazole-2-carboxylate (280 mg, 0.95 mmol) in tetrahydrofuran (10 mL) and water (2 mL) was added lithium hydroxide monohydrate (200 mg, 4.8 mmol). The reaction mixture was stirred at 25° C. for 3 h and subsequently concentrated under reduced pressure. The residue was adjusted to pH=5 by additional of hydrochloric acid (2 N). The resulting mixture was extracted with ethyl acetate (3×20 mL). The combined organic layers were washed with water (20 mL), brine (20 mL), dried over anhydrous sodium sulfate and concentrated under reduced pressure to afford crude 7,7-difluoro-5-phenyl-5,6-dihydropyrrolo[1,2-b][1,2,4]triazole-2-carboxylic acid as a yellow solid (240 mg, 95%), used in the next step without further purification.

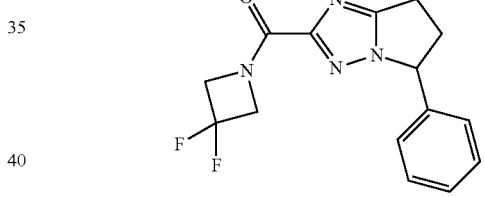

Step 12: (3,3-difluoroazetidin-1-yl)-(7,7-difluoro-1-phenyl-5,6-dihydropyrrolo[1,2-b][1,2,4]triazol-2-yl)methanone A mixture of 7,7-difluoro-5-phenyl-5,6-dihydropyrrolo[1,2-b][1,2,4]triazole-2-carboxylic acid (40 mg, 0.15 mmol), 1-(3-dimethylaminopropyl)-3-ethylcarbodiimidehydrochloride (30 mg. 0.18 mmol), 1-hydroxybenzotriazole (20 mg, 0.18 mmol) and 3,3-difluoroazetidine hydrochloride (0.02 g, 0.18 mmol) in N,N-dimethylformamide (4 mL) was stirred at 25° C. for 16 h and subsequently concentrated under reduced pressure. The residue was purified by RP-HPLC (acetonitrile 30-60%/0.05% ammonium hydroxide in water) to afford (3,3-difluoroazetidin-1-yl)-(7,7-difluoro-5-phenyl-5,6-dihydropyrrolo[1,2-b][1,2,4]triazol-2-yl)methanone (10 mg, 30%) as a yellow solid. $^1$H NMR (400 MHz, CD$_3$OD) δ 7.45-7.42 (m, 3H), 7.28-7.25 (m, 2H), 5.94-5.89 (m, 1H), 4.98-4.93 (m, 2H), 4.53 (t, J=12.0 Hz, 2H), 3.90-3.82 (m, 1H), 3.27-3.19 (m, 1H). LCMS $R_T$=0.713 min, m/z=340.9 [M+H]$^+$.

LCMS (5 to 95% acetonitrile in water+0.03% trifluoacetic acid over 1.5 mins) retention time: 0.713 min, ESI+ found [M+H]=340.9.

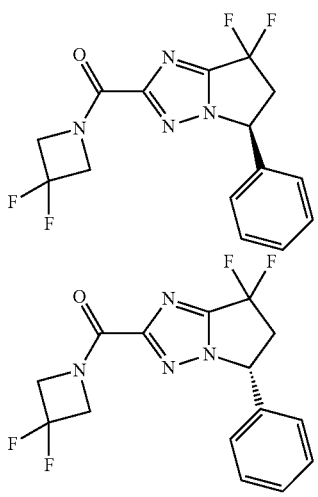

Step 13: (S)-(7,7-difluoro-5-phenyl-6,7-dihydro-5H-pyrrolo[1,2-b][1,2,4]triazol-2-yl)(3,3-difluoroazetidin-1-yl)methanone and & (R)-(7,7-difluoro-5-phenyl-6,7-dihydro-5H-pyrrolo[1,2-b][1,2,4]triazol-2-yl)(3,3-difluoro azetidin-1-yl)methanone Racemic (3,3-difluoroazetidin-1-yl)-(7,7-difluoro-5-phenyl-5,6-dihydropyrrolo[1,2-b][1,2,4] triazol-2-yl)methanone (30 mg, 0.09 mmol) was separated by chrial SFC to arbitrarily afford: (S)-(7,7-difluoro-5-phenyl-6,7-dihydro-5H-pyrrolo[1,2-b][1,2,4]triazol-2-yl)(3,3-difluoro azetidin-1-yl)methanone (peak 1, retention time=3.080 min) (6.3 mg, 21%) as white solids. $^1$H NMR (400 MHz, CD$_3$OD) δ 7.46-7.37 (m, 3H), 7.30-7.20 (m, 2H), 5.94-5.86 (m, 1H), 4.96-4.92 (m, 2H), 4.51 (t, J=12.0 Hz. 2H), 3.91-3.82 (m, 1H), 3.27-3.23 (m, 1H). LCMS R$_T$=1.024 min, m/z=341.1 [M+H]$^+$.

LCMS (10 to 80% acetonitrile in water+0.03% trifluoacetic acid over 2.0 mins) retention time: 1.025 min, ESI+ found [M+H]=341.1.

(R)-(7,7-difluoro-5-phenyl-6,7-dihydro-5H-pyrrolo[1,2-b][1,2,4]triazol-2-yl)(3,3-difluoro azetidin-1-yl)methanone (peak 2, retention time=3.545 min) (5.8 mg, 19%) as white solid. $^1$H NMR (400 MHz, CD$_3$OD) δ 7.44-7.39 (m, 3H), 7.25-7.23 (m, 2H), 5.94-5.86 (m, 1H), 4.97-4.91 (m, 2H), 4.51 (t, J=12.0 Hz. 2H), 3.88-3.78 (m, 1H), 3.26-3.21 (m, 1H). LCMS R$_T$=1.025 min, m/z=341.2 [M+H]$^+$.

LCMS (10 to 80% acetonitrile in water+0.03% trifluoacetic acid over 2.0 mins) retention time: 1.025 min, ESI+ found [M+H]=341.2.

SFC conditions: Column: ChiralPak AD-3 150×4.6 mm I.D., 3 um; Mobile phase: A: CO$_2$ B: Ethanol (0.05% DEA); Gradient: from 5% to 40% of B in 5.5 min and hold 40% for 3 min, then 5% of B for 1.5 min; Flow rate: 2.5 mL/min; Column temperature: 40° C.

SFC 1:

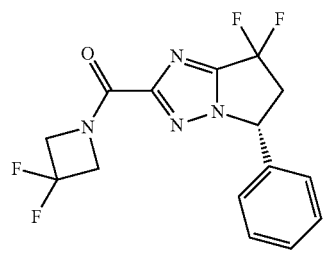 [SMILES: O=C(c1nc2n(n1)[C@@H](c1ccccc1)CC2(F)F)N1CC(F)(F)C1]

(3,3-difluoroazetidin-1-yl)-[(5R)-7,7-difluoro-5-phenyl-5,6-dihydropyrrolo[1,2-b][1,2,4]triazol-2-yl]methanone (6.0 mg, 39% yield)

Purification:
SFC condition: Column: Chiralpak IG 150×21.2 mm I.D., Mobile phase: A: CO2 B: Methanol (0.1% NH4OH) Isocratic: 15%: 70 mL/min Column temperature: 40° C.

Analytical:
Peak 2: Acquisition Method 15_Isocratic 10% MeOH, UV Wavelength: PDA Single 220.0 nm, Column: Chiralpak IG, Run Time: 2.5 Minutes, Co-Solvent: MeOH w/0.1% NH4OH Injection Volume: 2.00 ul, ColumnTemp: 40.0

Example 2

Method #2

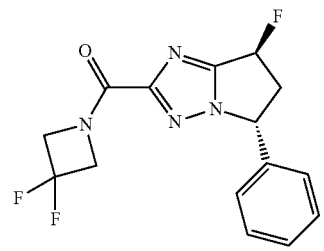 [SMILES: O=C(c1nc2n(n1)[C@@H](c1ccccc1)C[C@@H]2F)N1CC(F)(F)C1]

(3,3-difluoroazetidin-1-yl)-[rac-(5R,7S)-7-fluoro-5-phenyl-6,7-dihydro-5H-pyrrolo[1,2-b][1,2,4]triazol-2-yl]methanone

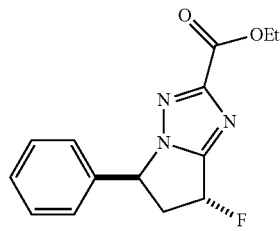

Step 1: trans-ethyl 7-fluoro-5-phenyl-6,7-dihydro-5H-pyrrolo[1,2-b][1,2,4]triazole-2-carboxylate To a solution of cis-ethyl-7-hydroxy-5-phenyl-6,7-dihydro-5H-pyrrolo[1,2-b][1,2,4]triazole-2-carboxylate (100 mg, 0.37 mmol) in dichloromethane (8 mL) was added diethylaminosulfur trifluoride (176.9 mg, 1.10 mmol) at 0° C. The reaction mixture was stirred at 0° C. for 2 h and then quenched by addition of water (20 mL). The mixture was extracted with dichloromethane (3×20 mL). The combined organic layers were washed with water (20 mL), brine (20 mL), dried over sodium sulfate and concentrated under reduced pressure. The residue was purified by preparative TLC (50% ethyl acetate in petroleum ether, $R_f$=0.5) to afford trans-ethyl-7-fluoro-5-phenyl-6,7-dihydro-5H-pyrrolo[1,2-b][1,2,4]triazole-2-carboxylate (30 mg, 30%) as light yellow oil. $^1$H NMR (400 MHz, CDCl$_3$) δ 7.40-7.37 (m, 3H), 7.14-7.12 (m, 2H), 6.14 (d, J=5.2 Hz, 0.5H), 6.00 (d, J=5.2 Hz, 0.5H), 5.74-5.71 (m, 1H), 4.51-4.45 (m, 2H), 3.42-3.35 (m, 1H), 3.07-2.96 (m, 1H), 1.42 (t, J=7.2 Hz. 3H).

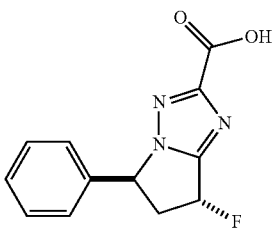

Step 2: trans-7-fluoro-5-phenyl-6,7-dihydro-5H-pyrrolo[1,2-b][1,2,4]triazole-2-carboxylic acid To a solution of trans-ethyl-7-fluoro-5-phenyl-6,7-dihydro-5H-pyrrolo[1,2-b][1,2,4]triazole-2-carboxylate (30 mg, 0.11 mol) in tetrahydrofuran (4 mL) and water (1 mL) was added lithium hydroxide monohydrate (14 mg, 0.33 mmol). The reaction mixture was stirred at 25° C. for 2 h and then concentrated under reduced pressure. The residue was adjusted to pH=5 by addition of hydrochloric acid (2 N). The mixture was extracted with ethyl acetate (3×20 mL). The combined organic layers were washed with water (20 mL), brine (20 mL), dried over anhydrous sodium sulfate and concentrated under reduced pressure to afford crude trans-7-fluoro-5-phenyl-6,7-dihydro-5H-pyrrolo[1,2-b][1,2,4]triazole-2-carboxylic acid as white solid (13 mg. 48%), used in the next step without further purification.

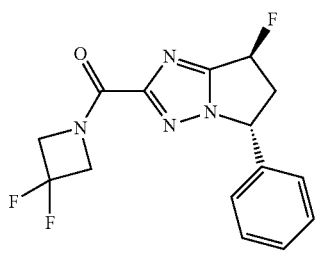 [SMILES: O=C(c1nc2n(n1)[C@@H](c1ccccc1)C[C@@H]2F)N1CC(F)(F)C1]

Step 3: (3,3-difluoroazetidin-1-yl)-[(5R,7S)-7-fluor-5-phenyl-6,7-dihydro-5H-pyrrolo[1,2-b][1,2,4]triazol-2-yl]methanone (trans mixture)

A mixture of trans-7-fluoro-5-phenyl-6,7-dihydro-5H-pyrrolo[1,2-b][1,2,4]triazole-2-carboxylic acid (13 mg, 0.05 mmol), 3,3-difluoroazetidine hydrochloride (14 mg, 0.11 mmol), 1-(3-dimethylaminopropyl)-3-ethylcarbodiimidehydrochloride (15 mg, 0.08 mmol) and 1-hydroxybenzotriazole (8 mg, 0.06 mmol) in N,N-dimethylformamide (2 mL) was stirred at 30° C. for 12 h. The mixture was concentrated under reduced pressure and the residue was purified by RP-HPLC (35 to 65% acetonitrile in water+0.05% ammonia water) to afford (3,3-difluoroazetidin-1-yl)-[(5R,7S)-7-fluoro-5-phenyl-6,7-dihydro-5H-pyrrolo[1,2-b][1,2,4] triazol-2-yl]methanone (trans mixture) (11.6 mg, 68%) as a white solid. $^1$H NMR (400 MHz, CD$_3$OD) δ 7.44-7.38 (m, 3H), 7.28-7.24 (m, 2H), 6.26-6.10 (m, 1H). 5.88-5.84 (m, 1H), 4.95-4.92 (m, 2H), 4.51 (t, J=12.0 Hz, 2H), 3.45-3.30 (m, 1H), 3.16-3.04 (m, 1H). LCMS $R_T$=0.961 min, m/z=323.2 [M+H]$^+$.

LCMS (10 to 80% acetonitrile in water+0.03% trifluoacetic acid over 2 mins) retention time 0.961 min, ESI+ found [M+H]=323.2.

Example 3

Method #3

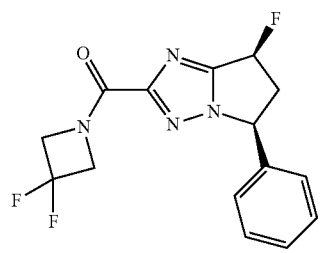 [SMILES: O=C(c1nc2n(n1)[C@H](c1ccccc1)C[C@@H]2F)N1CC(F)(F)C1]

(3,3-difluoroazetidin-1-yl)-[(5S,7S)-7-fluoro-5-phenyl-6,7-dihydro-5H-pyrrolo[1,2-b][1,2,4]triazol-2-yl]methanone (cis mixture)

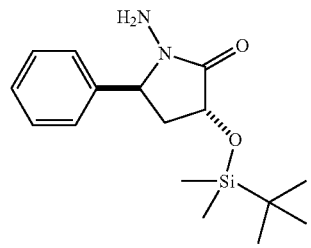

Step 1: trans-1-amino-3-((tert-butyldimethylsilyl)oxy)-5-phenylpyrrolidin-2-one

To a solution of tans-3-[tert-butyl(dimethyl)silyl]oxy-5-phenyl-pyrrolidin-2-one (7.0 g, 24.0 mmol) in N,N-dimethylformamide (200 mL) was added sodium hydride (1.44 g., 36.0 mmol) at 0° C. and the mixture was stirred at 0° C. for 20 min. Then o-(diphenylphosphoryl)hydroxylamine (8.40 g, 36.03 mmol) was added. The reaction mixture was stirred at 25° C. for 16 hours. The mixture was filtered and the filtrate was concentrated under reduced pressure to afford trans-1-amino-3-[tert-butyl(dimethyl)silyl]oxy-5-phenyl-pyrrolidin-2-one (7.0 g, 95.1%) as a yellow oil, use in the next step without further purification. LCMS $R_T$=0.775 min, m/z=307.0 [M+H]$^+$.

LCMS (5 to 95% acetonitrile in water+0.03% trifluoacetic acid over 1.5 mins) retention time 0.775 min, ESI+ found [M+H]=307.0.

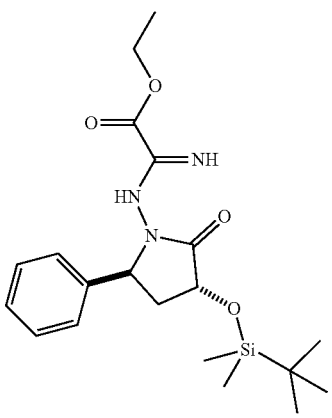 [SMILES: CCOC(=O)C(=N)NN1C(=O)[C@H](O[Si](C)(C)C(C)(C)C)C[C@H]1c1ccccc1]

Step 2: trans-ethyl 2-(3-((tert-butyldimethylsilyl)oxy)-2-oxo-5-phenylpyrrolidin-1-yl)amino)-2-iminoacetate To a solution of trans-1-amino-3-[tert-butyl(dimethyl)silyl]oxy-5-phenyl-pyrrolidin-2-one (7.0 g, 22.8 mmol) in ethanol (150 mL) was added ethyl 2-ethoxy-2-imino-acetate (6.63 g, 45.7 mmol). The reaction mixture was stirred at 60° C. for 16 h and subsequently concentrated under reduced pressure to afford crude trans-ethyl 2-(3-((tert-butyldimethylsilyl)oxy)-2-oxo-5-phenylpyrrolidin-1-yl)amino)-2-iminoacetate (8.50 g, 92%) as a yellow oil, used in the next step without further purification.

LCMS $R_T$=2.154 min, m/n=406.3 [M+H]$^+$.

LCMS (0 to 60% acetonitrile in water+0.03% trifluoacetic acid over 3.0 mins) retention time 2.143 min, ESI+ found [M+H]=406.3.

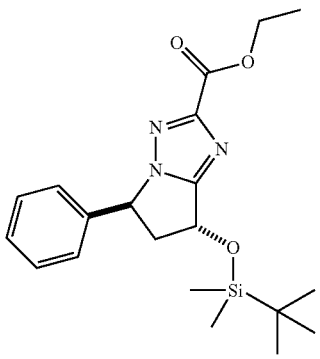

Step 3: trans-ethyl 7-((tert-butyldimethylsilyl)oxy)-5-phenyl-6,7-dihydro-5H-pyrrolo[1,2-b][1,2,4]triazole-2-carboxylate To a solution of ethyl 2-[[trans-3-[tert-butyl(dimethyl)silyl]oxy-2-oxo-5-phenyl-pyrrolidin-1-yl]amino]-2-iminoacetate (8.5 g, 21.0 mmol) in toluene (100 mL) was added p-toluenesulfonic acid (4.4 g, 25.2 mmol). The reaction mixture was stirred at 120° C. for 16 and subsequently concentrated under reduced pressure to afford crude trans-ethyl 7-((tert-butyldimethylsilyl)oxy)-5-phenyl-6,7-dihydro-5H-pyrrolo[1,2-b][1,2,4]triazole-2-carboxylate (7.5 g, 92.3%) as a yellow oil, used in the next step without further purification. LCMS $R_T$=1.022 min, m/z=374.2 [M+H]$^+$.

LCMS (10 to 80% acetonitrile in water+0.03% trifluoacetic acid over 2 mins) retention time 1.022 min, ESI+ found [M+H]=374.2.

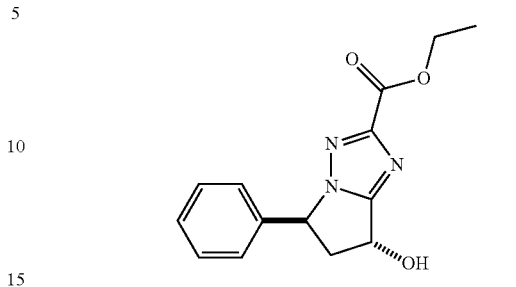

Step 4: trans-ethyl 7-hydroxy-5-phenyl-6,7-dihydro-5H-pyrrolo[1,2-b][1,2,4]triazole-2-carboxylate To a solution of ethyl trans-7-[tert-butyl(dimethyl)silyl]oxy-5-phenyl-6,7-dihydro-5H-pyrrolo[1,2-b][1,2,4]triazole-2-carboxylate (7.0 g, 18.06 mmol) in tetrahydrofuran (120 mL) was added tetrabutylammonium fluoride (1 N in THF, 18.06 mL, 18.06 mmol). The reaction mixture was stirred at 40° C. for 3 h and subsequently concentrated under reduced pressure to afford crude trans-ethyl 7-hydroxy-5-phenyl-6,7-dihydro-5H-pyrrolo[1,2-b][1,2,4]triazole-2-carboxylate (3.5 g, 57%) as a yellow oil, used in the next step without further purification. $^1$H NMR (400 MHz, CDCl$_3$): δ 7.39-7.35 (m, 3H), 7.14-7.12 (m, 2H), 5.73-5.70 (m, 1H), 5.54-5.51 (m, 1H), 4.47-4.40 (m, 2H), 3.24-3.21 (m, 1H), 3.05-3.00 (m, 1H), 1.41-1.36 (m, 3H).

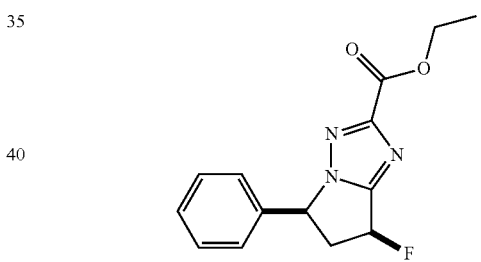

Step 5: cis-ethyl 7-fluoro-5-phenyl-6,7-dihydro-5H-pyrrolo[1,2-b][1,2,4]triazole-2-carboxylate To a solution of trans-ethyl 7-hydroxy-5-phenyl-6,7-dihydro-5H-pyrrolo[1,2-b][1,2,4]triazole-2-carboxylate (100 mg, 0.37 mmol) in dichloromethane (8 mL) was added diethylaminosulfur trifluoride (176.9 mg, 1.10 mmol) at 0° C. The reaction mixture was stirred at 0° C. for 2 h and subsequently quenched by addition of water (20 mL). The resulting mixture was extracted with dichloromethane (3×20 mL). The combined organic layers were washed with water (20 mL), brine (20 mL), dried over sodium sulfate and concentrated under reduced pressure. The residue was purified by preparative TLC (50% ethyl acetate in petroleum ether, $R_f$=0.5) to afford cis-ethyl-7-fluoro-5-phenyl-6,7-dihydro-5H-pyrrolo[1,2-b][1,2,4]triazole-2-carboxylate (54 mg, 54%) as a light yellow oil. $^1$H NMR (400 MHz, CDCl$_3$) δ 7.44-7.31 (m, 3H), 7.25-7.17 (m, 2H), 6.09 (dd, J=1.4 Hz, 7.2 Hz, 1H), 5.95 (dd, J=1.4 Hz, 7.2 Hz, 1H), 5.52-5.47 (m, 1H), 4.53-4.37 (m, 2H), 3.74-3.54 (m, 1H), 3.05-2.82 (m, 1H), 1.48-1.33 (m, 3H).

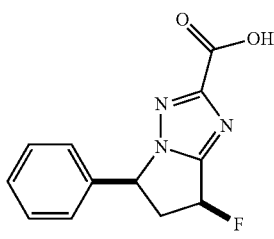

Step 6: cis-7-fluoro-5-phenyl-6,7-dihydro-5H-pyrrolo[1,2-b][1,2,4]triazole-2-carboxylic acid To a solution of cis-ethyl-7-fluoro-5-phenyl-6,7-dihydro-5H-pyrrolo[1,2-b][1,2,4]triazole-2-carboxylate (54 mg. 0.20 mol) in tetrahydrofuran (4 mL) and water (1 mL) was added lithium hydroxide monohydrate (25 mg, 0.59 mmol). The reaction mixture was stirred at 25° C. for 2 h and subsequently concentrated under reduced pressure. The residue was adjusted to pH=5 by addition of hydrochloric acid (2 N. The resulting mixture was extracted with ethyl acetate (3×10 mL). The combined organic layers were washed with water (10 mL), brine (10 mL), dried over anhydrous sodium sulfate and concentrated under reduced pressure to afford crude cis-7-fluoro-5-phenyl-6,7-dihydro-5H-pyrrolo[1,2-b][1,2,4]triazole-2-carboxylic acid (45 mg, 93%) as a white solid, used in the next step without further purification.

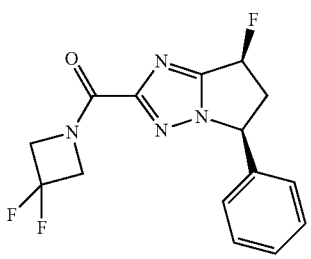 [SMILES: O=C(c1nc2n(n1)[C@H](c1ccccc1)C[C@@H]2F)N1CC(F)(F)C1]

Step 7: (3,3-difluoroazetidin-1-yl)-[rac-(5S,7S)-7-fluoro-5-phenyl-6,7-dihydro-5H-pyrrolo[1,2-b][1,2,4]triazol-2-yl]methanone (cis mixture)

A mixture of cis-7-fluoro-5-phenyl-6,7-dihydro-5H-pyrrolo[1,2-b][1,2,4]triazole-2-carboxylic acid (20 mg, 0.08 mmol), 3,3-difluoroazetidine hydrochloride (12 mg. 0.08 mmol). 1-(3-dimethylaminopropyl)-3-ethylcarbodiimidehydrochloride (19 mg, 0.10 mmol) and 1-hydroxybenzotriazole (11 mg, 0.08 mmol) in N,N-dimethylformamide (5 mL) was stirred at 25° C. for 12 h. The mixture was concentrated under reduced pressure and the residue was purified by RP-HPLC (35 to 65% acetonitrile in water+0.05% ammonia water) to afford (3,3-difluoroazetidin-1-yl)-[(5S,7S)-7-fluoro-5-phenyl-6,7-dihydro-5H-pyrrolo[1,2-b][1,2,4]triazol-2-yl]methanone (cis mixture) (13.5 mg, 51%) as a white solid. $^1$H NMR (400 MHz, CD$_3$OD) δ 7.44-7.38 (m, 3H), 7.28-7.24 (m, 2H), 6.17-6.02 (m, 1H). 5.65-5.62 (m, 1H), 4.95-4.92 (m, 2H), 4.52 (t, J=12.0 Hz, 2H), 3.82-3.68 (m, 1H), 2.86-2.76 (m, 1H). LCMS R$_T$=1.670 min, m/z=323.1 [M+H]$^+$.

LCMS (10 to 80% acetonitrile in water+0.03% trifluoacetic acid over 2 mins) retention time 1.670 min, ESI+ found [M+H]=323.1.

Example 4

Method #4

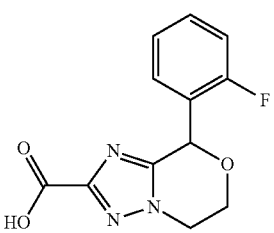 [SMILES: O=C(O)c1nc2n(n1)CCOC2c1ccccc1F]

(3,3-difluoroazetidin-1-yl)-(7-phenyl-6,7-dihydro-5H-pyrrolo[1,2-b][1,2,4]triazol-2-yl)methanone

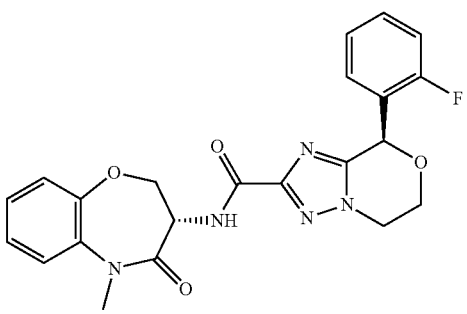 [SMILES: CN1C(=O)[C@@H](NC(=O)c2nc3n(n2)CCO[C@@H]3c2ccccc2F)COc2ccccc21]

Step 1: 1-amino-3-phenylpyrrolidin-2-one

To a solution of tert-butyl N-(2-oxo-3-phenyl-pyrrolidin-1-yl)carbamate (1.4 g, 5.1 mmol) in ethyl acetate (20 mL) was added HCl (4N in ethyl acetate, 12.0 mL, 48.0 mmol). The mixture was stirred at 20° C. for 3 h and concentrated under reduced pressure. The residue was slowly quenched by addition of saturated sodium bicarbonate (30 mL). The resulting solution was extracted with ethyl acetate (3×50 mL). The combined organic layers were dried over sodium sulfate and concentrated to give crude 1-amino-3-phenyl-pyrrolidin-2-one (590 mg. 66%) as a white solid, used as is in the next step.

Step 2: ethyl 2-imino-2-((2-oxo-3-phenylpyrrolidin-1-yl)amino)acetate

To a solution of 1-amino-3-phenyl-pyrrolidin-2-one (590 mg, 3.35 mmol) in ethanol (10 mL) was added ethyl 2-ethoxy-2-imino-acetate (1458 mg, 10.04 mmol). The mixture was stirred at 40° C. for 12 h and concentrated under reduced pressure to obtain crude ethyl (2Z)-2-amino-2-(2-oxo-3-phenyl-pyrrolidin-1-yl)imino-acetate (1370 mg, 100%), used as is in the next step.

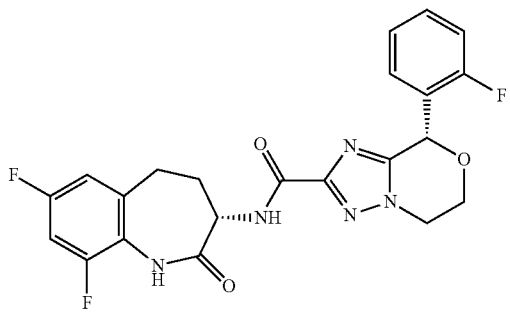 [SMILES: O=C(N[C@H]1CCc2cc(F)cc(F)c2NC1=O)c1nc2n(n1)CCO[C@H]2c1ccccc1F]

Step 3: Ethyl 7-phenyl-6,7-dihydro-5H-pyrrolo[1,2-b][1,2,4]triazole-2-carboxylate A solution of ethyl (2Z)-2-amino-2-(2-oxo-3-phenyl-pyrrolidin-1-yl)imino-acetate (1370 mg, 4.98 mmol) in phosphorus oxychloride (5 mL) as stirred at 120° C. for 1 h. After cooled, the mixture was slowly quenched by addition of saturated sodium bicarbonate (20 mL) and extracted with dichloromethane (3×20 mL). The combined organic layers were washed with brine (30 mL), dried over sodium sulfate and concentrated under reduced pressure. The residue was purified by column chromatography (silica gel, 100-200 mesh, 0 to 50% ethyl acetate in petroleum ether) to afford ethyl 7-phenyl-6,7-dihydro-5H-pyrrolo[1,2-b][1,2,4]triazole-2-carboxylate (390 mg, 31%) as a light yellow solid. $^1$H NMR (400 MHz, CDCl$_3$) δ7.40-7.14 (m, 5H), 4.45 (q, J=8.0 Hz, 4H), 4.40-4.36 (m, 1H), 4.26-4.23 (m, 1H), 3.29-3.22 (m, 1H), 2.78-2.70 (m, 1H), 1.40 (t, J=7.2 Hz, 3H). LCMS R$_T$=1.95 min, m/z=258.1 [M+H]$^+$.

LCMS (0 to 60% acetonitrile in water+0.05% ammonium hydroxide over 3 mins) retention time 1.95 min, ESI+ found [M+H]=258.1.

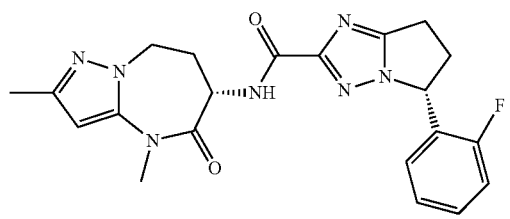 [SMILES: Cc1cc2n(n1)CC[C@H](NC(=O)c1nc3n(n1)[C@@H](c1ccccc1F)CC3)C(=O)N2C]

Step 4: 7-phenyl-6,7-dihydro-5H-pyrrolo[1,2-b][1,2,4]triazole-2-carboxylic acid

A mixture of ethyl (7S)-7-phenyl-6,7-dihydro-5H-pyrrolo[1,2-b][1,2,4] triazole-2-carboxylate (340 mg, 1.32 mmol) and lithium hydroxide hydrate (555 mg, 13.22 mmol) in tetrahydrofuran (5 mL) and water (5 mL) was stirred at 20° C. for 12 h. The organic solvent was evaporated under reduced pressure and the aqueous residue was adjusted to pH=2-3 by addition of 20% HCl. The mixture was extracted with dichloromethane (5×30 mL). The combined organic layers were dried over sodium sulfate and concentrated under reduced pressure to afford the crude 7-phenyl-6,7-dihydro-5H-pyrrolo[1,2-b][1,2,4]triazole-2-carboxylic acid (260 mg, 85%) as a yellow solid, used as is in the next step.

Step 5: (3,3-difluoroazetidin-1-yl)-(7-phenyl-6,7-dihydro-5H-pyrrolo[1,2-b][1,2,4]triazol-2-yl)methanone A mixture of 3,3-difluoroazetidine hydrochloride (31 mg, 0.24 mmol), 1H-benzo[d][1,2,3]triazol-1-ol (9 mg, 0.070 mmol), 1-(3-dimethylaminopropyl)-3-ethylcarbodiimidehydrochloride (63 mg, 0.33 mmol) and 7-phenyl-6,7-dihydro-5H-pyrrolo[1,2-b][1,2,4]triazole-2-carboxylic acid (50 mg, 0.22 mmol) in N,N-dimethylformamide (3 mL) was stirred at 25° C. for 3 h. The mixture was concentrated under reduced pressure and the residue was purified by RP-HPLC (acetonitrile 20-50%/0.05% ammonia hydroxide in water) to afford (3,3-difluoroazetidin-1-yl)-(7-phenyl-6,7-dihydro-5H-pyrrolo[1,2-b][1,2,4]triazol-2-yl)methanone (13 mg, 19%) as a white solid. $^1$H NMR (400 MHz, CD$_3$OD) δ 7.39-7.32 (m, 2H). 7.31-7.24 (m, 3H), 4.99-4.92 (m, 2H), 4.57-4.47 (m, 3H), 4.45-4.37 (m, 1H), 4.32-4.23 (m, 1H), 3.30-3.24 (m, 1H), 2.75-2.63 (m, 1H). LCMS R$_T$=0.782 min, m/z=304.9 [M+H]$^+$.

LCMS (5 to 95% acetonitrile in water+0.03% trifluoroacetic acid over 1.5 mins) retention time 0.782 min, ESI+ found [M+H]=304.9.

Example 5

Method #5

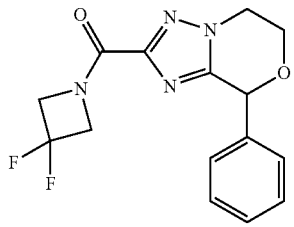 [SMILES: O=C(c1nc2n(n1)CCOC2c1ccccc1)N1CC(F)(F)C1]

(3,3-difluoroazetidin-1-yl)-(8-phenyl-6,8-dihydro-5H-[1,2,4]triazolo[5,1-c][1,4]oxazin-2-yl)methanone

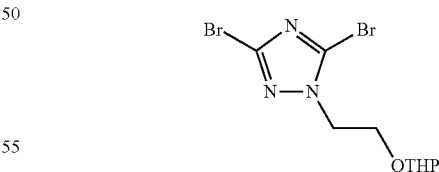

Step 1: 3,5-dibromo-1-(2-tetrahydropyran-2-yloxy-ethyl)-1,2,4-triazole

To a solution of 3,5-dibromo-1H-1,2,4-triazole (10 g, 44.1 mmol) in acetonitrile (100 mL) was added 2-(2-bromoethoxy)tetrahydro-2H-pyran (8.0 mL, 52.9 mmol) and N,N-diisopropylethylamine (8.45 mL, 48.5 mmol). The mixture was stirred at 90° C. for 3 h and concentrated under reduced pressure. The residue was diluted with ethyl acetate (300 mL), washed saturated sodium bicarbonate (2×50 mL), brine (2×50 mL), dried over sodium sulfate and concentrated under reduced pressure. The residue was purified by column chromatography (silica gel, 100-200 mesh, 0 to 20% ethyl acetate in petroleum ether) to afford 3,5-dibromo-1-(2-tetrahydropyran-2-yloxyethyl)-1,2,4-triazole (13 g, 83%) as a colorless oil, used as is in the next step.

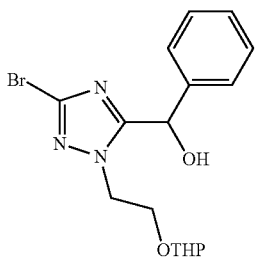

Step 2: [5-bromo-2-(2-tetrahydropyran-2-yloxyethyl)-1,2,4-triazol-3-yl]-phenyl-methanol To a solution of 3,5-dibromo-1-(2-tetrahydropyran-2-yloxyethyl)-1,2,4-triazole (2.0 g, 5.6 mmol) in tetrahydrofuran (20 mL) was added n-butyllithium (2.5 M in hexanes. 2.6 mL, 6.5 mmol) at −78° C. The mixture was stirred at −78° C. for 1 h and then a solution of benzaldehyde (1.2 g, 11.3 mmol) in THF (2 mL) was added. After addition, the mixture was stirred at −78° C. for another 1 h and then quenched by addition of saturated ammonium chloride (10 mL). The resulting mixture was diluted with ethyl acetate (100 mL), washed with water (20 mL), brine (20 mL), dried over sodium sulfate and concentrated under reduced pressure. The residue was purified by column chromatography (silica gel, 100-200 mesh, 0 to 30% ethyl acetate in petroleum ether) to afford [5-bromo-2-(2-tetrahydropyran-2-yloxyethyl)-1,2,4-triazol-3-yl]-phenyl-methanol (1.5 g, 69.7%) as a light yellow oil, used as is in the next step.

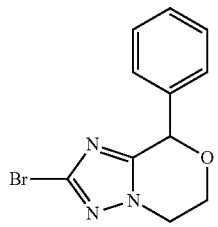 [SMILES: Brc1nc2n(n1)CCOC2c1ccccc1]

Step 3: 2-bromo-8-phenyl-6,8-dihydro-5H-[1,2,4]triazolo[5,1-c][1,4]oxazine

A mixture of [5-bromo-2-(2-tetrahydropyran-2-yloxyethyl)-1,2,4-triazol-3-yl]-phenyl-methanol (1.5 g, 3.92 mmol) and p-toluenesulfonic acid (863 mg, 5.02 mmol) in toluene (50 mL) was heated at reflux for 5 h. After cooled, the reaction was diluted with ethyl acetate (100 mL), washed with sodium hydroxide (1N. 20 mL), brine (20 mL), dried over sodium sulfate and concentrated under reduced pressure. The residue was purified by column chromatography (silica gel, 100-200 mesh, 0 to 40% ethyl acetate in petroleum ether) to afford 2-bromo-8-phenyl-6,8-dihydro-5H-[1,2,4]triazolo[5,1-c][1,4]oxazine (800 mg., 73%) as a yellow oil. LCMS $R_T$=0.642 min, m/z=281.6 [M+H]$^+$.

LCMS (5 to 95% acetonitrile in water+0.03% trifluoacetic acid over 1.5 mins) retention time 0.642 min, ESI+ found [M+H]=281.6

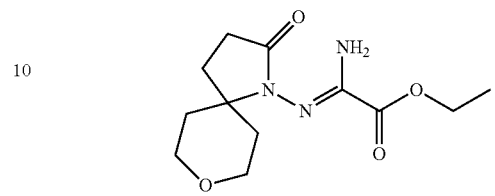

Step 4: methyl 8-phenyl-6,8-dihydro-5H-[1,2,4]triazolo[5,1-c][1,4]oxazine-2-carboxylate A mixture of 1,1'-bis(diphenylphosphino)ferrocene palladium dichlororide (13 mg, 0.02 mmol), 2-bromo-8-phenyl-6,8-dihydro-5H-[1,2,4]triazolo[5,1-c][1,4]oxazine (300 mg, 1.07 mmol) and triethylamine (1.45 mL, 10.7 mmol) in methanol (30 mL) was heated at 70° C. for 12 h under CO (40 psi). The mixture was filtered and the filtrate was concentrated under reduced pressure. The residue was purified by column chromatography (silica gel, 100-200 mesh, 0 to 50% ethyl acetate in petroleum ether) to afford methyl 8-phenyl-6,8-dihydro-5H-[1,2,4]triazolo[5,1-c][1,4]oxazine-2-carboxylate (100 mg, 20%) as a brown oil.

LCMS $R_T$=0.682 min, m/z=259.9 [M+H]$^+$.

LCMS (5 to 95% acetonitrile in water+0.03% trifluoacetic acid over 1.5 mins) retention time 0.682 min, ESI+ found [M+H]=259.9

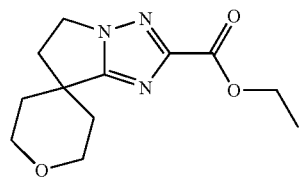 [SMILES: CCOC(=O)c1nc2n(n1)CCC21CCOCC1]

Step 5: 8-phenyl-6,8-dihydro-5H-[1,2,4]triazolo[5,1-c][1,4]oxazine-2-carboxylic acid A mixture of methyl 8-phenyl-6,8-dihydro-5H-[1,2,4]triazolo[5,1-c][1,4]oxazine-2-carboxylate (50 mg, 0.11 mmol) and lithium hydroxide (8 mg, 0.32 mmol) in tetrahydrofuran (4 mL) and water (1 mL) was stirred at 25° C. for 1 h. The mixture was adjusted to pH=3 by addition of 2N HCl and extracted with ethyl acetate (2×10 mL). The combined organic layers were concentrated under reduced pressure to afford crude 8-phenyl-6,8-dihydro-5H-[1,2,4]triazolo[5,1-c][1,4]oxazine-2-carboxylic acid (25 mg, 94% crude yield) as a yellow solid, used as is in the next step.

Step 6: (3,3-difluoroazetidin-1-yl)-(8-phenyl-6,8-dihydro-5H-[1,2,4]triazolo[5,1-c][1,4]oxazin-2-yl)methanone A mixture of 3,3-difluoroazetidine hydrochloride (14.9 mg, 0.12 mmol), 1H-benzo[d][1,2,3]triazol-1-ol (4.3 mg, 0.030 mmol), 1-(3-dimethylaminopropyl)-3-ethylcarbodiimidehydrochloride (30 mg, 0.16 mmol) and 8-phenyl-6,8-dihydro-5H-[1,2,4]triazolo[5,1-c][1,4]oxazine-2-carboxylic acid (26 mg, 0.10 mmol) in N,N-dimethylformamide (2 mL) was stirred at 30° C. for 15 h. The mixture was concentrated under reduced pressure and the residue was purified by RP-HPLC (acetonitrile 30-60%/0.05% ammonia hydroxide in water) to afford (3,3-difluoroazetidin-1-yl)-(8-phenyl-6,8-dihydro-5H-[1,2,4]triazolo[5,1-c][1,4]oxazin-2-yl)methanone (2.65 mg, 8%) as a yellow oil. ¹H NMR (400 MHz, CD₃OD) δ 7.43-7.36 (m, 5H), 5.97 (s, 1H), 4.54-4.43 (m, 4H), 4.43-4.14 (m, 4H).

LCMS $R_T$=1.559 min, m/z=321.1 [M+H]⁺.

LCMS (10 to 80% acetonitrile in water+0.05% ammonium hydroxide over 3 minutes) retention time 1.559 min, ESI+ found [M+H]=321.1.

Example 6

Method #6

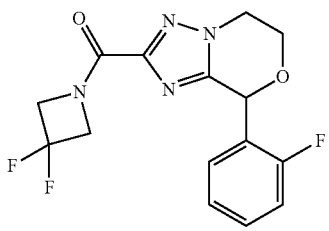 [SMILES: O=C(c1nc2n(n1)CCOC2c1ccccc1F)N1CC(F)(F)C1]

(3,3-difluoroazetidin-1-yl)-[8-(2-fluorophenyl)-6,8-dihydro-5H-[1,2,4]triazolo[5,1-c][1,4]oxazin-2-yl]methanone

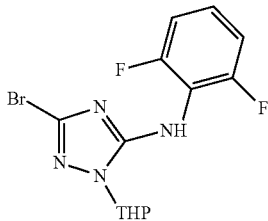

Step 1: (3-bromo-1-(2-((tetrahydro-2H-pyran-2-yl)oxy)ethyl)-1H-1,2,4-triazol-1-yl)(2-fluorophenyl)methanol To a solution of 3,5-dibromo-1-(2-tetrahydropyran-2-yloxyethyl)-1,2,4-triazole (2.0 g, 5.6 mmol) in tetrahydrofuran (20 mL) was added n-butyllithium (2.5 M in hexanes, 2.6 mL, 6.5 mmol) at −78° C. The mixture was stirred at −78° C. for 1 h and then a solution of 2-fluorobenzaldehyde (1.4 g, 11.27 mmol) in THF (2 mL) was added. After addition, the mixture was stirred at −78° C. for another 1 h and then quenched by addition of saturated ammonium chloride (10 mL). The resulting mixture was diluted with ethyl acetate (100 mL), washed with water (20 mL), brine (20 mL), dried over sodium sulfate and concentrated under reduced pressure. The residue was purified by column chromatography (silica gel, 100-200 mesh, 0 to 20% ethyl acetate in petroleum ether) to afford [5-bromo-2-(2-tetrahydropyran-2-yloxyethyl)-1,2,4-triazol-3-yl]-(2-fluorophenyl)methanol (1.0 g, 44%) as a light yellow oil. LCMS $R_T$=0.64 min, m/z=401.7 [M+H]⁺. LCMS (5 to 95% acetonitrile in water+0.03% trifluoacetic acid over 1.5 mins) retention time 0.64 min, ESI+ found [M+H]=401.7.

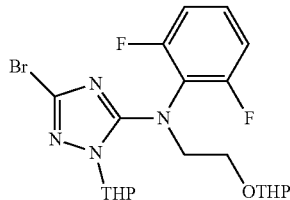

Step 2: 2-bromo-8-(2-fluorophenyl)-6,8-dihydro-5H-[1,2,4]triazolo[5,1-c][1,4]oxazine A mixture of [5-bromo-2-(2-tetrahydropyran-2-yloxyethyl)-1,2,4-triazol-3-yl]-(2-fluorophenyl)methanol (1000 mg, 2.5 mmol) and p-toluenesulfonic acid (546 mg, 3.17 mmol) in toluene (20 mL) was heated at reflux for 3 h. The mixture was concentrated under reduced pressure, and the residue was purified by column chromatography (silica gel, 100-200 mesh, 0 to 30% ethyl acetate in petroleum ether) to give 2-bromo-8-(2-fluorophenyl)-6,8-dihydro-5H-[1,2,4]triazolo[5,1-c][1,4]oxazine (300 mg, 40.3%) as yellow solid, used as is in the next step.

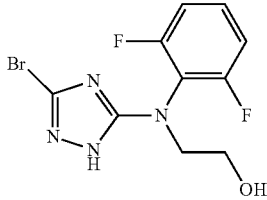 [SMILES: OCCN(c1nc(Br)n[nH]1)c1c(F)cccc1F]

Step 3: Methyl 8-(2-fluorophenyl)-6,8-dihydro-5H-[1,2,4]triazolo[5,1-c][1,4]oxazine-2-carboxylate A mixture of 2-bromo-8-(2-fluorophenyl)-6,8-dihydro-5H-[1,2,4]triazolo[5,1-c][1,4]oxazine (290 mg, 0.97 mmol), 1,1'-bis(diphenylphosphino)ferrocene palladium dichloride (13 mg, 0.02 mmol), and triethylamine (1.31 mL, 9.73 mmol) in methanol (10 mL) was heated at 80° C. for 16 h under CO (25 psi) and filtered. The filtrate was concentrated under reduced pressure and the residue was purified by column chromatography (silica gel, 100-200 mesh, 100% dichloromethane) to give methyl 8-(2-fluorophenyl)-6,8-dihydro-5H-[1,2,4]triazolo[5,1-c][1,4]oxazine-2-carboxylate (200 mg, 74%) as colorless oil. LCMS $R_T$=0.59 min, m/z=277.8 [M+H]⁺.

LCMS (5 to 95% acetonitrile in water+0.03% trifluoacetic acid over 1.5 mins) retention time 0.59 min, ESI+ found [M+H]=277.8.

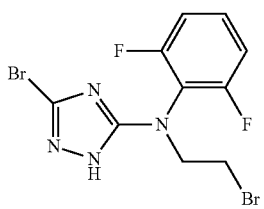 [SMILES: Fc1cccc(F)c1N(CCBr)c1nc(Br)n[nH]1]

Step 4: 8-(2-fluorophenyl)-6,8-dihydro-5H-[1,2,4]triazolo[5,1-c][14]oxazine-2-carboxylic acid A mixture of methyl 8-(2-fluorophenyl)-6,8-dihydro-5H-[1,2,4]triazolo[5,1-c][1,4]oxazine-2-carboxylate (200 mg, 0.72 mmol) and potassium hydroxide (80 mg, 1.44 mml) in ethanol (20 mL) and water (5 mL) was stirred at 25° C. for 1 h. The ethanol was evaporated under reduced pressure and the aqueous residue was adjusted to pH=3 by addition of 2N HCl. The solution was extracted with ethyl acetate (2×10 mL). The combined organic layers were concentrated to give crude 8-(2-fluorophenyl)-6,8-dihydro-5H-[1,2,4]triazolo[5,1-c][1,4]oxazine-2-carboxylic acid (180 mg, 94%) as a yellow solid, used as is in the next step.

Step 5: (3,3-difluoroazetidin-1-yl)-[8-(2-fluorophenyl)-6,8-dihydro-5H-[1,2,4]triazolo[5,1-c][1,4]oxazin-2-yl]methanone A mixture of 3,3-difluoroazetidine hydrochloride (14 mg, 0.11 mmol), 1-hydroxybenzotriazole (12 mg, 0.09 mmol), 1-(3-dimethylaminopropyl)-3-ethylcarbodiimidehydrochloride (17 mg, 0.09 mmol) and 8-(2-fluorophenyl)-6,8-dihydro-5H-[1,2,4]triazolo[5,1-c][1,4]oxazine-2-carboxylic acid (20 mg, 0.08 mmol) in N,N-dimethylformamide (3 mL) was stirred at 25° C. for 12 h. The mixture was concentrated under reduced pressure and the residue was purified by RP-HPLC (acetonitrile 20% to 50%/0.05% ammonia hydroxide in water) to afford (3,3-difluoroazetidin-1-yl)-[8-(2-fluorophenyl)-6,8-dihydro-5H-[1,2,4]triazolo[5,1-c][1,4]oxazin-2-yl]methanone (6.0 mg, 23%) as a white solid. $^1$H NMR (400 MHz, DMSO-$d_6$) δ 7.47 (d, J=6.4 Hz, 1H), 7.38 (t, J=6.8 Hz, 1H), 7.30-7.18 (m, 2H), 6.18 (s. 1H), 4.81-4.73 (m, 2H), 4.57-4.31 (m, 4H), 4.29-4.08 (m, 2H). LC-MS $R_T$=1.713 min, m/z=339.2 [M+H]$^+$.

LCMS (0 to 60% acetonitrile in water+0.03% trifluoroacetic acid over 3.0 mins) retention time 1.713 min, ESI+ found [M+H]=339.2.

Example 7

Method #7

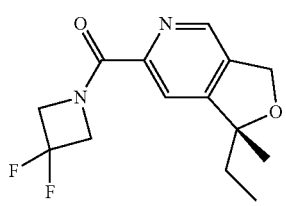 [SMILES: CC[C@@]1(C)OCc2cnc(C(=O)N3CC(F)(F)C3)cc21]

(3,3-difluoroazetidin-1-yl)-[(1R)-1-ethyl-1-methyl-3H-furo[3,4-c]pyridin-6-yl]methanone

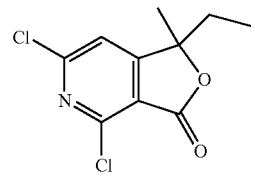

4,6-dichloro-1-ethyl-1-methylfuro[3,4-c]pyridin-3(1H)-one n-BuLi (2.5 M in hexane, 16 mL, 40 mmol) was added dropwise to a solution of diisopropylamine (4.7 g, 46.5 mmol) at −78° C. The mixture was stirred at −78° C. for 40 min and a solution of 2,6-dichloronicotinic acid (3 g, 15.6 mmol) in tertahydrofuran (30 mL) was added dropwise to the reaction mixture at −78° C. and the resultant mixture was stirred at −78° C. for 3 h. Butanone (10 g, 139 mmol) was added dropwise to the reaction mixture at −78° C. and the reaction mixture was warmed slowly to RT and stirred for 16 h. The reaction mixture was cooled to 0° C., quenched with sat. ammonium chloride to pH 7 and acidified with 3 N HCl to pH 4. The mixture was extracted with ethyl acetate (30 mL×4). The combined organic layers were combined, dried over sodium sulphate and concentrated to dryness in vacuo. The residue was purified by column chromatography (silica gel, 100-200 mesh, 8:1 to 6:1 to 4:1 ethyl acetate: petroleum ether) to afford 4,6-dichloro-1-ethyl-1-methylfuro[3,4-c]pyridin-3(1H)-one as a brown solid (1.3 g, Yield 34%). LCMS: m/z=246.0/248.1 [M+1]. Column: MERCK RP18 (50-3). Mobile phase: $H_2O$ (0.01% TFA) (A)/ACN (0.01% TFA)(B) Elution program: Gradient from 10 to 95% of B in 1.8 min at 2.0 ml/min. Temperature: 45° C. 3 min gradient.

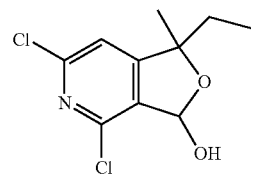

4,6-dichloro-1-ethyl-1-methyl-1,3-dihydrofuro[3,4-c]pyridin-3-ol

To a stirred suspension of 4,6-dichloro-1-ethyl-1-methylfuro[3,4-c]pyridin-3(1H)-one (1.3 g, 5.28 mmol) in toluene (30 mL) was added diisobutyl aluminium hydride (1 M in toluene, 12 mL, 12 mmol) at −78° C. The reaction mixture was stirred at −78° C. for 1.5 h and quenched with saturated ammonium chloride (50 ml) dropwise at −78° C. The mixture was warmed slowly to RT and stirred for 30 min. The reaction mixture was filtered and the filtrate was extracted with ethyl acetate (30 mL×3). The combined organic layers were combined, dried over sodium sulfate and concentrated to dryness in vacuo. The residue was purified by column chromatography (silica gel, 100-200 mesh, 4:1 to 2:1 ethyl acetate: petroleum ether) to afford 4,6-dichloro-1-ethyl-1-methyl-1,3-dihydrofuro[3,4-c]pyridin-3-ol (1 g, Yield 76%) as a colorless oil: LCMS: m/z=248.0/250.1 [M+1]. Column: MERCK RP18 (50-3). Mobile phase: $H_2O$ (0.01% TFA) (A)/ACN (0.01% TFA)(B) Elution program: Gradient from 10 to 95% of B in 1.8 min at 2.0 ml/min. Temperature: 45° C. 3 min gradient.

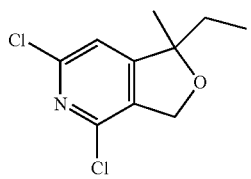

4,6-dichloro-1-ethyl-1-methyl-1,3-dihydrofuro[3,4-c]pyridine

To a stirred solution of 4,6-dichloro-1-ethyl-1-methyl-1,3-dihydrofuro[3,4-c]pyridin-3-ol (1 g, 4.06 mmol) in dichloromethane (10 ml) was added dropwise trifluoroacetic acid (1.5 mL. 20.1 mmol) at 0° C. and the mixture was stirred at 0° C. for 30 min. Triethylsilane (2 mL, 12.55 mmol) was added dropwise to the reaction mixture at 0° C. and the reaction mixture was warmed slowly to RT and stirred at RT for 2 h. The reaction mixture was concentrated to dryness in vacuo. The residue was dissolved in ethyl acetate (50 mL) and adjusted to pH=7 by addition of saturated sodium bicarbonate. The ethyl acetate layer was separated, dried over sodium sulphate and concentrated to dryness in vacuo. The residue was purified by column chromatography (silica gel, 100-200 mesh, 8:1 ethyl acetate: petroleum ether) to afford 4,6-dichloro-1-ethyl-1-methyl-1,3-dihydrofuro[3,4-c]pyridine (0.83 g, Yield 88%) was got as a white solid. LCMS: m/i=232.1/234.1 [M+1]. Column: MERCK RP18 (50-3). Mobile phase: $H_2O$ (0.01% TFA) (A)/ACN (0.01% TFA)(B) Elution program: Gradient from 10 to 95% of B in 1.8 min at 2.0 ml/min. Temperature: 45° C. 3 min gradient.

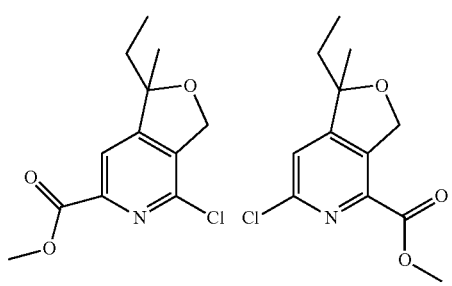

Methyl 4-chloro-1-ethyl-1-methyl-1,3-dihydrofuro [3,4-c]pyridine-6-carboxylate and methyl 6-chloro-1-ethyl-1-methyl-1,3-dihydrofuro[3,4-c]pyridine-4-carboxylate To a solution of 4,6-dichloro-1-ethyl-1-methyl-3H-furo [3,4-c]pyridine (0.50 g, 2.15 mmol) in methanol (10 mL) was added [1,1'-Bis(diphenylphosphino)ferrocene]palladium(II) dichloride (0.16 g, 0.22 mmol) and triethylamine (2.18 g, 21.54 mmol). The reaction mixture was stirred at 80° C. for 15 h under the carbon monoxide (25 psi). After cooling to RT the reaction mixture was concentrated to dryness in vacuo. The residue was purified by column chromatography (silica gel, 100-200 mesh, 0 to 30% ethyl acetate in petroleum ether) to afford methyl 4-chloro-1-ethyl-1-methyl-3H-furo[3,4-c]pyridine-6-carboxylate and methyl 6-chloro-1-ethyl-1-methyl-3H-furo[3,4-c]pyridine-4-carboxylate (140 mg (3:1 mixture), 0.55 mmol, 25.5% yield mixture) as a light yellow oil used as is in the next step without further purification.

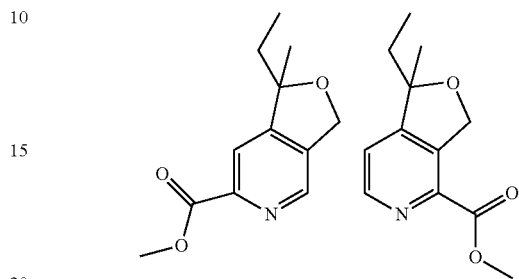

Methyl 1-ethyl-1-methyl-1,3-dihydrofuro[3,4-c] pyridine-6-carboxylate and methyl 1-ethyl-1-methyl-1,3-dihydrofuro[3,4-c]pyridine-4-carboxylate To a solution of methyl 4-chloro-1-ethyl-1-methyl-3H-furo[3,4-c]pyridine-6-carboxylate and methyl 6-chloro-1-ethyl-1-methyl-3H-furo[3,4-c]pyridine-4-carboxylate (140 mg, 0.55 mmol) in methanol (10 mL) was added 10% palladium (437 mg. 0.41 mmol) on carbon. The reaction mixture was hydrogenated (15 psi) at 20° C. for 1 h and then filtered through Celite. The filtrate was concentrated to dryness in vacuo to afford methyl 1-ethyl-1-methyl-3H-furo [3,4-c]pyridine-4-carboxylate and methyl 1-ethyl-1-methyl-3H-furo[3,4-c]pyridine-6-carboxylate (100 mg, 82.6% yield) as a yellow oil: LCMS (5 to 95% acetonitrile in water+0.03% trifluoacetic acid over 1.5 mins) retention time 0.65 min, ESI+ found [M+H]=222.

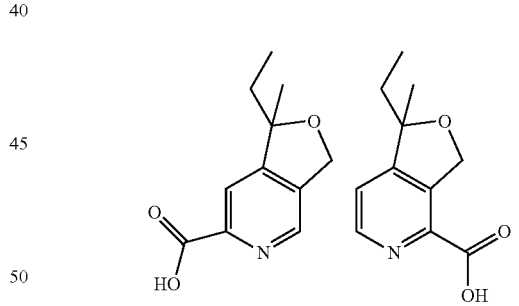

1-ethyl-1-methyl-1,3-dihydrofuro[3,4-c]pyridine-6-carboxylic acid and 1-ethyl-1-methyl-1,3-dihydrofuro[3,4-c]pyridine-4-carboxylic acid To a solution of methyl 1-ethyl-1-methyl-1,3-dihydrofuro [3,4-c]pyridine-6-carboxylate and methyl 1-ethyl-1-methyl-1,3-dihydrofuro[3,4-c]pyridine-4-carboxylate (100 mg, 0.46 mmol) in tetrahydrofuran (5 mL) and water (5 mL) was added lithium hydroxide monohydrate (202 mg, 4.81 mmol). The reaction mixture was stirred at 15° C. for 15 h and concentrated to dryness in vacuo. The residue was diluted with water (5 mL) and adjusted to pH=3 by addition of 1 M hydrochloric acid. The mixture was extracted with dichloromethane (3×15 mL). The combined organic layers were dried over sodium sulfate and concentrated to dryness in vacuo to afford 1-ethyl-1-methyl-1,3-dihydrofuro[3,4-c]pyridine-6-carboxylic acid and 1-ethyl-1-methyl-1,3-dihydrofuro[3,4-c]pyridine-4-carboxylic acid (50 mg, 50.5% yield) as a yellow oil used in the next step without further purification.

(3,3-difluoroazetidin-1-yl)-[(1R)-1-ethyl-1-methyl-3H-furo[3,4-c]pyridin-6-yl]methanone A mixture of 3,3-difluoroazetidine hydrochloride (34 mg, 0.27 mmol), 1-hydroxybenzotriazole (39 mg, 0.29 mmol), 1-(3-dimethylaminopropyl)-3-ethylcarbodiimidehydrochloride (55 mg, 0.29 mmol) and (1R)-1-ethyl-1-methyl-3H-furo[3,4-c]pyridine-6-carboxylic acid (50 mg, 0.24 mmol) in N,N-dimethylformamide (5 mL) was stirred at 25° C. for 12 h. The mixture was concentrated under reduced pressure and the residue was purified by RP-HPLC (acetonitrile 38% to 48%/0.05% ammonia hydroxide in water) to afford (3,3-difluoroazetidin-1-yl)-[(1R)-1-ethyl-1-methyl-3H-furo[3,4-c]pyridin-6-yl]methanone (29.6 mg, 43%) as a white solid. $^1$H NMR (400 MHz, CD$_3$OD) δ 8.56 (s, 1H), 7.92 (s, 1H), 5.20-5.12 (m, 2H), 5.06 (t. J=12.0 Hz, 2H), 4.54 (t, J=12.0 Hz, 2H), 1.87 (q, J=7.6 Hz, 2H), 1.48 (s, 3H), 0.79 (t, J=7.6 Hz, 3H). LC-MS R$_T$=1.699 min, m/z=283.1 [M+H]$^+$.

LCMS (10 to 80% acetonitrile in water+0.03% ammonium bicarbonate over 3.0 mins) retention time 1.699 min, ESI+ found [M+H]=283.1.

Example 8

Method #8

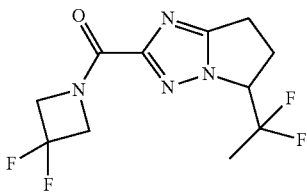 [SMILES: CC(F)(F)C1CCc2nc(C(=O)N3CC(F)(F)C3)nn21]

(3,3-difluoroazetidin-1-yl)-[5-(1,1-difluoroethyl)-6,7-dihydro-5H-pyrrolo[1,2-b][1,2,4]triazol-2-yl]methanone

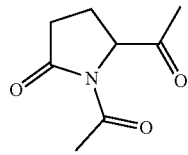

Step 1: 1,5-diacetylpyrrolidin-2-one

A mixture of D-glutamic acid (5.0 g, 33.98 mmol) and 4-dimethylaminopyridine (249.11 mg, 2.04 mmol) in acetic anhydride (10.9 mL, 115.54 mmol) and triethylamine (15.02 mL, 107.73 mmol) was stirred at 60° C. for 15 h and then concentrated under reduced pressure. The residue was purified by column chromatography (silica gel, 100-200 mesh, 0 to 40% ethyl acetate in petroleum ether) to afford 1,5-diacetylpyrrolidin-2-one (3.0 g, 52%) as yellow oil. $^1$H NMR (400 MHz, CDCl$_3$) δ 4.88-4.85 (m, 1H), 2.66-2.56 (m, 2H), 2.53 (s, 3H), 2.29-2.24 (m, 4H), 1.93-1.92 (m, 1H).

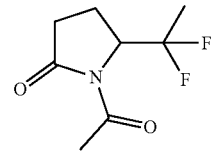

Step 2:
1-acetyl-5-(1,1-difluoroethyl)pyrrolidin-2-one

To a solution of 1,5-diacetylpyrrolidin-2-one (450 mg, 2.66 mmol) in dichloromethane (15 mL) was added diethylaminosulfur trifluoride (4.3 g, 26.6 mmol) at 25° C. The reaction mixture was stirred at 50° C. for 16 h and then concentrated under reduced pressure. The residue was purified by column chromatography (silica gel, 100-200 mesh, 0 to 20% ethyl acetate in petroleum ether) to afford 1-acetyl-5-(1,1-difluoroethyl)pyrrolidin-2-one (170 mg, 33%) as a yellow oil, used in the next step as is.

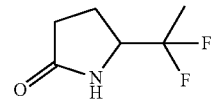

Step 3: 5-(1,1-difluoroethyl)pyrrolidin-2-one

To a solution of 1-acetyl-5-(1,1-difluoroethyl)pyrrolidin-2-one (60 mg, 0.30 mmol) in methanol (5 mL) was added sodium hydride (60%, 6 mg, 0.15 mmol). The reaction mixture was stirred at 25° C. for 12 h and subsequently concentrated under reduced pressure to afford crude of 5-(1,1-difluoroethyl)pyrrolidin-2-one (60 mg, 68%, 50% purity) as yellow oil, used in the next step without further purification.

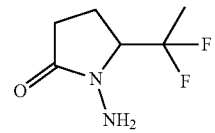

Step 4:
1-amino-5-(1,1-difluoroethyl)pyrrolidin-2-one

To a solution of 5-(1,1-difluoroethyl)pyrrolidin-2-one (60 mg, 0.4 mmol) in N,N-dimethylformamide (5 mL) was added sodium hydride (60%, 24 mg, 0.6 mmol) at 0° C. After addition, the mixture was stirred at 0° C. for 30 min and O-(diphenylphosphoryl)hydroxylamine (141 mg, 0.6 mmol) was added. The reaction mixture was stirred at 25° C. for 16 h and filtered. The filtrate was concentrated under reduced pressure and the residue was purified by preparative TLC (100% ethyl acetate in petroleum ether, R$_f$=0.4) to afford 1-amino-5-(1,1-difluoroethyl)pyrrolidin-2-one (30 mg, 45%) as a yellow oil.

LCMS R$_T$=0.716 min, m/z=165.1 [M+H]$^+$.

LCMS (0 to 60% acetonitrile in water+0.03% trifluoacetic acid over 3.0 mins) retention time 0.716 min, ESI+ found [M+H]=165.1.

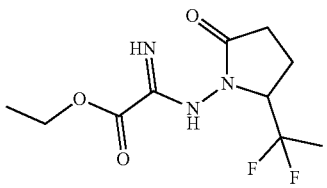 [SMILES: CCOC(=O)C(=N)NN1C(=O)CCC1C(C)(F)F]

Step 5: ethyl 2-[[2-(1,1-difluoroethyl)-5-oxo-pyrrolidin-1-yl]amino]-2-imino-acetate To a solution of 1-amino-5-(1,1-difluoroethyl)pyrrolidin-2-one (30 mg, 0.18 mmol) in ethanol (3 mL) was added ethyl 2-ethoxy-2-imino-acetate (80 mg, 0.55 mmol). The reaction mixture was stirred at 60° C. for 16 h and concentrated under reduced pressure to afford the crude ethyl 2-[[2-(1,1-difluoroethyl)-5-oxo-pyrrolidin-1-yl]amino]-2-imino-acetate (40 mg, 83%) as a yellow oil, used in the next step without further purification.

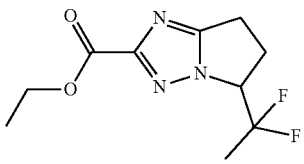 [SMILES: CCOC(=O)c1nc2n(n1)C(C(C)(F)F)CC2]

Step 6: ethyl 5-(1,1-difluoroethyl)-6,7-dihydro-5H-pyrrolo[1,2-b][1,2,4]triazole-2-carboxylate A mixture of ethyl 2-[[2-(1,1-difluoroethyl)-5-oxo-pyrrolidin-1-yl]amino]-2-imino-acetate (90 mg, 0.34 mmol) in phosphorus oxychloride (2.5 mL) was stirred at 120° C. for 1 h and subsequently quenched by addition of water (20 mL). The resulting mixture was extracted with dichloromethane (3×20 mL). The combined organic layers were washed with saturated aqueous sodium bicarbonate (20 mL), brine (20 mL), dried over anhydrous sodium sulfate and concentrated under reduced pressure. The residue was purified by column chromatography (silica gel, 100-200 mesh, 0 to 70% ethyl acetate in petroleum ether) to afford ethyl 5-(1,1-difluoroethyl)-6,7-dihydro-5H-pyrrolo[1,2-b][1,2,4]triazole-2-carboxylate (30 mg, 36%) as a light yellow oil. LCMS $R_T$=0.573 min, m/z=246.2 [M+H]$^+$.

LCMS (5 to 95% acetonitrile in water+0.03% trifluoacetic acid over 1.5 mins) retention time 0.573 min, ESI+ found [M+H]=246.2.

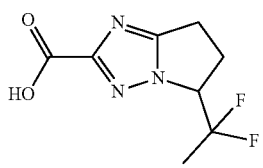

Step 7: 5-(1,1-difluoroethyl)-6,7-dihydro-5H-pyrrolo[1,2-b][1,2,4]triazole-2-carboxylic acid A mixture of ethyl 5-(1,1-difluoroethyl)-6,7-dihydro-5H-pyrrolo[1,2-b][1,2,4]triazole-2-carboxylate (30 mg, 0.12 mmol) and lithium hydroxide hydrate (41 mg, 0.98 mmol) in tetrahydrofuran/methanol/water (5 mL, 2:2:1) was stirred at 25° C. for 12 h and concentrated under reduced pressure. The residue was adjusted to pH=4-5 by addition of hydrochloric acid (1 M). The resulting mixture was concentrated under reduced pressure to give crude 5-(1,1-difluoroethyl)-6,7-dihydro-5H-pyrrolo[1,2-b][1,2,4]triazole-2-carboxylic acid (22 mg, 83%) as a yellow solid, used in the next step without further purification. LCMS $R_T$=0.819 min, m/z=218.1 [M+H]$^+$.

LCMS (0 to 60% acetonitrile in water+0.03% trifluoacetic acid over 2.0 mins) retention time 0.819 min, ESI+ found [M+H]=218.1.

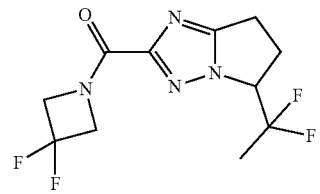 [SMILES: CC(F)(F)C1CCc2nc(C(=O)N3CC(F)(F)C3)nn21]

Step 8: (3,3-difluoroazetidin-1-yl)-[5-(1,1-difluoroethyl)-6,7-dihydro-5H-pyrrolo[1,2-b][1,2,4]triazol-2-yl]methanone A mixture of 5-(1,1-difluoroethyl)-6,7-dihydro-5H-pyrrolo[1,2-b][1,2,4]triazole-2-carboxylic acid (7 mg, 0.03 mmol), 1-hydroxybenzotriazole (7 mg. 0.05 mmol), 1-(3-dimethylaminopropyl)-3-ethylcarbodiimidehydrochloride (9 mg, 0.05 mmol) and 3,3-difluoroazetidine hydrochloride (4 mg, 0.03 mmol) in N,N-dimethylformamide (1 mL) was stirred at 25° C. for 4 h. The mixture was concentrated under reduced pressure and the residue was purified by RP-HPLC (acetonitrile 25-55%/0.05% ammonium hydroxide in water) to afford (3,3-difluoroazetidin-1-yl)-[5-(1,1-difluoroethyl)-6,7-dihydro-5H-pyrrolo[1,2-b][1,2,4]triazol-2-yl]methanone (4 mg, 42%) as a white solid. $^1$H NMR (400 MHz, CD$_3$OD) δ 4.98-4.95 (m, 2H), 4.90-4.83 (m, 1H), 4.52 (t, J=12.0 Hz, 2H), 3.03-2.94 (m, 3H), 2.88-2.85 (m, 1H), 1.82 (t, J=19.2 Hz, 3H). LC-MS $R_T$=0.738 min, m/z=292.9 [M+H]$^+$.

LCMS (5 to 95% acetonitrile in water+0.03% trifluoacetic acid over 1.5 mins) retention time 0.738 min, ESI+ found [M+H]=292.9.

Example 9

Method #9

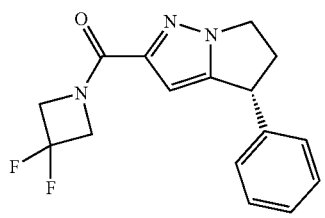 [SMILES: O=C(c1cc2n(n1)CC[C@@H]2c1ccccc1)N1CC(F)(F)C1]

(3,3-difluoroazetidin-1-yl)-[(4R)-4-phenyl-5,6-di-hydro-4H-pyrrolo[1,2-b]pyrazol-2-yl]methanone

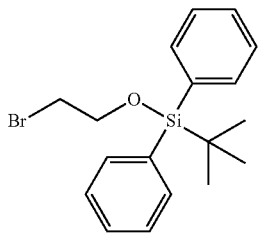 [SMILES: CC(C)(C)[Si](OCCBr)(c1ccccc1)c1ccccc1]

Step 1: (2-bromoethoxy)(tert-butyl)diphenylsilane

To a solution of 2-bromoethanol (2.0 g, 16.0 mmol) and imidazole (3.27 g. 48.0 mmol) in dichloromethane (20 mL) was added tert-butyldiphenylchlorosilane (4.4 g, 16.01 mmol) at 0° C. After addition, the reaction mixture was stirred at 25° C. for 16 h and subsequently concentrated under reduced pressure. The residue was purified by column chromatography (silica gel, 100-200 mesh, petroleum ether) to afford 2-bromoethoxy-tert-butyl-diphenyl-silane (3.1 g, 53%) as colorless oil. $^1$H NMR (400 MHz, CDCl$_3$) δ 7.68 (m, 4H), 7.47-7.37 (m, 6H). 3.93 (t, J=6.4 Hz, 2H), 3.43 (t, J=6.5 Hz, 2H), 1.08 (s, 9H).

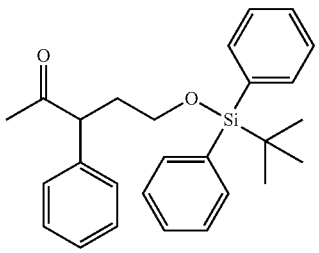 [SMILES: CC(=O)C(CCO[Si](c1ccccc1)(c1ccccc1)C(C)(C)C)c1ccccc1]

Step 2: 5-((tert-butyldiphenylsilyl)oxy)-3-phenyl-pentan-2-one

To a solution of phenylacetone (10.0 g, 74.5 mmol) in N,N-dimethylformamide (20 mL) was added sodium hydride (60%, 4.5 g, 111.8 mmol) at 0° C. After addition, the mixture was stirred at 25° C. for 15 min and 2-bromoethoxy-tert-butyl-diphenyl-silane (32.5 g, 89.4 mmol) was added. The resulting mixture was stirred at 25° C. for 18 h and subsequently quenched by addition of water (100 mL). The mixture was extracted with ethyl acetate (3×100 mL). The combined organic layers were washed with water (20 mL), brine (20 mL), dried over anhydrous sodium sulfate and concentrated under reduced pressure. The residue was purified by column chromatography (silica gel, 100-200 mesh, 0 to 20% ethyl acetate in petroleum ether) to afford 5-[tert-butyl(diphenyl)silyl]oxy-3-phenyl-pentan-2-one as yellow oil (6.0 g, 19%). $^1$H NMR (400 MHz. CDCl$_3$) δ 7.65-7.55 (m, 4H), 7.44-7.26 (m, 9H), 7.22-7.15 (m, 2H), 3.99 (t, J=7.2 Hz, 1H), 3.65-3.58 (m, 1H), 3.65-3.75 (m, 1H), 2.40-2.28 (m, 1H), 2.05 (s, 3H), 1.90-1.80 (m, 1H), 1.05 (s, 9H).

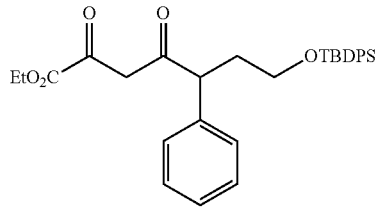

Step 3: ethyl 7-((tert-butyldiphenylsilyl)oxy)-2,4-dioxo-5-phenylheptanoate

To a solution of 5-[tert-butyl(diphenyl)silyl]oxy-3-phenyl-pentan-2-one (5.75 g, 13.8 mmol) in tetrahydrofuran (60 mL) was added potassium tert-butoxide (1.0 M in tetrahydrofuran, 20.7 mL, 20.7 mmol) at 0° C. After addition, the mixture was stirred at 25° C. for 30 min and diethyl oxalate (3.0 g, 20.7 mmol) was added. The resulting mixture was stirred at 25° C. for 2 h and concentrated under reduced pressure. The residue was purified by column chromatography (silica gel, 100-200 mesh, 0 to 50% ethyl acetate in petroleum ether) to afford ethyl 7-[tert-butyl(diphenyl)silyl]oxy-2,4-dioxo-5-phenyl-heptanoate as a brown oil (6.0 g, 84%), used as is in the next step.

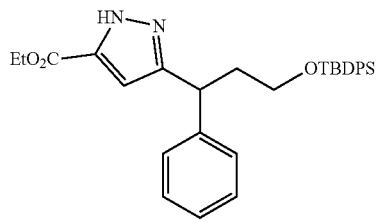

Step 4: ethyl 3-(3-((tert-butyldiphenylsilyl)oxy)-1-phenylpropyl)-1H-pyrazole-5-carboxylate A mixture of hydrazine monohydrate (684 mg, 11.6 mmol) and ethyl 7-[tert-butyl(diphenyl)silyl]oxy-2,4-dioxo-5-phenyl-heptanoate (6.0 g, 11.6 mmol) in ethanol (120 mL) was stirred at 25° C. for 5 h and concentrated under reduced pressure. The residue was purified by column chromatography (silica gel 100-200 mesh, 0 to 50% ethyl acetate in petroleum ether) to afford ethyl 3-[3-[tert-butyl(diphenyl)silyl]oxy-1-phenyl-propyl]-1H-pyrazole-5-carboxylate (1.8 g, 30%) as a light yellow oil. LCMS R$_T$=1.036 min, m/z=513.1 [M+H]$^+$.

LCMS (5 to 95% acetonitrile in water+0.03% trifluoacetic acid over 1.5 mins) retention time 1.036 min, ESI+ found [M+H]=513.1.

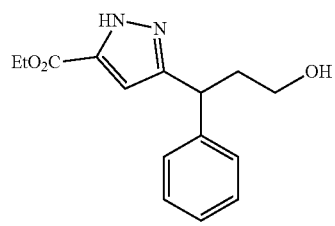 [SMILES: CCOC(=O)c1cc(C(CCO)c2ccccc2)n[nH]1]

Step 5: ethyl 3-(3-hydroxy-1-phenylpropyl)-1H-pyrazole-5-carboxylate

To a solution of ethyl 3-[3-[tert-butyl(diphenyl)silyl]oxy-1-phenyl-propyl]-1H-pyrazole-5-carboxylate (1.80 g, 3.5 mmol) in tetrahydrofuran (40 mL) was added tetrabutylammonium fluoride (1.0 N in tetrahydrofuran, 3.9 mL, 3.9 mmol). The mixture was stirred at 25° C. for 5 h and then concentrated under reduced pressure. The residue was purified by column chromatography (silica gel, 100-200 mesh, 0 to 50% ethyl acetate in petroleum ether) to afford ethyl 3-(3-hydroxy-1-phenyl-propyl)-1H-pyrazole-5-carboxylate as a light yellow oil (800 mg, 83%), used as is in the next step.

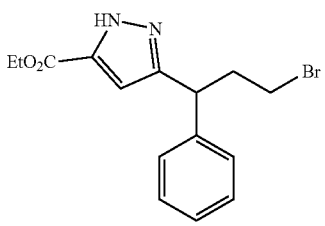 [SMILES: CCOC(=O)c1cc(C(CCBr)c2ccccc2)n[nH]1]

Step 6: ethyl 3-(3-bromo-1-phenylpropyl)-1H-pyrazole-5-carboxylate

A mixture of phosphorusoxybromide (815 mg, 2.84 mmol) and ethyl 5-(3-hydroxy-1-phenyl-propyl)-1H-pyrazole-3-carboxylate (650 mg, 2.37 mmol) in acetonitrile (20 mL) was heated at 50° C. for 15 h and subsequently concentrated under reduced pressure to afford crude ethyl 5-(3-bromo-1-phenyl-propyl)-1H-pyrazole-3-carboxylate as brown solid (790 mg, 98%). This crude was used in the next step without further purification.

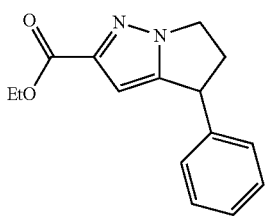 [SMILES: O=C(O)c1cc2n(n1)CCC2c1ccccc1]

Step 7: ethyl 4-phenyl-5,6-dihydro-4H-pyrrolo[1,2-b]pyrazole-2-carboxylate

A mixture of ethyl 5-(3-bromo-1-phenyl-propyl)-1H-pyrazole-3-carboxylate (790 mg, 2.34 mmol) and potassium carbonate (2.59 g, 18.74 mmol) in N,N-dimethylformamide (20 mL) was stirred at 25° C. for 5 h and filtered. The filtrate was concentrated under reduced pressure and the residue was purified by preparative TLC (50% ethyl acetate in petroleum ether, $R_f$=0.5) to afford ethyl 4-phenyl-5,6-dihydro-4H-pyrrolo[1,2-b]pyrazole-2-carboxylate (400 mg, 67%) as a brown oil. LCMS $R_T$=0.850 min, m/z=257.0 [M+H]$^+$.

LCMS (5 to 95% acetonitrile in water+0.03% trifluoacetic acid over 1.5 mins) retention time 0.850 min, ESI+ found [M+H]=257.0.

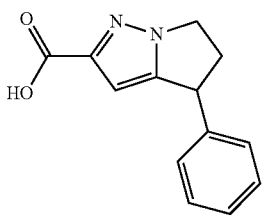

Step 8: 4-phenyl-5,6-dihydro-4H-pyrrolo[1,2-b]pyrazole-2-carboxylic acid

A mixture of ethyl 4-phenyl-5,6-dihydro-4H-pyrrolo[1,2-b]pyrazole-2-carboxylate (400 mg, 1.56 mmol) and lithium hydroxide monohydrate (196 mg, 4.68 mmol) in tetrahydrofuran (8 mL)/water (2 mL) was stirred at 25° C. for 2 h and concentrated under reduced pressure. The residue was adjusted to pH=5 by addition of hydrochloric acid (2 N). The resulting mixture was extracted with ethyl acetate (3×10 mL). The combined organic layers were washed with water (20 mL), brine (20 mL), dried over anhydrous sodium sulfate and concentrated under reduced pressure to afford crude 4-phenyl-5,6-dihydro-4H-pyrrolo[1,2-b]pyrazole-2-carboxylic acid as a brown solid (340 mg, 95%), used in the next step without further purification.

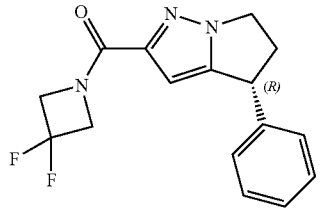

Step 9: (3,3-difluoroazetidin-1-yl)-[(4R)-4-phenyl-5,6-dihydro-4H-pyrrolo[1,2-b]pyrazol-2-yl]methanone A mixture of 4-phenyl-5,6-dihydro-4H-pyrrolo[1,2-b]pyrazole-2-carboxylic acid (100 mg, 0.44 mmol), 1-hydroxybenzotriazole (65 mg, 0.48 mmol), 1-(3-dimethylaminopropyl)-3-ethylcarbodiimidehydrochloride (126 mg, 0.66 mmol) and 3,3-difluoroazetidine hydrochloride (68 mg, 0.53 mmol) in N,N-dimethylformamide (4 mL) was stirred at 25° C. for 15 h. The mixture was concentrated under reduced pressure and the residue was purified by RP-HPLC (acetonitrile 40-70%/0.05% ammonium hydroxide in water) to afford (3,3-difluoroazetidin-1-yl)-(4-phenyl-5,6-dihydro-4H-pyrrolo[1,2-b]pyrazol-2-yl)methanone as a white solid (45 mg, 34%). LCMS $R_T$=1.824 min, m/z=304.1 [M+H]$^+$.

LCMS (10 to 80% acetonitrile in water+0.03% trifluoacetic acid over 2.0 mins) retention time: 1.824 min, ESI+ found [M+H]=304.1

The racemic (3,3-difluoroazetidin-1-yl)-(4-phenyl-5,6-dihydro-4H-pyrrolo[1,2-b]pyrazol-2-yl)methanone (45 mg, 0.15 mmol) was further separated by chiral SFC to afford arbitrarily assigned: (3,3-difluoroazetidin-1-yl)-[(4R)-4-phenyl-5,6-dihydro-4H-pyrrolo[1,2-b]pyrazol-2-yl] methanone (peak 2, retention time=2.757 min) as a white solid (19 mg, 42%). $^1$H NMR (400 MHz, CD$_3$OD) δ 7.35-7.30 (m, 2H), 7.30-7.21 (m, 3H). 6.44 (s, 1H), 4.96-4.85 (m, 2H), 4.51-4.47 (m, 3H), 4.40-4.28 (m 1H), 4.28-4.20 (m, 1H), 3.14-3.05 (m, 1H), 2.57-2.50 (m, 1H). LCMS $R_T$=1.040 min, m/z=304.2 [M+H]$^+$.

LCMS (10 to 80% acetonitrile in water+0.03% trifluoacetic acid over 2.0 mins) retention time: 1.040 min, ESI+ found [M+H]=304.2

SFC condition: Column: OJ (250 mm*30 mm, 5um); Mobile phase: A: $CO_2$ B: 0.1% NH3H2O ETOH; Gradient: from 20% to 20% of B; Flow rate: 60 mL/min. Column temperature: 40° C.

Example 10

Method #10

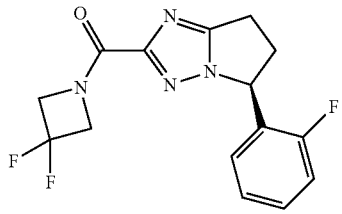 [SMILES: O=C(c1nc2n(n1)[C@H](c1ccccc1F)CC2)N1CC(F)(F)C1]

(3,3-difluoroazetidin-1-yl)-[(5S)-5-(2-fluorophenyl)-6,7-dihydro-5H-pyrrolo[1,2-b][1,2,4]triazol-2-yl]methanone

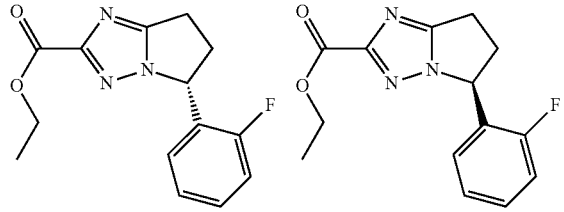

Step 1: (R)-ethyl 5(2-fluorophenyl)-6,7-dihydro-5H-pyrrolo[1,2-b][1,2,4]triazole-2-carboxylate and (S)-ethyl 5-(2-fluorophenyl)-6,7-dihydro-5H-pyrrolo[1,2-b][1,2,4]triazole-2-carboxylate Racemic ethyl 5-(2-fluorophenyl)-6,7-dihydro-5H-pyrrolo[1,2-b][1,2,4]triazole-2-carboxylate (7.1 g, 25.79 mmol) was separated by chrial SFC to afford arbitrarily assigned:
(R)-ethyl 5-(2-fluorophenyl)-6,7-dihydro-5H-pyrrolo[1,2-b][1,2,4]triazole-2-carboxylate (Peak 1, Retention time=3.325 min) (3.0 g, 42%) as a yellow oil.
(S)-ethyl 5-(2-fluorophenyl)-6,7-dihydro-5H-pyrrolo[1,2-b][1,2,4]triazole-2-carboxylate (Peak 2, Retention time=3.560 min) (2.8 g, 39%) as a yellow oil.

SFC condition: Column: ChiralPak AD-3 150×4.6 mm I.D., 3 um Mobile phase: A: CO2 B: Ethanol (0.05% DEA) Gradient: from 5% to 40% of B in 5.5 min and hold 40% for 3 min, then 5% of B for 1.5 min Flow rate: 2.5 mL/min Column temperature: 40° C.

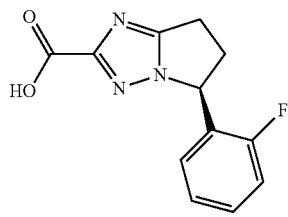 [SMILES: O=C(O)c1nc2n(n1)[C@H](c1ccccc1F)CC2]

Step 2: (S)-5-(2-fluorophenyl)-6,7-dihydro-5H-pyrrolo[1,2-b][1,2,4]triazole-2-carboxylic acid To a solution of ethyl (5S)-5-(2-fluorophenyl)-6,7-dihydro-5H-pyrrolo[1,2-b][1,2,4]triazole-2-carboxylate (2.0 g, 7.27 mmol) in tetrahydrofuran (50 mL)/water (10 mL) was added lithium hydroxide hydrate (870 mg, 36.33 mmol) portion-wise. The reaction mixture was stirred at 25° C. for 12 h and then concentrated under reduce pressure. The aqueous residue was diluted with ice water (20 mL) and adjusted to pH=3 by addition of hydrochloric acid (1 N). The solid product was collected by filtration and dried in vacuo to afford crude (5S)-5-(2-fluorophenyl)-6,7-dihydro-5H-pyrrolo[1,2-b][1,2,4]triazole-2-carboxylic acid (1.6 g, 89%) as a white solid used as is in the next step.

$^1$H NMR (400 MHz, DMSO-d$_6$) δ 13.19 (br s, 1H), 7.48-7.40 (m, 1H), 7.31-7.20 (m, 3H), 5.80-5.76 (m, 1H), 3.25-3.17 (m, 1H), 3.11-2.97 (m, 2H), 2.64-2.58 (m, 1H). LCMS $R_T$=0.586 min, m/z=248.0 [M+H]$^+$.

LCMS (5 to 95% acetonitrile in water+0.03% trifluoroacetic acid over 1.5 mins) retention time 0.586 min, ESI+ found [M+H]=248.0.

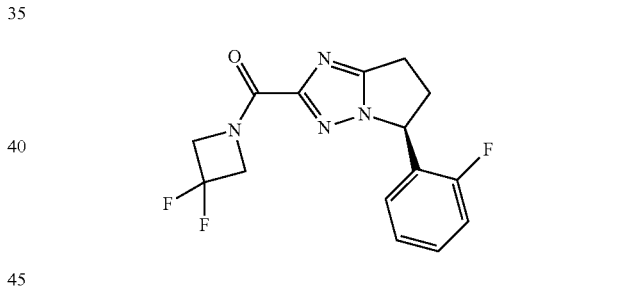

Step 3: (3,3-difluoroazetidin-1-yl)-[(5S)-5(2-fluorophenyl)-6,7-dihydro-5H-pyrrolo[1,2-b][1,2,4]triazol-2-yl]methanone A mixture of (5S)-5-(2-fluorophenyl)-6,7-dihydro-5H-pyrrolo[1,2-b][1,2,4]triazole-2-carboxylic acid (20 mg, 0.08 mmol). 3,3-difluoroazetidine hydrochloride (15 mg, 0.11 mmol), 1-hydroxybenzotriazole (14 mg, 0.10 mmol) and 1-(3-dimethylaminopropyl)-3-ethylcarbodiimidehydrochloride (19 mg, 0.10 mmol) in N,N-dimethylformamide (3 mL) was stirred at 25° C. for 15 h. The mixture was concentrated under reduced pressure and the residue was purified by RP-HPLC (acetonitrile 22-52%/0.05% ammonium hydroxide in water) to afford (3,3-difluoroazetidin-1-yl)-[(5S)-5-(2-fluorophenyl)-6,7-dihydro-5H-pyrrolo[1,2-b][1,2,4]triazol-2-yl]methanone (7.2 mg, 27%) as a white solid. $^1$H NMR (400 MHz, CD$_3$OD) δ 7.43-7.36 (m, 1H), 7.23-7.10 (m, 3H), 5.80-5.77 (m, 1H), 4.96-4.86 (m, 2H), 4.48 (t, J=12.0 Hz, 2H), 3.38-3.31 (m, 1H), 3.19-3.02 (m, 2H), 2.70-2.67 (m, 1H). LCMS $R_T$=1.738 min, m/z=323.2 [M+H]$^+$.

LCMS (0 to (60/o acetonitrile in water+0.03% trifluoroacetic acid over 3.0 mins) retention time 1.738 min, ESI+ found [M+H]=323.2.

Example 11

Method #11

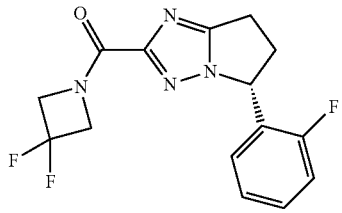 [SMILES: O=C(c1nc2n(n1)[C@@H](c1ccccc1F)CC2)N1CC(F)(F)C1]

(3,3-difluoroazetidin-1-yl)-[(5R)-5-(2-fluorophenyl)-6,7-dihydro-5H-pyrrolo[1,2-b][1,2,4]triazol-2-yl]methanone

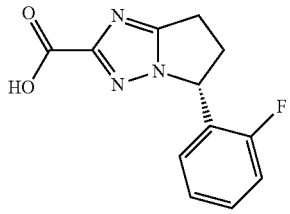 [SMILES: O=C(O)c1nc2n(n1)[C@@H](c1ccccc1F)CC2]

Step 1: (R)-5-(2-fluorophenyl)-6,7-dihydro-5H-pyrrolo[1,2-b][1,2,4]triazole-2-carboxylic acid To a solution of ethyl (5R)-5-(2-fluorophenyl)-6,7-dihydro-5H-pyrrolo[1,2-b][1,2,4]triazole-2-carboxylate (1.0 g, 3.63 mmol) in tetrahydrofuran (30 mL)/water (15 mL) was added lithium hydroxide hydrate (870 mg, 36.33 mmol) portionwise. The reaction mixture was stirred at 25° C. for 12 h and then concentrated under reduce pressure. The aqueous residue was diluted with ice water (20 mL) and adjusted to pH=3 by addition of hydrochloric acid (1 N). The solid product was collected by filtration and dried in vacuo to afford (5R)-5-(2-fluorophenyl)-6,7-dihydro-5H-pyrrolo[1,2-b][1,2,4]triazole-2-carboxylic acid (700 mg, 78%) as a white solid, used in the next step without further purification. LCMS $R_T$=0.986 min, m/z=248.2 [M+H].

LCMS (0 to 60% acetonitrile in water+0.03% trifluoroacetic acid over 2.0 mins) retention time 0.986 min, ESI+ found [M+H]=248.2.

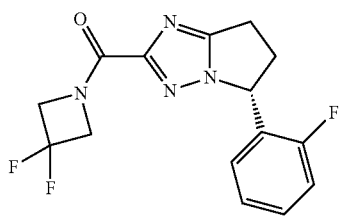 [SMILES: O=C(c1nc2n(n1)[C@@H](c1ccccc1F)CC2)N1CC(F)(F)C1]

Step 2: (3,3-difluoroazetidin-1-yl)-[(5R)-5-(2-fluorophenyl)-6,7-dihydro-H-pyrrolo[1,2-b][1,2,4]triazol-2-yl]methanone A mixture of (5R)-5-(2-fluorophenyl)-6,7-dihydro-5H-pyrrolo[1,2-b][1,2,4]triazole-2-carboxylic acid (20 mg, 0.08 mmol), 3,3-difluoroazetidine hydrochloride (15 mg, 0.11 mmol), 1-hydroxybenzotriazole (14 mg, 0.10 mmol) and 1-(3-dimethylaminopropyl)-3-ethylcarbodiimidehydrochloride (19 mg. 0.10 mmol) in N,N-dimethylformamide (3 mL) was stirred at 25° C. for 15 h. The mixture was concentrated under reduced pressure and the residue was purified by RP-HPLC (acetonitrile 22-52%/0.05% ammonium hydroxide in water) to afford ((3,3-difluoroazetidin-1-yl)-[(5R)-5-(2-fluorophenyl)-6,7-dihydro-5H-pyrrolo[1,2-b][1,2,4]triazol-2-yl]methanone (7.4 mg, 28%) as a white solid. $^1$H NMR (400 MHz, CD$_3$OD) δ 7.44-7.35 (m, 1H), 7.22-7.10 (m, 3H), 5.80-5.77 (m, 1H), 4.94-4.87 (m, 1H), 4.85-4.79 (m, 1H), 4.48 (t, J=12.0 Hz, 2H), 3.36-3.31 (m, 1H), 3.20-3.01 (m, 2H), 2.75-2.65 (m, 1H). LCMS $R_T$=1.737 min, m/z=323.2 [M+H]$^+$.

LCMS (0 to 60% acetonitrile in water+0.03% trifluoroacetic acid over 3.0 mins) retention time 1.737 min, ESI+ found [M+H]=323.2.

Example 12

Method #12

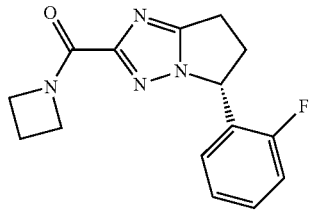 [SMILES: O=C(c1nc2n(n1)[C@@H](c1ccccc1F)CC2)N1CCC1]

Azetidin-1-yl-[(5R)-5-(2-fluorophenyl)-6,7-dihydro-5H-pyrrolo[1,2-b][1,2,4]triazol-2-yl]methanone Amide coupling was prepared in a similar fashion to Method #11 (G03093424, GNT_E425_1029).

The crude was purified by RP-HPLC (acetonitrile 20-50%/0.05% ammonium hydroxide in water) to afford azetidin-1-yl-[(5R)-5-(2-fluorophenyl)-6,7-dihydro-5H-pyrrolo[1,2-b][1,2,4]triazol-2-yl]methanone (7.8 mg. 33%) as a white solid.

$^1$H NMR (400 MHz, CD$_3$OD) δ 7.40-7.37 (m, 1H), 7.19-7.11 (m, 3H), 5.79-5.75 (m, 1H), 4.58-4.53 (m, 2H), 4.19-4.15 (m, 2H), 3.28-3.26 (m, 1H), 3.13-3.06 (m, 2H), 2.71-2.68 (m, 1H), 2.39-2.31 (m, 2H). LCMS $R_T$=0.680 min, m/z=287.0 [M+H]$^+$.

LCMS (5 to 95% acetonitrile in water+0.03% trifluoroacetic acid over 1.5 mins) retention time 0.680 min, ESI+ found [M+H]=287.0.

Example 13

Method #13

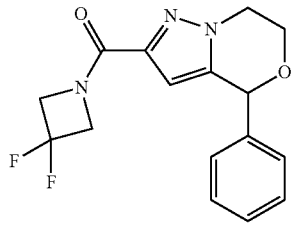

(3,3-difluoroazetidin-1-yl)-(4-phenyl-6,7-dihydro-4H-pyrazolo[5,1-c][1,4]oxazin-2-yl)methanone

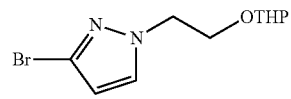

Step 1: 3-bromo-1-(2-((tetrahydro-2H-pyran-2-yl)oxy)ethyl)-1H-pyrazole

To a solution of 3-bromo-1H-pyrazole (5.0 g, 34.0 mmol) in acetonitrile (100 mL) was added cesium carbonate (16.6 g, 51.0 mmol) and 2-(2-bromoethoxy)tetrahydro-2h-pyran (7.5 g, 35.7 mmol). The mixture was stirred at 30° C. for 2 h and quenched by the addition of water (80 mL). The resulting mixture was extracted with ethyl acetate (3×100 mL). The combined organic layers were washed with water (20 mL), brine (20 mL), dried over anhydrous sodium sulfate and concentrated under reduced pressure. The residue was purified by column chromatography (silica gel, 100-200 mesh, 0 to 20% ethyl acetate in petroleum ether) to afford 3-bromo-1-(2-tetrahydropyran-2-yloxyethyl)pyrazole (5.5 g, 59%) as a yellow oil. $^1$HNMR (400 MHz, CDCl$_3$) δ 7.40 (d, J=2.4 Hz, 1H), 6.24 (d, J=1.2 Hz, 1H), 4.55-4.29 (m, 1H), 4.30-4.22 (m, 2H), 4.06-4.02 (m, 1H), 3.75-3.68 (m, 1H), 3.65-3.60 (m, 1H), 3.46-3.45 (m, 1H), 1.76-1.49 (m, 6H).

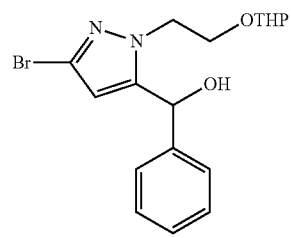

Step 2: (3-bromo-1-(2-((tetrahydro-2H-pyran-2-yl)oxy)ethyl)-1H-pyrazol-5-yl)(phenyl)methanol To a solution of lithium diisopropylamide (10.9 mL, 21.8 mmol) in tetrahydrofuran (100 mL) was added 3-bromo-1-(2-tetrahydropyran-2-yloxyethyl)pyrazole (4.0 g, 14.5 mmol) in tetrahydrofuran (2 mL) at −78° C. The resulting mixture was stirred at −78° C. for 30 min and benzaldehyde (1.8 g, 17.5 mmol) in tetrahydrofuran (2 mL) was added. The reaction mixture was allowed to warm to room temperature over 18 h and quenched by the addition of saturated aqueous ammonium chloride (20 mL). The mixture was extracted with ethyl acetate (3×100 mL). The combined organic layers were washed with water (50 mL), brine (50 mL), dried over anhydrous sodium sulfate and concentrated under reduced pressure. The residue was purified by column chromatography (silica gel, 100-200 mesh, 10 to 80% ethyl acetate in petroleum ether) to give [5-bromo-2-(2-tetrahydropyran-2-yloxyethyl)pyrazol-3-yl]-phenyl-methanol (3.5 g, 63%) as a colorless oil, used as is in the next step.

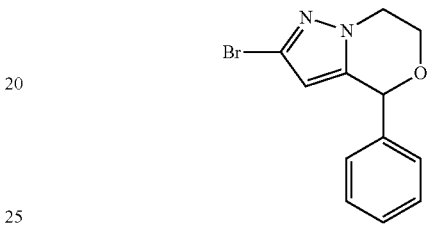

Step 3: 2-bromo-4-phenyl-6,7-dihydro-4H-pyrazolo[5,1-c][1,4]oxazine

To a solution of [5-bromo-2-(2-tetrahydropyran-2-yloxyethyl)pyrazol-3-yl]-phenyl-methanol (3.5 g, 9.18 mmol) was added p-toluenesulfonic acid (870 mg. 5.05 mmol). The reaction mixture was heated at reflux for 5 min and concentrated under reduced pressure. The residue was purified by column chromatography (silica gel, 100-200 mesh, 0 to 30% ethyl acetate in petroleum ether) to afford 2-bromo-4-phenyl-6,7-dihydro-4H-pyrazolo[5,1-c][1,4]oxazine (1.1 g, 43%) as a colorless oil. $^1$H NMR (400 MHz, CDCl$_3$) δ 7.43-7.34 (m, 5H), 5.83 (d, J=1.0 Hz, 1H), 5.71 (s, 1H). 4.36-4.28 (m, 2H), 4.24-4.17 (m, 1H), 4.15-4.08 (m, 1H).

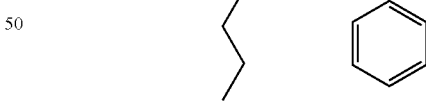

Step 4: butyl 4-phenyl-6,7-dihydro-4H-pyrazolo[5,1-c][1,4]oxazine-2-carboxylate A mixture of 2-bromo-4-phenyl-6,7-dihydro-4H-pyrazolo[5,1-c][1,4]oxazine (110 mg, 0.39 mmol), palladium(II) acetate (9 mg, 0.04 mmol), 1,3-bis(diphenylphosphino)propane (16 mg, 0.04 mmol) and triethylamine (0.55 mL, 3.94 mmol) in 1-butanol (5 mL) was stirred at 100° C. for 48 h under carbon monoxide (3.2 Mpa). The mixture was filtered and the filtrate was concentrated under reduced pressure. The residue was purified by preparative TLC (petroleum ether: ethyl acetate=3:1, R$_f$=0.3) to give butyl 4-phenyl-6, 7-dihydro-4H-pyrazolo[5,1-c][1,4]oxazine-2-carboxylate (50 mg, 42%), used as is in the next step.

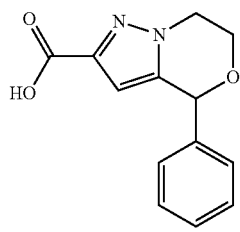 [SMILES: O=C(O)c1cc2n(n1)CCOC2c1ccccc1]

Step 5: 4-phenyl-6,7-dihydro-4H-pyrazolo[5,1-c][1,4]oxazine-2-carboxylic acid To a solution of butyl 4-phenyl-6,7-dihydro-4H-pyrazolo [5,1-c][1,4]oxazine-2-carboxylate (50 mg, 0.17 mmol) in tetrahydrofuran (4 mL)/water (2 mL) was added lithium hydroxide monohydrate (50 mg, 1.2 mmol). The reaction mixture was stirred at 30° C. for 12 h and subsequently concentrated under reduced pressure. The aqueous residue was diluted with water (10 mL) and adjusted to pH=5 by addition of hydrochloric acid (1 N). The resulting mixture was extracted with dichloromethane (3×10 mL). The combined organic layers were concentrated under reduced pressure to afford crude 4-phenyl-6,7-dihydro-4H-pyrazolo[5,1-c][1,4]oxazine-2-carboxylic acid (25 mg, 62%) as a white solid, used in the next step without further purification. LCMS $R_T$=0.867 min, m/z=245.1 [M+H]$^+$.

LCMS (10 to 80% acetonitrile in water+0.03% trifluoroacetic acid over 2.0 mins) retention time 0.867 min, ESI+ found [M+H]=245.1.

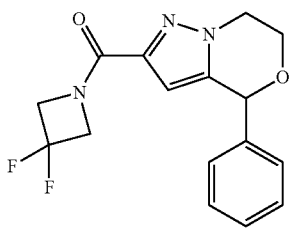 [SMILES: O=C(c1cc2n(n1)CCOC2c1ccccc1)N1CC(F)(F)C1]

Step 6: (3,3-difluoroazetidin-1-yl)-(4-phenyl-6,7-dihydro-4H-pyrazolo[5,1-c][1,4]oxazin-2-yl)methanone A mixture of 1-(3-dimethylaminopropyl)-3-ethylcarbodiimide hydrochloride (19 mg, 0.10 mmol) 3,3-difluoroazetidine hydrochloride (12 mg. 0.09 mmol), 1-hydroxybenzotriazole (13 mg, 0.10 mmol) and 4-phenyl-6,7-dihydro-4H-pyrazolo[5,1-c][1,4]oxazine-2-carboxylic acid (20 mg, 0.08 mmol) in N,N-dimethylformamide (3 mL) was stirred at 28° C. for 15 h. The mixture was concentrated under reduced pressure and the residue was purified by RP-HPLC (acetonitrile 25-55%/0.05% ammonium hydroxide in water) to afford (3,3-difluoroazetidin-1-yl)-(4-phenyl-6,7-dihydro-4H-pyrazolo[5,1-c][1,4]oxazin-2-yl)methanone (6.4 mg, 24%) as a white solid. $^1$H NMR (400 MHz, CD$_3$OD) δ 7.38 (m, 5H), 6.24 (s, 1H), 5.82 (s, 1H), 4.95-4.88 (m, 2H), 4.48-4.42 (m, 2H). 4.45-4.37 (m, 2H), 4.29-4.17 (m, 2H). LCMS $R_T$=1.729 min, m/z=320.1 [M+H]$^+$.

LCMS (10 to 80% acetonitrile in water+0.05% ammonium bicarbonate over 3 mins) retention time 1.729 min, ESI+ found [M+H]=320.1.

Example 14

Method #14

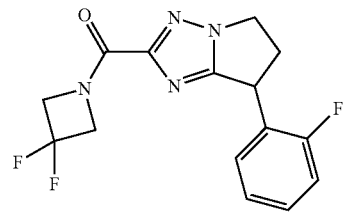

(3,3-difluoroazetidin-1-yl)-[7-(2-fluorophenyl)-6,7-dihydro-5H-pyrrolo[1,2-b][1,2,4]triazol-2-yl]methanone

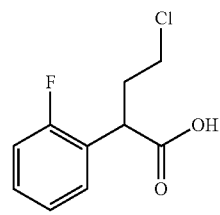 [SMILES: O=C(O)C(CCCl)c1ccccc1F]

Step 1: 4-chloro-2-(2-(2-fluorophenyl)butanoic acid

To a stirred solution of 2-(2-fluorophenyl)acetic acid (10.0 g, 64.9 mmol) in tetrahydrofuran (300 mL) was added n-butyllithium (2.5 M in hexanes, 51.9 mL, 129.8 mmol) dropwise at −78° C. The resulting mixture was stirred for 20 min at −78° C. and 1 h at 0° C., and subsequently 1-bromo-2-chloroethane (5.59 mL, 64.9 mmol) was added. The reaction mixture was allowed to warm to 25° C. over 15 h and quenched by addition of hydrochloric acid (1 N, 100 mL). The mixture was extracted with ethyl acetate (3×150 mL). The combined organic layers were washed with brine (200 mL) and concentrated under reduced pressure. The residue was purified by column chromatography (silica gel, 100-200 mesh, dichloromethane) to afford 4-chloro-2-(2-fluorophenyl)butanoic acid (9.5 g, 68%) as a yellow oil. $^1$HNMR (400 MHz, CD$_3$OD) δ 7.41-7.24 (m, 2H), 7.21-6.98 (m, 2H), 4.18-4.08 (m, 1H), 3.63-3.55 (m, 1H), 3.46-3.38 (m, 1H), 2.58-2.47 (m, 1H), 2.25-2.10 (m, 1H).

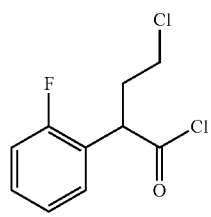 [SMILES: O=C(Cl)C(CCCl)c1ccccc1F]

Step 2: 4-chloro-2-(2-fluorophenyl)butanoyl chloride

To a mixture of 4-chloro-2-(2-fluorophenyl)butanoic acid (1.0 g, 4.62 mmol) in dichloromethane (6 mL), one drop N,N-dimethylformamide and oxalyl chloride (1.97 mL, 23.2 mmol) was added dropwise. The mixture was stirred at 25° C. for 1.5 h and concentrated under reduced pressure (below 30° C.) to afford crude 4-chloro-2-(2-fluorophenyl)butanoyl chloride (1.08 g, 99%) as a yellow oil, use in the next step without further purification.

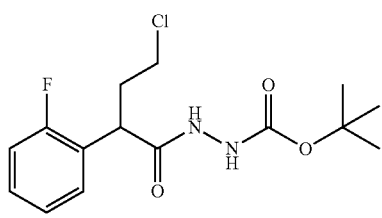 [SMILES: CC(C)(C)OC(=O)NNC(=O)C(CCCl)c1ccccc1F]

Step 3: tert-butyl 2-(4-chloro-2-(2-fluorophenyl) butanoyl)hydrazinecarboxylate To a solution of triethylamine (0.81 mL, 13.78 mmol) and tert-butyl hydrazinecarboxylate (1.21 g, 9.19 mmol) in tetrahydrofuran (30 mL) was added 4-chloro-2-(2-fluorophenyl)butanoyl chloride (1.08 g, 4.59 mmol) in tetrahydrofuran (3 mL) at 0° C. The resulting mixture was stirred at 0° C. for 2 h and subsequently diluted with water (150 mL) and ethyl acetate (200 mL). The separated organic layer was washed with 1 N hydrochloric acid (2×30 mL) and brine (30 mL), dried over anhydrous sodium sulfate and concentrated under reduced pressure. The residue was purified by column chromatography (silica gel, 100-200 mesh, 0 to 4% methanol in dichloromethane) to afford tert-butyl 2-(4-chloro-2-(2-fluorophenyl)butanoyl)hydrazinecarboxylate (1.07 g, 70%) as a yellow oil.

LCMS RT=0.741 min, m/z=230.8 [M−100+H].

LCMS (5 to 95% acetonitrile in water+0.03% trifluoroacetic acid over 1.5 mins) retention time 0.741 min, ESI+ found [M−100+H]=230.8.

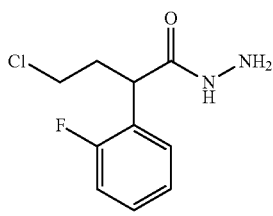 [SMILES: NNC(=O)C(CCCl)c1ccccc1F]

Step 4: 4-chloro-2-(2-fluorophenyl)butanehydrazide

To s solution of tert-butyl N-[[4-chloro-2-(2-fluorophenyl)butanoyl]amino]carbamate (1.07 g, 3.2 mmol) in ethyl acetate (2.0 mL) was added hydrochloric acid (4.0 N in ethyl acetate, 10.0 mL, 40.0 mmol). The mixture was stirred for 1.5 h and concentrated under reduced pressure. The residue was diluted with ethyl acetate (60 mL), washed with saturated aqueous sodium bicarbonate (20 mL), brine (20 mL), dried over sodium sulfate and concentrated under reduced pressure to afford crude 4-chloro-2-(2-fluorophenyl)butanehydrazide (740 mg, 100%) as a yellow oil. LCMS RT=0.591 min, m/z=230.8 [M+H]$^+$.

LCMS (5 to 95% acetonitrile in water+0.03% trifluoroacetic acid over 1.5 mins) retention time 0.591 min, ESI+ found [M+H]=230.8.

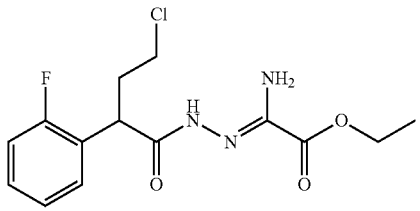 [SMILES: CCOC(=O)/C(N)=N/NC(=O)C(CCCl)c1ccccc1F]

Step 5: (Z)-ethyl 2-amino-2-(2-(4-chloro-2-(2-fluorophenyl)butanoyl)hydrazono)acetate To a solution of 4-chloro-2-(2-fluorophenyl)butanehydrazide (746 mg, 3.23 mmol) in ethanol (10 mL) was added ethyl 2-ethoxy-2-imino-acetate (469 mg, 3.23 mmol). The mixture was stirred at 25° C. for 2 h and then filtered. The solid was dried in vacuo to afford crude (Z)-ethyl 2-amino-2-(2-(4-chloro-2-(2-fluorophenyl)butanoyl)hydrazono)acetate (650 mg, 61%) as a white solid, used in the next step without any further purification. LCMS RT=0.786 min, m/z=329.9 [M+H]$^+$.

LCMS (5 to 95% acetonitrile in water+0.03% trifluoroacetic acid over 1.5 mins) retention time 0.786 min, ESI+ found [M+H]=329.9.

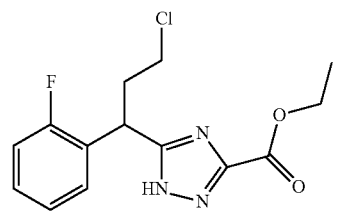 [SMILES: CCOC(=O)c1n[nH]c(C(CCCl)c2ccccc2F)n1]

Step 6: ethyl 5-(3-chloro-1-(2-fluorophenyl)propyl)-1H-1,2,4-triazole-3-carboxylate A mixture of ethyl (2E)-2-amino-2-[[4-chloro-2-(2-fluorophenyl)butanoyl]hydrazono]acetate (650 mg, 1.97 mmol) and phosphorus oxychloride (8.0 mL, 85.57 mmol) was stirred at 120° C. for 1.5 h and subsequently quenched by addition of water (50 mL). The resulting mixture was extracted with ethyl acetate (2×50 mL). The combined organic layers were dried over sodium sulfate and concentrated under reduced pressure to afford crude ethyl 5-[3-chloro-1-(2-fluorophenyl)propyl]-1H-1,2,4-triazole-3-carboxylate (614 mg, 100%) as a colorless oil, used in the next step without further purification. LCMS $R_T$=0.716 min, m/z=311.9 [M+H].

LCMS (5 to 95% acetonitrile in water+0.03% trifluoroacetic acid over 1.5 mins) retention time 0.716 min, ESI+ found [M+H]=311.9.

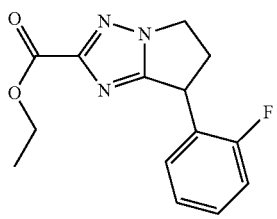 [SMILES: CCOC(=O)c1nc2n(n1)CCC2c1ccccc1F]

Step 7: ethyl 7-(2-fluorophenyl)-6,7-dihydro-5H-pyrrolo[1,2-b][1,2,4]triazole-2-carboxylate To a solution of ethyl 5-[3-chloro-1-(2-fluorophenyl)propyl]-1H-1,2,4-triazole-3-carboxylate (614 mg, 1.97 mmol) in N,N-dimethylformamide (4 mL) was added potassium carbonate (272 mg, 1.97 mmol). The reaction mixture was stirred at 25° C. for 15 h and filtered. The filtrate was concentrated under reduced pressure and the residue was purified by column chromatography (silica gel, 100-200 mesh, 0 to 3% methanol in dichloromethane) to afford ethyl 7-(2-fluorophenyl)-6,7-dihydro-5H-pyrrolo[1,2-b][1,2,4]triazole-2-carboxylate (450 mg, 83%) as a yellow oil. $^1$H NMR (400 MHz, CD$_3$OD) δ 7.41-7.25 (m, 2H), 7.22-7.08 (m, 2H), 4.76-4.72 (m, 1H), 4.49-4.28 (m, 4H). 3.38-3.33 (m, 1H), 2.84-2.66 (m, 1H), 1.38 (t, J=7.2 Hz, 3H).

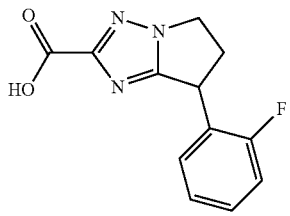 [SMILES: O=C(O)c1nc2n(n1)CCC2c1ccccc1F]

Step 8: 7-(2-fluorophenyl)-6,7-dihydro-5H-pyrrolo[1,2-b][1,2,4]triazole-2-carboxylic acid A mixture of ethyl 7-(2-fluorophenyl)-6,7-dihydro-5H-pyrrolo[1,2-b][1,2,4]triazole-2-carboxylate (450 mg, 1.63 mmol) and lithium hydroxide monohydrate (141 mg, 3.37 mmol) in tetrahydrofuran (30 mL)/water (7 mL) was stirred at 25° C. for 2 h and concentrated under reduced pressure. The aqueous residue was diluted with water (10 mL) and adjusted to pH=5 by addition of 1N HCl. The resulting mixture was extracted with dichloromethane (4×50 mL). The combined organic layers were dried over sodium sulfate and concentrated under reduced pressure to afford crude 7-(2-fluorophenyl)-6,7-dihydro-5H-pyrrolo[1,2-b][1,2,4]triazole-2-carboxylic acid (200 mg, 50%), used in the next step without further purification. LCMS R$_T$=0.658 min, m/z=247.9 [M+H]$^+$.

LCMS (5 to 95% acetonitrile in water+0.03% trifluoroacetic acid over 1.5 mins) retention time 0.658 min, ESI+ found [M+H]=247.9.

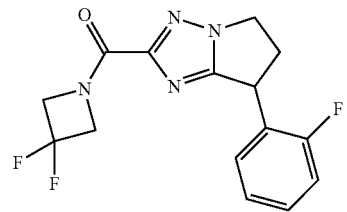

Step 9: 3-bromo-1-(2-((tetrahydro-2H-pyran-2-yl)oxy)ethyl)-1H-pyrazole

A mixture of 7-(2-fluorophenyl)-6,7-dihydro-5H-pyrrolo[1,2-b][1,2,4]triazole-2-carboxylic acid (40 mg, 0.16 mmol), 3,3-difluoroazetidine hydrochloride (21 mg, 0.16 mmol), 1-hydroxybenzotriazole (22 mg, 0.16 mmol) and 1-(3-dimethylaminopropyl)-3-ethylcarbodiimidehydrochloride (31 mg, 0.16 mmol) in N,N-dimethylformamide (4 mL) was stirred at 25° C. for 2 h. The mixture was concentrated under reduced pressure and the residue was purified by RP-HPLC (acetonitrile 25-55%/0.05% ammonium hydroxide in water) to afford (3,3-difluoroazetidin-1-yl)-[7-(2-fluorophenyl)-6,7-dihydro-5H-pyrrolo[1,2-b][1,2,4]triazol-2-yl]methanone (11.1 mg, 21%) as a white solid. $^1$H NMR (400 MHz, CD$_3$OD) δ 7.47-7.23 (m, 2H), 7.21-6.94 (m, 2H). 5.02-4.91 (m, 2H), 4.78-4.68 (m, 1H), 4.50 (t, J=12.0 Hz, 2H), 4.44-4.37 (m, 1H), 4.33-4.18 (m, 1H), 3.40-3.32 (m, 1H), 2.74-2.63 (m, 1H). LCMS R$_T$=1.626 min, m/z=323.1 [M+H]$^+$.

LCMS (10 to 80% acetonitrile in water+0.05% ammonium bicarbonate over 3 mins) retention time 1.626 min, ESI+ found [M+H]=323.1.

Example 15

SFC 2

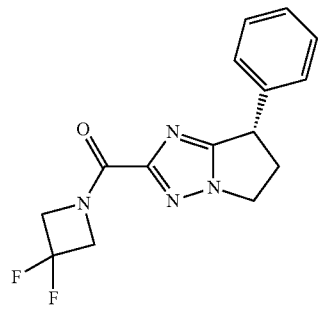 [SMILES: O=C(c1nc2n(n1)CC[C@H]2c1ccccc1)N1CC(F)(F)C1]

(3,3-difluoroazetidin-1-yl)-[(7S)-7-phenyl-6,7-dihydro-5H-pyrrolo[1,2-b][1,2,4]triazol-2-yl]methanone was prepared according to Method #4 and the following SFC purification (5 mg, 38% yield).

Purification:

SFC condition: Column: Chiralpak IG 150×21.2 mm I.D., Mobile phase: A: CO2 B: Methanol (0.1% NH4OH) Isocratic: 25%: 70 mL/min Column temperature: 40° C.

Analytical:

Isocratic 20% MeOH, UV Wavelength: PDA Single 220.0 nm, Column: Chiralcel OX, Run Time: 2.5 Minutes, Co-Solvent: MeOH w/0.1% NH4OH, ColumnTemp: 40.0

Example 16

Method #16

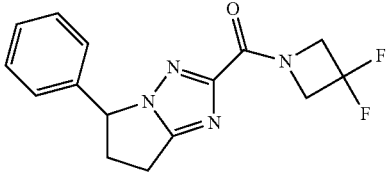 [SMILES: O=C(c1nc2n(n1)C(c1ccccc1)CC2)N1CC(F)(F)C1]

Step 1: (3,3-difluoroazetidin-1-yl)-(5-phenyl-6,7-dihydro-H-pyrrolo[1,2-b][1,2,4]triazol-2-yl)methanone To a solution of 5-phenyl-6,7-dihydro-5H-pyrrolo[1,2-b][1,2,4]triazole-2-carboxylic acid (25.0 mg, 0.109 mmol) in N,N-dimethylformamide (1.09 mL) was added 3,3 difluoroazetidine (9.89 mg, 0.076 mmol), trimethylamine (0.07 mL, 0.436 mmol) and 1-[bis(dimethylamino)methylene]-1H-1,2,3-triazolo[4,5-b]pyridinium 3-oxide hexafluorophosphate (94.0 mg, 0.24 mmol). The reaction mixture was stirred at RT for 16 h. The crude mixture was evaporated under reduced pressure and purified by RP-HPLC affording (3,3-difluoroazetidin-1-yl)-(5-phenyl-6,7-dihydro-5H-pyrrolo[1,2-b][1,2,4]triazol-2-yl)methanone (21.1 mg, 64%) as a white powder: 1H NMR (400 MHz, DMSO-d6) δ 7.45-7.33 (m, 3H), 7.26-7.17 (m, 2H), 5.66-5.54 (m, 1H), 4.85 (m, 2H), 4.45 (t. J=12.6 Hz, 2H), 3.24-3.14 (m, 2H), 3.14-3.05 (m, 1H), 2.99 (m, 1H). LC-MS $R_T$=4.26 min, m/z=305.11 (M+H)$^+$.

LCMS (2 to 98% acetonitrile in water+0.1% formic acid over 10 mins) retention time 4.26 min, ESI+ found [M+H]=305.1

Example 17

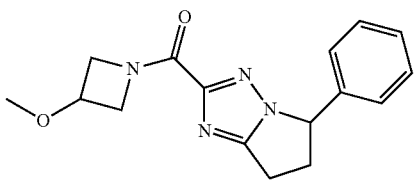 [SMILES: COC1CN(C(=O)c2nc3n(n2)C(c2ccccc2)CC3)C1]

(3-methoxyazetidin-1-yl)-(5-phenyl-6,7-dihydro-5H-pyrrolo[1,2-b][1,2,4]triazol-2-yl)methanone Method A (18.4 mg, 56% yield).

1H NMR (400 MHz, DMSO-d6) δ 7.49-7.29 (m, 3H), 7.26-7.15 (m, 2H), 5.64-5.51 (m, 1H). 4.67-4.52 (m, 1H), 4.23-4.19 (m, 2H), 4.20-4.15 (m, 1H), 3.87-3.73 (m, 1H), 3.21 (s, 3H), 3.13-3.03 (m, 2H), 3.03-2.93 (m, 2H). LC-MS $R_T$=3.94 min. m/z=299.14 (M+H)$^+$.

LCMS (2 to 98% acetonitrile in water+0.1% formic acid over 10 mins) retention time 3.94 min, ESI+ found [M+H]=299.1

Example 18

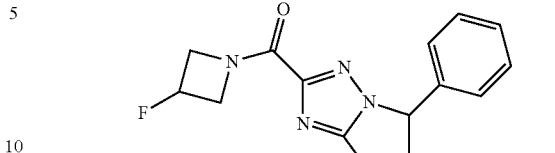

(3-fluoroazetidin-1-yl)-(5-phenyl-6,7-dihydro-5H-pyrrolo[1,2-b][1,2,4]triazol-2-yl)methanone Method A (10.5 mg, 33% yield).

1H NMR (400 MHz, DMSO-d6) δ 7.45-7.31 (m, 3H), 7.25-7.17 (m, 2H), 5.64-5.54 (m, 1H), 4.86-4.68 (m, 1H), 4.55-4.27 (m, 2H), 4.14-3.98 (m, 1H), 3.29-3.28 (m, 1H), 3.24-3.15 (m, 1H), 3.13-3.04 (m, 1H), 3.04-2.92 (m, 1H), 2.60-2.52 (m, 1H). LC-MS $R_T$=4.01 min, m/z=287.12 (M+H)$^+$.

LCMS (2 to 98% acetonitrile in water+0.1% formic acid over 10 mins) retention time 4.01 min, ESI+ found [M+H]=287.1

Example 19

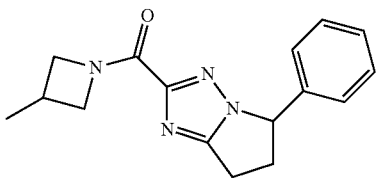 [SMILES: CC1CN(C(=O)c2nc3n(n2)C(c2ccccc2)CC3)C1]

(3-methylazetidin-1-yl)-(5-phenyl-6,7-dihydro-5H-pyrrolo[1,2-b][1,2,4]triazol-2-yl)methanone Method A (14.8 mg, 48% yield).

1H NMR (400 MHz, DMSO-d6) δ 7.44-7.31 (m, 3H), 7.23-7.16 (m, 2H), 5.56 (m, 1H), 4.58-4.44 (m, 1H). 4.18-4.06 (m, 1H), 4.02-3.91 (m, 1H), 3.60-3.49 (m, 1H), 3.30-3.14 (m, 2H), 3.12-3.02 (m, 1H), 3.02-2.91 (m, 1H), 2.74-2.63 (m, 1H), 1.22-1.15 (m, 3H). LC-MS $R_T$=4.36 min, m/z=283.14 (M+H)$^+$.

LCMS (2 to 98% acetonitrile in water+0.1% formic acid over 10 mins) retention time 4.36 min, ESI+ found [M+H]=283.1

Example 20

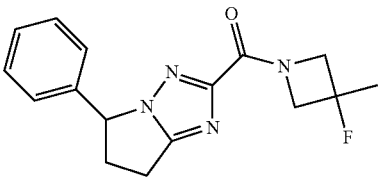 [SMILES: CC1(F)CN(C(=O)c2nc3n(n2)C(c2ccccc2)CC3)C1]

(3-fluoro-3-methyl-azetidin-1-yl)-(5-phenyl-6,7-dihydro-5H-pyrrolo[1,2-b][1,2,4]triazol-2-yl)methanone Method A (12.3 mg, 38% yield).

1H NMR (400 MHz, DMSO-d6) δ 7.43-7.32 (m, 3H), 7.26-7.17 (m, 2H), 5.58 (dd, J=8.3, 5.7 Hz, 1H), 4.55-4.46 (m, 2H), 4.15-4.03 (m, 2H), 3.29-3.27 (m, 1H), 3.17 (m, 1H), 3.13-3.03 (m, 1H), 3.03-2.93 (m, 1H), 1.64-1.50 (m, 3H). LC-MS $R_T$=4.69 min, m/z=301.14 (M+H)$^+$.

LCMS (2 to 98% acetonitrile in water+0.1% formic acid over 10 mins) retention time 4.69 min, ESI+ found [M+H]=301.1

Example 21

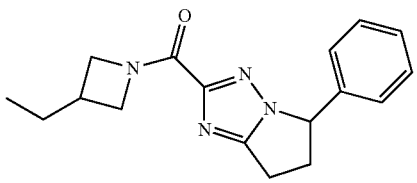 [SMILES: CCC1CN(C(=O)c2nc3n(n2)C(c2ccccc2)CC3)C1]

(3-ethylazetidin-1-yl)-(5-phenyl-6,7-dihydro-5H-pyrrolo[1,2-b][1,2,4]triazol-2-yl)methanone Method A (5.2 mg, 16% yield).

1H NMR (400 MHz, DMSO-d6) δ 7.45-7.30 (m, 3H), 7.26-7.11 (m, 2H), 5.63-5.50 (m, 1H), 4.55-4.43 (m, 1H), 4.13-3.94 (m, 2H), 3.64-3.53 (m, 1H), 3.30-3.25 (m, 1H), 3.25-3.12 (m, 1H), 3.12-3.02 (m, 1H). 3.02-2.91 (m, 1H), 2.58-2.52 (m, 1H), 1.60-1.49 (m, 2H). 0.87-0.79 (m, 3H). LC-MS $R_T$=5.03 min, m/z=297.16 (M+H)$^+$.

LCMS (2 to 98% acetonitrile in water+0.1% formic acid over 10 mins) retention time 5.03 min, ESI+ found [M+H]=297.1

Example 22

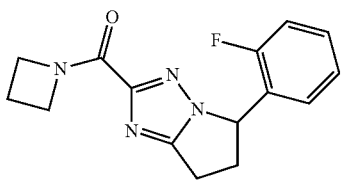 [SMILES: O=C(c1nc2n(n1)C(c1ccccc1F)CC2)N1CCC1]

Azetidin-1-yl-[5-(2-fluorophenyl)-6,7-dihydro-5H-pyrrolo[1,2-b][1,2,4]triazol-2-yl]methanone Method A (4.0 mg, 17% yield).

LC-MS $R_T$=4.17 min, m/z=287.12 (M+H)$^+$.

LCMS (2 to 98% acetonitrile in water+0.1% formic acid over 10 mins) retention time 4.17 min, ESI+ found [M+H]=287.1

Example 23

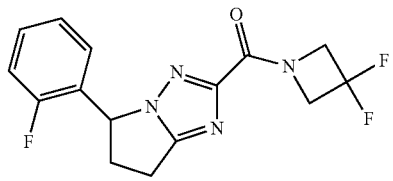 [SMILES: O=C(c1nc2n(n1)C(c1ccccc1F)CC2)N1CC(F)(F)C1]

(3,3-difluroroazetidin-1-yl)-[5-(2-fluorophenyl)-6,7-dihydro-5H-pyrrolo[1,2-b][1,2,4]triazol-2-yl]methanone Method A (16.0 mg, 62% yield).

1H NMR (400 MHz, DMSO-d6) δ 7.44 (m, 1H), 7.33-7.11 (m, 3H), 5.80 (m, J=8.6, 5.6 Hz, 1H), 4.92-4.79 (m, 2H), 4.45 (m, 2H), 3.26-3.15 (m, 1H), 3.13-2.94 (m, 2H), 2.69-2.54 (m, 1H). LC-MS $R_T$=4.64 min, m/z=323.1 (M+H)$^+$.

LCMS (2 to 98% acetonitrile in water+0.1% formic acid over 10 mins) retention time 4.64 min, ESI+ found [M+H]=323.1

Example 24

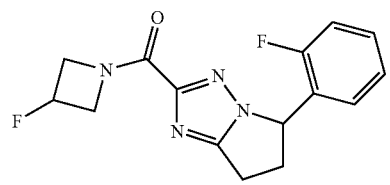 [SMILES: O=C(c1nc2n(n1)C(c1ccccc1F)CC2)N1CC(F)C1]

(3-fluoroazetidin-1-yl)-[5-(2-fluorophenyl)-6,7-dihydro-5H-pyrrolo[1,2-b][1,2,4]triazol-2-yl]methanone Method A (14.0 mg, 57% yield).

1H NMR (400 MHz, DMSO-d6) δ 7.51-7.35 (m, 1H), 7.33-7.12 (m, 3H), 5.78 (dd, J=8.6, 5.6 Hz, 1H), 5.58-5.27 (m, 1H), 4.89-4.64 (m, 1H), 4.54-4.23 (m, 2H), 4.15-3.93 (m, 1H), 3.25-3.13 (m, 1H), 3.13-2.94 (m, 2H), 2.66-2.51 (m, 1H). LC-MS $R_T$=4.20 min, m/z=305.11 (M+H)$^+$.

LCMS (2 to 98% acetonitrile in water+0.1% formic acid over 10 mins) retention time 4.20 min, ESI+ found [M+H]=305.1

Example 25

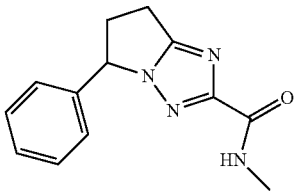 [SMILES: CNC(=O)c1nc2n(n1)C(c1ccccc1)CC2]

N-methyl-5-phenyl-6,7-dihydro-5H-pyrrolo[1,2-b][1,2,4]triazole-2-carboxamide

Method A (11.8 mg, 38% yield).

Example 26

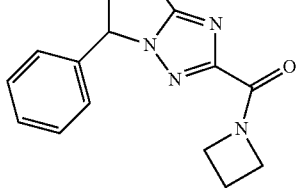

azetidin-1-yl-(5-phenyl-6,7-dihydro-5H-pyrrolo[1,2-b][1.2.4]triazol-2-yl)methanone Method A (1.8 mg, 5% yield).

Example 27

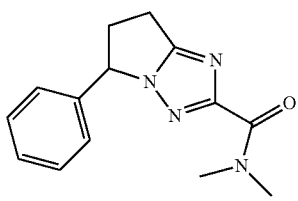 [SMILES: CN(C)C(=O)c1nc2n(n1)C(c1ccccc1)CC2]

N,N-dimethyl-5-phenyl-6,7-dihydro-5H-pyrrolo[1,2-b][1,2,4]triazole-2-carboxamide Method A (17.6 mg, 53% yield).

Example 28

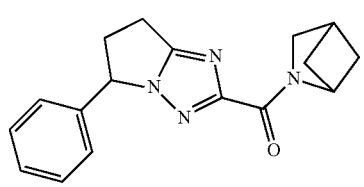 [SMILES: O=C(c1nc2n(n1)C(c1ccccc1)CC2)N1CC2CC1C2]

2-azabicyclo[2.1.1]hexan-2-yl-(5-phenyl-6,7-dihydro-5H-pyrrolo[1,2-b][1,2,4]triazol-2-yl)methanone Method A (21.2 mg, 59% yield).

Example 29

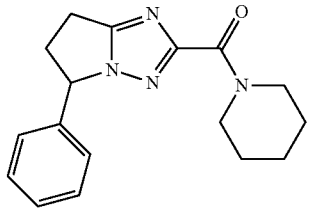 [SMILES: O=C(c1nc2n(n1)C(c1ccccc1)CC2)N1CCCCC1]

(5-phenyl-6,7-dihydro-5H-pyrrolo[1,2-b][1,2,4]triazol-2-yl)-(1-piperidyl)methanone Method A (21.5 mg, 59% yield).

Example 30

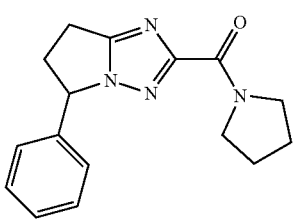 [SMILES: O=C(c1nc2n(n1)C(c1ccccc1)CC2)N1CCCC1]

(5-phenyl-6,7-dihydro-5H-pyrrolo[1,2-b][1,2,4]triazol-2-yl)-pyrrolidin-1-yl-methanone Method A (19.2 mg, 56% yield).

Example 31

SFC 3

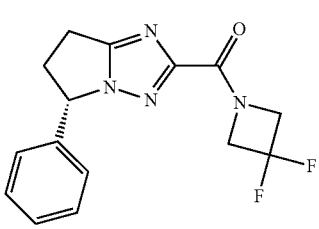 [SMILES: O=C(c1nc2n(n1)[C@H](c1ccccc1)CC2)N1CC(F)(F)C1]

(3,3-difluoroazetidin-1-yl)-[rac-(5S)-5-phenyl-6,7-dihydro-5H-pyrrolo[1,2-b][1,2,4]triazol-2-yl]methanone (8.6 mg, 33% yield)
Purification:
SFC condition: Column: Chiralpak IC 150×30.0 mm I.D 5 uM., Mobile phase: A: CO2 B: Methanol (0.1% NH4OH) Isocratic: 35%: 150 mL/min Column temperature: 40° C.

Analytical

Peak 1, Isocratic 30% MeOH, UV Wavelength: PDA Single 254.0 nm, Column: Chiralpak IC, Run Time: 2.5 Minutes, Co-Solvent: MeOH w/0.1% NH4OH, ColumnTemp: 40.0° C.

Example 32

SFC 4

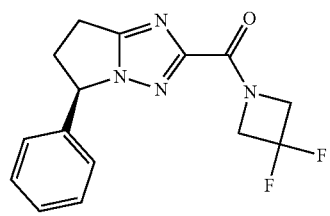 [SMILES: O=C(c1nc2n(n1)[C@@H](c1ccccc1)CC2)N1CC(F)(F)C1]

(3,3-difluoroazetidin-1-yl)-[rac-(5R)-5-phenyl-6,7-dihydro-5H-pyrrolo[1,2-b][1,2,4]triazol-2-yl]methanone (7.8 mg, 30% yield)
Purification:
SFC condition: Column: Chiralpak IC 150×30.0 mm I.D 5 uM., Mobile phase: A: CO2 B: Methanol (0.1% NH4OH) Isocratic: 35%: 150 ml/min Column temperature: 40° C.
Analytical
Peak 2, Isocratic 30% MeOH, UV Wavelength: PDA Single 254.0 nm, Column: Chiralpak IC, Run Time: 2.5 Minutes, Co-Solvent: MeOH w/0.1% NH4OH, ColumnTemp: 40.0° C.

Examples 33-48

Prepared According to One of Methods #1-16 as Described Above. See Also Table 1 Below Example 49

Method #16

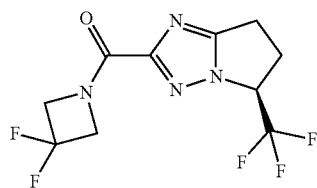 [SMILES: O=C(c1nc2n(n1)[C@H](C(F)(F)F)CC2)N1CC(F)(F)C1]

(3-difluoroazetidin-1-yl)-[(5S)-5-(trifluoromethyl)-6,7-dihydro-5H-pyrrolo[1,2-b][1,2,4]triazol-2-yl] methanone

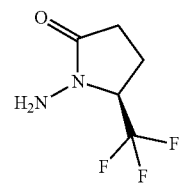

Step 1:
(S)-1-amino-5-(trifluoromethyl)pyrrolidin-2-one

To a solution of o-(diphenylphosphoryl)hydroxylamine (41.1 g, 176.4 mmol) in N,N-dimethylformamide (900 mL) was added sodium hydride (60%. 9.4 g, 235.1 mmol) at 25° C. The reaction mixture was stirred at 25° C. for 2 h and filtered. The filtrate was concentrated under reduced pressure to give (5S)-1-amino-5-(trifluoromethyl)pyrrolidin-2-one (19.5 g, 99%) as a light yellow oil which was used in the next step without further purification.

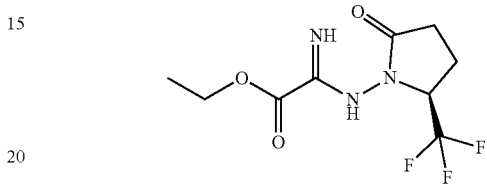

Step 2: (S)-ethyl 2-imino-2-((2-oxo-5-(trifluoromethyl)pyrrolidin-1-yl)amino)acetate To a solution of (5S)-1-amino-5-(trifluoromethyl)pyrrolidin-2-one (30.0 g, 178.4 mmol) in ethanol (280 mL) was added ethyl 2-ethoxy-2-imino-acetate (38.9 g. 267.7 mmol). The reaction mixture was stirred at 60° C. for 15 h and concentrated under reduced pressure to afford crude ethyl 2-imino-2-[[(5S)-2-oxo-5-(trifluoromethyl)pyrrolidin-1-yl] amino]acetate as a yellow oil (38.0 g, 80%) which was used in the next step without further purification.

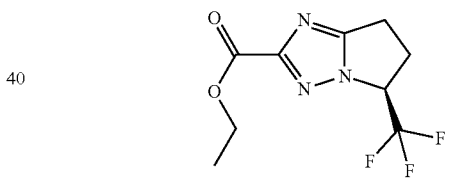

Step 3: (S)-ethyl 5-(trifluoromethyl)-6,7-dihydro-5H-pyrrolo[1,2-b][1,2,4]triazole-2-carboxylate A mixture of phosphorus oxychloride (284.2 g. 1853.6 mmol) and ethyl 2-imino-2-[[(5S)-2-oxo-5-(trifluoromethyl)pyrrolidin-1-yl]amino]acetate (37.5 g. 140.3 mmol) was heated at 110° C. for 1 h and concentrated under reduced pressure. The residue was poured into water (50 mL) and adjusted to pH=10 by addition of saturated aqueous sodium bicarbonate. The resulting mixture was extracted with ethyl acetate (3×200 mL). The combined organic layers were dried and concentrated under reduced pressure. The residue was purified by column chromatography (silica gel, 100-200 mesh, 0 to 50% ethyl acetate in petroleum ether) to afford ethyl (5S)-5-(trifluoromethyl)-6,7-dihydro-5H-pyrrolo[1,2-b][1,2,4]triazole-2-carboxylate as a white solid (22.0 g. 63%).

LCMS (5 to 95% acetonitrile in water+0.03% trifluoacetic acid over 1.5 mins) retention time 0.508 min, ESI+ found [M+H]=250.0.

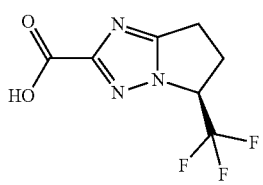 [SMILES: O=C(O)c1nc2n(n1)[C@H](C(F)(F)F)CC2]

Step 4: (S)-5-(trifluoromethyl)-6,7-dihydro-5H-pyrrolo[1,2-b][1,2,4]triazole-2-carboxylic acid To a solution of ethyl (5S)-5-(trifluoromethyl)-6,7-dihydro-5H-pyrrolo[1,2-b][1,2,4]triazole-2-carboxylate (8.0 g, 32.1 mmol) in tetrahydrofuran (80 mL) was added a solution of lithium hydroxide monohydrate (4.0 g, 96.3 mmol) in water (40 mL). The mixture was stirred at 25° C. for 16 h and concentrated under reduced pressure to remove the organic solvent. The residue was diluted with water (30 mL) and washed with ethyl acetate (30 mL). The aqueous layer was adjusted to pH=3 by addition of aqueous hydrochloric acid (4 N). The crude product was collected by filtration and dried in vacuo to give (5S)-5-(trifluoromethyl)-6,7-dihydro-5H-pyrrolo[1,2-b][1,2,4]triazole-2-carboxylic acid as a white solid (6.0 g, 85%).

LCMS (5 to 95% acetonitrile in water+0.03% trifluoacetic acid over 2 mins) retention time 0.729 min, ESI+ found [M+H]=222.2.

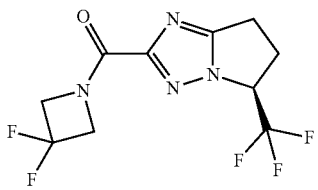 [SMILES: O=C(c1nc2n(n1)[C@H](C(F)(F)F)CC2)N1CC(F)(F)C1]

Step 5: (3,3-difluoroazetidin-1-yl)-[(5S)-5-(trifluoromethyl)-6,7-dihydro-5H-pyrrolo[1,2-b][1,2,4]triazol-2-yl]methanone A mixture of (5S)-5-(trifluoromethyl)-6,7-dihydro-5H-pyrrolo[1,2-b][1,2,4]triazole-2-carboxylic acid (60 mg, 0.27 mmol). 1-(3-dimethylaminopropyl)-3-ethylcarbodiimidehydrochloride (68 mg, 0.35 mmol), 1-hydroxybenzotriazole (37 mg. 0.27 mmol), 3,3-difluoroazetidine hydrochloride (53 mg, 0.41 mmol) and N,N-diisopropylethylamine (70 mg, 0.54 mmol) in N,N-dimethylformamide (3.5 mL) was stirred at 25 (2 for 4 h and concentrated under reduced pressure. The residue was purified by RP-HPLC (acetonitrile 25-55%/0.05% ammonia hydroxide in water) to afford (3,3-difluoroazetidin-1-yl)-[(5S)-5-(trifluoromethyl)-6,7-dihydro-5H-pyrrolo[1,2-b][1,2,4]triazol-2-yl]methanone (33.8 mg, 42%) as a white solid. $^1$H NMR (400 MHz, CD$_3$OD) δ 5.30-5.26 (m, 1H), 4.99-4.92 (m, 2H), 4.56-4.50 (m, 2H), 3.13-3.02 (m, 23), 2.88-2.87 (m, 1H). LCMS R$_T$=1.294 min, m/z=297.1 [M+H]$^+$.

LCMS (10 to 80% acetonitrile in water+0.1% ammonia water over 3.0 mins) retention time 1.294 min, ESI+ found [M+H]=297.1.

Example 50

Method 17

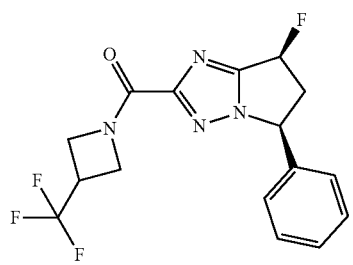 [SMILES: O=C(c1nc2n(n1)[C@H](c1ccccc1)C[C@@H]2F)N1CC(C(F)(F)F)C1]

[rac-(5S,7S)-7-fluoro-5-phenyl-6,7-dihydro-5H-pyrrolo[1,2-b][1,2,4]triazol-2-yl]-[3-(trifluoromethyl)azetidin-1-yl]methanone A mixture of cis-7-fluoro-5-phenyl-6,7-dihydro-5H-pyrrolo[1,2-b][1,2,4]triazole-2-carboxylic acid (25 mg, 0.10 mmol), 3-(trifluoromethyl)azetidine hydrochloride (18 mg, 0.11 mmol), HATU (44 mg, 0.11 mmol) and N-ethyl-N-isopropylpropan-2-amine (0.07 mL, 0.40 mmol) in N,N-dimethylformamide (0.5 mL) was stirred at 25° C. for 12 h. Isopropyl acetate was added to the reaction mixture. The resulting solution was washed with water (2×20 mL) and saturated aqueous sodium chloride solution. The organic was dried over magnesium sulfate, filtered, and concentrated. The residue was further purified by preparative RP-HPLC (20-60% acetonitrile in water+0.1% formic acid) to afford [rac-(5S,7S)-7-fluoro-5-phenyl-6,7-dihydro-5H-pyrrolo[1,2-b][1,2,4]triazol-2-yl]-[3-(trifluoromethyl)azetidin-1-yl]methanone (20.5 mg, 56%) as a white solid. $^1$H NMR (400 MHz, DMSO-d$_6$) δ 7.49-7.32 (m, 3H), 7.29-7.16 (m, 2H), 6.21 (ddt, J=56.5, 7.2, 1.9 Hz, 1H), 5.70 (ddd, J=9.0, 6.7, 3.0 Hz, 1H), 4.72 (dt, J=13.1, 9.7 Hz, 1H), 4.45 (td, J=9.7, 5.4 Hz, 1H), 4.29 (t, J=9.9 Hz, 1H), 4.02 (dd, J=10.7, 5.4 Hz, 1H), 3.87-3.55 (m, 2H), 2.85-2.54 (m, 1H). LCMS R$_T$=4.59 min, m/z=355.1 [M+H]$^+$.

LCMS (2 to 98% acetonitrile in water+0.1% formic acid over 10 mins) retention time 4.59 min, ESI+ found [M+H]=355.1

Example 51

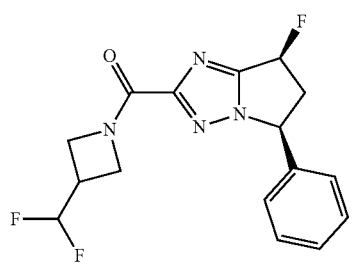 [SMILES: O=C(c1nc2n(n1)[C@H](c1ccccc1)C[C@@H]2F)N1CC(C(F)F)C1]

[3-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone Method 17 (12.9 mg. 38% yield)

$^1$H NMR (400 MHz, DMSO-d$_6$) δ 7.49-7.32 (m, 3H), 7.27-7.11 (m, 2H), 6.59-6.09 (m, 2H), 5.69 (ddd, J=8.9, 6.7, 3.0 Hz, 1H), 4.56 (q, J=9.0 Hz, 1H), 4.38 (td, J=11.0, 5.6 Hz, 1H), 4.14 (t, J=9.7 Hz, 1H), 3.95 (dd, J=10.5, 5.5 Hz, 1H), 3.72 (dddd, J=26.2, 15.5, 8.5, 7.1 Hz, 1H), 3.24-3.05 (m, 1H), 2.79-2.58 (m, 1H). LCMS R$_T$=4.22 min, m/z=337.1 [M+H]$^+$.

LCMS (2 to 98% acetonitrile in water+0.1% formic acid over 10 mins) retention time 4.22 min, ESI+ found [M+H]=337.1

Examples 52 and 53

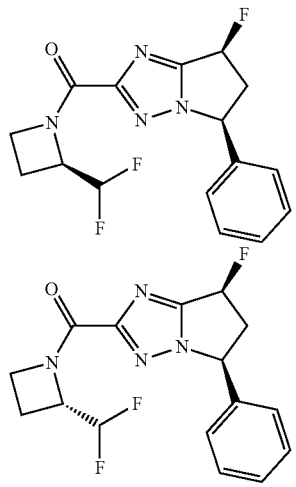

[rac-(2R)-2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone & [rac-(2S)-2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone

[2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone was prepared corresponding from 2-(difluoromethyl)azetidine 2,2,2-trifluoroacetate and rac-(5S,7S)-7-fluoro-5-phenyl-6,7-dihydro-5H-pyrrolo[1,2-b][1,2,4]triazole-2-carboxylic acid according to Method 17. The crude residue was further purified by chiral SFC (Chiralpak AD; 150×21.2 mm; 20% methanol isocratic elution with Carbon Dioxide) affording arbitrarily assigned two diastereomers as below:

[rac-(2R)-2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone (30.7 mg, 28.2%) as white solids

[rac-(2S)-2-(difluoromethyl)azetidin-11-yl]-[rac-(5 S,7S)-7-fluoro-5-phenyl-6,7-dihydro-5H-pyrrolo[1,2-b][1,2,4]triazol-2-yl]methanone (32.3 mg, 30.0%) as white solids Analytical data for the first eluting diastereomer (arbitrarily assigned 2R, 5S, 7S configuration): SFC R$_T$(Chiralpak AD, 15% methanol+0.1% ammonium hydroxide isocratic elution with Carbon Dioxide, 2.5 min method): 0.711 min, 100% purity, 100% ee: 1H NMR (400 MHz, DMSO-d6) δ 7.47-7.32 (m, 3H), 7.28-7.18 (m, 2H), 6.80-6.08 (m, 2H). 5.70 (td, J=8.8, 7.7, 2.8 Hz, 1H), 5.18-4.62 (m, 1H), 4.39 (dt, J=9.1, 6.5 Hz, 1H), 3.98 (dtd, J=38.7, 9.5, 6.0 Hz, 1H), 3.73 (dddd, J=26.1, 15.5, 8.5, 7.1 Hz, 1H), 2.78-2.51 (m, 1H), 2.42 (dddd, J=15.6, 11.7, 8.5, 5.7 Hz, 1H), 2.27 (dddd, J=11.5, 8.7, 6.1, 2.7 Hz, 1H). LCMS R$_T$=10.48 min, m/z=337.1 (M+H)$^+$.

LCMS (5 to 95% acetonitrile in water+0.1% formic acid over 30 mins) retention time 10.48 min, ESI+ found [M+H]=337.1

Analytical data for the second eluting diastereomer (arbitrarily assigned 2S, 5S, 7S configuration): SFC R$_T$(Chiralpak AD, 15% methanol+0.1% ammonium hydroxide isocratic elution with Carbon Dioxide, 2.5 min method): 0.990 min, 99.4% purity, 98.8% ee: $^1$H NMR (400 MHz. DMSO-d$_6$) δ 7.40 (dddd, J=10.6, 8.6, 6.7, 3.6 Hz, 3H), 7.31-7.16 (m, 2H), 6.78-6.02 (m, 2H), 5.70 (ddd, J=8.8, 6.7, 2.8 Hz. 1H), 5.32-4.62 (m, 1H), 4.38 (dd, J=8.5, 7.0 Hz, 1H), 4.11-3.84 (m, 1H), 3.73 (dddd, J=26.0, 15.4, 8.5, 7.1 Hz, 1H), 2.81-2.58 (m, 1H), 2.48-2.35 (m, 1H), 2.34-2.17 (m, 1H).

LCMS R$_T$=10.53 min, m/z=337.1 (M+H)$^+$.

LCMS (5 to 95% acetonitrile in water+0.1% formic acid over 30 mins) retention time 10.53 min, ESI+ found [M+H]=337.1

Example 54

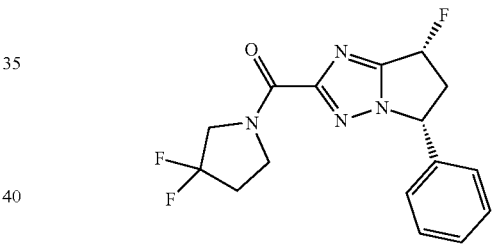

(3,3-difluoropyrrolidin-1-yl)-[rac-(5R,7R)-7-fluoro-5-phenyl-6,7-dihydro-5H-pyrrolo[1,2-b][1,2,4]triazol-2-yl]methanone Method 17 (63 mg, 89% yield)

The crude residue was further purified by chiral SFC (Whelko-01; 150×21.2 mm; 45% methanol isocratic elution with Carbon Dioxide) affording arbitrarily assigned diastereomers (3,3-difluoropyrrolidin-1-yl)-[rac-(5R,7R)-7-fluoro-5-phenyl-6,7-dihydro-5H-pyrrolo[1,2-b][1,2,4]triazol-2-yl]methanone (8.0 mg. 31%) as white solids Analytical data for the second eluting diastereomer (arbitrarily assigned 5R, 7R configuration): SFC R$_T$(Whelk-Ol S,S, 40% methanol+0.1% ammonium hydroxide isocratic elution with Carbon Dioxide, 2.5 min method): 1.311 min, 93% purity, 86% ee: $^1$H NMR (400 MHz, DMSO-d$_6$) δ 7.53-7.33 (m, 3H), 7.24 (ddd, J=7.8, 3.7, 1.5 Hz, 2H), 6.22 (ddd, J=56.5, 7.2, 1.9 Hz, 1H), 5.70 (td, J=8.0, 4.2 Hz, 1H), 4.22 (t, J=12.9 Hz, 1H), 4.05-3.96 (m, 1H), 3.91 (t, J=13.2 Hz. 1H), 3.85-3.61 (m, 2H), 2.69 (ddt, J=26.8, 15.2, 2.4 Hz, 1H), 2.49-2.31 (m, 2H). LCMS R$_T$=4.42 min, m/z=337.1 (M+H)$^+$.

LCMS (5 to 95% acetonitrile in water+0.1% formic acid over 10 mins) retention time 4.42 min, ESI+ found [M+H]=337.1

Example 55

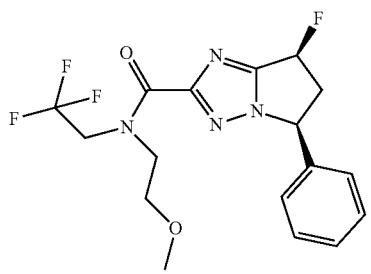 [SMILES: COCCN(CC(F)(F)F)C(=O)c1nc2n(n1)[C@H](c1ccccc1)C[C@@H]2F]

rac-(5S,7S)-7-fluoro-N-(2-methoxyethyl)-5-phenyl-N-(2,2,2-trifluoroethyl)-6,7-dihydro-5H-pyrrolo[1,2-b][1,2,4]triazole-2-carboxamide Method 17 (3.2 mg, 80 yield)
$^1$H NMR (400 MHz, DMSO-d$_6$) δ 7.47-7.33 (m, 3H), 7.27-7.18 (m, 2H), 6.36-6.03 (m, 1H). 5.68 (dddd, J=18.3, 15.5, 8.8, 3.7 Hz, 1H), 4.39 (qd, J=9.5, 6.4 Hz, 1H), 3.93-3.67 (m, 2H), 3.57-3.38 (m, 2H), 3.29-3.21 (m, 3H), 2.78-2.61 (m, 1H), 1.39 (dd, J=6.6, 1.4 Hz, 1H), 1.11 (dd, J=12.5, 6.6 Hz, 1H). LCMS R$_T$=4.89 min. m % z=387.2 (M+H)$^+$.

LCMS (2 to 98% acetonitrile in water+0.1% formic acid over 10 mins) retention time 4.89 min, ESI+ found [M+H]=387.2

Example 56

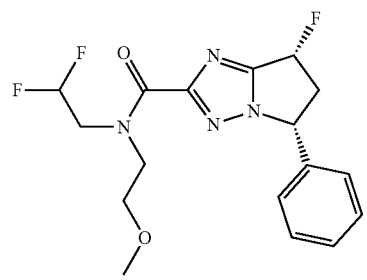 [SMILES: COCCN(CC(F)F)C(=O)c1nc2n(n1)[C@@H](c1ccccc1)C[C@H]2F]

rac-(5R,7R)—N-(2,2-difluoroethyl)-7-fluoro-N-(2-methoxyethyl)-5-phenyl-6,7-dihydro-5H-pyrrolo[1,2-b][1,2,4]triazole-2-carboxamide Method 17 (10 mg, 27% yield)
The crude residue was further purified by achiral SFC (Pyridyl Amide; 150×21.2 mm; 5-60% methanol elution with Carbon Dioxide) affording arbitrarily assigned diastereomers rac-(5R,7R)—N-(2,2-difluoroethyl)-7-fluoro-N-(2-methoxyethyl)-5-phenyl-6,7-dihydro-5H-pyrrolo[1,2-b][1,2,4]triazole-2-carboxamide
$^1$H NMR (400 MHz, DMSO-d) δ 7.56-7.05 (m, 5H), 6.50-5.95 (m, 2H), 5.69 (ddd, J=8.4, 6.7, 3.0 Hz, 1H), 4.14 (td, J=14.6, 4.0 Hz, 1H), 3.91 (tdd, J=14.8, 4.1, 2.7 Hz, 1H), 3.83-3.61 (m, 3H), 3.49 (dt, J=38.7, 5.6 Hz, 2H), 3.11 (s, 3H), 2.69 (ddtd, J=23.7, 13.9, 3.3, 1.8 Hz, 1H). LCMS R$_T$=4.57 min, m/z=369.2 (M+H)$^+$.

LCMS (5 to 95% acetonitrile in water+0.1% formic acid over 10 mins) retention time 4.57 min, ESI+ found [M+H]=369.2

Example 57

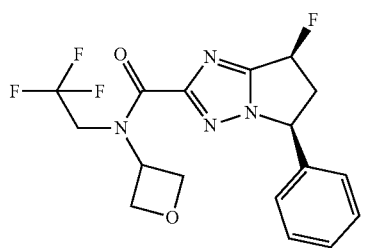 [SMILES: O=C(c1nc2n(n1)[C@H](c1ccccc1)C[C@@H]2F)N(CC(F)(F)F)C1COC1]

rac-(5S,7S)-7-fluoro-N-(oxetan-3-yl)-5-phenyl-N-(2,2,2-trifluoroethyl)-6,7-dihydro-5H-pyrrolo[1,2-b][1,2,4]triazole-2-carboxamide Method 17 (2 mg, 4% yield)
NO NMR
LCMS R$_T$=4.51 min, m/z=385.1 (M+H)$^+$.

LCMS (5 to 95% acetonitrile in water+0.1% formic acid over 10 mins) retention time 4.51 min, ESI+ found [M+H]=385.1

Example 58

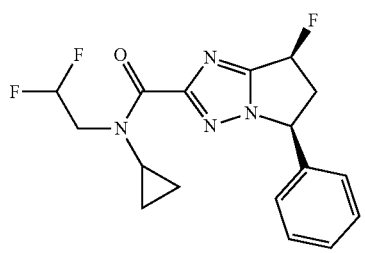 [SMILES: O=C(c1nc2n(n1)[C@H](c1ccccc1)C[C@@H]2F)N(CC(F)F)C1CC1]

rac-(5S,7S)—N-cyclopropyl-N-(2,2-difluoroethyl)-7-fluoro-5-phenyl-6,7-dihydro-5H-pyrrolo[1,2-b][1,2,4]triazole-2-carboxamide Method 17 (33.9 mg, 96% yield)
$^1$H NMR (400 MHz, DMSO-d6) δ 7.47-7.32 (m, 3H), 7.26-7.18 (m, 2H), 6.56-6.03 (m, 2H), 5.80-5.62 (m, 1H), 4.24-3.55 (m, 4H), 2.92 (s, 1H), 2.80-2.50 (m, 1H), 0.91-0.35 (m, 3H). LCMS R$_T$=4.68 min, m/z=351.1 (M+H)$^+$.

LCMS (5 to 95% acetonitrile in water+0.1% formic acid over 10 mins) retention time 4.68 min, ESI+ found [M+H]=351.1

Example 59

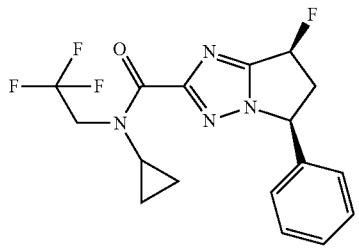 [SMILES: O=C(c1nc2n(n1)[C@H](c1ccccc1)C[C@@H]2F)N(CC(F)(F)F)C1CC1]

rac-(5S,7S)—N-cyclopropyl-7-fluoro-5-phenyl-N-(2,2,2-trifluoroethyl)-6,7-dihydro-5H-pyrrolo[1,2-b][1,2,4]triazole-2-carboxamide Method 17 (3.5 mg, 9% yield)

$^1$H NMR (400 MHz, DMSO-d$_6$) δ 7.54-7.25 (m, 3H), 7.33-7.10 (m, 2H), 6.23 (ddd, J=56.6, 7.1, 1.7 Hz, 1H). 5.84-5.60 (m, 1H), 4.95-4.19 (m, 2H), 3.75 (ddt, J=26.2, 15.5, 7.8 Hz, 1H), 2.92 (s, 1H), 2.84-2.45 (m, 1H), 0.97-0.43 (m, 4H). LCMS R$_T$=5.01 min, m/z=369.1 (M+H)$^+$.

LCMS (5 to 95% acetonitrile in water+0.1% formic acid over 10 mins) retention time 5.01 min, ESI+ found [M+H]=369.1

Example 60

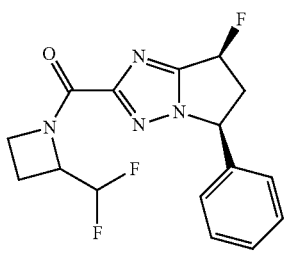 [SMILES: O=C(c1nc2n(n1)[C@H](c1ccccc1)C[C@@H]2F)N1CCC1C(F)F]

[2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone Method 17 (25.3 mg, 74% yield)

$^1$H NMR (400 MHz. DMSO-d6) δ 7.53-7.31 (m, 3H). 7.23 (td, J=7.9, 1.9 Hz, 2H), 6.63-6.07 (m, 2H), 5.70 (ddd, J=8.8, 5.4, 2.8 Hz, 1H), 5.32-4.61 (m, 1H), 4.39 (dp, J=9.6, 3.4 Hz, 1H), 4.08-3.87 (m, 1H), 3.73 (dddd, J=26.1, 15.5, 8.5, 7.2 Hz, 1H), 2.78-2.61 (m, 1H), 2.51-2.34 (m, 1H), 2.33-2.21 (m, 1H). LCMS R$_T$=4.46 min, m/z=337.1 (M+H)$^+$.

LCMS (5 to 95% acetonitrile in water+0.1% formic acid over 10 mins) retention time 4.46 min, ESI+ found [M+H]=337.1

Example 61

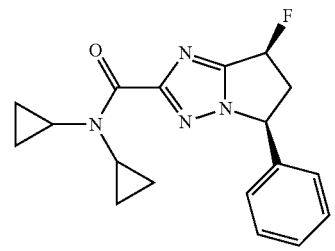 [SMILES: O=C(c1nc2n(n1)[C@H](c1ccccc1)C[C@@H]2F)N(C1CC1)C1CC1]

rac-(5S,7S)—N,N-dicyclopropyl-7-fluoro-5-phenyl-6,7-dihydro-5H-pyrrolo[1,2-b][1,2,4]triazole-2-carboxamide Method 17 (27.2 mg, 82% yield)

1H NMR (400 MHz, DMSO-d6) δ 7.46-7.30 (m, 3H), 7.23-7.15 (m, 2H), 6.20 (ddd, J=56.7, 7.1, 1.7 Hz, 1H), 5.68 (ddd, J=8.8, 6.7, 2.8 Hz, 1H), 3.73 (dddd, J=26.6, 15.5, 8.5, 7.1 Hz, 1H), 2.76-2.51 (m, 3H), 0.60 (m, 8H). LCMS R$_T$=4.40 min, m/z=327.2 (M+H)$^+$.

LCMS (5 to 95% acetonitrile in water+0.1% formic acid over 10 mins) retention time 4.40 min, ESI+ found [M+H]=327.2

Example 62

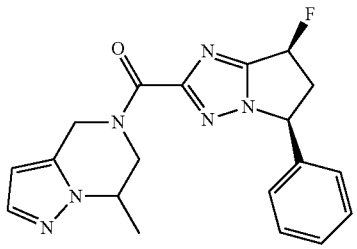 [SMILES: CC1CN(C(=O)c2nc3n(n2)[C@H](c2ccccc2)C[C@@H]3F)Cc2ccnn21]

(7-methyl-6,7-dihydro-4H-pyrazolo[1,5-a]pyrazin-5-yl)-[rac-(5S,7S)-7-fluoro-5-phenyl-6,7-dihydro-5H-pyrrolo[1,2-b][1,2,4]triazol-2-yl]methanone Method 17 (39.1 mg, 99% yield)

$^1$H NMR (400 MHz, DMSO-d$_6$) δ 7.52-7.31 (m, 4H), 7.26 (dt, J=8.7, 3.1 Hz, 2H), 6.42-5.94 (m, 2H), 5.71 (t, J=6.6 Hz. 1H), 5.11-4.91 (m, 1H), 5.05-4.71 (m, 1H), 4.37 (dq, J=13.1, 6.6 Hz, 1H), 4.26-4.06 (m, 1H), 4.02-3.62 (m, 2H), 2.87-2.57 (m, 1H), 1.50-1.21 (m, 3H). LCMS R$_T$=4.05 min, m/z=367.2 (M+H)$^+$.

LCMS (5 to 95% acetonitrile in water+0.1% formic acid over 10 mins) retention time 4.05 min, ESI+ found [M+H]=367.2

Example 63

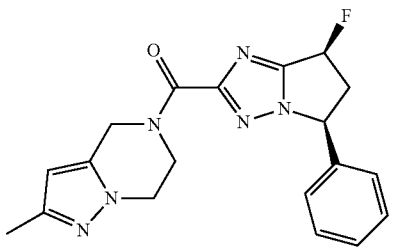 [SMILES: Cc1cc2n(n1)CCN(C(=O)c1nc3n(n1)[C@H](c1ccccc1)C[C@@H]3F)C2]

(2-methyl-6,7-dihydro-4H-pyrazolo[1,5-a]pyrazin-5-yl)-[rac-(5S,7S)-7-fluoro-5-phenyl-6,7-dihydro-5H-pyrrolo[1,2-b][1,2,4]triazol-2-yl]methanone Method 17 (28.7 mg, 77% yield)

$^1$H NMR (400 MHz, DMSO-d6) δ 7.52-7.33 (m, 3H), 7.26 (ddd, J=8.0, 3.5, 1.5 Hz, 2H), 6.23 (ddt J=56.5, 7.2, 2.3 Hz, 1H), 5.78-5.63 (m, 1H), 4.94 (s, 1H), 4.81 (d, J=2.8 Hz, 1H), 4.19-4.01 (m, 4H), 3.74 (ddt, J=25.8, 15.5, 7.8 Hz, 1H), 2.79-2.62 (m, 1H), 2.12 (d, J=8.8 Hz, 3H). LCMS $R_T$=4.01 min, m % z=367.2 (M+H)$^+$.

LCMS (5 to 95% acetonitrile in water+0.1% formic acid over 10 mins) retention time 4.01 min, ESI+ found [M+H]=367.2

Examples 64 and 65

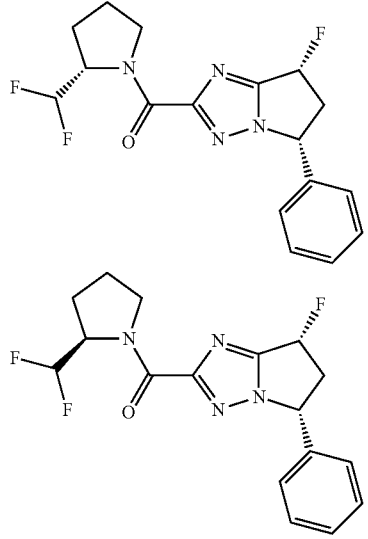

[rac-(2S)-2-(difluoromethyl)pyrrolidin-1-yl]-[rac-(5R,7R)-7-fluoro-5-phenyl-6,7-dihydro-5H-pyrrolo[1,2-b][1,2,4]triazol-2-yl]methanone & [rac-(2R)-2-(difluoromethyl)pyrrolidin-1-yl]-[rac-(5R,7R)-7-fluoro-5-phenyl-6,7-dihydro-H-pyrrolo[1,2-b][1,2,4]triazol-2-yl]methanone

[2-(difluoromethyl)pyrrolidin-1-yl]-[rac-(5R,7R)-7-fluoro-5-phenyl-6,7-dihydro-5H-pyrrolo[1,2-b][1,2,4]triazol-2-yl]methanone was prepared according to Method 17. The crude residue was further purified by chiral SFC (Whelko-01; 150×21.2 mm; 45% methanol isocratic elution with Carbon Dioxide) affording arbitrarily assigned two diastereomers as below:

[rac-(2S)-2-(difluoromethyl)pyrrolidin-1-yl]-[rac-(5R,7R)-7-fluoro-5-phenyl-6,7-dihydro-5H-pyrrolo[1,2-b][1,2,4]triazol-2-yl]methanone (10.9 mg, 15%) as white solids

[rac-(2R)-2-(difluoromethyl)pyrrolidin-1-yl]-[rac-(5R,7R)-7-fluoro-5-phenyl-6,7-dihydro-5H-pyrrolo[1,2-b][1,2,4]triazol-2-yl]methanone (9.5 mg, 13%) as white solids Analytical data for the fourth eluting diastereomer (arbitrarily assigned 2S, 5R, 7R configuration): SFC $R_T$ (Whelk-Ol S,S, 35% methanol+0.1% ammonium hydroxide isocratic elution with Carbon Dioxide, 2.5 min method): 1.559 min, 100% purity, 100% ee: $^1$H NMR (400 MHz, DMSO-d$_6$) δ 7.47-7.33 (m, 3H), 7.23 (ddd, J=7.4, 3.8, 1.5 Hz, 2H), 6.59-5.98 (m, 2H), 5.70 (ddt, J=9.4, 6.5, 2.9 Hz, 1H), 5.16-4.43 (m, 1H), 3.86-3.62 (m, 3H), 2.77-2.61 (m, 1H), 2.16-1.79 (m, 4H). LCMS $R_T$=4.72 min, m/z=351.1 (M+H)$^+$.

LCMS (5 to 95% acetonitrile in water+0.1% formic acid over 10 mins) retention time 4.72 min, ESI+ found [M+H]=351.1

Analytical data for the third eluting diastereomer (arbitrarily assigned 2R, 5R, 7R configuration): SFC $R_T$ (Whelk-Ol S,S, 35% methanol+0.1% ammonium hydroxide isocratic elution with Carbon Dioxide, 2.5 min method): 1.272 min, 100% purity, 100% ee: $^1$H NMR (400 MHz. DMSO-d$_6$) δ 7.47-7.33 (m, 3H), 7.22 (tt, J=8.5, 1.6 Hz, 2H), 6.51-5.99 (m, 2H), 5.70 (ddd, J=9.5, 7.0, 3.0 Hz, 1H), 5.12-4.38 (m, 1H), 3.88-3.61 (m, 3H), 2.77-2.60 (m, 1H), 2.16-1.78 (m, 4H). LCMS $R_T$=4.71 min, m/z=351.2 (M+H)$^+$.

LCMS (5 to 95% acetonitrile in water+0.1% formic acid over 10 mins) retention time 4.71 min, ESI+ found [M+H]=351.2

Example 66

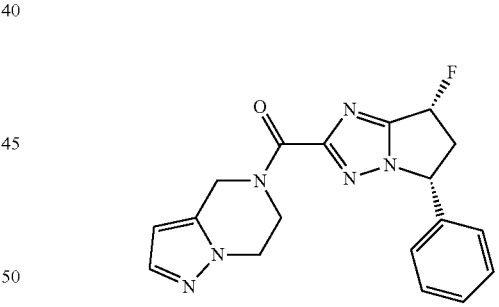

6,7-dihydro-4H-pyrazolo[1,5-a]pyrazin-5-yl-[rac-(5R,7R)-7-fluoro-5-phenyl-6,7-dihydro-5H-pyrrolo[1,2-b][1,2,4]triazol-2-yl]methanone 6,7-dihydro-4H-pyrazolo[1,5-a]pyrazin-5-yl-[rac-(5R,7R)-7-fluoro-5-phenyl-6,7-dihydro-5H-pyrrolo[1,2-b][1,2,4]triazol-2-yl]methanone was prepared according to Method 17. The crude residue was further purified by chiral SFC (Chiralpak IC; 150×21.2 mm; 50% methanol isocratic elution with Carbon Dioxide) affording arbitrarily assigned diastereomers as below:

6,7-dihydro-4H-pyrazolo[1,5-a]pyrazin-5-yl-[rac-(5R,7R)-7-fluoro-5-phenyl-6,7-dihydro-5H-pyrrolo[1,2-b][1,2,4]triazol-2-yl]methanone (7.5 mg, 28%) as white solids Analytical data for this second eluting diastereomer (arbitrarily assigned 5R, 7R configuration): SFC $R_T$(Chiralpak IC, 40% methanol+0.1% ammonium hydroxide isocratic elution with Carbon Dioxide, 2.5 min method): 1.583 min, 100% purity, 100% ee: $^1$H NMR (400 MHz, DMSO-$d_6$) δ 7.48-7.34 (m, 4H), 7.30-7.23 (m, 2H), 6.39-6.00 (m, 2H), 5.70 (dtd, J=8.9, 6.2, 2.9 Hz, 1H), 5.02 (s, 1H), 4.88 (d, J=2.2 Hz, 1H), 4.27-4.00 (m, 4H), 3.75 (dddd, J=26.3, 14.6, 8.9, 7.3 Hz, 1H), 2.71 (ddd, J=26.7, 15.3, 2.6 Hz, 1H). LCMS $R_T$=3.84 min, m/z=353.2 (M+H)$^+$.

LCMS (5 to 95% acetonitrile in water+0.1% formic acid over 10 mins) retention time 3.84 min, ESI+ found [M+H]=353.2

Example 67

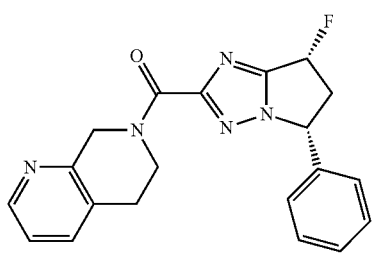 [SMILES: O=C(c1nc2n(n1)[C@@H](c1ccccc1)C[C@H]2F)N1CCc2cccnc2C1]

6,8-dihydro-5H-1,7-naphthyridin-7-yl-[rac-(5R,7R)-7-fluoro-5-phenyl-6,7-dihydro-5H-pyrrolo[1,2-b][1,2,4]triazol-2-yl]methanone 6,8-dihydro-5H-1,7-naphthyridin-7-yl-[rac-(5R,7R)-7-fluoro-5-phenyl-6,7-dihydro-5H-pyrrolo[1,2-b][1,2,4]triazol-2-yl]methanone was prepared according to Method 17. The crude residue was further purified by chiral SFC (Whelko-01; 150×21.2 mm; 50% methanol isocratic elution with Carbon Dioxide) affording arbitrarily assigned diastereomers as below:

6,8-dihydro-5H-1,7-naphthyridin-7-yl-[rac-(5R,7R)-7-fluoro-5-phenyl-6,7-dihydro-5H-pyrrolo[1,2-b][1,2,4]triazol-2-yl]methanone (6.8 mg, 25%) as white solids Analytical data for this second eluting diastereomer (arbitrarily assigned 5R, 7R configuration): SFC $R_T$ (Whelk-O1 S,S, 45% methanol+0.1% ammonium hydroxide isocratic elution with Carbon Dioxide, 2.5 min method): 2.053 min, 100% purity, 100% ee: $^1$H NMR (400 MHz, DMSO-d6) δ 8.38 (ddd, J=25.5, 4.7, 1.6 Hz, 1H), 7.61 (ddd, J=7.8, 4.6, 1.6 Hz, 1H), 7.48-7.33 (m, 3H), 7.30-7.19 (m, 3H), 6.37-6.08 (m, 1H), 5.70 (dtd, J=8.5, 5.6, 3.0 Hz, 1H), 4.83 (d, J=29.7 Hz, 2H). 4.03-3.84 (m, 2H), 3.84-3.63 (m, 1H), 2.89 (t, J=5.9 Hz, 2H), 2.79-2.62 (m, 1H). LCMS $R_T$=3.44 min, m/z=364.2 (M+H)$^+$.

LCMS (5 to 95% acetonitrile in water+0.1% formic acid over 10 mins) retention time 3.44 min, ESI+ found [M+H]=364.2

Example 68

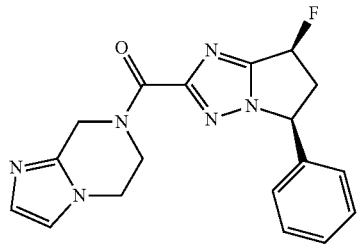

6,8-dihydro-5H-imidazo[1,2-a]pyrazin-7-yl-[rac-(5S,7S)-7-fluoro-5-phenyl-6,7-dihydro-5H-pyrrolo[1,2-b][1,2,4]triazol-2-yl]methanone Method 17 (23.0 mg, 65% yield)

$^1$H NMR (400 MHz, DMSO-$d_6$) δ 7.58-7.26 (m, 3H), 7.38-7.11 (m, 2H), 7.12 (d, J=1.2 Hz, 1H), 6.89 (dd. J=14.9, 1.3 Hz, 1H), 6.23 (ddd, J=56.6, 7.2, 1.9 Hz, 1H), 5.70 (tt, J=7.3, 3.4 Hz, 1H), 4.87 (d, J=63.2 Hz, 2H), 4.09 (dt, J=12.6, 3.7 Hz, 4H), 3.91-3.58 (m, 1H), 2.71 (ddt, J=26.7, 15.2, 2.4 Hz, 1H). LCMS $R_T$=2.44 min, m/z=353.2 (M+H)$^+$.

LCMS (5 to 95% acetonitrile in water+0.1% formic acid over 10 mins) retention time 2.44 min, ESI+ found [M+H]=353.2

Example 69

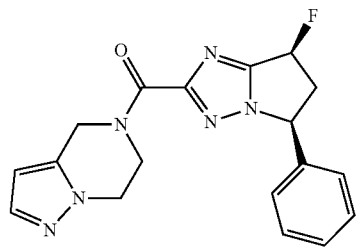 [SMILES: O=C(c1nc2n(n1)[C@H](c1ccccc1)C[C@@H]2F)N1CCn2nccc2C1]

6,7-dihydro-4H-pyrazolo[1,5-a]pyrazin-5-yl-[rac-(5S,7S)-7-fluoro-5-phenyl-6,7-dihydro-5H-pyrrolo[1,2-b][1,2,4]triazol-2-yl]methanone Method 17 (25.1 mg, 65% yield)

$^1$H NMR (400 MHz, DMSO-$d_6$) δ 7.55-7.26 (m, 4H), 7.26 (dd, J=7.4, 2.9 Hz, 2H), 6.42-5.97 (m, 2H), 5.70 (ddt, J=9.2, 5.7, 2.9 Hz, 1H), 5.02 (s, 1H), 4.88 (d, J=1.9 Hz, 1H), 4.29-4.00 (m, 4H), 3.75 (ddt, J=25.8, 15.5, 7.8 Hz, 1H), 2.82-2.61 (m, 1H). LCMS $R_T$=3.83 min, m/z=353.2 (M+H)$^+$.

LCMS (5 to 95% acetonitrile in water+0.1% formic acid over 10 mins) retention time 3.83 min, ESI+ found [M+H]=353.2

Example 70

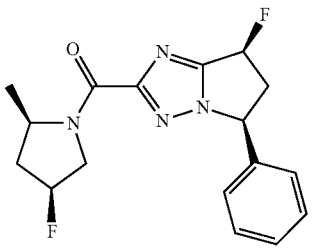 [SMILES: C[C@@H]1C[C@H](F)CN1C(=O)c1nc2n(n1)[C@H](c1ccccc1)C[C@@H]2F]

[rac-(2R,4S)-4-fluoro-2-methyl-pyrrolidin-1-yl]-[rac-(5S,7S)-7-fluoro-5-phenyl-6,7-dihydro-5H-pyrrolo[1,2-b][1,2,4]triazol-2-yl]methanone {arbitrarily assigned (2R, 4S), (5S, 7S) configuration}

Method 17 (22.7 mg, 68% yield)

$^1$H NMR (400 MHz, DMSO-d$_6$) δ 7.54-7.25 (m, 3H), 7.23 (tt, J=6.6, 2.0 Hz, 2H), 6.41-6.03 (m, 1H), 5.69 (td, J=8.2, 7.6, 2.9 Hz, 1H), 5.33 (dt, J=53.6, 4.5 Hz, 1H), 4.54 (dp. J=126.8, 7.2, 6.8 Hz, 1H), 4.22-3.62 (m, 3H), 2.84-2.59 (m, 1H), 2.46-2.12 (m, 1H), 1.96 (ddd, J=28.5, 19.6, 14.5 Hz, 1H), 1.40-1.02 (m, 3H). LCMS R$_T$=4.36 min, m/z=333.2 (M+H)$^+$.

LCMS (5 to 95% acetonitrile in water+0.1% formic acid over 10 mins) retention time 4.36 min, ESI+ found [M+H]=333.2

Example 71

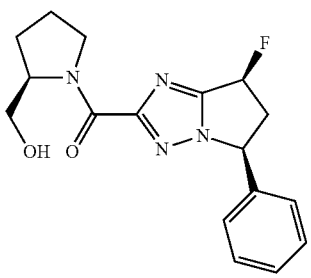 [SMILES: O=C(c1nc2n(n1)[C@H](c1ccccc1)C[C@@H]2F)N1CCC[C@@H]1CO]

[rac-(5S,7S)-7-fluoro-5-phenyl-6,7-dihydro-5H-pyrrolo[1,2-b][1,2,4]triazol-2-yl]-[rac-(2R)-2-(hydroxymethyl)pyrrolidin-1-yl]methanone (arbitrarily assigned 2R, 5S, 7S) configuration Method 17 (12.5 mg, 37% yield)

$^1$H NMR (400 MHz, DMSO-d$_6$) δ 7.59-7.31 (m, 3H), 7.28-7.11 (m, 2H), 6.20 (ddt, J=56.6, 7.2, 2.0 Hz, 1H), 5.68 (ddt, J=8.6, 5.7, 2.7 Hz, 1H), 4.86-4.67 (m, 1H), 4.45 (s, 1H), 4.12 (dd, J=7.1, 3.8 Hz, 1H), 3.90-3.41 (m, 3H), 3.31 (s, 2H). 2.84-2.52 (m, 1H), 2.07-1.65 (m, 3H). LCMS R$_T$=3.65 min, m/z=331.2 (M+H)$^+$.

LCMS (5 to 95% acetonitrile in water+0.1% formic acid over 10 mins) retention time 3.65 min, ESI+ found [M+H]=331.2

Example 72

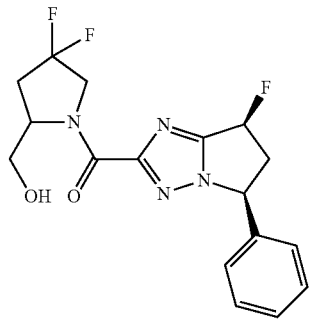 [SMILES: O=C(c1nc2n(n1)[C@H](c1ccccc1)C[C@@H]2F)N1CC(F)(F)CC1CO]

[4,4-difluoro-2-(hydroxymethyl)pyrrolidin-1-yl]-[rac-(5S,7S)-7-fluoro-5-phenyl-6,7-dihydro-5H-pyrrolo[1,2-b][1,2,4]triazol-2-yl]methanone (arbitrarily assigned 5S, 7S configuration)

Method 17 (24.5 mg, 66% yield)

$^1$H NMR (400 MHz, DMSO-d6) δ 7.47-7.32 (m, 3H), 7.29-7.18 (m, 2H), 6.22 (dddd. J=56.5, 7.2, 3.5, 1.9 Hz, 1H), 5.74-5.65 (m, 1H), 5.04 (L, J=5.5 Hz, 1H), 4.87 (s, 1H), 4.48-4.29 (m, 2H), 4.10 (ddt, J=31.6, 21.2, 10.7 Hz, 1H), 3.86-3.63 (m, 1H), 3.59 (q, J=5.1 Hz, 1H), 3.43-3.17 (m, 2H), 2.78-2.61 (m, 1H). LCMS R$_T$=4.06 min, m/z=366.9 (M+H)$^+$.

LCMS (5 to 95% acetonitrile in water+0.1% formic acid over 10 mins) retention time 4.06 min, ESI+ found [M+H]=366.9

Example 73

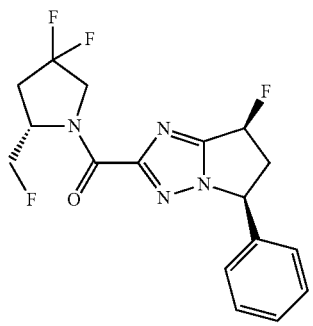 [SMILES: O=C(c1nc2n(n1)[C@H](c1ccccc1)C[C@@H]2F)N1CC(F)(F)C[C@H]1CF]

[rac-(2S)-4,4-difluoro-2-(fluoromethyl)pyrrolidin-1-yl]-[rac-(5S,7S)-7-fluoro-5-phenyl-6,7-dihydro-5H-pyrrolo[1,2-b][1,2,4]triazol-2-yl]methanone (arbitrarily assigned 2S, 5S, 7S configuration)

Method 17 (22.3 mg, 60% yield)

$^1$H NMR (400 MHz, DMSO-d6) δ 7.41 (dddd. J=12.0, 7.2, 5.9, 2.2 Hz. 3H), 7.29-7.19 (m, 2H), 6.22 (dddd, J=56.5, 7.2, 3.3, 1.9 Hz, 1H), 5.70 (ddt, J=8.8, 5.7, 2.7 Hz, 1H), 5.19 (s, 1H). 4.75-4.51 (m, 2H), 4.55-4.32 (m, 1H), 4.29-4.06 (m, 1H). 3.92-3.64 (m, 1H), 2.96-2.61 (m, 2H), 2.50-2.37 (m, 1H). LCMS R$_T$=4.75 min, m/z=368.9 (M+H)$^+$.

LCMS (5 to 95% acetonitrile in water+0.1% formic acid over 10 mins) retention time 4.75 min, ESI+ found [M+H]=368.9

Example 74

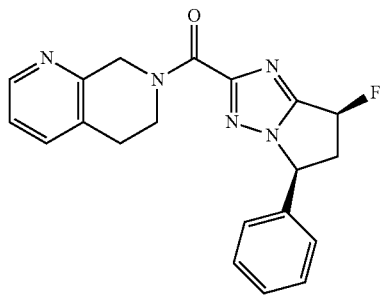 [SMILES: O=C(c1nc2n(n1)[C@H](c1ccccc1)C[C@@H]2F)N1CCc2cccnc2C1]

6,8-dihydro-5H-1,7-naphthyridin-7-yl-[rac-(5 S,7S)-7-fluoro-5-phenyl-6,7-dihydro-5H-pyrrolo[1,2-b][1,2,4]triazol-2-yl]methanone (arbitrarily assigned 5S, 7S configuration)

Method 17 (27.3 mg, 74% yield)
$^1$H NMR (400 MHz, DMSO-d6) δ 8.38 (dddd, J=25.7, 4.7, 1.7 Hz, 1H), 7.61 (ddd, J=7.7, 4.8, 1.6 Hz, 1H), 7.48-7.32 (m, 3H), 7.30-7.19 (m, 3H), 6.37-6.11 (m, 1H), 5.75-5.65 (m, 1H), 4.83 (d, J=29.7 Hz, 2H), 3.99-3.80 (m, 2H). 3.85-3.65 (m, 1H), 2.95-2.85 (m, 2H), 2.79-2.63 (m, 1H).
LCMS $R_T$=3.44 min, m/z=363.9 (M+H)$^+$.
LCMS (5 to 95% acetonitrile in water+0.1% formic acid over 10 mins) retention time 3.44 min, ESI+ found [M+H]=363.9

Example 75

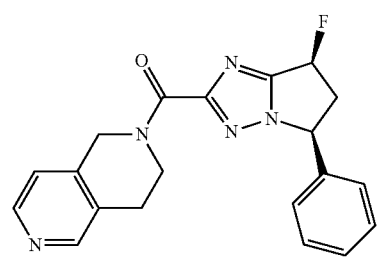 [SMILES: O=C(c1nc2n(n1)[C@H](c1ccccc1)C[C@@H]2F)N1CCc2cnccc2C1]

3,4-dihydro-1H-2,6-naphthyridin-2-yl-[rac-(5S,7S)-7-fluoro-5-phenyl-6,7-dihydro-5H-pyrrolo[1,2-b][1,2,4]triazol-2-yl]methanone (arbitrarily assigned 5S, 7S configuration)

Method 17 (20.3 mg, 55% yield)
$^1$H NMR (400 MHz, DMSO-d6) δ 8.43-8.29 (m, 2H), 7.48-7.33 (m, 3H), 7.32-6.99 (m, 3H), 6.23 (ddt, J=56.6, 7.6, 2.5 Hz, 1H), 5.70 (qd, J=8.1, 3.1 Hz, 1H), 4.92-4.76 (m, 2H), 4.03-3.64 (m, 3H), 2.88 (t, J=5.9 Hz, 2H), 2.79-2.63 (m, 1H). LCMS $R_T$=2.65 min, m/z=363.9 (M+H)$^+$.

LCMS (5 to 95% acetonitrile in water+0.1% formic acid over 10 mins) retention time 2.65 min, ESI+ found [M+H]=363.9

Example 76

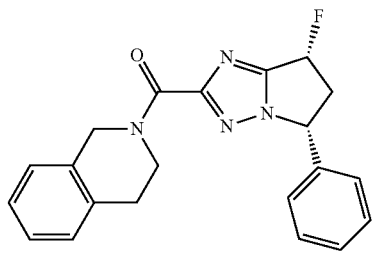 [SMILES: O=C(c1nc2n(n1)[C@@H](c1ccccc1)C[C@H]2F)N1CCc2ccccc2C1]

3,4-dihydro-1H-isoquinolin-2-yl-[rac-(5R,7R)-7-fluoro-5-phenyl-6,7-dihydro-5H-pyrrolo[1,2-b][1,2,4]triazol-2-yl]methanone 3,4-dihydro-1H-isoquinolin-2-yl-[rac-(5R,7R)-7-fluoro-5-phenyl-6,7-dihydro-5H-pyrrolo[1,2-b][1,2,4]triazol-2-yl]methanone was prepared according to Method 17. The crude residue was further purified by chiral SFC (Whelko-01; 150×21.2 mm; 50% methanol isocratic elution with Carbon Dioxide) affording arbitrarily assigned diastereomers as below:

3,4-dihydro-1H-isoquinolin-2-yl-[rac-(5R,7R)-7-fluoro-5-phenyl-6,7-dihydro-5H-pyrrolo[1,2-b][1,2,4]triazol-2-yl]methanone (9.6 mg, 36%) as white solids Analytical data for this second eluting diastereomer (arbitrarily assigned 5R, 7R configuration): SFC $R_T$ (Whelk-Ol S,S, 45% methanol+0.1% ammonium hydroxide isocratic elution with Carbon Dioxide, 2.5 min method): 1.752 min, 100% purity. 100% ee: $^1$H NMR (400 MHz, DMSO-d6) δ 7.48-7.33 (m, 3H), 7.30-6.97 (m, 6H), 6.23 (ddd, J=56.6, 7.2, 1.9 Hz, 1H), 5.70 (dq, J=7.1, 3.2 Hz, 1H), 4.78 (s, 2H), 3.92-3.65 (m, 3H), 2.87 (q, J=6.4 Hz, 2H), 2.79-2.62 (m, 1H). LCMS $R_T$=5.03 min, m/z=363.1 (M+H)$^+$.

LCMS (5 to 95% acetonitrile in water+0.1% formic acid over 10 mins) retention time 5.03 min, ESI+ found [M+H]=363.1

Example 77

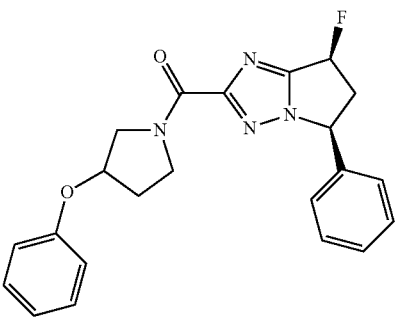 [SMILES: O=C(c1nc2n(n1)[C@H](c1ccccc1)C[C@@H]2F)N1CCC(Oc2ccccc2)C1]

(3-phenoxypyrrolidin-1-yl)-[rac-(5S,7S)-7-fluoro-5-phenyl-6,7-dihydro-5H-pyrrolo[1,2-b][1,2,4]triazol-2-yl]methanone (arbitrarily assigned 5S, 7S configuration)

Method 17 (31.6 mg, 67% yield)

$^1$H NMR (400 MHz, DMSO-d6) δ 7.47-7.33 (m, 3H), 7.38-7.15 (m, 4H), 7.01-6.89 (m, 3H), 6.35-6.04 (m, 1H), 5.75-5.62 (m, 1H), 5.09 (qd, J=4.5, 2.4 Hz, 1H), 4.07-3.89 (m, 1H), 3.84-3.51 (m, 4H), 2.77-2.58 (m, 1H), 2.29-2.05 (m, 2H). LCMS $R_T$=5.08 min, m/z=393.1 (M+H)$^+$.

LCMS (5 to 95% acetonitrile in water+0.1% formic acid over 10 mins) retention time 5.08 min, ESI+ found [M+H]=393.1

Example 78

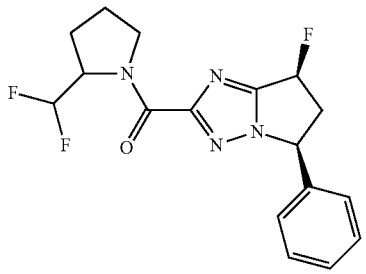 [SMILES: O=C(c1nc2n(n1)[C@H](c1ccccc1)C[C@@H]2F)N1CCCC1C(F)F]

[2-(difluoromethyl)pyrrolidin-1-yl]-[rac-(5S,7S)-7-fluoro-5-phenyl-6,7-dihydro-5H-pyrrolo[1,2-b][1,2,4]triazol-2-yl]methanone (arbitrarily assigned 5S, 7S configuration)

Method 17 (4.1 mg, 10% yield)

$^1$H NMR (400 MHz, DMSO-d$_6$) δ 7.57-7.23 (m, 3H), 7.22 (ddt, J=8.5, 5.3, 1.5 Hz, 2H), 6.68-5.90 (m, 2H), 5.70 (td, J=7.7, 6.5, 2.8 Hz, 1H), 4.69-4.33 (m, 1H), 3.96-3.54 (m, 3H), 2.87-2.50 (m, 1H), 2.25-1.63 (m, 4H). LCMS $R_T$=4.71 min, m/z=351.1 (M+H)$^+$.

LCMS (5 to 95% acetonitrile in water+0.1% formic acid over 10 mins) retention time 4.71 min, ESI+ found [M+H]=351.1

Example 79

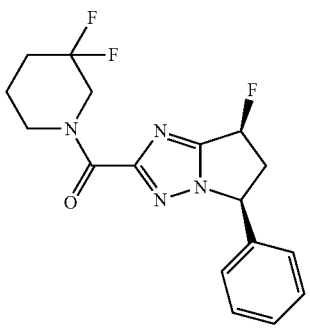 [SMILES: O=C(c1nc2n(n1)[C@H](c1ccccc1)C[C@@H]2F)N1CCCC(F)(F)C1]

(3,3-difluoro-1-piperidyl)-[rac-(5S,7S)-7-fluoro-5-phenyl-6,7-dihydro-5H-pyrrolo[1,2-b][1,2,4]triazol-2-yl]methanone Method 17 (30.9 mg, 69% yield)

$^1$H NMR (400 MHz, DMSO-d6) δ 7.47-7.28 (m, 3H), 7.28-7.19 (m, 2H), 6.37-6.07 (m, 1H), 5.74-5.63 (m, 1H), 4.07 (t, J=11.8 Hz, 1H), 3.96 (t, J=12.0 Hz, 1H), 3.83-3.58 (m, 3H), 2.70 (dddd, J=26.7, 15.2, 3.1, 1.9 Hz, 1H), 2.09 (qt, J=13.1, 6.7 Hz, 2H), 1.70 (td, J=6.8, 3.9 Hz, 2H). LCMS $R_T$=4.50 min, m/z=351.1 (M+H)$^+$.

LCMS (5 to 95% acetonitrile in water+0.1% formic acid over 10 mins) retention time 4.50 min, ESI+ found [M+H]=351.1

Example 80

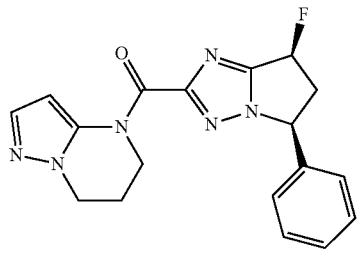 [SMILES: O=C(c1nc2n(n1)[C@H](c1ccccc1)C[C@@H]2F)N1CCCn2nccc21]

6,7-dihydro-5H-pyrazolo[1,5-a]pyrimidin-4-yl-[rac-(5S,7S)-7-fluoro-5-phenyl-6,7-dihydro-5H-pyrrolo[1,2-b][1,2,4]triazol-2-yl]methanone Method 17 (24.6 mg, 69% yield)

$^1$H NMR (400 MHz, DMSO-d6) δ 7.48-7.33 (m, 4H), 7.31-7.23 (m, 2H), 6.64 (s, 1H), 6.24 (ddd, J=56.5, 7.1, 1.9 Hz, 1H), 5.71 (ddd. J=8.6, 6.7, 3.1 Hz, 1H), 4.16 (t. J=6.1 Hz. 2H), 4.02 (tq, J=12.9, 7.3, 6.5 Hz, 2H), 3.76 (dddd, J=25.7, 15.4, 8.5, 7.2 Hz, 1H), 2.80-2.63 (m, 1H), 2.14 (p, J=6.0 Hz, 2H). LCMS $R_T$=3.97 min. m/z=353.1 (M+H)$^+$.

LCMS (5 to 95% acetonitrile in water+0.1% formic acid over 10 mins) retention time 3.97 min, ESI+ found [M+H]=353.1

Example 81

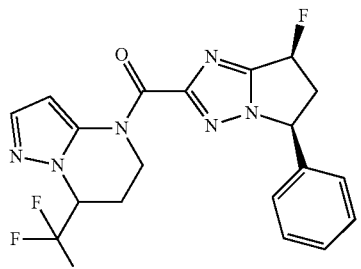

[rac-(5S,7S)-7-fluoro-5-phenyl-6,7-dihydro-5H-pyrrolo[1,2-b][1,2,4]triazol-2-yl]-[7-(trifluoromethyl)-6,7-dihydro-5H-pyrazolo[1,5-a]pyrimidin-4-yl]methanone Method 17 (16.1 mg, 36% yield)
¹H NMR (400 MHz, DMSO-d₆) δ 7.56 (s, 1H), 7.56-7.26 (m, 3H), 7.38-7.16 (m, 2H), 6.58 (s, 1H), 6.40-6.07 (m, 1H), 5.73 (ddt, J=9.4, 6.1, 2.9 Hz, 1H). 5.35 (q. J=7.2, 6.3 Hz, 1H), 4.19 (t, J=15.5 Hz, 1H), 4.13-3.86 (m, 1H), 3.76 (dddd, J=25.9, 15.5, 8.0, 6.9 Hz, 1H), 2.88-2.60 (m, 1H), 2.42 (dh, J=14.9, 4.8 Hz, 2H). LCMS R$_T$=4.71 min, m/z=421.1 (M+H)⁺.

LCMS (5 to 95% acetonitrile in water+0.1% formic acid over 10 mins) retention time 4.71 min, ESI+ found [M+H]=421.1

Example 82

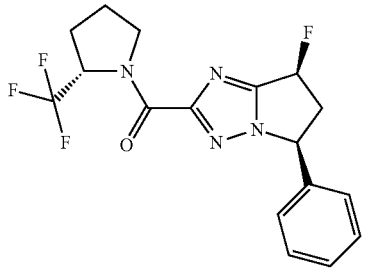 [SMILES: O=C(c1nc2n(n1)[C@H](c1ccccc1)C[C@@H]2F)N1CCC[C@H]1C(F)(F)F]

[rac-(5S,7S)-7-fluoro-5-phenyl-6,7-dihydro-5H-pyrrolo[1,2-b][1,2,4]triazol-2-yl]-[rac-(2S)-2-(trifluoromethyl)pyrrolidin-1-yl]methanone (arbitrarily assigned 2S, 5S, 7S configuration)

Method 17 (32.2 mg, 72% yield)
¹H NMR (400 MHz, DMSO-d6) δ 7.41 (dtd, J=12.2, 6.8, 2.3 Hz, 3H), 7.28-7.14 (m, 2H), 6.36-6.05 (m, 1H), 5.76-5.67 (m, 1H), 5.04 (td, J=8.4, 4.2 Hz, 1H), 3.89-3.64 (m, 3H), 2.69 (ddt. J=27.3, 18.9, 2.9 Hz, 1H). 2.18-2.08 (m, 1H), 2.10-1.90 (m, 3H). LCMS R$_T$=4.94 min, m/z=369.1 (M+H)⁺.

LCMS (5 to 95% acetonitrile in water+0.1% formic acid over 10 mins) retention time 4.94 min, ESI+ found [M+H]=369.1

Example 83

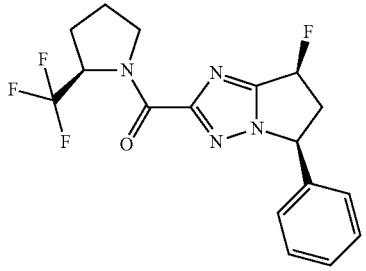 [SMILES: O=C(c1nc2n(n1)[C@H](c1ccccc1)C[C@@H]2F)N1CCC[C@@H]1C(F)(F)F]

[rac-(5S,7S)-7-fluoro-5-phenyl-6,7-dihydro-5H-pyrrolo[1,2-b][1,2,4]triazol-2-yl]-[rac-(2R)-2-(trifluoromethyl)pyrrolidin-1-yl]methanone (arbitrarily assigned 2R, 5S, 7S configuration)

Method 17 (30.2 mg, 67% yield)
¹H NMR (400 MHz, DMSO-d6) δ 7.40 (ddtt, J=12.4, 9.5, 7.2, 2.1 Hz, 3H), 7.30-7.11 (m, 2H), 6.38-6.09 (m, 1H), 5.80-5.65 (m, 1H), 5.04 (td. J=8.3, 4.1 Hz, 1H), 3.92-3.48 (m, 3H), 2.78-2.61 (m, 1H), 2.18-2.08 (m, 1H), 2.06-1.78 (m, 3H). LCMS R$_T$=4.94 min, m/z=369.1 (M+H)⁺.

LCMS (5 to 95% acetonitrile in water+0.1% formic acid over 10 mins) retention time 4.94 min, ESI+ found [M+H]=369.1

Example 84

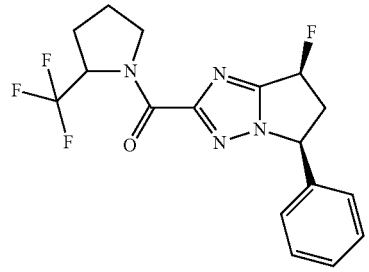 [SMILES: O=C(c1nc2n(n1)[C@H](c1ccccc1)C[C@@H]2F)N1CCCC1C(F)(F)F]

[rac-(5S,7S)-7-fluoro-5-phenyl-6,7-dihydro-5H-pyrrolo[1,2-b][1,2,4]triazol-2-yl]-[2-(trifluoromethyl)pyrrolidin-1-yl]methanone Method 17 (33.9 mg, 52% yield)
¹H NMR (400 MHz, DMSO-d6) δ 7.49-7.31 (m, 3H), 7.28-7.14 (m, 2H), 6.36-6.10 (m, 1H), 5.82-5.63 (m, 1H), 5.11-4.98 (m, 1H), 3.89-3.49 (m, 3H), 2.78-2.61 (m, 1H), 2.18-2.08 (m, 1H), 2.06-1.90 (m, 3H). LCMS R$_T$=4.94 min, m/z=369.1 (M+H)⁺.

LCMS (5 to 95% acetonitrile in water+0.1% formic acid over 10 mins) retention time 4.94 min, ESI+ found [M+H]=369.1

Examples 85 and 86

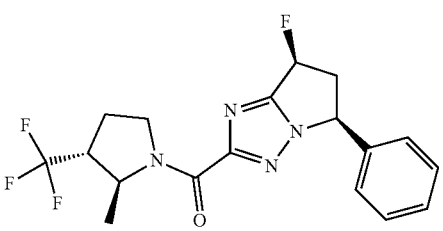

[rac-(5S,7S)-7-fluoro-5-phenyl-6,7-dihydro-5H-pyrrolo[1,2-b][1,2,4]triazol-2-yl]-[rac-(2S,3R)-2-methyl-3-(trifluoromethyl)pyrrolidin-1-yl]methanone & [rac-(5S,7S)-7-fluoro-5-phenyl-6,7-dihydro-5H-pyrrolo[1,2-b][1,2,4]triazol-2-yl]-[rac-(2S,3S)-2-methyl-3-(trifluoromethyl)pyrrolidin-1-yl]methanone

[rac-(5S,7S)-7-fluoro-5-phenyl-6,7-dihydro-5H-pyrrolo[1,2-b][1,2,4]triazol-2-yl]-[2-methyl-3-(trifluoromethyl)pyrrolidin-1-yl]methanone was prepared according to Method 17. The crude residue was further purified by chiral SFC (Whelko-01 150×21.2 mm; 40% methanol+0.1% ammonium hydroxide isocratic elution with Carbon Dioxide) affording arbitrarily assigned two diastereomers as below:
[rac-(5S,7S)-7-fluoro-5-phenyl-6,7-dihydro-5H-pyrrolo[1,2-b][1,2,4]triazol-2-yl-[rac-(2S,3R)-2-methyl-3-(trifluoromethyl)pyrrolidin-1-yl]methanone (1.9 mg, 4%) as white solids
[rac-(5S,7S)-7-fluoro-5-phenyl-6,7-dihydro-5H-pyrrolo[1,2-b][1,2,4]triazol-2-yl]-[rac-(2S,3S)-2-methyl-3-(trifluoromethyl)pyrrolidin-1-yl]methanone (2.6 mg, 10%) as white solids
Analytical data for the third eluting diastereomer {arbitrarily assigned (2S, 3R). (5S, 7S) configuration}: SFC $R_T$(Whelk-Ol S,S, 30% methanol+0.1% ammonium hydroxide isocratic elution with Carbon Dioxide, 2.5 min method): 1.594 min, 100% purity, 100% ee: $^1$H NMR (400 MHz, DMSO-d$_6$) δ 7.53-7.33 (m, 3H). 7.22 (dt, J=7.8, 1.7 Hz, 2H), 6.22 (dddd, J=56.6, 10.6, 7.1, 1.9 Hz, 1H), 5.83-5.57 (m, 1H), 4.67 (dt, J=106.6, 6.7 Hz, 1H), 4.00 (td, J=9.4, 7.9, 3.1 Hz, 1H), 3.91-3.45 (m, 2H), 2.85-2.53 (m, 1H), 2.33-1.95 (m, 2H), 1.15 (ddd, J=36.4, 6.5, 1.9 Hz, 3H). LCMS $R_T$=5.07 min, m/z=383.1 (M+H)$^+$.
LCMS (5 to 95% acetonitrile in water+0.1% formic acid over 30 mins) retention time 5.07 min, ESI+ found [M+H]=383.1
Analytical data for the fourth eluting diastereomer {arbitrarily assigned (2S. 3S), (5S, 7S) configuration}: SFC $R_T$(Whelk-Ol S,S, 30% methanol+0.1% ammonium hydroxide isocratic elution with Carbon Dioxide, 2.5 min method): 1.732 min, 100% purity, 100% ee: $^1$H NMR (400 MHz, DMSO-d$_6$) δ 7.54-7.25 (m, 3H), 7.39-7.11 (m, 2H), 6.22 (dddd, J=56.6, 12.7, 7.2, 1.8 Hz, 1H), 5.83-5.56 (m, 1H), 4.70 (dp, J=141.9, 6.6 Hz, 1H), 4.09-3.84 (m, 1H), 3.91-3.47 (m, 2H), 2.86-2.53 (m, 1H), 2.33-1.89 (m, 2H). 1.30-0.93 (m, 4H). LCMS $R_T$=5.08 min, m/z=383.1 (M+H)$^+$.
LCMS (5 to 95% acetonitrile in water+0.1% formic acid over 30 mins) retention time 5.08 min, ESI+ found [M+H]=383.1

Example 87

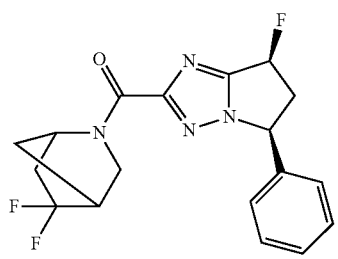 [SMILES: O=C(c1nc2n(n1)[C@H](c1ccccc1)C[C@@H]2F)N1CC2CC1CC2(F)F]

(5,5-difluoro-2-azabicyclo[2.2.1]heptan-2-yl)-[rac-(5S,7S)-7-fluoro-5-phenyl-6,7-dihydro-5H-pyrrolo[1,2-b][1,2,4]triazol-2-yl]methanone Method 17 (28.4 mg, 66% yield)
$^1$H NMR (400 MHz, DMSO-d6) δ 7.47-7.32 (m, 3H), 7.27-7.19 (m, 2H), 6.21 (dddt, J=56.6, 7.4, 4.6, 1.7 Hz, 1H), 5.69 (tt, J=6.9, 2.7 Hz, 1H), 5.07-4.57 (m, 1H), 3.77 (s, 1H), 3.83-3.63 (m, 1H), 3.54-3.39 (m, 1H), 2.97 (d, J=6.8 Hz, 1H), 2.78-2.60 (m, 1H), 2.25 (s, 1H), 2.20-2.01 (m, 1H), 1.90 (d, J=13.0 Hz, 2H). LCMS $R_T$=4.52 min, m % z=363.1 (M+H)$^+$.
LCMS (5 to 95% acetonitrile in water+0.1% formic acid over 10 mins) retention time 4.52 min, ESI+ found [M+H]=363.1

Example 88

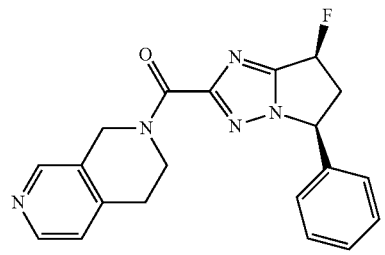 [SMILES: O=C(c1nc2n(n1)[C@H](c1ccccc1)C[C@@H]2F)N1CCc2ccncc2C1]

3,4-dihydro-1H-2,7-naphthyridin-2-yl-[rac-(5 S,7S)-7-fluoro-5-phenyl-6,7-dihydro-5H-pyrrolo[1,2-b][1,2,4]triazol-2-yl]methanone Method 17 (17.1 mg, 43% yield)
$^1$H NMR (400 MHz, DMSO-d6) δ 8.56-8.15 (m, 2H), 7.49-7.34 (m, 3H), 7.31-7.14 (m, 3H), 6.23 (ddd, J=56.6, 7.1, 1.9 Hz, 1H), 5.75-5.65 (m, 1H), 4.84 (d, J=13.5 Hz, 2H), 3.97-3.82 (m, 1H), 3.86-3.78 (m, 1H), 3.83-3.65 (m, 1H), 2.88 (q, J=5.8, 4.1 Hz, 2H), 2.80-2.60 (m, 1H). LCMS $R_T$=2.71 min, m/z=364.1 (M+H)$^+$.
LCMS (5 to 95% acetonitrile in water+0.1% formic acid over 10 mins) retention time 2.71 min, ESI+ found [M+H]=364.1

Example 89

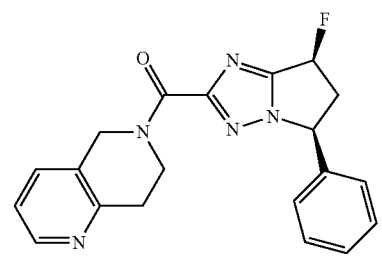 [SMILES: O=C(c1nc2n(n1)[C@H](c1ccccc1)C[C@@H]2F)N1CCc2ncccc2C1]

7,8-dihydro-5H-1,6-naphthyridin-6-yl-[rac-(5S,7S)-7-fluoro-5-phenyl-6,7-dihydro-5H-pyrrolo[1,2-b][1,2,4]triazol-2-yl]methanone Method 17 (23.4 mg, 59% yield)
$^1$H NMR (400 MHz, DMSO-d6) δ 8.40 (dd, J=4.7, 2.0 Hz, 1H), 7.70 (dd, J=7.8, 1.7 Hz, 1H), 7.51-7.33 (m, 3H), 7.30-7.17 (m, 3H), 6.23 (dtd, J=56.5, 6.6, 6.0, 1.9 Hz, 1H), 5.70 (tdd, J=9.6, 7.0, 3.0 Hz, 1H), 4.84 (d, J=12.4 Hz, 2H), 4.06-3.85 (m, 2H), 3.85-3.65 (m, 1H), 2.96 (dt, J=8.0, 4.2 Hz, 2H), 2.80-2.62 (m, 1H). LCMS $R_T$=2.81 min, m/z=364.1 (M+H)$^+$.
LCMS (5 to 95% acetonitrile in water+0.1% formic acid over 10 mins) retention time 2.81 min, ESI+ found [M+H]=364.1

Example 90

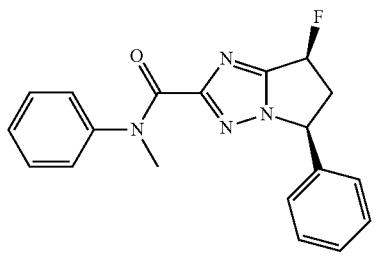 [SMILES: CN(C(=O)c1nc2n(n1)[C@H](c1ccccc1)C[C@@H]2F)c1ccccc1]

rac-(5S,7S)-7-fluoro-N-methyl-N,5-diphenyl-6,7-dihydro-5H-pyrrolo[1,2-b][1,2,4]triazole-2-carboxamide Method 17 (29.8 mg, 75% yield)
$^1$H NMR (400 MHz, DMSO-d$_6$) δ 7.42-7.13 (m, 6H), 7.15 (s. 2H), 6.80 (s, 2H), 6.05 (dd, J=56.7, 6.8 Hz, 1H), 5.54 (s, 1H), 3.81-3.50 (m, 1H), 3.38 (s, 3H), 2.64-2.47 (m, 1H). LCMS $R_T$=4.55 min, m/z=337.1 (M+H)$^+$.
LCMS (5 to 95% acetonitrile in water+0.1% formic acid over 10 mins) retention time 4.55 min, ESI+ found [M+H]=337.1

Example 91

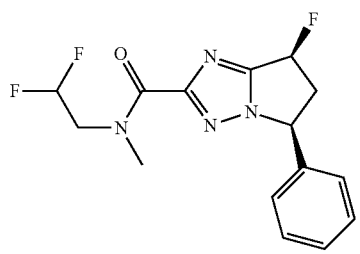 [SMILES: CN(CC(F)F)C(=O)c1nc2n(n1)[C@H](c1ccccc1)C[C@@H]2F]

rac-(5S,7S)—N-(2,2-difluoroethyl)-7-fluoro-N-methyl-5-phenyl-6,7-dihydro-5H-pyrrolo[1,2-b][1,2,4]triazole-2-carboxamide Method 17 (32.0 mg, 80% yield)
$^1$H NMR (400 MHz, DMSO-d$_6$) δ 7.57-7.23 (m, 3H), 7.23 (ddt, J=8.0, 5.6, 1.6 Hz, 2H), 6.63-5.98 (m, 2H), 5.69 (t, J=7.5 Hz, 1H), 4.09 (td, J=15.0, 3.9 Hz, 1H), 3.90 (td, J=15.4, 4.0 Hz, 1H), 3.83-3.58 (m, 1H), 3.22-3.00 (m, 3H), 2.80-2.58 (m, 1H). LCMS $R_T$=4.30 min, m/z=325.1 (M+H)$^+$.
LCMS (5 to 95% acetonitrile in water+0.1% formic acid over 10 mins) retention time 4.30 min, ESI+ found [M+H]=325.1

Example 92

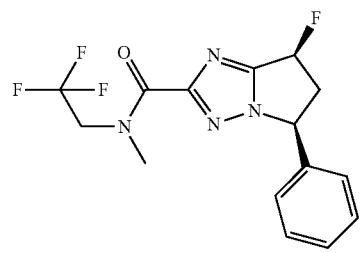 [SMILES: CN(CC(F)(F)F)C(=O)c1nc2n(n1)[C@H](c1ccccc1)C[C@@H]2F]

rac-(5S,7S)-7-fluoro-N-methyl-5-phenyl-N-(2,2,2-trifluoroethyl)-6,7-dihydro-5H-pyrrolo[1,2-b][1,2,4]triazole-2-carboxamide Method 17 (34.2 mg, 68% yield)
$^1$H NMR (400 MHz, DMSO-d6) δ 7.47-7.32 (m, 3H), 7.29-7.16 (m, 2H), 6.22 (dddd, J=56.6, 7.2, 4.1, 1.9 Hz, 1H), 5.76-5.65 (m, 1H), 4.74 (qd, J=9.3, 6.1 Hz, 1H), 4.37 (q, J=9.6 Hz, 1H), 3.74 (dddd, J=25.8, 15.5, 8.5, 7.2 Hz, 1H), 3.15 (d, J=46.5 Hz. 3H), 2.78-2.61 (m, 1H). LCMS $R_T$=4.62 min, m/z=343.1 (M+H)$^+$.
LCMS (5 to 95% acetonitrile in water+0.1% formic acid over 10 mins) retention time 4.62 min, ESI+ found [M+H]=343.1

Example 93

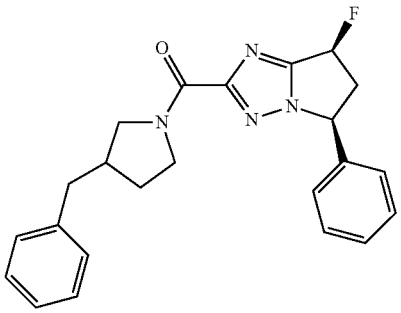 [SMILES: O=C(c1nc2n(n1)[C@H](c1ccccc1)C[C@@H]2F)N1CCC(Cc2ccccc2)C1]

(3-benzylpyrrolidin-1-yl)-[rac-(5S,7S)-7-fluoro-5-phenyl-6,7-dihydro-5H-pyrrolo[1,2-b][1,2,4]triazol-2-yl]methanone Method 17 (21.1 mg, 42% yield)
$^1$H NMR (400 MHz, DMSO-d$_6$) δ 7.53-7.06 (m, 10H), 6.19 (ddt, J=56.6, 7.2, 2.1 Hz, 1H), 5.68 (ddd, J=8.7, 5.1, 1.9 Hz, 1H), 3.95-3.49 (m, 2H), 3.46-3.33 (m, 1H), 3.14 (dd, J=12.2, 8.2 Hz, 1H), 2.77-2.59 (m, 4H), 2.46 (m, 1H), 1.91 (dq. J=10.9, 6.3 Hz, 1H), 1.77-1.44 (m, 1H). LCMS $R_T$=5.38 min, m/z=391.1 (M+H)$^+$.

Example 94

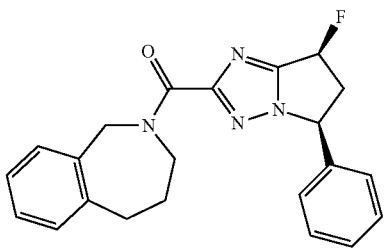 [SMILES: O=C(c1nc2n(n1)[C@H](c1ccccc1)C[C@@H]2F)N1CCCc2ccccc2C1]

[rac-(5S,7S)-7-fluoro-5-phenyl-6,7-dihydro-5H-pyrrolo[1,2-b][1,2,4]triazol-2-yl]-(1,3,4,5-tetrahydro-2-benzazepin-2-yl)methanone Method 17 (38.0 mg, 76% yield)

$^1$H NMR (400 MHz, DMSO-d$_6$) δ 7.57-6.76 (m, 9H), 6.45-6.01 (m, 2H), 5.65 (dddd. J=15.2, 8.3, 6.9, 2.9 Hz, 1H), 4.96-4.52 (m, 2H), 4.19-3.56 (m, 1H), 3.09-2.87 (m, 2H), 2.84-2.56 (m, 1H), 1.74 (d, J=28.7 Hz, 2H). LCMS R$_t$=5.15 min, m/z=377.1 (M+H)$^+$.

LCMS (5 to 95% acetonitrile in water+0.1% formic acid over 10 mins) retention time 5.15 min, ESI+ found [M+H]=377.1

Example 95

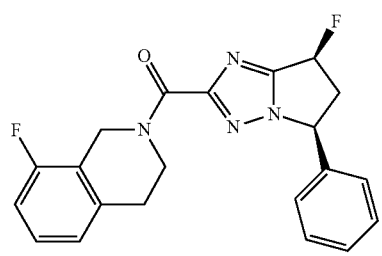 [SMILES: O=C(c1nc2n(n1)[C@H](c1ccccc1)C[C@@H]2F)N1CCc2cccc(F)c2C1]

(8-fluoro-3,4-dihydro-1H-isoquinolin-2-yl)-[rac-(5S,7S)-7-fluoro-5-phenyl-6,7-dihydro-5H-pyrrolo[1,2-b][1,2,4]triazol-2-yl]methanone Method 17 (34.2 mg, 68% yield)

$^1$H NMR (400 MHz, DMSO-d6) δ 7.48-7.32 (m, 3H), 7.25 (tt, J=7.9, 1.5 Hz, 3H), 7.05 (tt, J=13.0, 8.9 Hz, 2H), 6.23 (ddd, J=56.6, 7.2, 1.9 Hz, 1H), 5.75-5.66 (m, 1H), 4.82 (d, J=33.7 Hz, 2H), 3.93-3.80 (m, 2H), 3.83-3.65 (m, 1H), 2.90 (t, J=5.9 Hz, 2H), 2.79-2.58 (m, 1H). LCMS R$_T$=5.15 min, m/z=381.1 (M+H)$^+$.

LCMS (5 to 95% acetonitrile in water+0.1% formic acid over 10 mins) retention time 5.15 min, ESI+ found [M+H]=381.1

Example 96

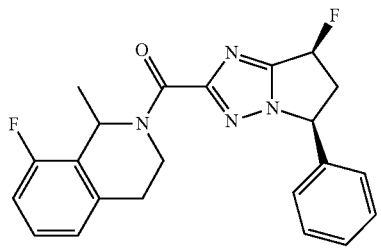 [SMILES: CC1c2c(F)cccc2CCN1C(=O)c1nc2n(n1)[C@H](c1ccccc1)C[C@@H]2F]

(8-fluoro-1-methyl-3,4-dihydro-1H-isoquinolin-2-yl)-[rac-(5S,7S)-7-fluoro-5-phenyl-6,7-dihydro-5H-pyrrolo[1,2-b][1,2,4]triazol-2-yl]methanone Method 17 (36.9 mg, 74% yield)

$^1$H NMR (400 MHz, DMSO-d$_6$) δ 7.56-7.24 (m, 3H), 7.39-7.10 (m, 3H), 7.19-6.90 (m, 2H), 6.44-6.04 (m, 1H), 5.84-5.25 (m, 2H), 4.63-3.96 (m, 1H), 3.56 (m, 2H), 3.02-2.55 (m, 3H), 1.62-1.36 (m, 3H). LCMS R$_T$=5.41 min, m/z=395.1 (M+H)$^+$.

LCMS (5 to 95% acetonitrile in water+0.1% formic acid over 10 mins) retention time 5.41 min, ESI+ found [M+H]=395.1

Example 97

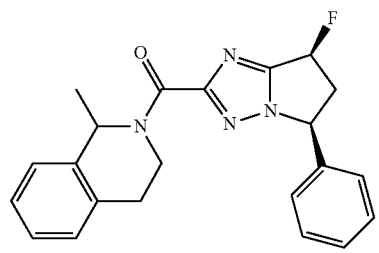 [SMILES: CC1c2ccccc2CCN1C(=O)c1nc2n(n1)[C@H](c1ccccc1)C[C@@H]2F]

(1-methyl-3,4-dihydro-1H-isoquinolin-2-yl)-[rac-(5S,7S)-7-fluoro-5-phenyl-6,7-dihydro-5H-pyrrolo[1,2-b][1,2,4]triazol-2-yl]methanone Method 17 (30.8 mg, 81% yield)

$^1$H NMR (400 MHz, DMSO-d$_6$) δ 7.48-7.32 (m, 3H), 7.32-6.98 (m, 6H), 6.23 (dddd, J=56.6, 7.1, 4.3, 1.9 Hz, 1H), 5.75-5.64 (m, 1H), 5.56 (m, 1H), 4.04 (m, 1H), 3.75 (m, 2H), 3.01-2.62 (m, 3H), 1.50 (dd, J=24.3, 6.8 Hz, 3H). LCMS R$_T$=5.28 min, m/z=377.1 (M+H)$^+$.

LCMS (5 to 95% acetonitrile in water+0.1% formic acid over 10 mins) retention time 5.28 min, ESI+ found [M+H]=377.1

Example 98

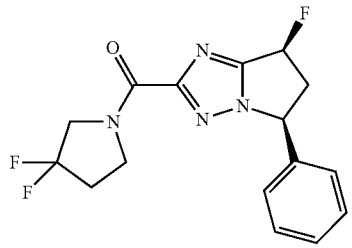 [SMILES: O=C(c1nc2n(n1)[C@H](c1ccccc1)C[C@@H]2F)N1CCC(F)(F)C1]

(3,3-difluoropyrrolidin-1-yl)-[rac-(5S,7S)-7-fluoro-5-phenyl-6,7-dihydro-5H-pyrrolo[1,2-b][1,2,4]triazol-2-yl]methanone Method 17 (28.9 mg, 85% yield)

$^1$H NMR (400 MHz, DMSO-d6) δ 7.48-7.33 (m, 3H), 7.25 (ddd, J=7.9, 3.7, 1.5 Hz, 2H), 6.23 (ddd, J=56.5, 7.2, 1.9 Hz, 1H), 5.76-5.66 (m, 1H), 4.23 (t, J=12.9 Hz, 1H), 4.01 (td, J=7.4, 1.8 Hz, 1H), 3.91 (t, J=13.2 Hz, 1H), 3.84-3.64 (m, 2H), 3.43-3.19 (m, 1H), 2.70 (ddt, J=26.8, 15.3, 2.3 Hz, 1H), 2.51-2.38 (m, 1H). LCMS $R_T$=4.42 min, m/z=337.1 (M+H)$^+$.

LCMS (5 to 95% acetonitrile in water+0.1% formic acid over 10 mins) retention time 4.42 min, ESI+ found [M+H]=337.1

Example 99

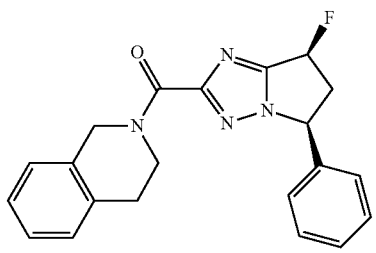 [SMILES: O=C(c1nc2n(n1)[C@H](c1ccccc1)C[C@@H]2F)N1CCc2ccccc2C1]

3,4-dihydro-1H-isoquinolin-2-yl-[rac-(5S,7S)-7-fluoro-5-phenyl-6,7-dihydro-5H-pyrrolo[1,2-b][1,2,4]triazol-2-yl]methanone Method 17 (30.3 mg, 84% yield)

$^1$H NMR (400 MHz, DMSO-d6) δ 7.48-7.33 (m, 3H), 7.29-7.11 (m, 6H), 6.23 (ddd, J=56.6, 7.2, 1.9 Hz, 1H), 5.69 (tdd, J=7.7, 5.8, 3.0 Hz, 1H), 4.78 (s, 2H), 3.93-3.65 (m, 3H), 3.44 (s, OH), 2.87 (q, J=6.4 Hz, 2H), 2.79-2.62 (m, 1H). LCMS $R_T$=5.03 min, m/z=363.1 (M+H)$^+$.

LCMS (5 to 95% acetonitrile in water+0.1% formic acid over 10 mins) retention time 5.03 min, ESI+ found [M+H]=363.1

Example 100

Method B

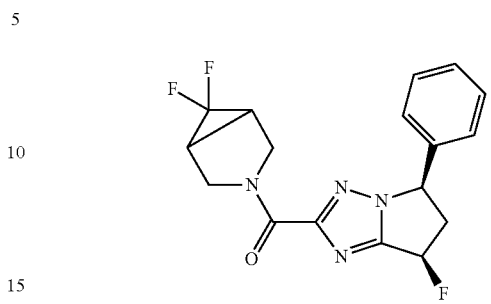

(6,6-difluoro-3-azabicyclo[3.1.0]hexan-3-yl)-[rac-(5R,7R)-7-fluoro-5-phenyl-6,7-dihydro-5H-pyrrolo[1,2-b][1,2,4]triazol-2-yl]methanone (23.5 mg, 68% yield)

$^1$H NMR (400 MHz, DMSO-d6) δ 7.48-7.35 (m, 3H), 7.23 (dt, J=8.0, 1.6 Hz, 2H), 6.27 (dd, J=7.2, 1.9 Hz, 1H), 6.13 (dd, J=7.1, 1.9 Hz, 1H), 5.69 (ddd, J=10.4, 5.5, 2.6 Hz, 1H). 4.15 (dd, J=12.1, 6.4 Hz, 1H), 4.08-3.97 (m, 2H), 3.83-3.64 (m, 2H), 2.72-2.54 (m, 2H). LCMS $R_T$=4.39 min, m/z=349.1 [M+H]$^+$.

Example 101

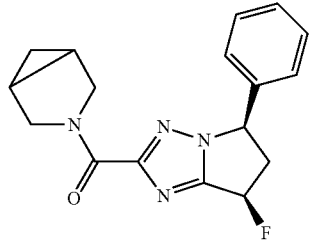 [SMILES: O=C(c1nc2n(n1)[C@@H](c1ccccc1)C[C@H]2F)N1CC2CC2C1]

3-azabicyclo[3.1.0]hexan-3-yl-[rac-(5R,7R)-7-fluoro-5-phenyl-6,7-dihydro-5H-pyrrolo[1,2-b][1,2,4]triazol-2-yl]methanone (15.8 mg, 51% yield)

$^1$H NMR (400 MHz, DMSO-d6) δ 7.41-7.24 (m, 3H), 7.20-7.08 (m, 2H), 6.19 (dd, J=7.2, 1.8 Hz, 1H), 6.05 (dd, J=7.2, 1.8 Hz. 1H), 5.60 (ddt, J=8.4, 4.6, 2.4 Hz, 1H), 3.85-3.69 (m, 2H), 3.72-3.54 (m, 2H), 3.36 (dd, J=12.1, 4.2 Hz, 1H), 1.58-1.45 (m, 2H), 0.69-0.54 (m, 1H), −0.01 (q, J=4.3 Hz, 1H). LCMS $R_T$=4.26 min, m/z=313.1 [M+H]$^+$.

Example 102

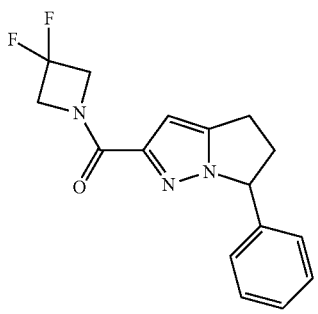 [SMILES: O=C(c1cc2n(n1)C(c1ccccc1)CC2)N1CC(F)(F)C1]

(3,3-difluoroazetidin-1-yl)-(6-phenyl-5,6-dihydro-4H-pyrrolo[1,2-b]pyrazol-2-yl)methanone A mixture of 6-phenyl-5,6-dihydro-4H-pyrrolo[1,2-b]pyrazole-2-carboxylic acid (30 mg. 0.13 mmol), 1-hydroxybenzotriazole (18 mg, 0.13 mmol), 1-(3-dimethylaminopropyl)-3-ethylcarbodiimidehydrochloride (38 mg, 0.20 mmol) and 3,3-difluoroazetidine hydrochloride (34 mg, 0.26 mmol) in N,N-dimethylformamide (3 mL) was stirred at 25° C. for 5 h. The mixture was filtered and the filtrated was concentrated under reduced pressure. The residue was purified by RP-HPLC (acetonitrile 30-60%/0.05% ammonia hydroxide in water) to afford (3,3-difluoroazetidin-1-yl)-(6-phenyl-5,6-dihydro-4H-pyrrolo[1,2-b]pyrazol-2-yl)methanone (12.7 mg, 31%) as a white solid. $^1$H NMR (400 MHz, CD$_3$OD) δ 7.42-7.27 (m, 3H), 7.08 (d, J=8.0 Hz. 2H), 6.59 (s, 1H), 5.54-5.48 (m, 1H), 4.81-4.62 (m, 2H), 4.44 (t, J=12.0 Hz, 2H), 3.19-2.94 (m, 3H), 2.55-2.46 (m, 1H). LCMS R$_T$=0.862 min, m/z=304.0 [M+H]$^+$.

LCMS (5 to 95% acetonitrile in water+0.03% trifluoacetic acid over 1.5 mins) retention time 0.862 min, ESI+ found [M+H]=304.0.

Example 103

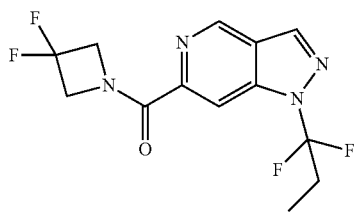 [SMILES: CCC(F)(F)n1ncc2cnc(C(=O)N3CC(F)(F)C3)cc21]

(3,3-difluoroazetidin-1-yl)-[1-(1,1-difluoropropyl)pyrazolo[4,3-c]pyridin-6-yl]methanone

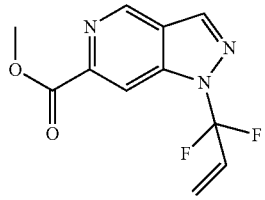 [SMILES: C=CC(F)(F)n1ncc2cnc(C(=O)OC)cc21]

Step 1: methyl 1-(1,1-difluoroallyl)-1H-pyrazolo[4,3-c]pyridine-6-carboxylate To a stirred solution of methyl 1H-pyrazolo[4,3-c]pyridine-6-carboxylate (100 mg, 0.56 mmol) in toluene (3 mL) was added triethylamine (114 mg, 1.13 mmol) and 3-bromo-3,3-difluoropropene (133 mg, 0.85 mmol). The reaction was stirred at 60° C. for 19 h. After cooled to room temperature, the mixture was diluted with water (10 mL) and extracted with ethyl acetate (3×10 mL). The combined organic layers were washed with brine (10 mL), dried and concentrated under reduced pressure. The residue was purified by preparative TLC (20% ethyl acetate in petroleum ether, R$_f$=0.5) to afford methyl 1-(1,1-difluoroallyl)pyrazolo[4,3-c]pyridine-6-carboxylate (40 mg, 28%) as light yellow solid.

LCMS (0 to 60% acetonitrile in water+0.05% ammonia hydroxide over 3.0 mins) retention time 1.186 min, ESI+ found [M+H]=254.1.

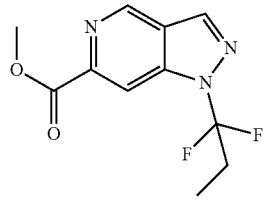 [SMILES: CCC(F)(F)n1ncc2cnc(C(=O)OC)cc21]

Step 2: methyl 1-(1,1-difluoropropyl)-1H-pyrazolo[4,3-c]pyridine-6-carboxylate A mixture of methyl 1-(1,1-difluoroallyl)pyrazolo[4,3-c]pyridine-6-carboxylate (100 mg, 0.39 mmol) and palladium (10% on carbon, 60 mg) in methanol (3 mL) was hydrogenated (15 psi) at 25° C. for 3 h and filtered. The filtrate was concentrated under reduced pressure to afford crude methyl 1-(1,1-difluoropropyl)pyrazolo[4,3-c]pyridine-6-carboxylate (60 mg, 60%) as a white solid.

LCMS (5 to 95% acetonitrile in water+0.03% trifluoacetic acid over 1.5 mins) retention time 1.237 min, ESI+ found [M+H]=256.2.

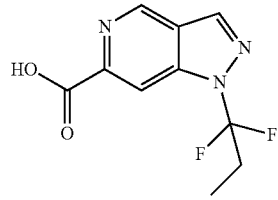 [SMILES: CCC(F)(F)n1ncc2cnc(C(=O)O)cc21]

Step 3: 1-(1,1-difluoropropyl)-1H-pyrazolo[4,3-c]pyridine-6-carboxylic acid

A mixture of methyl 1-(1,1-difluoropropyl)pyrazolo[4,3-c]pyridine-6-carboxylate (60 mg, 0.24 mmol) and lithium hydroxide hydrate (15 mg, 0.35 mmol) in tetrahydrofuran (2 mL) and water (0.60 mL) was stirred at 0° C. for 3 h and concentrated under reduce pressure. The residue was diluted with water (15 mL) and adjusted to pH=4 by addition of aqueous hydrochloric acid (1 N). The resulting mixture was extracted with ethyl acetate (2×15 mL). The combined organic layers were washed with brine (10 mL), dried and concentrated under reduced pressure to afford 1-(1,1-difluoropropyl)pyrazolo[4,3-c]pyridine-6-carboxylic acid (70 mg, two batches combined, 60%) as light yellow solid which would be used directly for next step.

LCMS (0 to (60% acetonitrile in water+0.03% trifluoacetic acid over 2 mins) retention time 0.910 min, ESI+ found [M+H]=241.8.

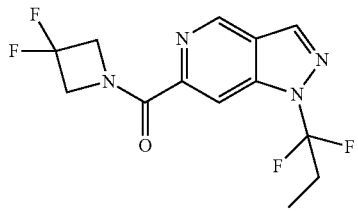 [SMILES: CCC(F)(F)n1ncc2cnc(C(=O)N3CC(F)(F)C3)cc21]

Step 4: (3,3-difluoroazetidin-1-yl)-[1-(1,1-difluoropropyl)pyrazolo[4,3-c]pyridin-6-yl]methanone A mixture of 1-(1,1-difluoropropyl)pyrazolo[4,3-c]pyridine-6-carboxylic acid (35 mg, 0.15 mmol) and 3,3-difluoroazetidine hydrochloride (23 mg, 0.17 mmol) and 1-hydroxybenzotriazole (24 mg, 0.17 mmol) and 1-(3-dimethylaminopropyl)-3-ethylcarbodiimidehydrochloride (34 mg, 0.17 mmol) in N,N-dimethylformamide (1.5 mL) was stirred at 25° C. for 3 h and concentrated under reduced pressure. The residue (from two batches) was purified by RP-HPLC (acetonitrile 35-65% acetonitrile/0.05% ammonia hydroxide in water) to afford (3,3-difluoroazetidin-1-yl)-[1-(1,1-difluoropropyl)pyrazolo[4,3-c]pyridin-6-yl]methanone (9.5 mg, 21%) as light yellow solid. $^1$H NMR (400 MHz, CD$_3$OD) δ 9.20 (s, 1H), 8.49 (s, 2H), 5.14 (t, J=12.0 Hz, 2H), 4.57 (t, J=12.0 Hz, 2H), 2.85-2.78 (m, 2H), 1.18 (t, J=7.6 Hz, 3H). LCMS R$_T$=1.137 min, m/z=317.1 [M+H]$^+$.

LCMS (10 to 80% acetonitrile in water+0.03% trifluoacetic acid over 1.5 mins) retention time 1.137 min, ESI+ found [M+H]=317.1.

Example 104

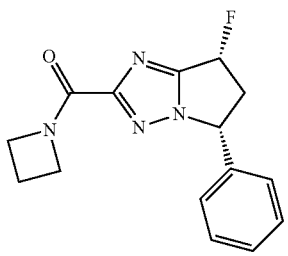 [SMILES: O=C(c1nc2n(n1)[C@@H](c1ccccc1)C[C@H]2F)N1CCC1]

azetidin-1-yl-[rac-(5R,7R)-7-fluoro-5-phenyl-6,7-dihydro-5H-pyrrolo[1,2-b][1,2,4]triazol-2-yl]methanone A mixture of cis-7-fluoro-5-phenyl-6,7-dihydro-5H-pyrrolo[1,2-b][1,2,4]triazole-2-carboxylic acid (20 mg, 0.08 mmol), 1-hydroxybenzotriazole (12 mg, 0.08 mmol), 1-(3-dimethylaminopropyl)-3-ethylcarbodiimidehydrochloride (23 mg, 0.12 mmol) and azetidine hydrochloride (11 mg, 0.12 mmol) in N,N-dimethylformamide (2 mL) was stirred under 25° C. for 16 h and concentrated under reduced pressure. The residue was purified by RP-HPLC (25-55% acetonitrile/0.05% ammonia hydroxide in water) to afford azetidin-1-yl-[(5R,7R)-7-fluoro-5-phenyl-6,7-dihydro-5H-pyrrolo[1,2-b][1,2,4]triazol-2-yl]methanone (6.3 mg, 27%) as a white solid. $^1$H NMR (400 MHz, CD$_3$OD) δ 7.42-7.34 (m, 3H), 7.35-7.23 (m, 2H), 6.16-6.14 (m, 0.5H). 6.02-6.00 (m, 0.5H), 5.64-5.58 (m, 1H), 4.63-4.56 (m, 2H), 4.21-4.17 (m,2H) 3.77-3.68 (m, 1H), 2.85-2.73 (m, 1H), 2.41-2.32 (m, 2H). LCMS R$_T$=0.957 min, m/z=287.2 [M+H]$^+$.

LCMS (10 to 80% acetonitrile in water+0.03% trifluoacetic acid over 2 mins) retention time 0.957 min, ESI+ found [M+H]=287.2.

Example 105

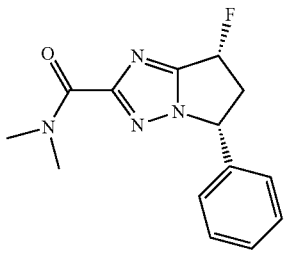 [SMILES: CN(C)C(=O)c1nc2n(n1)[C@@H](c1ccccc1)C[C@H]2F]

rac-(5R,7R)-7-fluoro-N,N-dimethyl-5-phenyl-6,7-dihydro-5H-pyrrolo[1,2-b][1,2,4]triazole-2-carboxamide A mixture of cis-7-fluoro-5-phenyl-6,7-dihydro-5H-pyrrolo[1,2-b][1,2,4]triazole-2-carboxylic acid (20 mg, 0.08 mmol), N,N-dimethylamine (2.0 mL, 2 mmol, 1 M in tetrahydrofuran), 1-(3-dimethylaminopropyl)-3-ethylcarbodiimidehydrochloride (23 mg, 0.12 mmol) and 1-hydroxybenzotriazole (11 mg, 0.08 mmol) in N,N-dimethylformamide (2.0 mL) was stirred under 25 OC for 16 h and concentrated under reduced pressure. The residue was purified by RP-HPLC (23-53% acetonitrile/0.05% ammonia hydroxide in water) to afford (5R,7R)-7-fluoro-N,N-dimethyl-5-phenyl-6,7-dihydro-5H-pyrrolo[1,2-b][1,2,4]triazole-2-carboxamide (11.92 mg, 54%) as a white solid. $^1$H NMR (400 MHz, CD$_3$OD) δ 7.39-7.34 (m, 3H), 7.24-7.22 (m, 2H), 6.42-6.12 (m, 0.5H), 6.05-5.98 (m, 0.5H), 5.59-5.58 (m, 1H), 3.75-3.68 (m, 1H), 3.70 (s, 3H), 3.18 (s, 3H), 2.82-2.75 (m, 1H). LCMS R$_T$=0.925 min, m/z=275.3 [M+H]$^+$.

LCMS (10 to 80% acetonitrile in water+0.03% trifluoacetic acid over 2 mins) retention time 0.925 min, ESI+ found [M+H]=275.3.

RIP1 Kinase Inhibition Assays (Biochemical Assay):

The compounds of the present invention were tested for their capacity to inhibit RIP K activity as described below.

Enzyme assay: The ability of the receptor interacting protein kinase (RIPK1) to catalyze the hydrolysis of adenosine-5'-triphosphate (ATP) is monitored using the Transcreener ADP (adenosine-5'-diphosphate) assay (BellBrook Labs). Purified human RIP1 kinase domain (2-375) (50 nM) derived from a baculovirus-infected insect cell expression system is incubated with test compounds for 2 hours in 50 mM Hepes buffer (pH 7.5) containing 30 mM MgCl$_2$, 1 mM dithiothreitol, 50 uM ATP, 0.002% Brij-35, and 0.5% dimethyl sulfoxide (DMSO). Reactions are quenched by the addition of 1× Bell Brooks Stop buffer B (20 mM Hepes (ph7.5), 40 mM ethylenediaminetetraacetic acid and 0.02% Brij-35) containing an additional 12 mM EDTA and 55 ug/mL ADP2 antibody and 4 nM ADP-AlexaFluor® 633 tracer. The tracer bound to the antibody is displaced by the ADP generated during the RIP1K reaction, which causes a decrease in fluorescence polarization that is measured by laser excitation at 633 nm with a FP microplate reader M1000. Fractional activity was plotted against test article concentration. Using Genedata Screener software (Genedata; Basel, Switzerland), the data were fit to the tight-binding apparent inhibition constant ($K_i^{app}$) Morrison equation [Williams, J. W. and Morrison, J. F. (1979) The kinetics of reversible tight-binding inhibition. Methods Enzymol 63: 437-67]. The following equation was used to calculate fractional activity and $K_i^{app}$:

$$\text{Fractional activity} = \frac{v_i}{v_o} = 1 - \frac{([E]_T + [I]_T + K_i^{app}) - \sqrt{([E]_T + [I]_T + K_i^{app})^2 - 4[E]_T[I]_T}}{2[E]_T}$$

where $[E]_T$ and $[I]_T$ are the total concentrations of active enzyme and test article, respectively.

Exemplary compounds of the present invention are provided in the following Tables along with their physiochemical characterization and in vitro RIP1 kinase inhibitory activity data. "Method" in the first column of each table refers to the synthetic method(s) used to prepare each compound as shown in the Examples above. In certain examples, chiral column retention times (min) are provided for certain stereoisomers.

TABLE 1

| Compound Example # Method | RIP1 Ki (µM) | Structure and Name | Stereo-chemistry | $^1$H NMR Data | MS (m/z) retention time |
|---|---|---|---|---|---|
| Example 1 Method #1 | 0.057 | 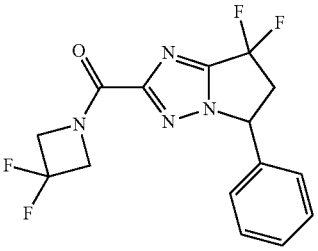 [SMILES: O=C(c1nc2n(n1)C(c1ccccc1)CC2(F)F)N1CC(F)(F)C1]<br>(3,3-difluoroazetidin-1-yl)-(7,7-difluoro-5-phenyl-5,6-dihydropyrrolo[1,2-b][1,2,4]triazol-2-yl)methanone | Mixture of Enantiomers | $^1$H NMR (400 MHz, CD$_3$OD) δ 7.45-7.42 (m, 3H), 7.28-7.25 (m, 2H), 5.94-5.89 (m, 1H), 4.98-4.93 (m, 2H), 4.53 (t, J = 12.0 Hz, 2H), 3.90-3.82 (m, 1H), 3.27-3.19 (m, 1H). | 340.9 0.713 min |
| Example 1a Method #1 SFC 1 | 0.008 | 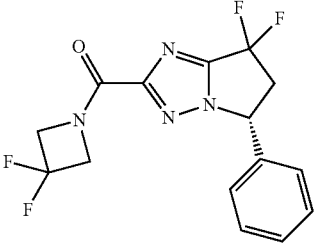 [SMILES: O=C(c1nc2n(n1)[C@@H](c1ccccc1)CC2(F)F)N1CC(F)(F)C1]<br>(3,3-difluoroazetidin-1-yl)-[(5R)-7,7-difluoro-5-phenyl-5,6-dihydropyrrolo[1,2-b][1,2,4]triazol-2-yl]methanone | Single Unknown Stereoisomer | $^1$H NMR (400 MHz, DMSO-d$_6$) δ 7.55-7.35 (m, 3H), 7.33-7.13 (m, 2H), 6.11-5.95 (m, 1H), 4.99-4.77 (m, 2H), 4.59-4.32 (m, 2H), 4.02-3.75 (m, 1H), 3.29-3.19 (m, 1H). | 341.1 5.66 min |
| Example 1b Method #1 | >10 | 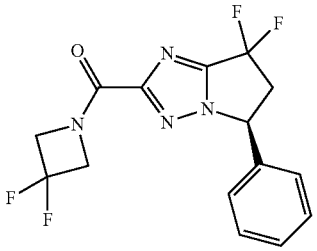 [SMILES: O=C(c1nc2n(n1)[C@H](c1ccccc1)CC2(F)F)N1CC(F)(F)C1]<br>(S)-(7,7-difluoro-5-phenyl-6,7-dihydro-5H- | Single Unknown Stereoisomer | $^1$H NMR (400 MHz, CD$_3$OD) δ 7.46-7.37 (m, 3H), 7.30-7.20 (m, 2H), 5.94-5.86 (m, 1H), 4.96-4.92 (m, 2H), 4.51 (t, J = 12.0 Hz, 2H), 3.91-3.82 (m, 1H), 3.27-3.23 (m, 1H). | 341.1 1.024 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| | | pyrrolo[1,2-b][1,2,4]triazol-2-yl)(3,3-difluoroazetidin-1-yl)methanone | | | |
| Example 2 Method #2 | 0.478 | (3,3-difluoroazetidin-1-yl)-[rac-(5R,7S)-7-fluoro-5-phenyl-6,7-dihydro-5H-pyrrolo[1,2-b][1,2,4]triazol-2-yl]methanone | Mixture of Enantiomers | ¹H NMR (400 MHz, CD₃OD) δ 7.44-7.38 (m, 3H), 7.28-7.24 (m, 2H), 6.26-6.10 (m, 1H), 5.88-5.84 (m. 1H), 4.95-4.92 (m, 2H), 4.51 (t, J = 12.0 Hz, 2H), 3.45-3.30 (m, 1H), 3.16-3.04 (m, 1H). | 323.2 0.961 min |
| Example 3 Method #3 | 0.009 | (3,3-difluoroazetidin-1-yl)-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, CD₃OD) δ 7.44-7.38 (m, 3H), 7.28-7.24 (m, 2H), 6.17-6.02 (m, 1H), 5.65-5.62 (m, 1H), 4.95-4.92 (m, 2H), 4.52 (t, J = 12.0 Hz, 2H), 3.82-3.68 (m, 1H), 2.86-2.76 (m, 1H). | 323.1 1.670 min |
| Example 4 Method #4 | 0.205 | (3,3-difluoroazetidin-1-yl)-(7-phenyl-6,7-dihydro-5H-pyrrolo[1,2-b][1,2,4]triazol-2-yl)methanone | Mixture of Enantiomers | ¹H NMR (400 MHz, CD₃OD) δ 7.39-7.32 (m, 2H), 7.31-7.24 (m, 3H), 4.99-4.92 (m, 2H), 4.57-4.47 (m, 3H), 4.45-4.37 (m, 1H), 4.32-4.23 (m, 1H), 3.30-3.24 (m, 1H), 2.75-2.63 (m, 1H). | 304.9 0.782 min |
| Example 5 Method #5 | 0.768 | (3,3-difluoroazetidin-1-yl)-(8-phenyl-6,8-dihydro-5H- | Mixture of Enantiomers | ¹H NMR (400 MHz, CD₃OD) δ 7.43-7.36 (m, 5H), 5.97 (s, 1H), 4.54-4.43 (m, 4H), 4.43-4.14 (m, 4H). | 321.1 1.559 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| | | [1,2,4]triazolo[5,1-c][1,4]oxazin-2-yl]methanone | | | |
| Example 6 Method #6 | 0.722 | (3,3-difluoroazetidin-1-yl)-[8-(2-fluorophenyl)-6,8-dihydro-5H-[1,2,4]triazolo[5,1-c][1,4]oxazin-2-yl]methanone | Mixture of Enantiomers | ¹H NMR (400 MHz, DMSO-d₆) δ 7.47 (d, J = 6.4 Hz, 1H), 7.38 (t, J = 6.8 Hz, 1H), 7.30-7.18 (m, 2H), 6.18 (s, 1H), 4.81-4.73 (m, 2H), 4.57-4.31 (m, 4H), 4.29-4.08 (m, 2H). | 339.2 1.713 min |
| Example 7 Method #7 | 1.982 | (3,3-difluoroazetidin-1-yl)-[(1R)-1-ethyl-1-methyl-3H-furo[3,4-c]pyridin-6-yl]methanone | Single Unknown Stereoisomer | ¹H NMR (400 MHz, CD₃OD) δ 8.56 (s, 1H), 7.92 (s, 1H), 5.20-5.12 (m, 2H), 5.06 (t, J = 12.0 Hz, 2H), 4.54 (t, J = 12.0 Hz, 2H), 1.87 (q, J = 7.6 Hz, 2H), 1.48 (s, 3H), 0.79 (t, J = 7.6 Hz, 3H). | 283.1 1.699 min |
| Example 8 Method #8 | 8.69 | (3,3-difluoroazetidin-1-yl)-[5-(1,1-difluoroethyl)-6,7-dihydro-5H-pyrrolo[1,2-b][1,2,4]triazol-2-yl]methanone | Mixture of Enantiomers | ¹H NMR (400 MHz, CD₃OD) δ 4.98-4.95 (m, 2H), 4.90-4.83 (m, 1H), 4.52 (t, J = 12.0 Hz, 2H), 3.03-2.94 (m, 3H), 2.88-2.85 (m, 1H), 1.82 (t, J = 19.2 Hz, 3H). | 292.9 0.738 min |
| Example 9 Method #9 | 2.655 | (3,3-difluoroazetidin-1-yl)-[(4R)-4-phenyl-6-dihydro-4H-pyrrolo[1,2-b]pyrazol-2-yl]methanone | Single Unknown Stereoisomer | ¹H NMR (400 MHz, CD₃OD) δ 7.35-7.30 (m, 2H), 7.30-7.21 (m, 3H), 6.44 (s, 1H), 4.96-4.85 (m, 2H), 4.51-4.47 (m, 3H), 4.40-4.28 (m 1H), 4.28-4.20 (m, 1H), 3.14-3.05 (m, 1H), 2.57-2.50 (m, 1H). | 304.2 1.040 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 10 Method #10 | >10 | 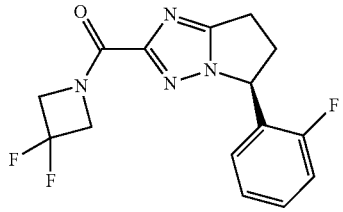<br>(3,3-difluoroazetidin-1-yl)-[(5S)-5-(2-fluorophenyl)-6,7-dihydro-5H-pyrrolo[1,2-b][1,2,4]triazol-2-yl]methanone | Single Unknown Stereoisomer | ¹H NMR (400 MHz, CD₃OD) δ 7.43-7.36 (m, 1H), 7.23-7.10 (m, 3H), 5.80-5.77 (m, 1H), 4.96-4.86 (m, 2H), 4.48 (t, J = 12.0 Hz, 2H), 3.38-3.31 (m, 1H), 3.19-3.02 (m, 2H), 2.70-2.67 (m, 1H). | 323.2 1.738 min |
| Example 11 Method #11 | 0.009 | 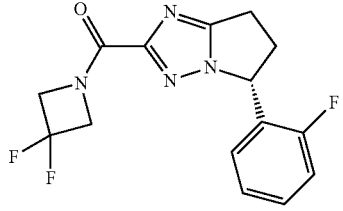<br>(3,3-difluoroazetidin-1-yl)-[(5R)-5-(2-fluorophenyl)-6,7-dihydro-5H-pyrrolo[1,2-b][1,2,4]triazol-2-yl]methanone | Single Unknown Stereoisomer | ¹H NMR (400 MHz, CD₃OD) δ 7.44-7.35 (m, 1H), 7.22-7.10 (m, 3H), 5.80-5.77 (m, 1H), 4.94-4.87 (m, 1H), 4.85-4.79 (m, 1H), 4.48 (t, J = 12.0 Hz, 2H), 3.36-3.31 (m, 1H), 3.20-3.01 (m, 2H), 2.75-2.65 (m, 1H). | 323.2 1.737 min |
| Example 12 Method #12 | 0.137 | 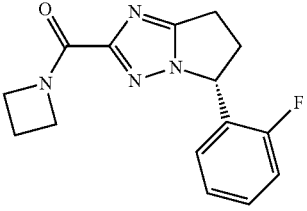<br>azetidin-1-yl-[(5R)-5-(2-fluorophenyl)-6,7-dihydro-5H-pyrrolo[1,2-b][1,2,4]triazol-2-yl]methanone | Single Unknown Stereoisomer | ¹H NMR (400 MHz, CD₃OD) δ 7.40-7.37 (m, 1H), 7.19-7.11 (m, 3H), 5.79-5.75 (m, 1H), 4.58-4.53 (m, 2H), 4.19-4.15 (m, 2H), 3.28-3.26 (m, 1H), 3.13-3.06 (m, 2H), 2.71-2.68 (m, 1H), 2.39-2.31 (m, 2H). | 287.0 0.680 min |
| Example 13 Method #13 | 1.135 | 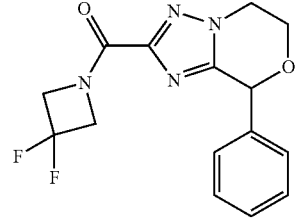<br>(3,3-difluoroazetidin-1-yl)-(4-phenyl-6,7-dihydro-4H-pyrazolo[5,1-c][1,4]oxazin-2-yl)methanone | Mixture of Enantiomers | ¹H NMR (400 MHz, CD₃OD) δ 7.38 (s, 5H), 6.24 (s, 1H), 5.82 (s, 1H), 4.95-4.88 (m, 2H), 4.48-4.42 (m, 2H), 4.45-4.37 (m, 2H), 4.29-4.17 (m, 2H). | 320.1 1.729 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 14 Method #14 | 0.233 | 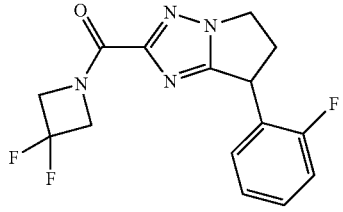 (3,3-difluoroazetidin-1-yl)-[7-(2-fluorophenyl)-6,7-dihydro-5H-pyrrolo[1,2-b][1,2,4]triazol-2-yl]methanone | Mixture of Enantiomers | ¹H NMR (400 MHz, CD₃OD) δ 7.47-7.23 (m, 2H), 7.21-6.94 (m, 2H), 5.02-4.91 (m, 2H), 4.78-4.68 (m, 1H), 4.50 (t, J = 12.0 Hz, 2H), 4.44-4.37 (m, 1H), 4.33-4.18 (m, 1H), 3.40-3.32 (m, 1H), 2.74-2.63 (m, 1H). | 323.1 1.626 min |
| Example 15 Method #4 SFC 2 | 0.066 | 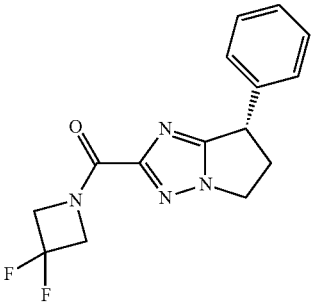 [SMILES: O=C(c1nc2n(n1)CC[C@H]2c1ccccc1)N1CC(F)(F)C1] (3,3-difluoroazetidin-1-yl)-[(7S)-7-phenyl-6,7-dihydro-5H-pyrrolo[1,2-b][1,2,4]triazol-2-yl]methanone | Single Unknown Stereoisomer | 1H NMR (400 MHz, DMSO-d6) δ 7.42-7.23 (m, 5H), 4.96-4.72 (m, 2H), 4.61-4.15 (m, 4H), 3.25-3.09 (m, 1H, 2.73-2.53 (m, 1H). | 305.1 4.98 min |
| Example 16 Method #16 | 0.105 | 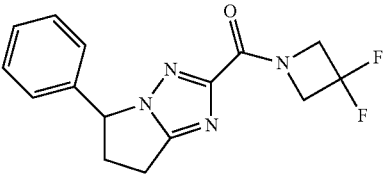 (3,3-difluoroazetidin-1-yl)-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.45-7.33 (m, 3H), 7.26-7.17 (m, 2H), 5.66-5.54 (m, 1H), 4.85(m, 2H), 4.45 (t, J = 12.6 Hz, 2H), 3.24-3.14 (m, 2H), 3.14-3.05 (m, 1H), 2.99 (m, 1H). | 305.1 4.26 min |
| Example 17 Method #16 | 1.366 | 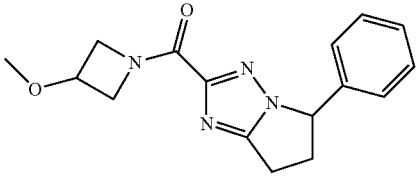 (3-methoxyazetidin-1-yl)-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.49-7.29 (m, 3H), 7.26-7.15 (m, 2H), 5.64-5.51 (m, 1H), 4.67-4.52 (m, 1H), 4.23-4.19 (m, 2H), 4.20-4.15 (m, 1H), 3.87-3.73 (m, 1H), 3.21 (s, 3H), 3.13-3.03 (m, 2H), 3.03-2.93 (m, 2H). | 299.1 3.94 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 18 Method #16 | 0.343 | 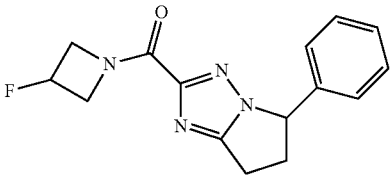<br>(3-fluoroazetidin-1-yl)-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.45-7.31 (m, 3H), 7.25-7.17 (m, 2H), 5.64-5.54 (m, 1H), 4.86-4.68 (m, 1H), 4.55-4.27 (m, 2H), 4.14-3.98 (m, 1H), 3.29-3.28 (m, 1H), 3.24-3.15 (m, 1H), 3.13-3.04 (m, 1H), 3.04-2.92 (m, 1H), 2.60-2.52 (m, 1H). | 287.1 4.01 min |
| Example 19 Method #16 | 0.465 | 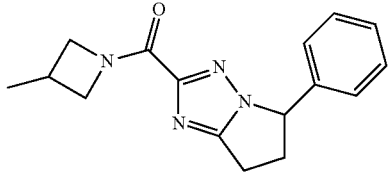<br>(3-methylazetidin-1-yl)-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.44-7.31 (m, 3H), 7.23-7.16 (m, 2H), 5.56 (m, 1H), 4.58-4.44 (m, 1H), 4.18-4.06 (m, 1H), 4.02-3.91 (m, 1H), 3.60-3.49 (m, 1H), 3.30-3.14 (m, 2H), 3.12-3.02 (m, 1H), 3.02-2.91 (m, 1H), 2.74-2.63 (m, 1H), 1.22-1.15 (m, 3H). | 283.1 4.36 min |
| Example 20 Method #16 | 0.271 | 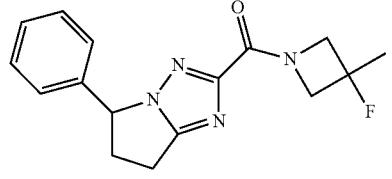<br>(3-fluoro-3-methyl-azetidin-1-yl)-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.43-7.32 (m, 3H), 7.26-7.17 (m, 2H), 5.58 (dd, J = 8.3, 5.7 Hz, 1H), 4.55-4.46 (m, 2H), 4.15-4.03 (m, 2H), 3.29-3.27 (m, 1H), 3.17 (m, 1H), 3.13-3.03 (m, 1H), 3.03-2.93 (m, 1H), 1.64-1.50 (m, 3H). | 301.1 4.69 min |
| Example 21 Method #16 | 1.357 | 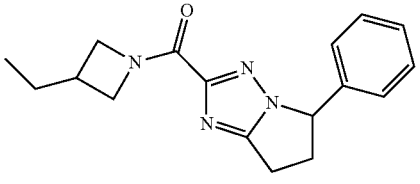<br>(3-ethylazetidin-1-yl)-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.45-7.30 (m, 3H), 7.26-7.11 (m, 2H), 5.63-5.50 (m, 1H), 4.55-4.43 (m, 1H), 4.13-3.94 (m, 2H), 3.64-3.53 (m, 1H), 3.30-3.25 (m, 1H), 3.25-3.12 (m, 1H), 3.12-3.02 (m, 1H), 3.02-2.91 (m, 1H), 2.58-2.52 (m, 1H), 1.60-1.49 (m, 2H), 0.87-0.79 (m, 3H). | 297.1 5.03 min |

TABLE 1-continued

| Compound Example # Method | RIP1 Ki (μM) | Structure and Name | Stereo- chemistry | ¹H NMR Data | MS (m/z) retention time |
|---|---|---|---|---|---|
| Example 22 Method #16 | 0.511 | azetidin-1-yl-[5-(2-fluorophenyl)-6,7-dihydro-5H-pyrrolo[1,2-b][1,2,4]triazol-2-yl]methanone | Mixture of Enantiomers | | 287.1 4.17 min |
| Example 23 Method #16 | 0.044 | (3,3-difluoroazetidin-1-yl)-[5-(2-fluorophenyl)-6,7-dihydro-5H-pyrrolo[1,2-b][1,2,4]triazol-2-yl]methanone | Mixture of Enantiomers | 1H NMR (400 MHz, DMSO-d6) δ 7.44 (m, 1H), 7.33-7.11 (m, 3H), 5.80(m, J = 8.6, 5.6 Hz, 1H), 4.92-4.79 (m, 2H), 4.45 (m, 2H), 3.26-3.15 (m, 1H), 3.13-2.94(m, 2H), 2.69-2.54 (m, 1H). | 323.1 4.64 min |
| Example 24 Method #16 | 0.194 | (3-fluoroazetidin-1-yl)-[5-(2-fluorophenyl)-6,7-dihydro-5H-pyrrolo[1,2-b][1,2,4]triazol-2-yl]methanone | Mixture of Enantiomers | 1H NMR (400 MHz, DMSO-d6) δ 7.51-7.35 (m, 1H), 7.33-7.12 (m, 3H), 5.78 (dd, J = 8.6, 5.6 Hz, 1H), 5.58-5.27 (m, 1H), 4.89-4.64 (m, 1H), 4.54-4.23 (m, 2H), 4.15-3.93 (m, 1H), 3.25-3.13 (m, 1H), 3.13-2.94 (m, 2H), 2.66-2.51 (m, 1H). | 305.1 4.20 min |
| Example 25 Method #16 | 3.6 | N-methyl-5-phenyl-6,7-dihydro-5H-pyrrolo[1,2-b][1,2,4]triazole-2-carboxamide | Mixture of Enantiomers | 1H NMR (400 MHz, DMSO-d6) δ 8.36 (d, J = 5.1 Hz, 1H), 7.45-7.30 (m, 4H), 7.29-7.18 (m, 2H), 5.56 (dd, J = 8.3, 5.8 Hz, 1H), 2.71 (d, J = 4.8 Hz, 3H), 2.69-2.66 (m, 1H), 2.60-2.52 (m, 1H) | 243.1 3.19 min |

TABLE 1-continued

| Compound Example # Method | RIP1 Ki (μM) | Structure and Name | Stereo- chemistry | ¹H NMR Data | MS (m/z) retention time |
|---|---|---|---|---|---|
| Example 26 Method #16 | 0.530 | 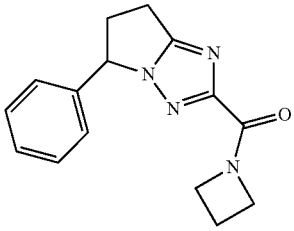<br>azetidin-1-yl-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.44-7.30 (m, 3H), 7.27-7.05 (m, 2H), 5.64-5.47 (m, 0H), 4.48-4.32 (m, 2H), 4.06-3.90 (m, 2H), 3.26-2.53 (m, 1H), 2.23 (s, 1H), 1.04 (s, 1H). | 269.1 3.64 min |
| Example 27 Method #16 | 2.2 | 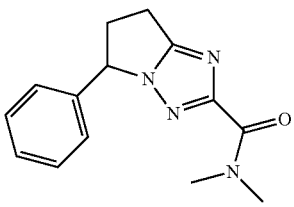<br>N,N-dimethyl-5-phenyl-6,7-dihydro-5H-pyrrolo[1,2-b][1,2,4]triazole-2-carboxamide | Mixture of Enantiomers | 1H NMR (400 MHz, DMSO-d6) δ 7.45-7.30 (m, 3H), 7.25-7.18 (m, 2H), 5.56 (dd, J = 8.3, 5.7 Hz, 1H), 3.19 (dddd, J = 13.0, 9.4, 8,3, 4.9 Hz, 1H), 3.14-3.06 (m, 1H), 3.05 (s, 3H), 3.03-2.96 (m, 1H), 2.95 (s, 3H), 2.59-2.52 (m, 1H). | 257.1 3.37 min |
| Example 28 Method #16 | 8.9 | 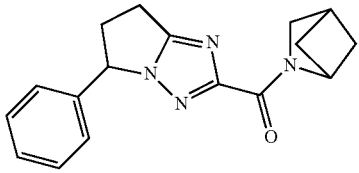<br>2-azabicyclo[2.1.1]hexan-2-yl-(5-phenyl-6,7-dihydro-5H-pyrrolo[1,2-b][1,2,4]triazol-2-yl)methanone | Mixture of Enantiomers | 1H NMR (400 MHz, DMSO-d6) δ 7.45-7.31 (m, 3H), 7.29-7.15 (m, 2H), 5.62-4.68 (m, 1H), 3.71 (d, J = 1.0 Hz, 1H), 3.41 (ddt, J = 1.5, 1.0, 0.5 Hz, 1H), 3.21-3.05 (m, 3H), 3.04-2.93 (m, 2H), 2.88 (dddd, J = 7.9, 4.8, 2.5, 1.4 Hz, 1H), 1.96 (dd, J = 16.4, 4.3 Hz, 2H), 1.43-1.26 (m, 2H). | 295.1 3.92 min |
| Example 29 Method #16 | 5.4 | 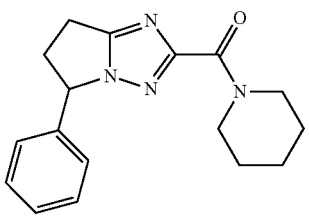<br>(5-phenyl-6,7-dihydro-5H-pyrrolo[1,2-b][1,2,4]triazol-2-yl)-(1-piperidyl)methanone | Mixture of Enantiomers | 1H NMR (400 MHz, DMSO-d6) δ 7.44-7.31 (m, 3H), 7.24-7.19 (m, 2H), 5.55 (dd, J = 8.3, 5.7 Hz, 1H), 3.61-3.52 (m, 2H), 3.52-3.42 (m, 2H), 3.25-2.86 (m, 3H), 2.61-2.52 (m, 1H), 1.65-1.56 (m, 2H), 1.56-1.38 (m, 4H). | 297.1 4.11 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 30 Method #16 | 6.4 | (5-phenyl-6,7-dihydro-5H-pyrrolo[1,2-b][1,2,4]triazol-2-yl)-pyrrolidin-1-yl-methanone | Mixture of Enantiomers | 1H NMR (400 MHz, DMSO-d6) δ 7.46-7.30 (m, 3H), 7.27-7.13 (m, 2H), 5.57 (dd, J = 8.3, 5.7 Hz, 1H), 3.72-3.60 (m, 2H), 3.50-3.40 (m, 2H), 3.24-3.13 (m, 1H), 3.13-2.90 (m, 2H), 2.61-2.51 (m, 1H), 1.94-1.68 (m, 4H). | 283.1 3.88 min |
| Example 31 Method #16 SFC 3 | 7.1 | (3,3-difluoroazetidin-1-yl)-[rac-(5S)-5-phenyl-6,7-dihydro-5H-pyrrolo[1,2-b][1,2,4]triazol-2-yl]methanone | Single Unknown Stereoisomer | 1H NMR (400 MHz, DMSO-d6) δ 7.46-7.31 (m, 3H), 7.26-7.16 (m, 2H), 5.67-5.53 (m, 1H), 4.95-4.76 (m, 2H), 4.45 (t, J = 12.5 Hz, 2H), 3.24-3.05 (m, 3H), 3.05-2.92 (m, 1H). | 305.1 4.49 min |
| Example 32 Method #16 SFC 4 | 0.066 | (3,3-difluoroazetidin-1-yl)-[rac-(SR)-5-phenyl-6,7-dihydro-5H-pyrrolo[1,2-b][1,2,4]triazol-2-yl]methanone | Single Unknown Stereoisomer | 1H NMR (400 MHz, DMSO-d6) δ 7.45-7.31 (m, 3H), 7.28-7.17 (m, 2H), 5.60 (dd, J = 8.4, 5.7 Hz, 1H), 4.94-4.79 (m, 2H), 4.45 (t, J = 12.6 Hz, 2H), 3.25-3.11 (m, 1H), 3.15-2.91 (m, 2H), 2.61-2.45 (m, 1H). | 305.1 4.49 min |
| Example 33 | 1.4 | 5-(2-fluorophenyl)-N,N-dimethyl-6,7-dihydro-5H-pyrrolo[1,2-b][1,2,4]triazole-2-carboxamide | Mixture of Enantiomers | ¹H NMR (400 MHz, DMSO-d6) δ 7.49-7.36 (m, 1H), 7.37-7.12 (m, 3H), 5.76 (dd, J = 8.6, 5.6 Hz, 1H), 3.24-3.16 (m, 1H), 3.04 (s, 3H), 2.95 (s, 3H), 2.87 (m, 2H), 2.59 (m, 1H). | 275.1 3.49 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 34 | 3.4 | 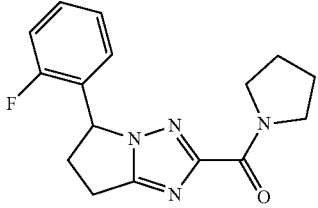<br>[5-(2-fluorophenyl)-6,7-dihydro-5H-pyrrolo[1,2-b][1,2,4]triazol-2-yl]-pyrrolidin-1-yl-methanone | Mixture of Enantiomers | ¹H NMR (400 MHz, DMSO-d6) δ 7.50-7.36 (m, 1H), 7.34-7.09 (m, 3H), 5.77 (dd, J = 8.6, 5.5 Hz, 1H), 3.71-3.57 (m, 2H), 3.44 (m, 2H), 3.17 (m, 1H), 3.14-2.98 (m, 2H), 2.58 (m, 1H), 1.97- 1.69 (m, 4H). | 301.1 3.98 min |
| Example 35 | 1.3 | 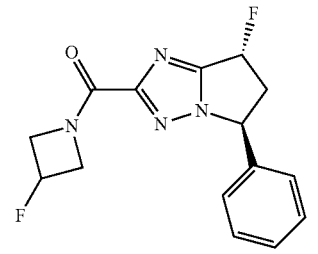<br>(3-fluoroazetidin-1-yl)-[rac-(5S,7R)-7-fluoro-5-phenyl-6,7-dihydro-5H-pyrrolo[1,2-b][1,2,4]triazol-2-yl]methanone | Mixture of Enantiomers | ¹H NMR (400 MHz, CD₃OD) δ 7.41-7.38 (m, 3H), 7.26-7.25 (m, 2H), 6.25-6.23 (m, 0.5H), 6.11-6.09 (m, 0.5H), 5.87-5.83 (m, 1H), 5.47-5.45 (m, 0.5H), 5.32-5.30 (m, 0.5H), 4.86-4.80 (m, 1H), 4.70-4.58 (m, 1H), 4.55-4.45 (m, 1H), 4.25-4.19 (m, 1H), 3.43-3.30 (m, 1H), 3.15-3.07 (m, 1H). | 304.9 0.772 min |
| Example 36 | 0.004 | 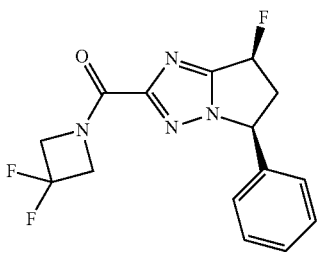<br>(3,3-difluoroazetidin-1-yl)-[rac-(5S,7S)-7-fluoro-5-phenyl-6,7-dihydro-5H-pyrrolo[1,2-b][1,2,4]triazol-2-yl]methanone | Single Unknown Stereoisomer | ¹H NMR (400 MHz, CD₃OD) δ 7.41-7.37 (m, 3H), 7.25-7.23 (m, 2H), 6.15 (d, J = 6.8 Hz, 0.5H), 6.02 (d, J = 7.2 Hz, 0.5H), 5.62-5.61 (m, 1H), 4.95-4.90 (m, 2H), 4.50 (t, J = 12.0 Hz, 2H), 3.76-3.68 (m, 1H), 2.85-2.74 (m, 1H). | 323.2 0.969 min |
| Example 37 | 1.4 | 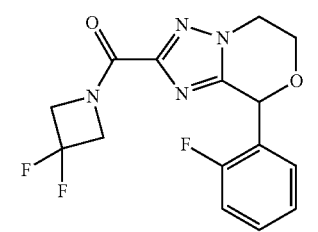<br>(3,3-difluoroazetidin-1-yl)-[4-(2-fluorophenyl)-6,7-dihydro-4H-pyrazolo[5,1-c][1,4]oxazin-2-yl]methanone | Mixture of Enantiomers | ¹H NMR (400 MHz, CD₃OD) δ 7.41-7.35 (m, 2H), 7.21-7.17 (m, 2H), 6.28 (s, 1H), 6.11 (s, 1H), 4.95-4.90 (m, 3H), 4.45-4.17 (m, 5H). | 338.1 1.802 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 38 | 0.048 | 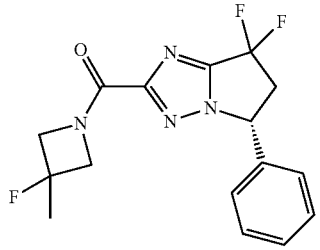<br>(3-fluoro-3-methyl-azetidin-1-yl)-[rac-(5R)-7,7-difluoro-5-phenyl-5,6-dihydropyrrolo[1,2-b][1,2,4]triazol-2-yl]methanone | Single Unknown Stereoisomer | ¹H NMR (400 MHz, CD$_3$OD) δ 7.44-7.42 (m, 3H), 7.27-7.25 (m, 2H), 5.93-5.88 (m, 1H), 4.73-4.58 (m, 2H), 4.27-4.19 (m, 2H), 3.87-3.83 (m, 1H), 3.31-3.24 (m, 1H), 1.67-1.59 (m, 3H). | 336.9 0.829 min |
| Example 39 | 0.032 | 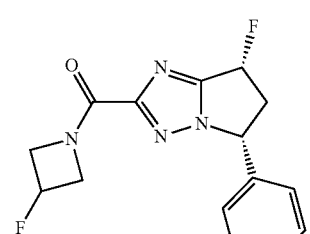<br>(3-fluoroazetidin-1-yl)-[rac-(5R,7R)-7-fluoro-5-phenyl-6,7-dihydro-5H-pyrrolo[1,2-b][1,2,4]triazol-2-yl]methanone | Mixture of Enantiomers | ¹H NMR (400 MHz, CD$_3$OD) δ 7.42-7.37 (m, 3H), 7.27-7.25 (m, 2H), 6.16-6.14 (m, 0.5H), 6.02-6.00 (m, 0.5H), 5.65-5.59 (m, 1H), 5.46-5.44 (m, 0.5H), 5.31-5.30 (m, 0.5H), 4.86-4.84 (m, 1H), 4.68-4.59 (m, 1H), 4.53-4.41 (m, 1H), 4.26-4.15 (m, 1H), 3.77-3.69 (m, 1H), 2.87-2.73 (m, 1H). | 305.2 0.908 min |
| Example 40 | 0.92 | 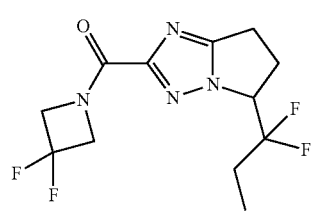 [SMILES: CCC(F)(F)C1CCc2nc(C(=O)N3CC(F)(F)C3)nn21]<br>(3,3-difluoroazetidin-1-yl)-[5-(1,1-difluoropropyl)-6,7-dihydro-5H-pyrrolo[1,2-b][1,2,4]triazol-2-yl]methanone | Mixture of Enantiomers | ¹H NMR (400 MHz, CD$_3$OD) δ 4.99-4.92 (m, 3H), 4.52 (t, J = 12.0 Hz, 2H), 3.03-2.84 (m, 4H), 2.27-2.07 (m, 2H), 1.12 (t, J = 7.2 Hz, 3H). | 307.1 0.932 min |
| Example 41 | 8 | 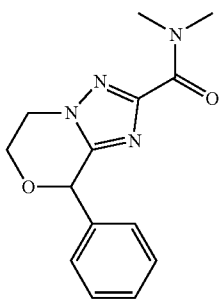 [SMILES: CN(C)C(=O)c1nc2n(n1)CCOC2c1ccccc1]<br>N,N-dimethyl-8-phenyl-6,8-dihydro-5H-[1,2,4]triazolo[5,1- | Mixture of Enantiomers | ¹H NMR (400 MHz, DMSO-d$_6$) δ 7.49-7.28 (m, 5H), 6.01 (s, 1H), 4.46-4.37 (m, 1H), 4.36-4.27 (m, 2H), 4.23-4.14 (m, 1H), 3.01 (s, 3H), 2.95 (s, 3H). | 273.1 3.31 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| | | c][1,4]oxazine-2-carboxamide | | | |
| Example 42 | 2.1 | 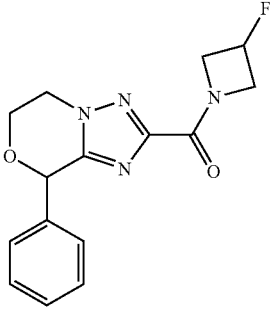 [SMILES: O=C(c1nc2n(n1)CCOC2c1ccccc1)N1CC(F)C1]<br>(3-fluoroazetidin-1-yl)-(8-phenyl-6,8-dihydro-5H-[1,2,4]triazolo[5,1-c][1,4]oxazin-2-yl)methanone | Mixture of Enantiomers | ¹H NMR (400 MHz, DMSO-d₆) δ 7.50-7.26 (m, 5H), 6.03 (s, 1H), 5.51-5.30 (m, 1H), 4.87-4.58 (m, 1H), 4.50-3.97 (m, 6H), 3.17 (d, J = 5.2 Hz, 1H). | 304.1 3.64 min |
| Example 43 | 5 | 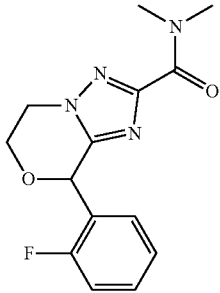 [SMILES: CN(C)C(=O)c1nc2n(n1)CCOC2c1ccccc1F]<br>8-(2-fluorophenyl)-N,N-dimethyl-6,8-dihydro-5H-[1,2,4]triazolo[5,1-c][1,4]oxazine-2-carboxamide | Mixture of Enantiomers | ¹H NMR (400 MHz, DMSO-d₆) δ 7.53-7.33 (m, 2H), 7.32-7.17 (m, 2H), 6.17 (s, 1H), 4.48-4.28 (m, 3H), 4.29-4.16 (m, 1H), 2.99 (s, 3H), 2.94 (s, 3H). | 291.1 3.26 min |
| Example 44 | 4.8 | 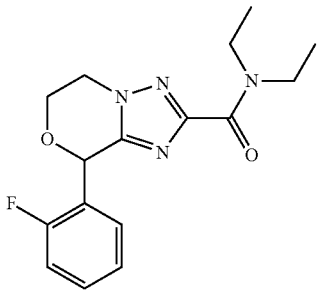 [SMILES: CCN(CC)C(=O)c1nc2n(n1)CCOC2c1ccccc1F]<br>N,N-diethyl-8-(2-fluorophenyl)-6,8-dihydro-5H-[1,2,4]triazolo[5,1-c][1,4]oxazine-2-carboxamide | Mixture of Enantiomers | ¹H NMR (400 MHz, DMSO-d₆) δ 7.56-7.32 (m, 2H), 7.33-7.14 (m, 2H), 6.17 (s, 1H), 4.47-4.15 (m, 4H), 3.43-3.34 (m, 2H), 3.30-3.25 (m, 3H), 1.22-0.94 (m, 6H). | 319.1 4.02 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 45 | 2.3 | 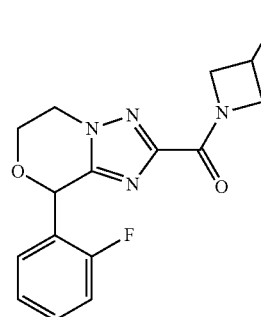<br>(3-fluoroazetidin-1-yl)-[8-(2-fluorophenyl)-6,8-dihydro-5H-[1,2,4]triazolo[5,1-c][1,4]oxazin-2-yl]methanone | Mixture of Enantiomers | ¹H NMR (400 MHz, DMSO-d$_6$) δ 7.55-7.43 (m, 1H), 7.43-7.35 (m, 1H), 7.32-7.18 (m, 2H), 6.18 (s, 1H), 5.51-5.27 (m, 1H), 4.79-4.61 (m, 1H), 4.49-4.27 (m, 5H), 4.27-4.16 (m, 1H), 4.12-3.96 (m, 1H). | 321.1 3.67 min |
| Example 46 | 0.917 | 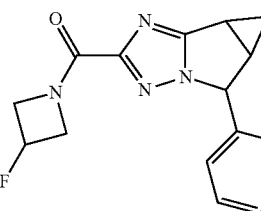<br>(3-fluoroazetidin-1-yl)-(5-phenyl-6,7,9-triazatricyclo[4.3.0.0²,⁴]nona-1(9),7-dien-8-yl)methanone | Mixture of Enantiomers | ¹H NMR (400 MHz, CD$_3$OD) δ 7.43-7.37 (m, 3H), 7.27-7.25 (m, 2H), 5.88 (d, J = 6.0 Hz, 1H), 5.47-5.45 (m, 0.5H), 5.32-5.30 (m, 0.5H), 4.85-4.82 (m, 1H), 4.63-4.47 (m, 2H), 4.24-4.18 (m, 1H), 2.98-2.94 (m, 1H), 2.67-2.64 (m, 1H), 1.29-1.23 (m, 1H), 0.82-0.79 (m, 1H). | 299.0 0.767 min |
| Example 47 | 0.195 | 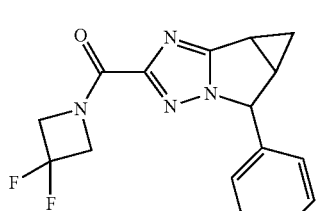<br>(3,3-difluoroazetidin-1-yl)-(5-phenyl-6,7,9-triazatricyclo[4.3.0.0²,⁴]nona-1(9),7-dien-8-yl)methanone | Mixture of Enantiomers | ¹H NMR (400 MHz, CD$_3$OD) δ 7.42-7.35 (m, 3H), 7.27-7.24 (m, 2H), 5.88 (d, J = 6.4 Hz, 1H), 4.96-4.91 (m, 2H), 4.49 (t, J = 12.0 Hz, 2H), 2.97-2.94 (m, 1H), 2.68-2.65 (m, 1H), 1.28-1.23 (m, 1H), 0.83-0.79 (m, 1H). | 317.1 0.808 min |

TABLE 1-continued

| Compound Example # Method | RIP1 Ki (μM) | Structure and Name | Stereo-chemistry | ¹H NMR Data | MS (m/z) retention time |
|---|---|---|---|---|---|
| Example 48 | 0.071 | (3-fluoroazetidin-1-yl)-[rac-(5R)-7,7-difluoro-5-phenyl-5,6-dihydropyrrolo[1,2-b][1,2,4]triazol-2-yl]methanone | Single Unknown Stereoisomer | ¹H NMR (400 MHz, CD₃OD) δ 7.45-7.38 (m, 3H), 7.26-7.24 (m, 2H), 5.93-5.88 (m, 1H), 5.47-5.45 (m, 0.5H), 5.32-5.30 (m, 0.5H), 4.92-4.90 (m, 1H), 4.65-4.59 (m, 1H), 4.52-4.42 (m, 1H), 4.26-4.19 (m, 1H), 3.87-3.83 (m, 1H), 3.31-3.21 (m, 1H). | 323.1 1.724 min |

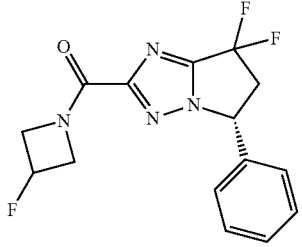

TABLE 2

| Compound Example # Method | RIP1 Ki (μM) | Stucture and Name | Stereo-chemistry | ¹H NMR Data | MS (m/z) retention time |
|---|---|---|---|---|---|
| Example 49 Method 16 | 5 | (3,3-difluoroazetidin-1-yl)-[rac-(5S)-5-(trifluoromethyl)-6,7-dihydro-5H-pyrrolo[1,2-b][1,2,4]triazol-2-yl]methanone | Single Known Stereoisomer | ¹H NMR (400 MHz, CD₃OD) δ 5.30-5.26 (m, 1H), 4.99-4.92 (m, 2H), 4.56-4.50 (m, 2H), 3.13-3.02 (m, 23), 2.88-2.87 (m, 1H) | 297.1 1.294 min |
| Example 50 Method 17 | 1.6 | [rac-(5S,7S)-7-fluoro-5-phenyl-6,7-dihydro-5H-pyrrolo[1,2-b][1,2,4]triazol-2-yl]-[3-(trifluoromethyl)azetidin-1-yl]methanone | Mixture of Enantiomers | ¹H NMR (400 MHz, DMSO-d₆) δ 7.49-7.32 (m, 3H), 7.29-7.16 (m, 2H), 6.21 (ddt, J = 56.5, 7.2, 1.9 Hz, 1H), 5.70 (ddd, J = 9.0, 6.7, 3.0 Hz, 1H), 4.72 (dt, J = 13.1, 9.7 Hz, 1H), 4.45 (td, J = 9.7, 5.4 Hz, 1H), 4.29 (t, J = 9.9 Hz, 1H), 4.02 (dd, J = 10.7, 5.4 Hz, 1H), 3.87-3.55 (m, 2H), 2.85-2.54 (m, 1H). | 355.1 4.59 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 51 Method 17 | 0.100 | [3-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d₆) δ 7.49-7.32 (m, 3H), 7.27-7.11 (m, 2H), 6.59-6.09 (m, 2H), 5.69 (ddd, J = 8.9, 6.7, 3.0 Hz, 1H), 4.56 (q, J = 9.0 Hz, 1H), 4.38 (td, J = 11.0, 5.6 Hz, 1H), 4.14 (t, J = 9.7 Hz, 1H), 3.95 (dd, J = 10.5, 5.5 Hz, 1H), 3.72 (dddd, J = 26.2, 15.5, 8 5, 7.1 Hz, 1H), 3.24-3.05 (m, 1H), 2.79-2.58 (m, 1H). | 337.1 4.22 min |
| Example 52 Method 17 | 0.005 | [rac-(2S)-2-(difluoromethyl)azelidin-1-yl]-[rac-(5S,7S)-7-fluoro-5-phenyl-6,7-dihydro-5H-pyrrolo[1.2-b][1,2,4]triazol-2-yl)methanone | Single Unknown Stereoisomer | ¹H NMR (400 MHz, DMSO-d₆) δ 7.40 (dddd, J = 10.6, 8.6, 6.7, 3.6 Hz, 3H), 7.31-7.16 (m, 2H), 6.78-6.02 (m, 2H), 5.70 (ddd, J = 8.8, 6.7, 2.8 Hz, 1H), 5.32-4.62 (m, 1H), 4.38 (dd, J = 8.5, 7.0 Hz, 1H), 4.11-3.84 (m, 1H), 3.73 (dddd, J = 26.0, 15.4, 8.5, 7.1 Hz, 1H), 2.81-2.58 (m, 1H), 2.48-2.35 (m, 1H), 2.34-2.17 (m, 1H). | 337.1 10.53 min |
| Example 53 Method 17 | 0.009 | [rac-(2R)-2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone | Single Unknown Stereoisomer | ¹H NMR (400 MHz, DMSO-d6) δ 7.47-7.32 (m, 3H), 7.28-7.18 (m, 2H), 6.80-6.08 (m, 2H), 5.70 (td, J = 8.8, 7.7, 2.8 Hz, 1H), 5.18-4.62 (m, 1H), 4.39 (dt, J = 9.1, 6.5 Hz, 1H), 3.98 (dtd, J = 38.7, 9.5, 6.0 Hz, 1H), 3.73 (dddd, J = 26.1, 15.5, 8.5, 7.1 Hz, 1H), 2.78-2.51 (m, 1H), 2.42 (dddd, J = 15.6, 11.7, 8.5, 5.7 Hz, 1H), 2.27 (dddd, J = 11.5, 8.7, 6.1, 2.7 Hz, 1H). | 337.1 10.48 min |
| Example 54 Method 17 | 0.011 | (3,3-difluoropyrrolidin-1-yl)-[rac-(5R,7R)-7-fluoro-5-phenyl-6,7-dihydro-5H-pyrrolo[1,2-b][1,2,4]triazol-2-yl]methanone | Single Unknown Stereoisomer | ¹H NMR (400 MHz, DMSO-d₆) δ 7.53-7.33 (m, 3H), 7.24 (ddd, J = 7.8, 3.7, 1.5 Hz, 2H), 6.22 (ddd, J = 56.5, 7.2, 1.9 Hz, 1H), 5.70 (td, J = 8.0, 4.2 Hz, 1H), 4.22 (t, J = 12.9 Hz, 1H), 4.05-3.96 (m, 1H), 3.91 (t, J = 13.2 Hz, 1H), 3 85-3.61 (m, 2H), 2.69 (ddt, J = 26.8, 15.2, 2.4 Hz, 1H), 2.49-2.31 (m, 2H). | 337.1 4.42 min |

TABLE 2-continued

| Compound Example # Method | RIP1 Ki (μM) | Structure and Name | Stereo-chemistry | ¹H NMR Data | MS (m/z) retention time |
|---|---|---|---|---|---|
| Example 55 Method 17 | 3.9 | rac-(5S,7S)-7-fluoro-N-(2-methoxyethyl)-5-phenyl-N-(2,2,2-trifluoroethyl)-6,7-dihydro-5H-pyrrolo[1,2-b][1,2,4]triazole-2-carboxamide | Mixture of Enantiomers | ¹H NMR (400 MHz, DMSO-$d_6$) δ 7.47-7.33 (m, 3H), 7.27-7.18 (m, 2H), 6.36-6.03 (m, 1H), 5.68 (dddd, J = 18.3, 15.5, 8.8, 3.7 Hz, 1H), 4.39 (qd, J = 9.5, 6.4 Hz, 1H), 3.93-3.67 (m, 2H), 3.57-3.38 (m, 2H), 3.29-3.21 (m, 3H) 2.78-2.61 (m, 1H), 1.39 (dd, J = 6.6, 1.4 Hz, 1H), 1.11 (dd, J = 12.5, 6.6 Hz, 1H). | 387.2 4.89 min |
| Example 56 Method 17 | 0.520 | rac-(5R,7R)-N-(2,2-difluoroethyl)-7-fluoro-N-(2-methoxyethyl)-5-phenyl-6,7-dihydro-5H-pyrrolo[1,2-b][1,2,4]triazole-2-carboxamide | Single Unknown Stereoisomer | ¹H NMR (400 MHz, DMSO-$d_6$) δ 7.56-7.05 (m, 5H), 6.50-5.95 (m, 2H), 5.69 (ddd, J = 8.4, 6.7, 3.0 Hz, 1H), 4.14 (td, J = 14.6, 4.0 Hz, 1H), 3.91 (tdd, J = 14.8, 4.1, 2.7 Hz, 1H), 3.83-3.61 (m, 3H), 3.49 (dt, J = 38.7, 5.6 Hz, 2H), 3.11 (s, 3H), 2.69 (ddtd, J = 23.7, 13.9, 3.3, 1.8 Hz, 1H). | 369.2 4.57 min |
| Example 57 Method 17 | 0.510 | rac-(5S,7S)-7-fluoro-N-(oxetan-3-yl)-5-phenyl-N-(2,2,2-trifluoroethyl)-6,7-dihydro-5H-pyrrolo[1,2-b][1,2,4]triazole-2-carboxamide | Mixture of Enantiomers | | 385.1 4.51 min |
| Example 58 Method 17 | 0.570 | rac-(5S,7S)-N-cyclopropyl-N-(2,2-difluoroethyl)-7-fluoro-5-phenyl-6,7-dihydro-5H-pyrrolo[1,2-b][1,2,4]triazole-2-carboxamide | Mixture of Enantiomers | 1H NMR (400 MHz, DMSO-d6) δ 7.47-7.32 (m, 3H), 7.26-7.18 (m, 2H), 6.56-6.03 (m, 2H), 5.80-5.62 (m, 1H), 4.24-3.55 (m, 4H), 2.92 (s, 1H), 2.80-2.50 (m, 1H), 0.91-0.35 (m, 3H). | 351.1 4.68 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 59 Method 17 | 2.2 | rac-(5S,7S)-N-cyclopropyl-7-fluoro-5-phenyl-N-(2,2,2-trifluoroethyl)-6,7-dihydro-5H-pyrrolo[1,2-b][1,2,4]triazole-2-carboxamide | Mixture of Enantiomers | ¹H NMR (400 MHz, DMSO-d₆) δ 7.54-7.25 (m, 3H), 7.33-7.10 (m, 2H), 6.23 (ddd, J = 56.6, 7.1, 1.7 Hz, 1H), 5.84-5.60 (m, 1H), 4.95-4.19 (m, 2H), 3.75 (ddt, J = 26.2, 15.5, 7.8 Hz, 1H), 2.92 (s, 1H), 2.84-2.45 (m, 1H), 0.97-0.43 (m, 4H). | 369.1 5.01 min |
| Example 60 Method 17 | 0.017 | [2-(difluoromethyl)azetidin-1-yl]-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-d6) δ 7.53-7.31 (m, 3H), 7.23 (td, J = 7.9, 1.9 Hz, 2H), 6.63-6.07 (m, 2H), 5.70 (ddd, J = 8.8, 5.4, 2.8 Hz, 1H), 5.32-4.61 (m, 1H), 4.39 (dp, J = 9.6, 3.4 Hz, 1H), 4.08-3.87 (m, 1H), 3.73 (dddd, J = 26.1, 15.5, 8.5, 7.2 Hz, 1H), 2.78-2.61 (m, 1H), 2.51-2.34 (m, 1H), 2.33-2.21 (m, 1H). | 337.1 4.46 min |
| Example 61 Method 17 | 3.2 | rac-(5S,7S)-N,N-dicyclopropyl-7-fluoro-5-phenyl-6,7-dihydro-5H-pyrrolo[1,2-b][1,2,4]triazole-2-carboxamide | Mixture of Enantiomers | ¹H NMR (400 MHz, DMSO-d6) δ 7.46-7.30 (m, 3H), 7.23-7.15 (m, 2H), 6.20 (ddd, J = 56.7, 7.1, 1.7 Hz, 1H), 5.68 (ddd, J = 8.8, 6.7, 2.8 Hz, 1H), 3.73 (dddd, J = 26.6, 15.5, 8.5, 7.1 Hz, 1H), 2.76-2.51 (m, 3H), 0.60 (m, 8H). | 327.2 4.40 min |
| Example 62 Method 17 | 0.130 | (7-methyl-6,7-dihydro-4H-pyrazolo[1,5-a]pyrazin-5-yl)-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-d₆) δ 7.52-7.31 (m, 4H), 7.26 (dt, J = 8.7, 3.1 Hz, 2H), 6.42-5.94 (m, 2H), 5.71 (t, J = 6.6 Hz, 1H), 5.11-4.91 (m, 1H), 5.05-4.71 (m, 1H), 4.37 (dq, J = 13.1, 6.6 Hz, 1H), 4.26-4.06 (m, 1H), 4.02-3.62 (m, 2H), 2.87-2.57 (m, 1H), 1.50-1.21 (m, 3H). | 367.2 4.05 min |

TABLE 2-continued

| Compound Example # Method | RIP1 Ki (μM) | Structure and Name | Stereo-chemistry | ¹H NMR Data | MS (m/z) retention time |
|---|---|---|---|---|---|
| Example 63 Method 17 | 2.3 | 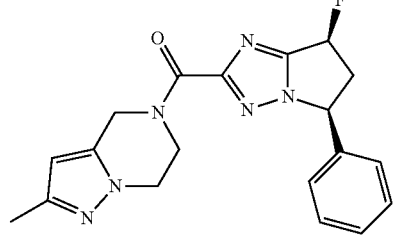<br>(2-methyl-6,7-dihydro-4H-pyrazolo[1,5-a]pyrazin-5-yl)-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.52-7.33 (m, 3H), 7.26 (ddd, J = 8.0, 3.5, 1.5 Hz, 2H), 6.23 (ddt, J = 56.5, 7.2, 2.3 Hz, 1H), 5.78-5.63 (m, 1H), 4.94 (s, 1H), 4.81 (d, J = 2.8 Hz, 1H), 4.19-4.01 (m, 4H), 3.74 (ddt, J = 25.8, 15.5, 7.8 Hz, 1H), 2.79-2.62 (m, 1H), 2.12 (d, J = 8.8 Hz, 3H). | 367.2 4.01 min |
| Example 64 Method 17 | 0.004 | 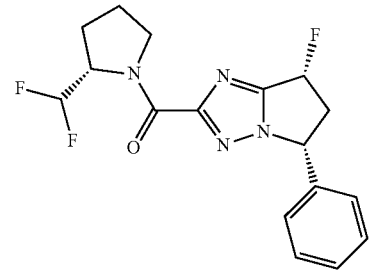 [SMILES: O=C(c1nc2n(n1)[C@@H](c1ccccc1)C[C@H]2F)N1CCC[C@H]1C(F)F]<br>[rac-(2S)-2-(difluoromethyl)pyrrolidin-1-yl]-[rac-(5R,7R)-7-fluoro-5-phenyl-6,7-dihydro-5H-pyrrolo[1,2-b][1,2,4]triazol-2-yl]methanone | Single Unknown Stereoisomer | ¹H NMR (400 MHz, DMSO-d₆) δ 7.47-7.33 (m, 3H), 7.23 (ddd, J = 7.4, 3.8. 1.5 Hz, 2H), 6.59-5.98 (m, 2H), 5.70 (ddt, J = 9.4, 6.5, 2.9 Hz, 1H), 5.16-4.43 (m, 1H), 3.86-3.62 (m, 3H), 2.77-2.61 (m, 1H), 2.16-1.79 (m, 4H). | 351.1 4.72 min |
| Example 65 Method 17 | 0.036 | 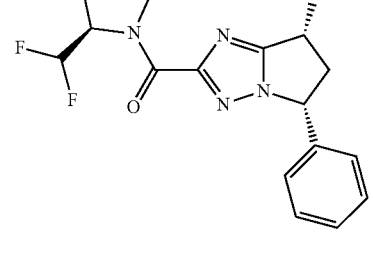<br>[rac-(2R)-2-(difluoromethyl)pyrrolidin-1-yl]-[rac-(5R,7R)-7-fluoro-5-phenyl-6,7-dihydro-5H-pyrrolo[1,2-b][1,2,4]triazol-2-yl]methanone | Single Unknown Stereoisomer | ¹H NMR (400 MHz, DMSO-d₆) δ 7.47-7.33 (m, 3H), 7.22 (tt, J = 8.5, 1.6 Hz, 2H), 6.51-5.99 (m, 2H), 5.70 (ddd, J = 9.5, 7.0, 3.0 Hz, 1H), 5.12-4.38 (m, 1H), 3.88-3.61 (m, 3H), 2.77-2.60 (m, 1H), 2.16-1.78 (m, 4H). | 351.2 4.71 min |
| Example 66 Method 17 | 0.015 | 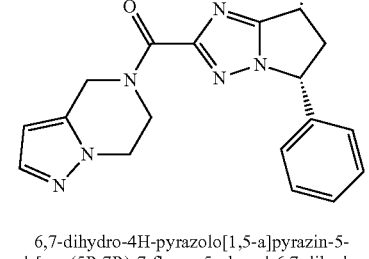<br>6,7-dihydro-4H-pyrazolo[1,5-a]pyrazin-5-yl-[rac-(5R,7R)-7-fluoro-5-phenyl-6,7-dihydro-5H-pyrrolo[1,2-b][1,2,4]triazol-2-yl]methanone | Single Unknown Stereoisomer | ¹H NMR (400 MHz, DMSO-d₆) δ 7.48-7.34 (m, 4H), 7.30-7.23 (m, 2H), 6.39-6.00 (m, 2H), 5.70 (dtd, J = 8.9, 6.2, 2.9 Hz, 1H), 5.02 (s, 1H), 4.88 (d, J = 2.2 Hz, 1H), 4.27-4.00 (m, 4H), 3.75 (dddd, J = 26.3, 14.6, 8.9, 7.3 Hz, 1H), 2.71 (ddd, J = 26.7, 15.3, 2.6 Hz, 1H). | 353.2 3.84 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 67 Method 17 | 0.005 | 6,8-dihydro-5H-1,7-naphthyridin-7-yl-[rac-(5R,7R)-7-fluoro-5-phenyl-6,7-dihydro-5H-pyrrollo[1,2-b][1,2,4]triazol-2-yl]methanone | Single Unknown Stereoisomer | ¹H NMR (400 MHz, DMSO-d6) δ 8.38 (ddd, J = 25.5, 4.7, 1.6 Hz, 1H), 7.61 (ddd, J = 7.8, 4.6, 1.6 Hz, 1H), 7.48-7.33 (m, 3H), 7.30-7.19 (m, 3H), 6.37-6.08 (m, 1H), 5.70 (dtd, J = 8.5, 5.6, 3.0 Hz, 1H), 4.83 (d, J = 29.7 Hz, 2H), 4.03-3.84 (m, 2H), 3.84-3.63 (m, 1H), 2.89 (t, J = 5.9 Hz, 2H), 2.79-2.62 (m, 1H). | 364.2 3.44 min |
| Example 68 Method 17 | 0.049 | 6,8-dihydro-5H-imidazo[1,2-a]pyrazin-7-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d₆) δ 7.58-7.26 (m, 3H), 7.38-7.11 (m, 2H), 7.12 (d, J = 1.2 Hz, 1H), 6.89 (dd, J = 14.9, 1.3 Hz, 1H), 6.23 (ddd,. J = 56.6, 7.2, 1.9 Hz, 1H), 5.70 (tt, J = 7.3, 3.4 Hz, 1H), 4.87 (d, J = 63.2 Hz, 2H), 4.09 (dt, J = 12.6, 3.7 Hz, 4H), 3.91-3.58 (m, 1H), 2.71 (ddt, J = 26.7, 15.2, 2.4 Hz, 1H). | 353.2 2.44 min |
| Example 69 Method 17 | 0.052 | 6,7-dihydro-4H-pyrazolo[1,5-a]pyrazin-5-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d₆) δ 7.55-7.26 (m, 4H), 7.26 (dd, J = 7.4, 2.9 Hz, 2H), 6.42-5.97 (m, 2H), 5.70 (ddt, J = 9.2, 5.7, 2.9 Hz, 1H), 5.02 (s, 1H), 4,88 (d, J = 1.9 Hz, 1H), 4.29-4.00 (m, 4H), 3.75 (ddt, J = 25.8, 15.5, 7.8 Hz, 1H), 2.82-2.61 (m, 1H). | 353.2 3.83 min |
| Example 70 Method 17 | 0.150 | [rac-(2R,4S)-4-fluoro-2-methyl-pyrrolidin-1-yl]-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d₆) δ 7.54-7.25 (m, 3H), 7.23 (tt, J = 6.6, 2.0 Hz, 2H), 6.41-6.03 (m, 1H), 5.69 (td, J = 8.2, 7.6, 2.9 Hz, 1H), 5.33 (dt, J = 53.6, 4.5 Hz, 1H), 4.54 (dp, J = 126.8, 7.2, 6.8 Hz, 1H), 4.22-3.62 (m, 3H), 2.84-2.59 (m, 1H), 2.46-2.12 (m, 1H), 1.96 (ddd, J = 28.5, 19.6, 14.5 Hz, 1H), 1.40-1.02 (m, 3H). | 333.2 4.36 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 71 Method 17 | 0.690 | 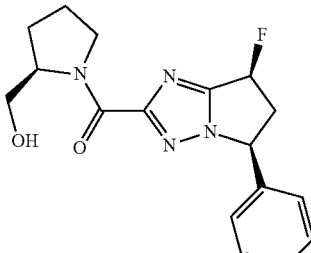 [rac-(5S,7S)-7-fluoro-5-phenyl-6,7-dihydro-5H-pyrrolo[1,2-b][1,2,4]triazol-2-yl]-[rac-(2R)-2-(hydroxymethyl) pyrrolidin-1-yl]methanone | Mixture of Enantiomers | ¹H NMR (400 MHz, DMSO-d₆) δ 7.59-7.31 (m, 3H), 7.28-7.11 (m, 2H), 6.20 (ddt, J = 56.6, 7.2, 2.0 Hz, 1H), 5.68 (ddt, J = 8.6, 5.7, 2.7 Hz, 1H), 4.86-4.67 (m, 1H), 4.45 (s, 1H), 4.12 (dd, 7.1, 3.8 Hz, 1H), 3.90-3.41 (m, 3H), 3.31 (s, 2H), 2 84-2.52 (m, 1H), 2.07-1.65 (m, 3H). | 331.2 3.65 min |
| Example 72 Method 17 | 3.9 | 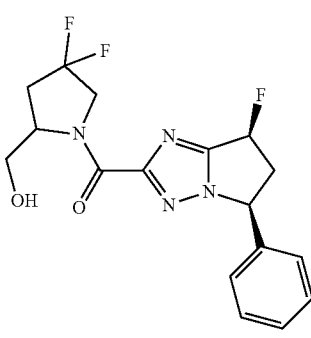 [4,4-difluoro-2-(hydroxymethyl) pyrrolodin-1-yl]-[rac-(5S,7S)-7-fluoro-5-phenyl-6,7-dihydro-5H-pyrrolo[1,2-b] [1,2,4]triazol-2-yl]methanone | Mixture of Diastereomers | ¹H NMR (400 MHz, DMSO-d6) δ 7.47-7.32 (m, 3H), 7.29-7.18 (m, 2H), 6.22 (dddd, J = 56.5, 7.2, 3.5, 1.9 Hz, 1H), 5.74-5.65 (m, 1H), 5.04 (t, J = 5.5 Hz, 1H), 4.87 (s, 1H), 4.48-4.29 (m, 2H), 4.10 (ddt, J = 31.6, 21.2, 10.7 Hz, 1H), 3.86-3.63 (m, 1H), 3.59 (q, J = 5.1 Hz, 1H), 3.43-3.17 (m, 2H), 2.78-2.61 (m, 1H). | 366.9 4.06 min |
| Example 73 Method 17 | 0.082 | 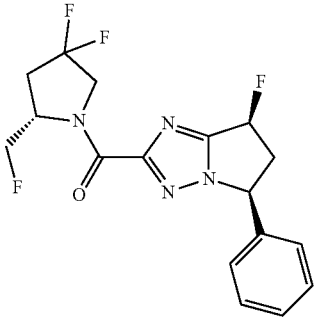 [SMILES: O=C(c1nc2n(n1)[C@H](c1ccccc1)C[C@@H]2F)N1CC(F)(F)C[C@H]1CF] [rac-(2S)-4,4-difluoro-2-(fluoromethyl) pyrrolidin-1-yl]-[rac-(5S,7S)-7-fluoro-5-phenyl-6,7-dihydro-5H-pyrrolo[1,2-b] [1,2,4]triazol-2-yl]methanone | Mixture of Enantiomers | ¹H NMR (400 MHz, DMSO-d6) δ 7.41 (dddd, J = 12.0, 7.2, 5.9, 2.2 Hz, 3H), 7.29-7.19 (m, 2H), 6.22 (dddd, J = 56.5, 7.2, 3.3, 1.9 Hz, 1H), 5.70 (ddt, J = 8 8, 5.7, 2.7 Hz, 1H), 5.19 (s, 1H), 4.75-4.51 (m, 2H), 4.55-4.32 (m, 1H), 4.29-4.06 (m, 1H), 3.92-3.64 (m, 1H), 2.96-2.61 (m, 2H), 2.50-2.37 (m, 1H). | 368.9 4.75 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 74 Method 17 | 0.024 | 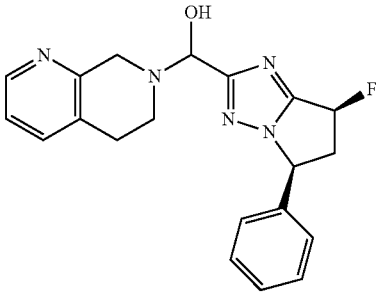 [SMILES: OC(c1nc2n(n1)[C@H](c1ccccc1)C[C@@H]2F)N1CCc2cccnc2C1]<br>6,8-dihydro-5H-1,7-naphthyridin-7-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 8.38 (dddd, J = 25.7, 4.7, 1.7 Hz, 1H), 7.61 (ddd, J = 7.7, 4.8, 1.6 Hz, 1H), 7.48-7.32 (m, 3H), 7.30-7.19 (m, 3H), 6.37-6.11 (m, 1H), 5.75-5.65 (m, 1H), 4.83 (d, J = 29.7 Hz, 2H), 3.99-3.80 (m, 2H), 3.85-3.65 (m, 1H), 2.95-2.85 (m, 2H), 2.79-2.63 (m, 1H). | 363.9 3.44 min |
| Example 75 Method 17 | 0.290 | 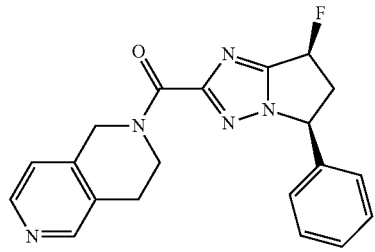 [SMILES: O=C(c1nc2n(n1)[C@H](c1ccccc1)C[C@@H]2F)N1CCc2cnccc2C1]<br>3,4-dihydro-1H-2,6-naphthyridin-2-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 8.43-8.29 (m, 2H), 7.48-7.33 (m, 3H), 7.32-6.99 (m, 3H), 6.23 (ddt, J = 56.6, 7.6. 2.5 Hz, 1H), 5.70 (qd, J = 8.1, 3.1 Hz, 1H), 4.92-4.76 (m, 2H), 4.03-3.64 (m, 3H), 2.88 (t, J = 5.9 Hz, 2H), 2.79-2.63 (m, 1H). | 363.9 2.65 min |
| Example 76 Method 17 | 0.031 | 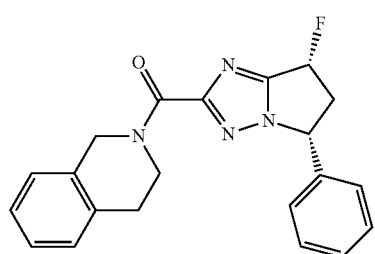<br>3,4-dihydro-1H-isoquinolin-2-yl-[rac-(5R,7R)-7-fluoro-5-phenyl-6,7-dihydro-5H-pyrrolo[1,2-b][1,2,4]triazol-1-yl]methanone | Single Unknown Stereoisomer | ¹H NMR (400 MHz, DMSO-d6) δ 7.48-7.33 (m, 3H), 7.30-6.97 (m, 6H), 6.23 (ddd, J = 56.6, 7.2, 1.9 Hz, 1H), 5.70 (dq, J = 7.1, 3.2 Hz, 1H), 4.78 (s, 2H), 3.92-3.65 (m, 3H), 2.87 (q, J = 6.4 Hz, 2H), 2.79-2.62 (m, 1H). | 363.1 5.03 min |
| Example 77 Method 17 | 0.061 | 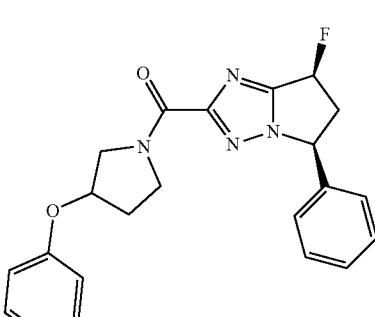<br>(3-phenoxypyrrolidin-1-yl)-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-d6) δ 7.47-7.33 (m, 3H), 7.38-7.15 (m, 4H), 7.01-6.89 (m, 3H), 6.35-6.04 (m, 1H), 5.75-5.62 (m, 1H), 5.09 (qd, J = 4.5, 2.4 Hz, 1H), 4.07-3.89 (m, 1H), 3.84-3.51 (m, 4H), 2.77-2.58 (m, 1H), 2.29-2.05 (m, 2H). | 393.1 5.08 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 78 Method 17 | 0.060 | [2-(difluoromethyl)pyrrolidin-1-yl]-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-d$_6$) δ 7.57-7.23 (m, 3H), 7.22 (ddt, J = 8.5, 5.3, 1.5 Hz, 2H), 6.68-5.90 (m, 2H), 5.70 (td, J = 7.7, 6.5, 2.8 Hz, 1H), 4.69-4.33 (m, 1H), 3.96-3.54 (m, 3H), 2.87-2.50 (m, 1H), 2.25-1.63 (m, 4H). | 351.1 4.71 min |
| Example 79 Method 17 | 0.790 | (3,3-difluoro-1-piperidyl)-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.47-7.28 (m, 3H), 7.28-7.19 (m, 2H), 6.37-6.07 (m, 1H), 5.74-5.63 (m, 1H), 4.07 (t, J = 11.8 Hz, 1H), 3.96 (t, J = 12.0 Hz, 1H), 3.83-3.58 (m, 3H), 2.70 (dddd, J = 26.7, 15.2, 3.1, 1.9 Hz, 1H), 2.09 (qt, J = 13.1, 6.7 Hz, 2H), 1.70 (td, J = 6.8, 3.9 Hz, 2H). | 351.1 4.50 min |
| Example 80 Method 17 | 0.100 | 6,7-dihydro-5H-pyrazolo[1,5-a]pyrimidin-4-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.48-7.33 (m, 4H), 7.31-7.23 (m, 2H), 6.64 (s, 1H), 6.24 (ddd, J = 56.5, 7.1, 1.9 Hz, 1H), 5.71 (ddd, J = 8.6, 6.7, 3.1 Hz, 1H), 4.16 (t, J = 6.1 Hz, 2H), 4.02 (tq, J = 12.9, 7.3, 6.5 Hz, 2H), 3.76 (dddd, J = 25.7, 15.4, 8.5, 7.2 Hz, 1H), 2.80-2.63 (m, 1H), 2.14 (p, J = 6.0 Hz, 2H). | 353.1 3.97 min |
| Example 81 Method 17 | 0.250 | [rac-(5S,7S)-7-fluoro-5-phenyl-6,7-dihydro-5H-pyrrolo[1,2-b][1,2,4]triazol-2-yl]-[7-(trifluoromethyl)-6,7-dihydro-5H-pyrazolo[1,5-a]pyrimidin-4-yl]methanone | Mixture of Diastereomers | ¹H NMR (400 MHz, DMSO-d$_6$) δ 7.56 (s, 1H), 7.56-7.26 (m, 3H), 7.38-7.16 (m, 2H), 6.58 (s, 1H), 6.40-6.07 (m, 1H), 5.73 (ddt, J = 9.4, 6.1, 2.9 Hz, 1H), 5.35 (q, J = 7.2, 6.3 Hz, 1H), 4.19 (t, J = 15.5 Hz, 1H), 4.13-3.86 (m, 1H), 3.76 (dddd, J = 25.9, 15.5, 8.0, 6.9 Hz, 1H), 2.88-2.60 (m, 1H), 2.42 (dh, J = 14.9, 4.8 Hz, 2H). | 421.1 4.71 min |

TABLE 2-continued

| Compound Example # Method | RIP1 Ki (μM) | Structure and Name | Stereo-chemistry | ¹H NMR Data | MS (m/z) retention time |
|---|---|---|---|---|---|
| Example 82 Method 17 | 0.450 | [rac-(5S,7S)-7-fluoro-5-phenyl-6,7-dihydro-5H-pyrrolo[1,2-b][1,2,4]triazol-2-yl]-[rac-(2S)-2-(trifluoromethyl)pyrrolidin-1-yl]methanone | Mixture of Enantiomers | ¹H NMR (400 MHz, DMSO-d6) δ 7.41 (dtd, J = 12.2, 6.8, 2.3 Hz, 3H), 7.28-7.14 (m, 2H), 6.36-6.05 (m, 1H), 5.76-5.67 (m, 1H), 5.04 (td, J = 8.4, 4.2 Hz, 1H), 3.89-3.64 (m, 3H), 2.69 (ddt, J = 27.3, 18.9, 2.9 Hz, 1H), 2.18-2.08 (m, 1H), 2.10-1.90 (m, 3H). | 369.1 4.94 min |
| Example 83 Method 17 | 0.350 | [rac-(5S,7S)-7-fluoro-5-phenyl-6,7-dihydro-5H-pyrrolo[1,2-b][1,2,4]triazol-2-yl]-[rac-(2R)-2-(trifluoromethyl)pyrrolidin-1-yl]methanone | Mixture of Enantiomers | ¹H NMR (400 MHz, DMSO-d6) δ 7.40 (ddtt, J = 12.4, 9.5, 7.2, 2.1 Hz, 3H), 7.30-7.11 (m, 2H), 6.38-6.09 (m, 1H), 5.80-5.65 (m, 1H), 5.04 (td, J = 8.3, 4.1 Hz, 1H), 3.92-3.48 (m, 3H), 2.78-2.61 (m, 1H), 2.18-2.08 (m, 1H), 2.06-1.78 (m, 3H). | 369.1 4.94 min |
| Example 84 Method 17 | 0.300 | [rac-(5S,7S)-7-fluoro-5-phenyl-6,7-dihydro-5H-pyrrolo[1,2-b][1,2,4]triazol-2-yl]-[2-(trifluoromethyl)pyrrolidin-1-yl]methanone | Mixture of Diastereomers | ¹H NMR (400 MHz, DMSO-d6) δ 7.49-7.31 (m, 3H), 7.28-7.14 (m, 2H), 6.36-6.10 (m, 1H), 5.82-5.63 (m, 1H), 5.11-4.98 (m, 1H), 3.89-3.49 (m, 3H), 2.78-2.61 (m, 1H), 2.18-2.08 (m, 1H), 2.06-1.90 (m, 3H). | 369.1 4.94 min |
| Example 85 Method 17 | 0.330 | [rac-(5S,7S)-7-fluoro-5-phenyl-6,7-dihydro-5H-pyrrolo[1,2-b][1,2,4]triazol-2-yl]-[rac-(2S,3R)-2-methyl-3-(trifluoromethyl)pyrrolidin-1-yl]methanone | Single Unknown Stereoisomer | ¹H NMR (400 MHz, DMSO-d₆) δ 7.53-7.33 (m, 3H), 7.22 (dt, J = 7.8, 1.7 Hz, 2H), 6.22 (dddd, J = 56.6, 10.6, 7.1, 1.9 Hz, 1H), 5.83-5.57 (m, 1H), 4.67 (dt, J = 106.6, 6.7 Hz, 1H), 4.00 (td, J = 9.4, 7.9, 3.1 Hz, 1H), 3.91-3.45 (m, 1H), 2.85-2.53 (m, 1H), 2.33-1.95 (m, 2H), 1.15 (ddd, J = 36.4, 6.5, 1.9 Hz, 3H). | 383.1 5.07 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 86 Method 17 | 0.005 | [rac-(5S,7S)-7-fluoro-5-phenyl-6,7-dihydro-5H-pyrrolo[1,2-b][1,2,4]triazol-2-yl]-[rac-(2S,3S)-2-methyl-3-(trifluoromethyl)pyrrolidin-1-yl]methanone | Single Unknown Stereoisomer | ¹H NMR (400 MHz, DMSO-d₆) δ 7.54-7.25 (m, 3H), 7.39-7.11 (m, 2H), 6.22 (dddd, J = 56.6, 12.7, 7.2, 1.8 Hz, 1H), 5.83-5.56 (m, 1H), 4.70 (dp, J = 141.9, 6.6 Hz, 1H), 4.09-3.84 (m, 1H), 3.91-3.47 (m, 2H), 2.86-2.53 (m, 1H), 2.33-1.89 (m, 2H), 1.30-0.93 (m, 4H). | 383.1 5.08 min |
| Example 87 Method 17 | 0.150 | (5,5-difluoro-2-azabicyclo[2.2.1]heptan-2-yl)-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-d6) δ 7.47-7.32 (m, 3H), 7.27-7.19 (m, 2H), 6.21 (dddt, J = 56.6, 7.4, 4.6, 1.7 Hz, 1H), 5.69 (tt, J = 6.9, 2.7 Hz, 1H), 5.07-4.57 (m, 1H), 3.77 (s, 1H), 3.83-3.63 (m, 1H), 3.54-3.39 (m, 1H), 2.97 (d, J = 6.8 Hz, 1H), 2.78-2.60 (m, 1H), 2.25 (s, 1H), 2.20-2.01 (m, 1H), 1.90 (d, J = 13.0 Hz, 2H). | 363.1 4.52 min |
| Example 88 Method 17 | 0.054 | 3,4-dihydro-1H-2,7-naphthyridin-2-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 8.56-8.15 (m, 2H), 7.49-7.34 (m, 5H), 7.31-7.14 (m, 5H), 6.23 (ddd, J = 56.6, 7.1, 1.9 Hz, 1H), 5.75-5.65 (m, 1H), 4.84 (d, J = 13.5 Hz, 2H), 3.97-3.82 (m, 1H), 3.86-3.78 (m, 1H), 3.83-3.65 (m, 1H), 2.88 (q, J = 5.8, 4.1 Hz, 2H), 2.80-2.60 (m, 1H) | 364.1 2.71 min |
| Example 89 Method 17 | 0.130 | 7,8-dihydro-5H-1,6-naphthyridin-6-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 8.40 (dd, J = 4.7, 2.0 Hz, 1H), 7.70 (dd, J = 7.8, 1.7 Hz, 1H), 7.51-7.33 (m, 3H), 7.30-7.17 (m, 3H), 6.23 (dtd, J = 56.5, 6.6, 6.0, 1.9 Hz, 1H), 5.70 (tdd, J = 9.6, 7.0, 3.0 Hz, 1H), 4.84 (d, J = 12.4 Hz, 2H), 4.06-3.85 (m, 2H), 3.85-3.65 (m, 1H), 2.96 (dt, J = 8.0, 4.2 Hz, 2H), 2.80-2.62 (m, 1H) | 364.1 2.81 min |

TABLE 2-continued

| Compound Example # Method | RIP1 Ki (μM) | Structure and Name | Stereo- chemistry | ¹H NMR Data | MS (m/z) retention time |
|---|---|---|---|---|---|
| Example 90 Method 17 | 0.620 | rac-(5S,7S)-7-fluoro-N-methyl-N,5-diphenyl-6,7-dihydro-5H-pyrrolo[1,2-b][1,2,4]triazole-2-carboxamide | Mixture of Enantiomers | ¹H NMR (400 MHz, DMSO-d$_6$) δ 7.42-7.13 (m, 6H), 7.15 (s, 2H), 6.80 (s, 2H), 6.05 (dd, J = 56.7, 6.8 Hz, 1H), 5.54 (s, 1H), 3.81-3.50 (m, 1H), 3.38 (s, 3H), 2.64-2.47 (m, 1H). | 337.1 4.55 min |
| Example 91 Method 17 | 0.042 | rac-(5S,7S)-N-(2,2-difluoroethyl)-7-fluoro-N-methyl-5-phenyl-6,7-dihydro-5H-pyrrolo[1,2-b][1,2,4]triazole-2-carboxamide | Mixture of Enantiomers | ¹H NMR (400 MHz, DMSO-d$_6$) δ 7.57-7.23 (m, 3H), 7.23 (ddt, J = 8.0, 5.6, 1.6 Hz, 2H), 6.63-5.98 (m, 2H), 5.69 (t, J = 7.5 Hz, 1H), 4.09 (td, J = 15.0, 3.9 Hz, 1H), 3.90 (td, J = 15.4, 4.0 Hz, 1H), 3.83-3.58 (m, 1H), 3.22-3.00 (m, 3H), 2.80-2.58 (m, 1H). | 325.1 4.30 min |
| Example 92 Method 17 | 0.100 | rac-(5S,7S)-7-fluoro-N-methyl-5-phenyl-N-(2,2,2-trifluoroethyl)-6,7-dihydro-5H-pyrrolo[1,2-b][1,2,4]triazole-2-carboxamide | Mixture of Enantiomers | ¹H NMR (400 MHz, DMSO-d6) δ 7.47-7.32 (m, 3H), 7.29-7.16 (m, 2H), 6.22 (dddd, J = 56.6, 7.2, 4.1, 1.9 Hz, 1H), 5.76-5.65 (m, 1H), 4.74 (qd, J = 9.3, 6.1 Hz, 1H), 4.37 (q, J = 9.6 Hz, 1H), 3.74 (dddd, J = 25.8, 15.5, 8.5, 7.2 Hz, 1H), 3.15 (d, J = 46.5 Hz, 3H), 2.78-2.61 (m, 1H). | 343.1 4.62 min |
| Example 93 Method 17 | 0.030 | (3-benzylpyrrolidin-1-yl)-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-d$_6$) δ 7.53-7.06 (m, 10H), 6.19 (ddt, J = 56.6, 7.2, 2.1 Hz, 1H), 5.68 (ddd, J = 8.7, 5.1, 1.9 Hz, 1H), 3.95-3.49 (m, 2H), 3.46-3.33 (m, 1H), 3.14 (dd, J = 12.2, 8.2 Hz, 1H), 2.77-2.59 (m, 4H), 2.46 (m, 1H), 1.91 (dq, J = 10.9, 6.3 Hz, 1H), 1.77-1.44 (m, 1H). | 391.1 5.38 min |

TABLE 2-continued

| Compound Example # Method | RIP1 Ki (μM) | Structure and Name | Stereo-chemistry | ¹H NMR Data | MS (m/z) retention time |
|---|---|---|---|---|---|
| Example 94 Method 17 | 0.160 | [rac-(5S,7S)-7-fluoro-5-phenyl-6,7-dihydro-5H-pyrrolo[1,2-b][1,2,4]triazol-2-yl]-(1,3,4,5-tetrahydro-2-benzazepin-2-yl)methanone | Mixture of Enantiomers | ¹H NMR (400 MHz, DMSO-$d_6$) δ 7.57-6.76 (m, 9H), 6.45-6.01 (m, 2H), 5.65 (dddd, J = 15.2, 8.3, 6.9, 2.9 Hz, 1H), 4.96-4.52 (m, 2H), 4.19-3.56 (m, 1H), 3.09-2.87 (m, 2H), 2.84-2.56 (m, 1H), 1.74 (d, J = 28.7 Hz, 2H). | 377.1 5.15 min |
| Example 95 Method 17 | 0.018 | (8-fluoro-3,4-dihydro-1H-isoquinolin-2-yl)-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.48-7.32 (m, 3H), 7.25 (tt, J = 7.9, 1.5 Hz, 3H), 7.05 (tt, J = 13.0, 8.9 Hz, 2H), 6.23 (ddd, J = 56.6, 7.2, 1.9 Hz, 1H), 5.75-5.66 (m, 1H), 4.82 (d, J = 33.7 Hz, 2H), 3.93-3.80 (m, 2H), 3.83-3.65 (m, 1H), 2.90 (t, J = 5.9 Hz, 2H), 2.79-2.58 (m, 1H). | 381.1 5.15 min |
| Example 96 Method 17 | 0.057 | (8-fluoro-1-methyl-3,4-dihydro-1H-isoquinolin-2-yl)-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-$d_6$) δ 7.56-7.24 (m, 3H), 7.39-7.10 (m, 3H), 7.19-6.90 (m, 2H), 6.44-6.04 (m, 1H), 5.84-5.25 (m, 2H), 4.63-3.96 (m, 1H), 3.56 (m, 2H), 3.02-2.55 (m, 3H), 1.62-1.36 (m, 3H). | 395.1 5.41 min |
| Example 97 Method 17 | 0.058 | (1-methyl-3,4-dihydro-1H-isoquinolin-2-yl)-[rac-(5S,7S)-7-fluoro-5-phenyl-6,7-dihydro-5H-pyrrolo[1,2-b][1,2,4]triazol-2-yl]methanone | Mixture of Diastereomers | ¹H NMR (400 MHz, DMSO-$d_6$) δ 7.48-7.32 (m, 3H), 7.32-6.98 (m, 6H), 6.23 (dddd, J = 56.6, 7.1, 4.3, 1.9 Hz, 1H), 5.75-5.64 (m, 1H), 5.56 (m, 1H), 4.04 (m, 1H), 3.75 (m, 2H), 3.01-2.62 (m, 3H), 1.50 (dd, 24.3, 6.8 Hz, 3H). | 377.1 5.28 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 98 Method 17 | 0.036 | (3,3-difluoropyrrolidin-1-yl)-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.48-7.33 (m, 3H), 7.25 (ddd, J = 7.9, 3.7, 1.5 Hz, 2H), 6.23 (ddd, J = 56.5, 7.2, 1.9 Hz, 1H), 5.76-5.66 (m, 1H), 4.23 (t, J = 12.9 Hz, 1H), 4.01 (td, J = 7.4, 1.8 Hz, 1H), 3.91 (t, J = 13.2 Hz, 1H), 3.84-3.64 (m, 2H), 3.43-3.19 (m, 1H), 2.70 (ddt, J = 26.8, 15.3, 2.3 Hz, 1H), 2.51-2.38 (m, 1H). | 337.1 4.42 min |
| Example 99 Method 17 | 0.013 | 3,4-dihydro-1H-isoquinolin-2-yl-[rac-(5S,7S)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.48-7.33 (m, 3H), 7.29-7.11 (m, 6H), 6.23 (ddd, J = 56.6, 7.2, 1.9 Hz, 1H), 5.69 (tdd, J = 7.7, 5.8, 3.0 Hz, 1H), 4.78 (s, 2H), 3.93-3.65 (m, 3H), 3.44 (s, 0H), 2.87 (q, J = 6.4 Hz, 2H), 2.79-2.62 (m, 1H). | 363.1 5.03 min |
| Example 100 Method B | 0.270 | (6,6-difluoro-3-azabicyclo[3.1.0]hexan-3-yl)-[rac-(5R,7R)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.48-7.35 (m, 3H), 7.23 (dt, J = 8.0, 1.6 Hz, 2H), 6.27 (dd, J = 7.2, 1.9 Hz, 1H), 6.13 (dd, J = 7.1, 1.9 Hz, 1H), 5.69 (ddd, J = 10.4, 5.5, 2.6 Hz, 1H), 4.15 (dd, J = 12.1, 6.4 Hz, 1H), 4.08-3.97 (m, 2H), 3.83-3.64 (m, 2H), 2.72-2.54 (m, 2H). | 349.1 4.39 min |
| Example 101 Method B | 0.082 | 3-azabicyclo[3.1.0]hexan-3-yl-[rac-(5R,7R)-7-fluoro-5-phenyl-6,7-dihydro-5H-pyrrolo[1,2-b][1,2,4]triazol-2-yl]methanone | Mixture of Enantiomers | ¹H NMR (400 MHz, DMSO-d6) δ 7.41-7.24 (m, 3H), 7.20-7.08 (m, 2H), 6.19 (dd, J = 7.2, 1.8 Hz, 1H), 6.05 (dd, J = 7.2, 1.8 Hz, 1H), 5.60 (ddt, J = 8.4, 4.6, 2.4 Hz, 1H), 3.85-3.69 (m, 2H), 3.72-3.54 (m, 2H), 3.36 (dd, J = 12.1, 4.2 Hz, 1H), 1.58-1.45 (m, 2H), 0.69-0.54 (m, 1H), −0.01 (q, J = 4.3 Hz, 1H). | 313.1 4.26 min |

TABLE 2-continued

| Compound Example # Method | RIP1 Ki (μM) | Stucture and Name | Stereo-chemistry | ¹H NMR Data | MS (m/z) retention time |
|---|---|---|---|---|---|
| Example 102 | 0.240 | 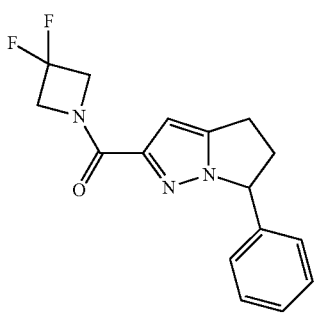 [SMILES: O=C(c1cc2n(n1)C(c1ccccc1)CC2)N1CC(F)(F)C1]<br>(3,3-difluoroazetidin-1-yl)-(6-phenyl-5,6-dihydro-4H-pyrrolo[1,2-b]pyrazol-2-yl)methanone | Mixture of Enantiomers | ¹H NMR (400 MHz, CD₃OD) δ 7.42-7.27 (m, 3H), 7.08 (d, J = 8.0 Hz, 2H), 6.59 (s, 1H), 5.54-5.48 (m, 1H), 4.81-4.62 (m, 2H), 4.44 (t, J = 12.0 Hz, 2H), 3.19-2.94 (m, 3H), 2.55-2.46 (m, 1H) | 297.1 1.294 min |
| Example 103 | 6.7 | 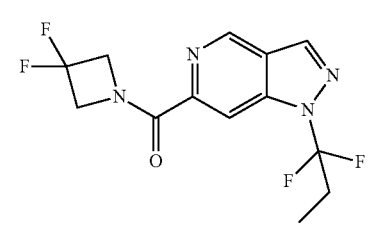<br>(3,3-difluoroazetidin-1-yl)-difluoropropyl)pyrazolo[4,3-c]pyridin-6-yl]methanone | No Stereo | ¹H NMR (400 MHz, CD₃OD) δ 9.20 (s, 1H), 8.49 (s, 2H), 5.14 (t, J = 12.0 Hz, 2H), 4.57 (t, J = 12.0 Hz, 2H), 2.85-2.78 (m, 2H), 1.18 (t, J = 7.6 Hz, 3H) | 317.1 1.137 min |
| Example 104 | 0.031 | 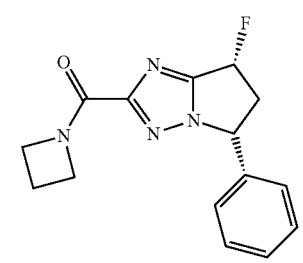<br>azetidin-1-yl-[rac-(5R,7R)-7-fluoro-5-phenyl-6,7-dihydro-5H-pyrrolo[1,2-b][1,2,4]triazol-2-yl]methanone | Mixture of Enantiomers | ¹H NMR (400 MHz, CD₃OD) δ 7.42-7.34 (m, 3H), 7.35-7.23 (m, 2H), 6.16-6.14 (m, 0.5H), 6.02-6.00 (m, 0.5H), 5.64-5.58 (m, 1H), 4.63-4.56 (m, 2H), 4.21-4.17 (m, 2H) 3.77-3.68 (m, 1H), 2.85-2.73 (m, 1H), 2.41-2.32 (m, 2H). | 287.2 0.957 min |
| Example 105 | 0.056 | 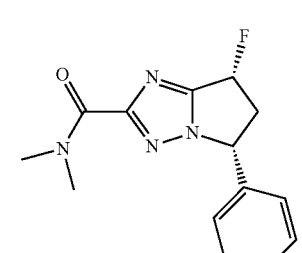<br>rac-(5R,7R)-7-fluoro-N,N-dimethyl-5-phenyl-6,7-dihydro-5H-pyrrolo[1,2-b][1,2,4]triazole-2-carboxamide | Mixture of Enantiomers | ¹H NMR (400 MHz, CD₃OD) δ 7.39-7.34 (m, 3H), 7.24-7.22 (m, 2H), 6.42-6.12 (m, 0.5H), 6.05-5.98 (m, 0.5H), 5.59-5.58 (m, 1H), 3.75-3.68 (m, 1H), 3.70 (s, 3H), 3.18 (s, 3H), 2.82-2.75 (m, 1H) | 275.3 0.925 min |

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

We claim:

1. A compound of Formula (I):

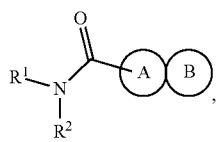

(I)

or a pharmaceutically acceptable salt thereof, wherein $R^1$ and $R^2$:

(a) are each independently selected from the group consisting of $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_1$-$C_6$ thioalkyl, $C_1$-$C_6$ alkyl-$N(R^N)_2$, phenyl, 5 to 6 membered heteroaryl, and 4 to 5 membered heterocyclyl;

(b) together with the adjacent amide N, form a 4 to 7 membered unsaturated heterocyclic ring optionally substituted by one or two $R^3$, wherein the unsaturated heterocyclic ring contains zero or one additional heteroatom selected from the group consisting of $NR^N$, O and S; or (c) together with the adjacent amide N, form a bicyclic heteroaryl moiety optionally substituted by one or two $R^3$, wherein the bicyclic heterocyclic moiety contains zero to three additional heteroatoms selected from the group consisting of N, O and S, wherein only one of the additional heteroatoms is O or S;

each $R^3$ is independently selected from the group consisting of F, Cl, $C_1$-$C_6$ alkyl, $C_3$-$C_6$ cycloalkyl, $C_1$-$C_6$ haloalkyl, $C_1$-$C_6$ alkoxy, $C_1$-$C_6$ haloalkoxy, $C_1$-$C_6$ hydroxyalkyl, and phenoxy; or, when $R^1$ and $R^2$ together with the adjacent amide N form a 6 membered ring, two $R^3$ may together form a 1 to 2 carbon bridge or a $C_3$-$C_5$ spirocycloalkyl;

each $R^N$ is independently selected from the group consisting of H, $C_1$-$C_6$ alkyl, $C_3$-$C_6$ cycloalkyl, $C_1$-$C_6$ alkoxy and $C_1$-$C_6$ haloalkyl; or two $R^N$ may together with the adjacent N form a 4-6 membered ring;

wherein

is selected from the group consisting of:

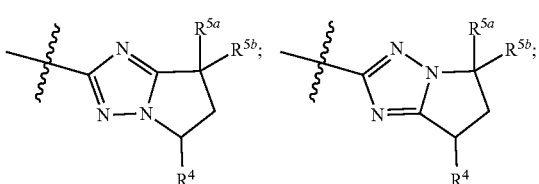

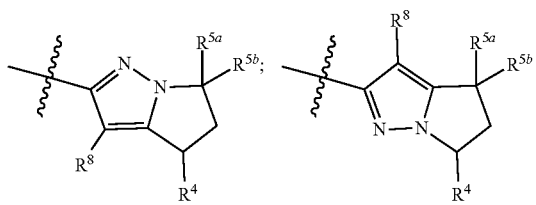

-continued

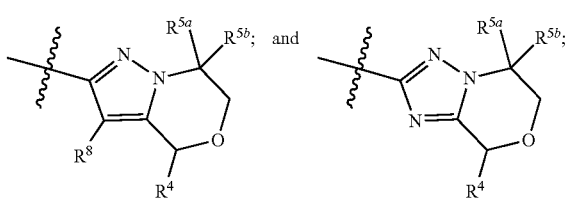

wherein $R^4$ is selected from the group consisting of phenyl and 5 to 6 membered heteroaryl, wherein the heteroaryl has one or two heteroatoms selected from O, S and N, and phenyl may be substituted by 1 to 3 substituents selected from the group consisting of halogen, $C_1$-$C_4$ alkyl, $C_1$-$C_4$ haloalkyl, $C_1$-$C_4$ alkoxy, $C_1$-$C_4$ haloalkoxy, and cyano;

each $R^{5a}$ and $R^{5b}$ is independently selected from the group consisting of H, F, Cl, $C_1$-$C_6$ alkyl, $C_3$-$C_4$ cycloalkyl, $C_1$-$C_6$ haloalkyl, $C_1$-$C_6$ alkoxy, $C_1$-$C_6$ haloalkoxy; and each $R^8$ is independently selected from the group consisting of H, halo, cyano, $C_1$-$C_4$ alkyl, $C_1$-$C_4$ haloalkyl, $C_1$-$C_4$ alkoxy, and $C_1$-$C_4$ haloalkoxy.

2. The compound of claim 1, or a pharmaceutically acceptable salt thereof, wherein $R^1$ and $R^2$ together with the adjacent amide N, form a 4 to 6 membered unsaturated heterocyclic ring optionally substituted by one or two $R^3$, containing zero or one additional heteroatom selected from the group consisting of O and S.

3. The compound of claim 1 having Formula (Ia):

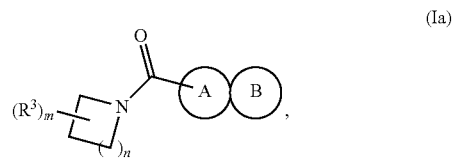

(Ia)

or a pharmaceutically acceptable salt thereof, wherein m is 0, 1 or 2; and n is 1, 2 or 3.

4. The compound of claim 3, or a pharmaceutically acceptable salt thereof, wherein n is 1.

5. The compound of claim 3, or a pharmaceutically acceptable salt thereof, wherein each $R^3$ is independently selected from the group consisting of methyl, ethyl, F and Cl.

6. The compound of claim 5, or a pharmaceutically acceptable salt thereof, wherein each $R^3$ is methyl or F.

7. The compound of claim 3, or a pharmaceutically acceptable salt thereof, wherein

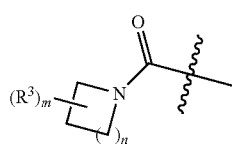
is selected from the group consisting of:
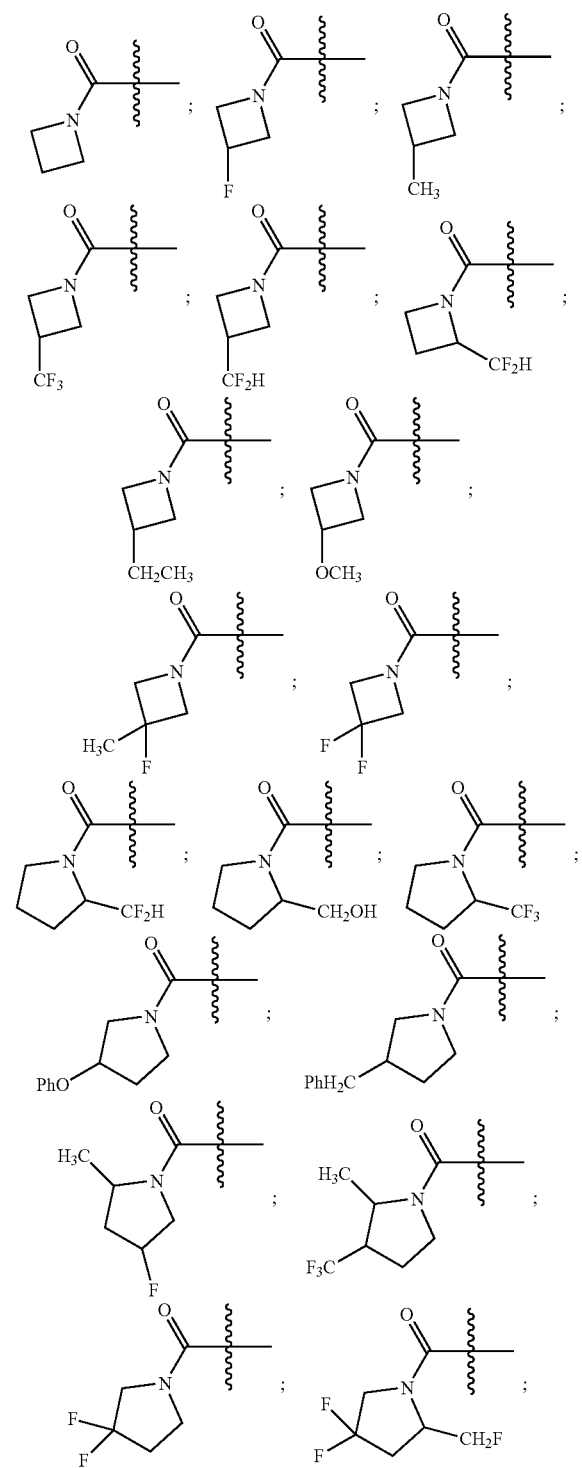
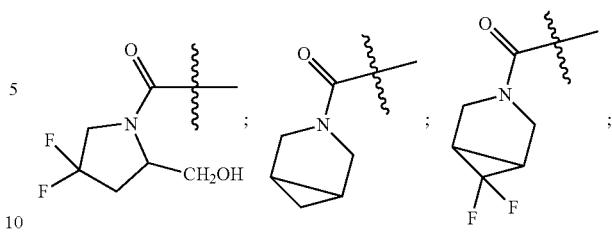
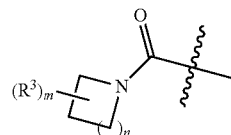
8. The compound of claim 3, or a pharmaceutically acceptable salt thereof, wherein
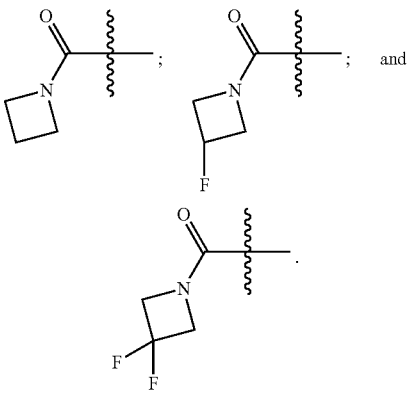
is selected from the group consisting of:
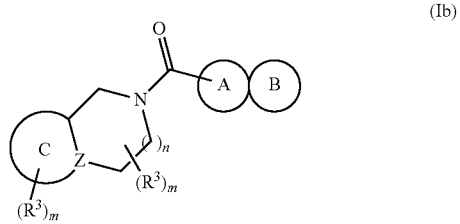
9. The compound of claim 1 having Formula (Ib) or (Ic):

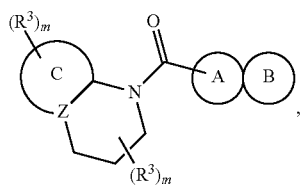

(Ic)

or a pharmaceutically acceptable salt thereof, wherein, in each instance, the C ring is phenyl or a 5 to 6 membered heteroaryl ring;
Z is C or N;
each $R^3$ is independently selected from the group consisting of F, Cl, $C_1$-$C_3$ alkyl, $C_3$-$C_5$ cycloalkyl, $C_1$-$C_3$ haloalkyl, $C_1$-$C_3$ alkoxy, and $C_1$-$C_3$ haloalkoxy;
n is 1 or 2; and
m is 0, 1 or 2.

10. The compound of claim 9, or a pharmaceutically acceptable salt thereof, wherein

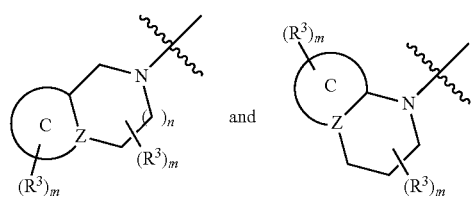

are independently selected from the group consisting of:

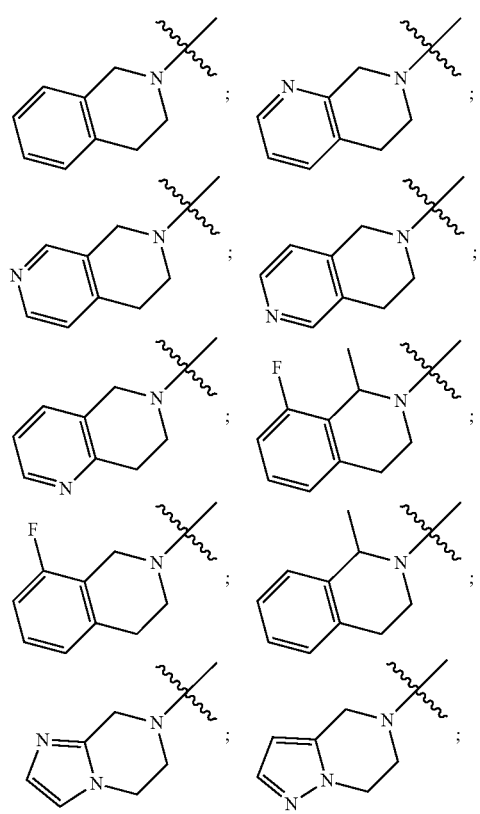

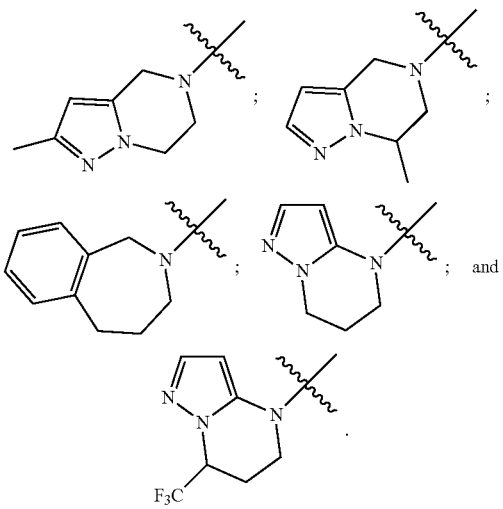

11. The compound of claim 1, or a pharmaceutically acceptable salt thereof, wherein $R^1$ is selected from the group consisting of $C_1$-$C_3$ alkyl, $C_3$-$C_5$ cycloalkyl, and $C_1$-$C_3$ haloalkyl; and $R^2$ is selected from the group consisting of $C_1$-$C_3$ alkyl, $C_3$-$C_5$ cycloalkyl, $C_1$-$C_4$ alkoxy, phenyl, and 4 to 5 membered heterocyclyl.

12. The compound of claim 11, or a pharmaceutically acceptable salt thereof, wherein $R^1$ is selected from the group consisting of methyl, cyclopropyl, —$CH_2CF_2H$ and —$CH_2CF_3$; and $R^2$ is selected from the group consisting of methyl, cyclopropyl, —$CH_2CH_2OCH_3$, phenyl, and oxetan-3-yl.

13. The compound of claim 1, or a pharmaceutically acceptable salt thereof, wherein

is selected from the group consisting of:

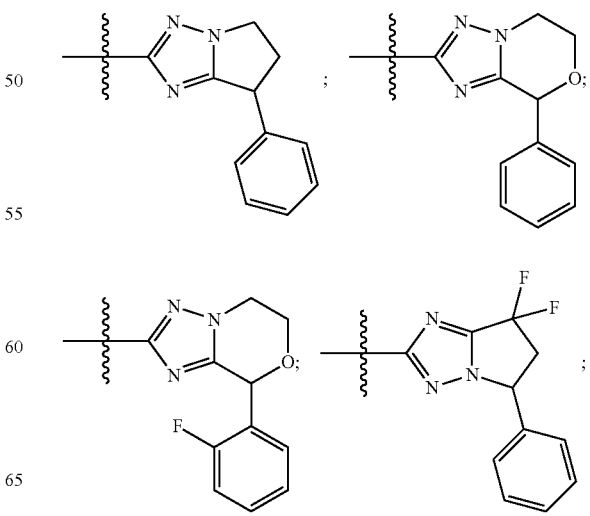

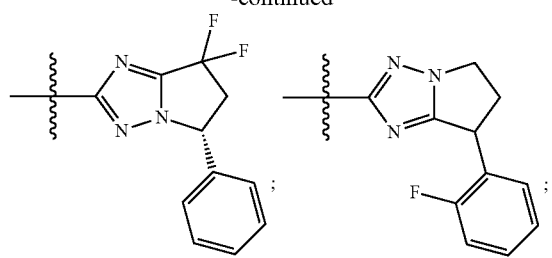
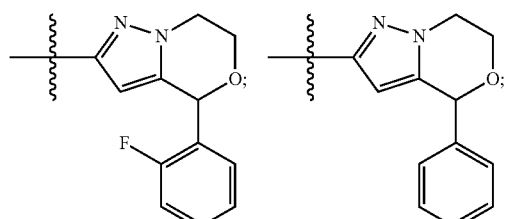
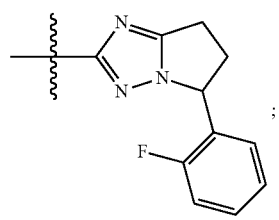
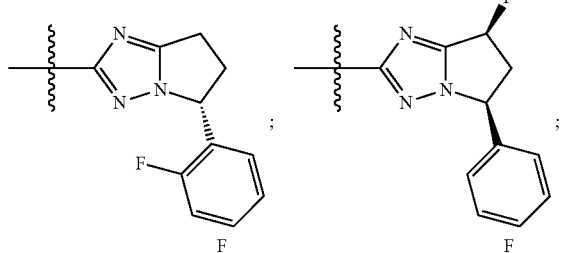
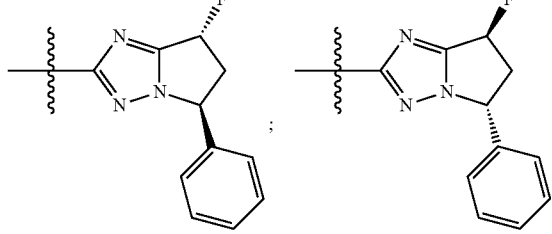
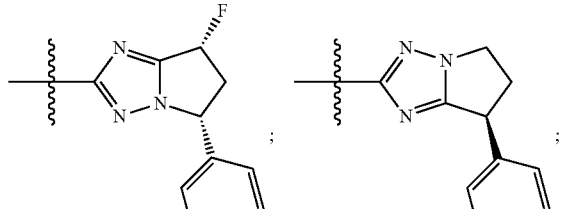
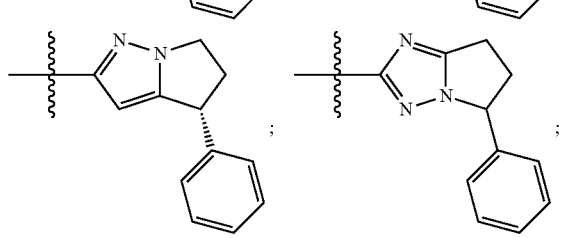
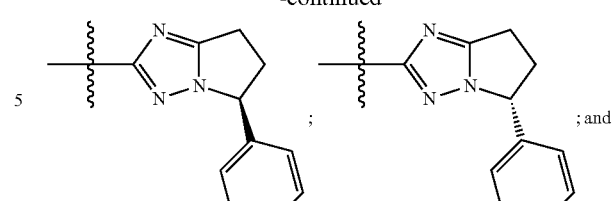
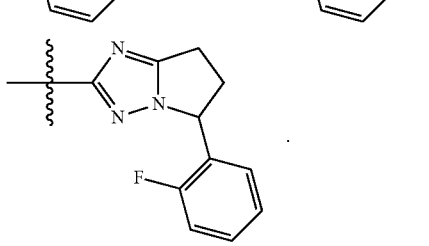
14. The compound of claim 1, or a pharmaceutically acceptable salt thereof, wherein
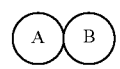
is selected from the group consisting of:
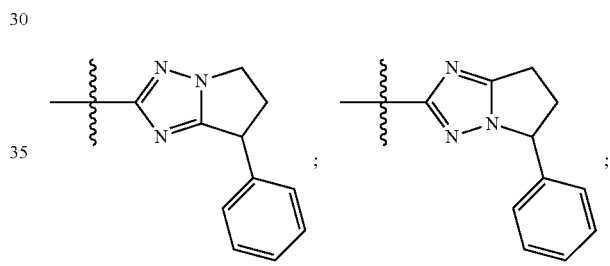
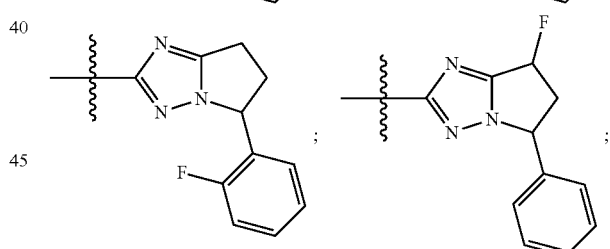
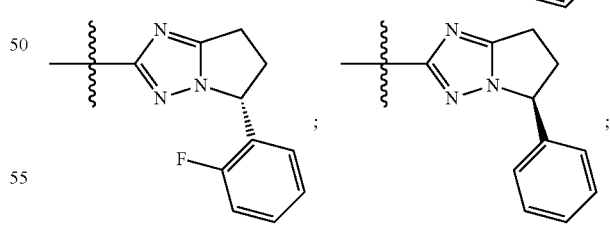
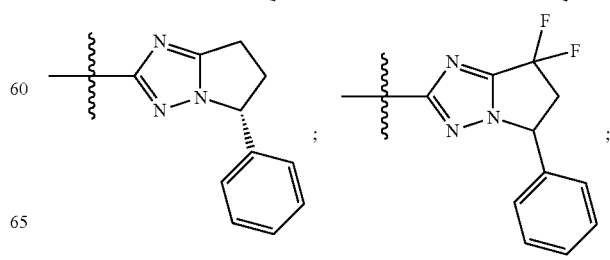

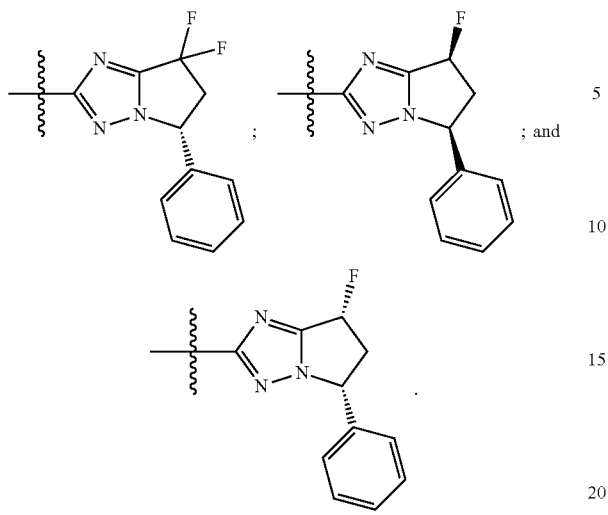
15. A compound, or a pharmaceutically acceptable salt thereof, wherein the compound is selected from the group consisting of:
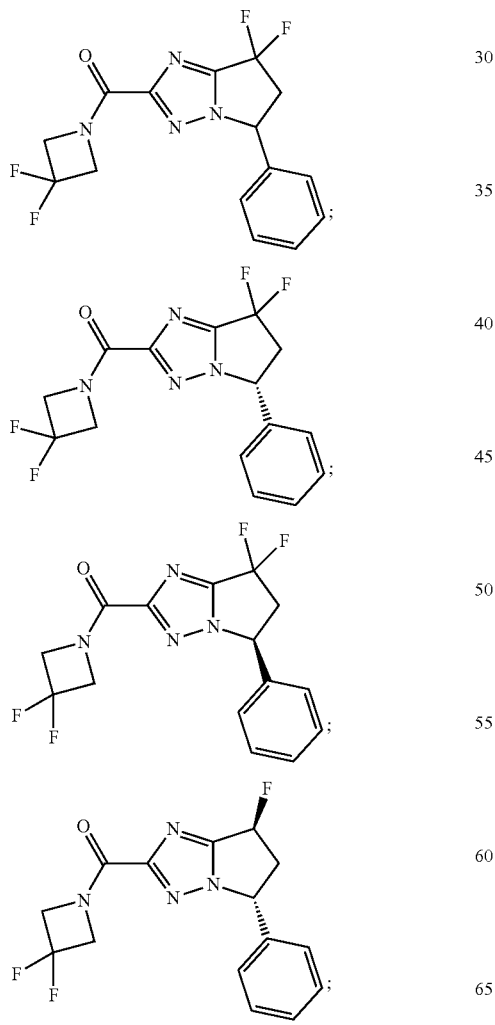
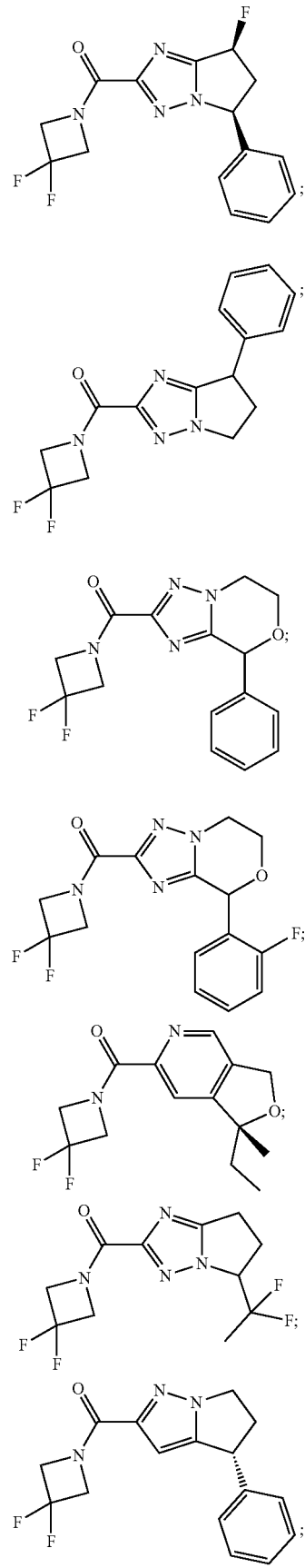

189
-continued
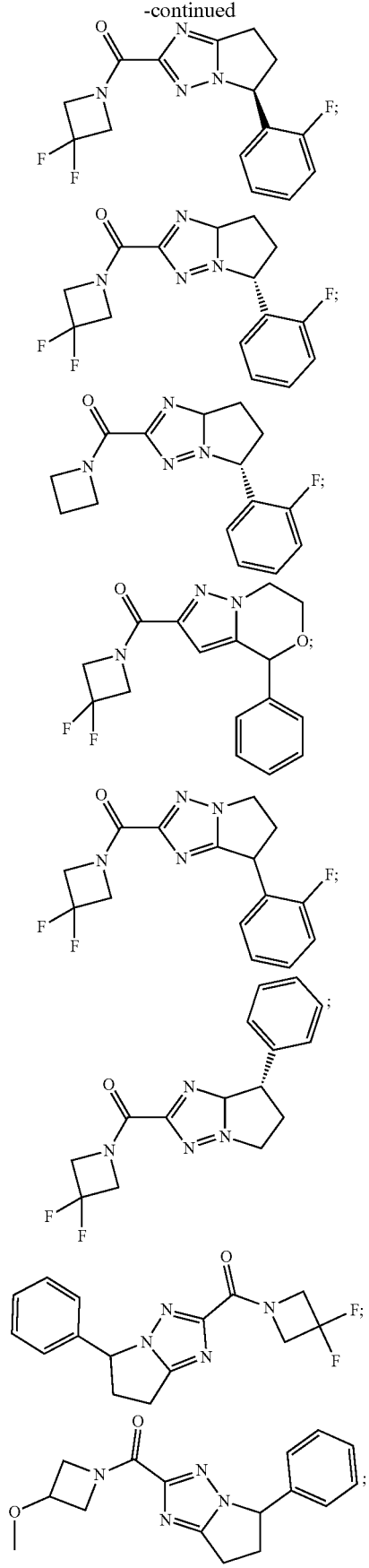
190
-continued
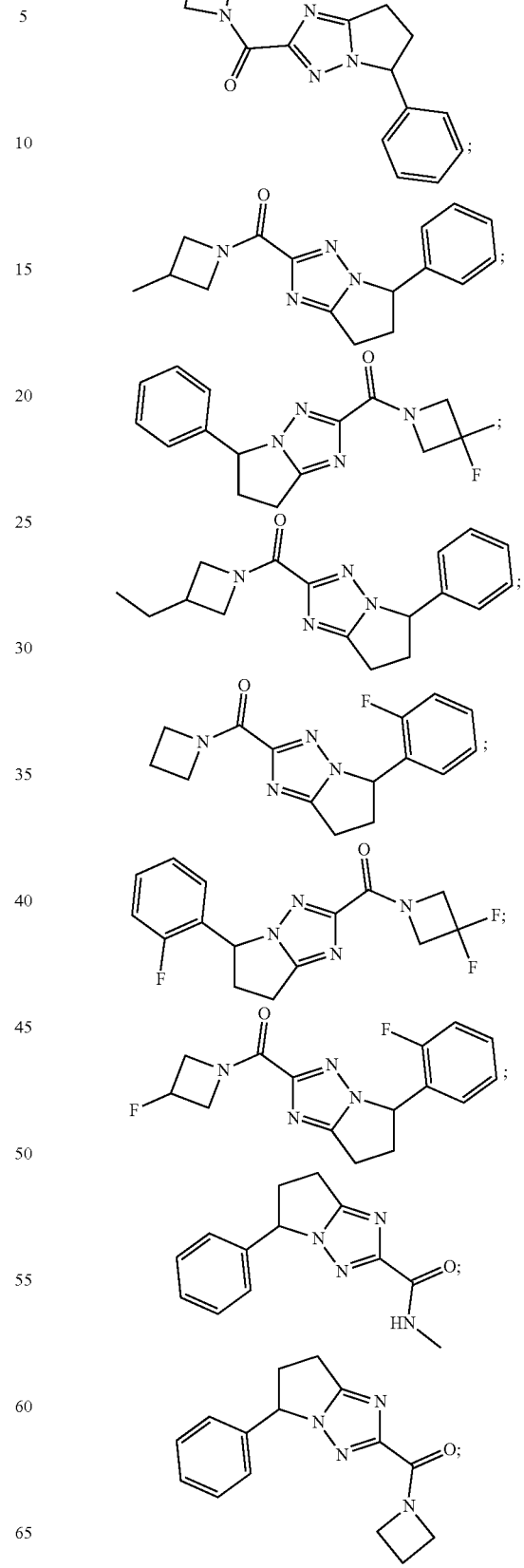

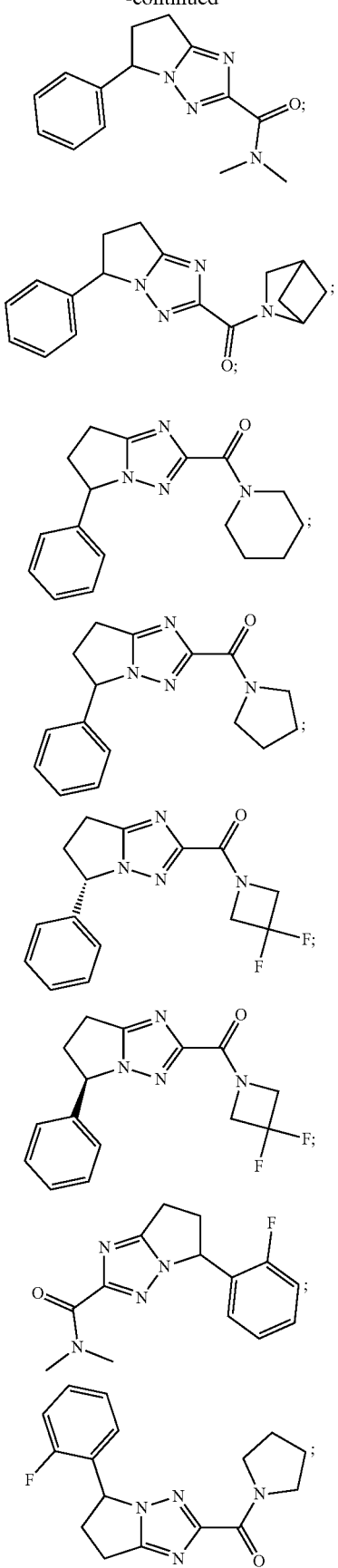
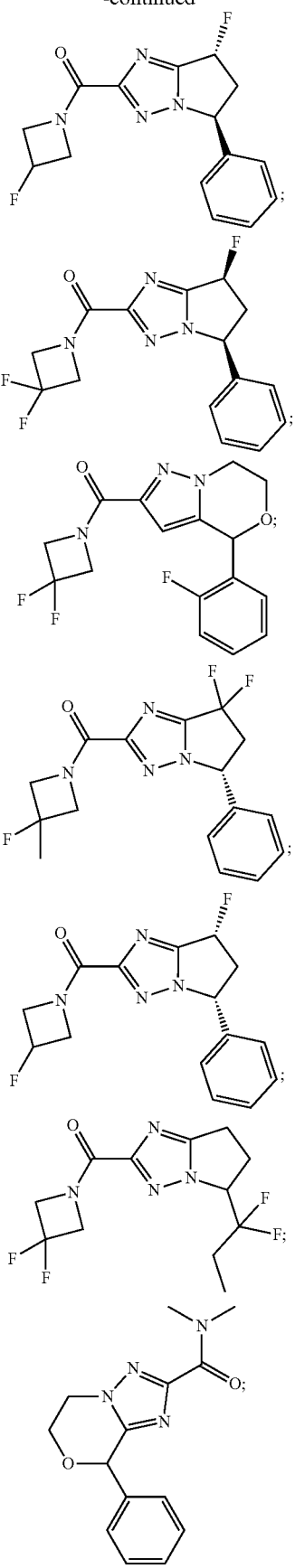

193
-continued
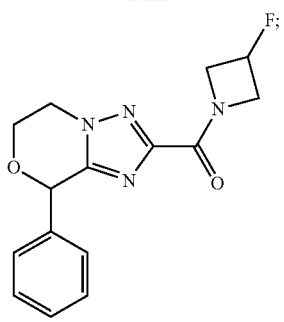
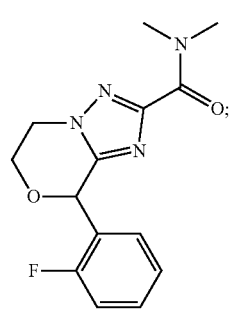
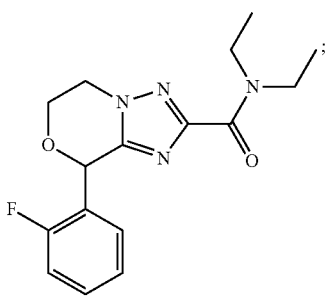
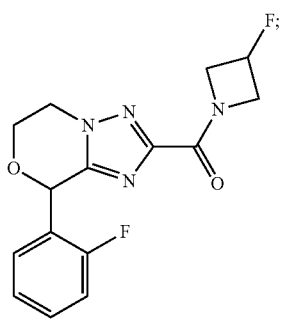
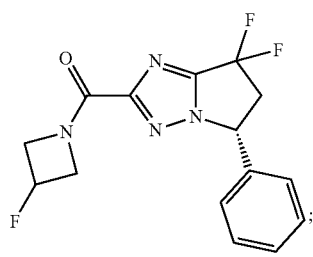
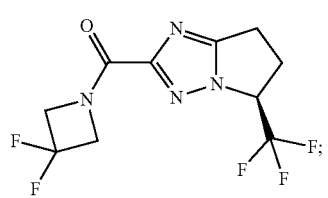
194
-continued
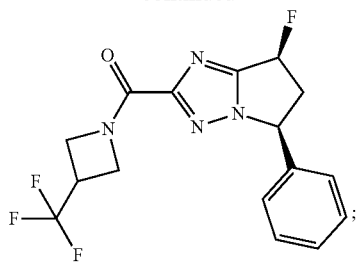
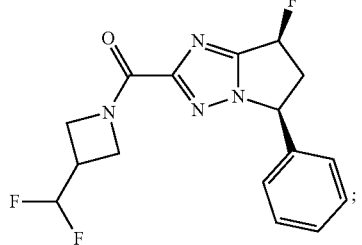
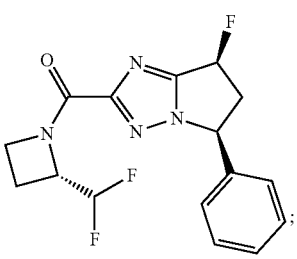
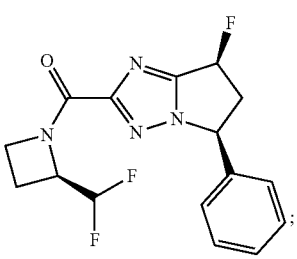
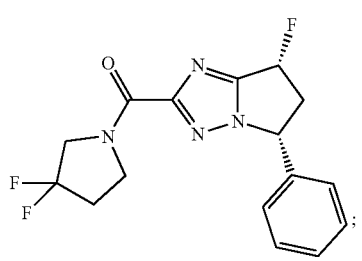
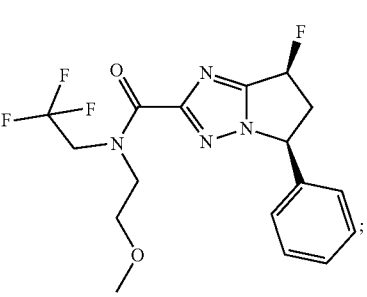

-continued
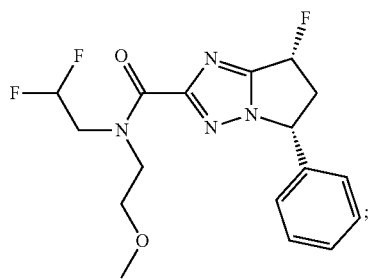
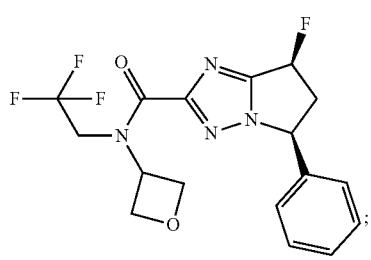
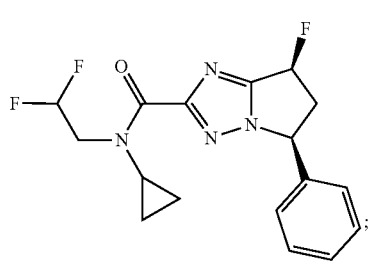
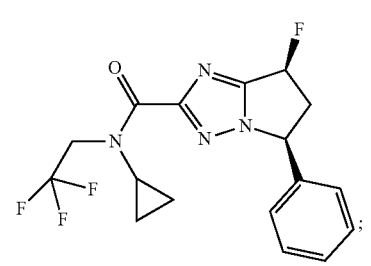
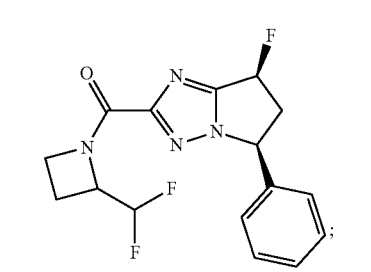
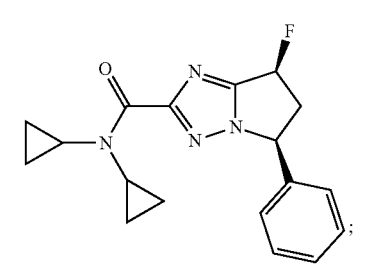
-continued
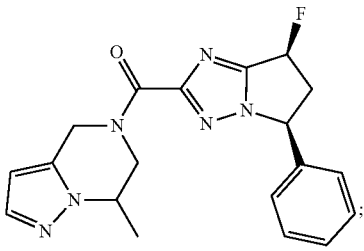
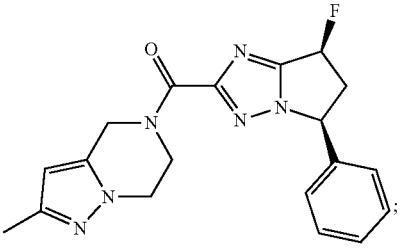
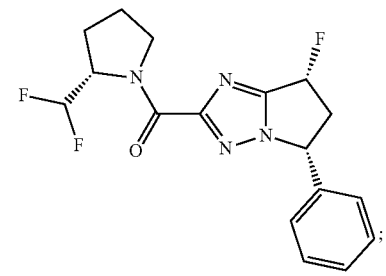
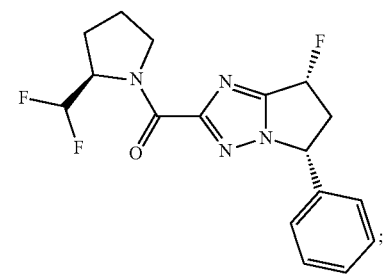
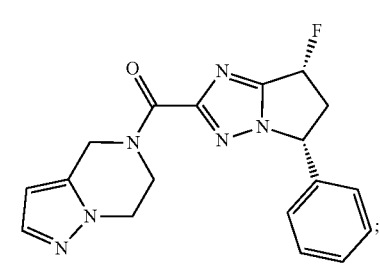
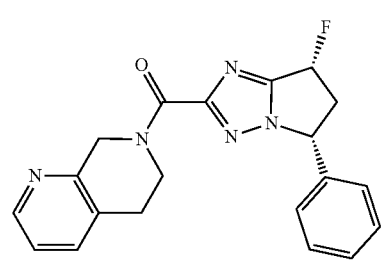

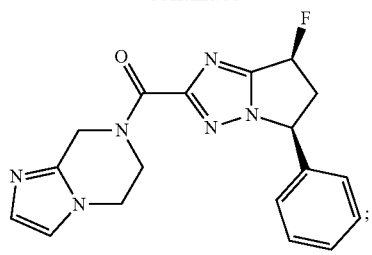
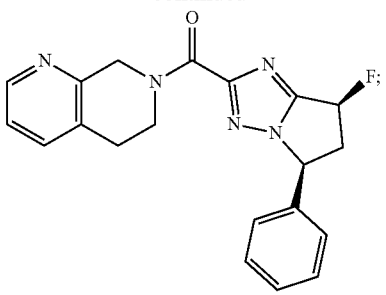
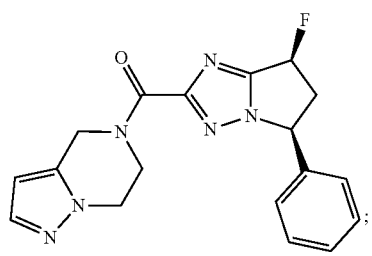
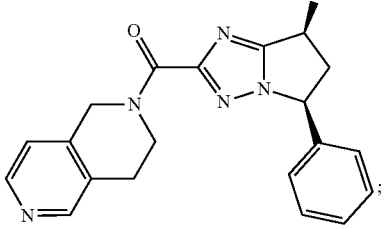
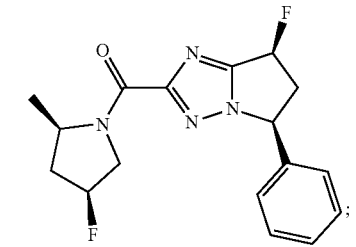
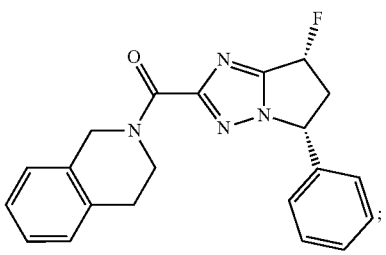
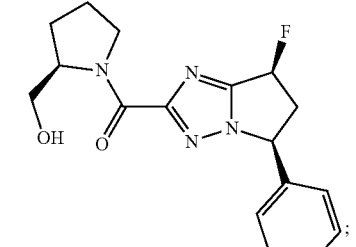
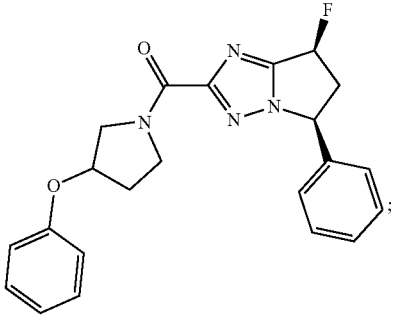
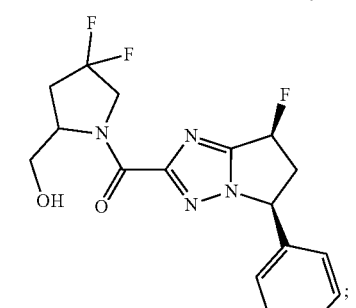
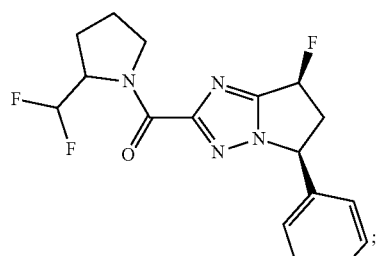
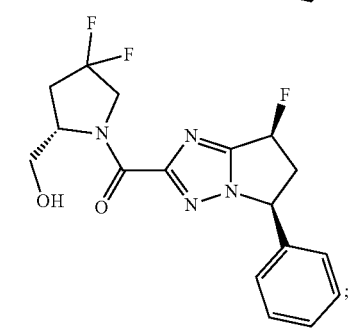
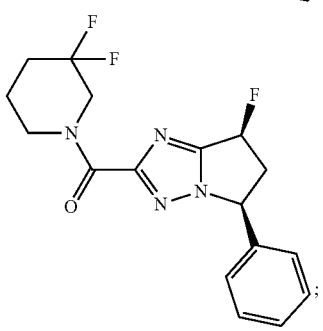

199
-continued
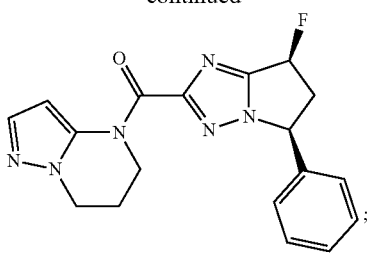
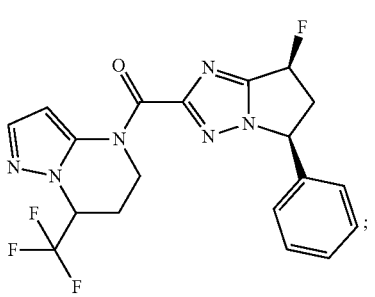
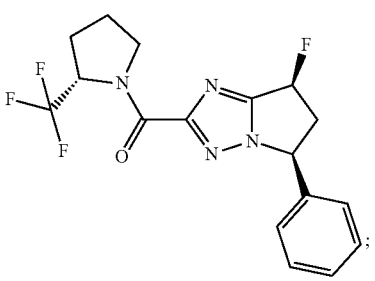
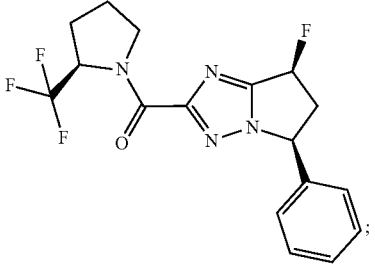
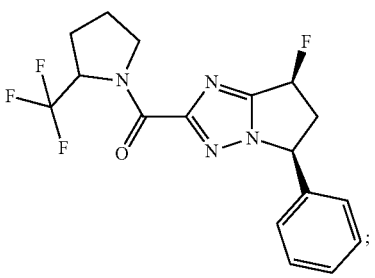
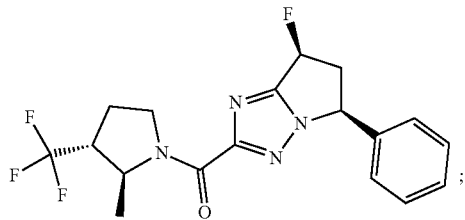
200
-continued
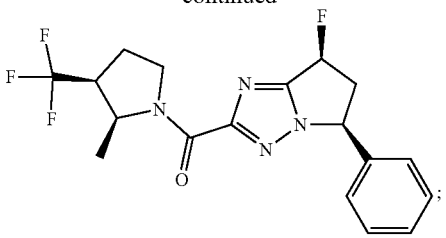
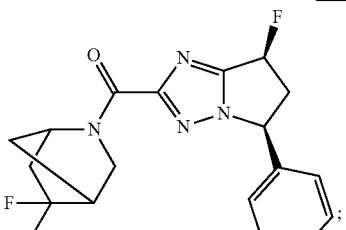
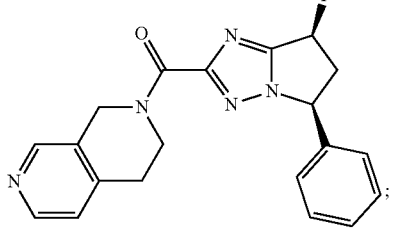
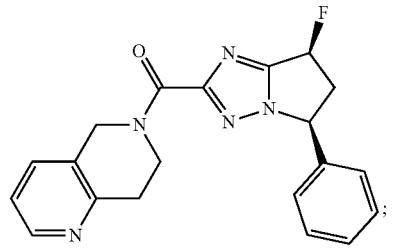
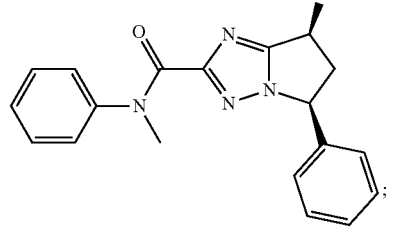
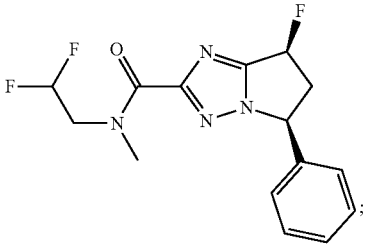
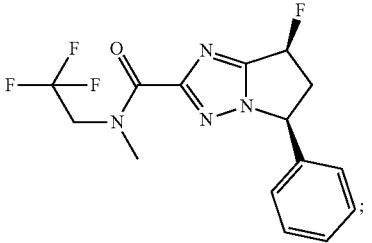

201
-continued
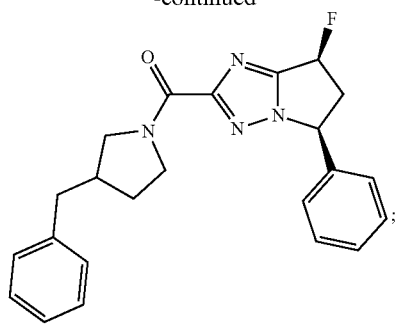
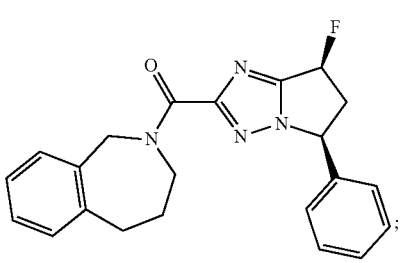
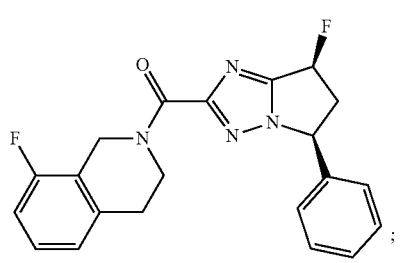
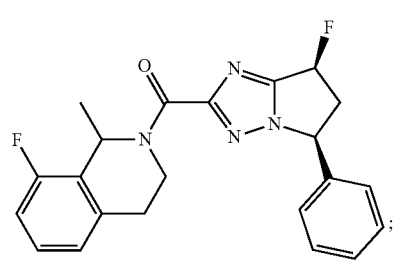
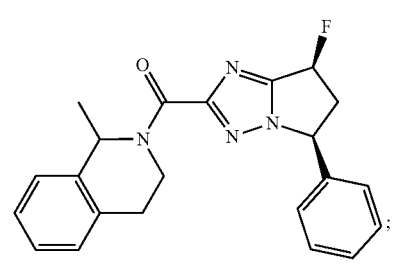
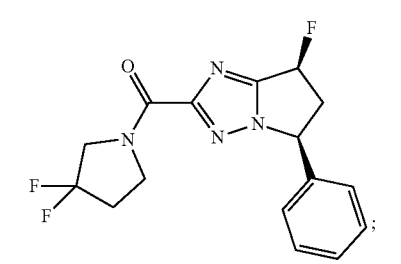
202
-continued
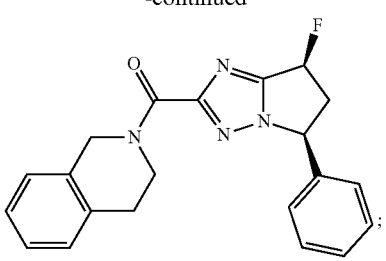
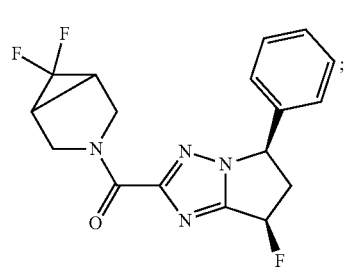
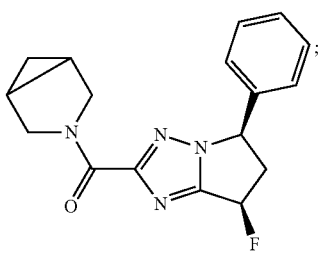
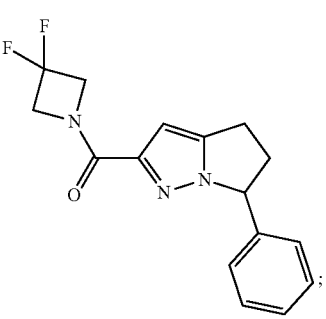
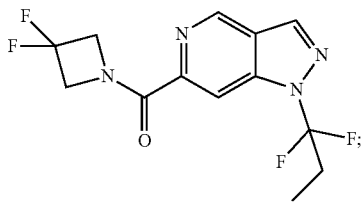
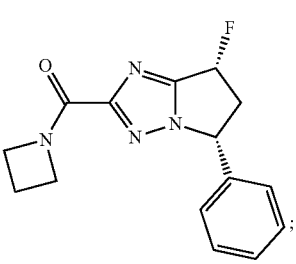

203
-continued
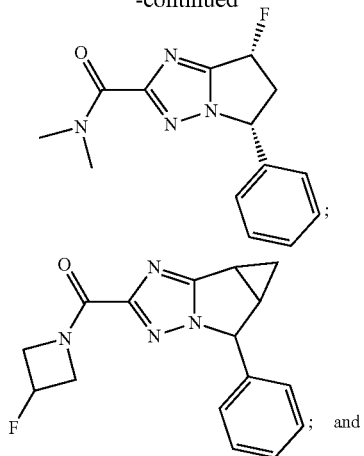
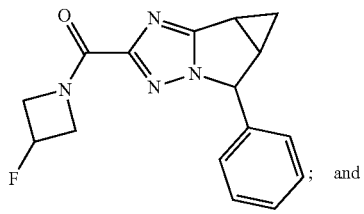
; and
204
-continued
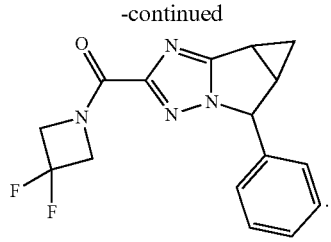
.
16. A pharmaceutical composition comprising a compound of claim 1, or a pharmaceutically acceptable salt thereof, and a therapeutically inert carrier.
17. A pharmaceutical composition comprising a compound of claim 15, or a pharmaceutically acceptable salt thereof, and a therapeutically inert carrier.
* * * * *